(12) United States Patent
Qin et al.

(10) Patent No.: US 9,540,400 B2
(45) Date of Patent: *Jan. 10, 2017

(54) COMPOUNDS AS DIACYLGLYCEROL ACYLTRANSFERASE INHIBITORS

(71) Applicant: GlaxoSmithKline Intellectual Property (No. 2) Limited, Brentford, Middlesex (GB)

(72) Inventors: Donghui Qin, Collegeville, PA (US); Mui Cheung, King of Prussia, PA (US); Hemant Joshi, Navi-Mumbai (IN); Raghuram Tangirala, Navi-Mumbai (IN); Sridhar Reddy Bethi, Navi-Mumbai (IN)

(73) Assignee: GlaxoSmithKline Intellectual Property (No.2) Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/996,318

(22) Filed: Jan. 15, 2016

(65) Prior Publication Data

US 2016/0200736 A1 Jul. 14, 2016

Related U.S. Application Data

(63) Continuation of application No. 14/695,206, filed on Apr. 24, 2015, now Pat. No. 9,273,069, which is a continuation of application No. 14/478,309, filed on Sep. 5, 2014, now Pat. No. 9,040,517, which is a continuation of application No. 14/118,976, filed as application No. PCT/US2012/038523 on May 18, 2012, now Pat. No. 8,859,536.

(60) Provisional application No. 61/503,728, filed on Jul. 1, 2011.

(30) Foreign Application Priority Data

May 20, 2011 (IN) .......................... 1452/DEL/2011

(51) Int. Cl.
*C07D 498/04* (2006.01)
*C07D 519/00* (2006.01)

(52) U.S. Cl.
CPC ........... *C07D 519/00* (2013.01); *C07D 498/04* (2013.01)

(58) Field of Classification Search
CPC ............................ C07D 498/04; C07D 519/00
See application file for complete search history.

(56) References Cited

U.S. PATENT DOCUMENTS

| 8,859,536 B2 | 10/2014 | Qin et al. |
| 9,040,517 B2 | 5/2015 | Cheung et al. |
| 2014/0148437 A1 | 5/2014 | Cheung et al. |
| 2015/0225425 A1 | 8/2015 | Cheung et al. |

*Primary Examiner* — Bruck Kifle
(74) *Attorney, Agent, or Firm* — Duke M. Fitch; Kathryn A. Lutomski; Edward R. Gimmi

(57) ABSTRACT

This invention relates to novel compounds which are inhibitors of acyl coenzymeA: diacylglycerol acyltransferase 1 (DGAT-1), to pharmaceutical compositions containing them, to processes for their preparation, and to their use in therapy for the prevention or treatment of diseases related to DGAT-1 dysfunction or where modulation of DGAT-1 activity may have therapeutic benefit including but not limited to obesity, obesity related disorders, hypertriglyceridemia, hyperlipoproteinemia, chylomicronemia, dyslipidemia, non-alcoholic steatohepatitis, diabetes, insulin resistance, metabolic syndrome, hepatitis C virus infection and acne or other skin disorders.

16 Claims, No Drawings

COMPOUNDS AS DIACYLGLYCEROL ACYLTRANSFERASE INHIBITORS

FIELD OF INVENTION

This invention relates to novel compounds which are inhibitors of acyl coenzymeA: diacylglycerol acyltransferase 1 (DGAT-1), to pharmaceutical compositions containing them, to processes for their preparation, and to their use in therapy for the prevention or treatment of diseases related to DGAT-1 dysfunction or where modulation of DGAT-1 activity may have therapeutic benefit including but not limited to obesity, obesity related disorders, hypertriglyceridemia, hyperlipoproteinemia, chylomicronemia, dyslipidemia, non-alcoholic steatohepatitis, diabetes, insulin resistance, metabolic syndrome, hepatitis C virus infection and acne or other skin disorders.

BACKGROUND OF THE INVENTION

Obesity is a medical condition that is reaching epidemic proportions among humans in a number of countries throughout the world. It is a condition that is also associated with or induces other diseases or conditions that disrupt life activities and lifestyles. Obesity is recognized as a serious risk factor for other diseases and conditions such as diabetes, hypertension, and arteriosclerosis. It is also known that increased body weight due to obesity can place a burden on joints, such as knee joints, causing arthritis, pain, and stiffness.

Because overeating and obesity have become such a problem in the general population, many individuals are now interested in losing weight, reducing weight, and maintaining a healthy body weight and desirable lifestyle. One approach to treating obesity is to reduce food intake and/or hyperlipidemia. It has been suggested that molecules which are developed to prevent the accumulation of triglyceride would not only reduce obesity but also have the additional beneficial effect of reducing insulin resistance, a primary factor contributing to the development of diabetes.

Acyl coenzymeA: diacylglycerol acyltransferase 1 (DGAT-1) is one of two known DGAT enzymes that catalyze the final step in mammalian triglyceride synthesis. DGAT-1 is an enzyme that is implicated in the development of both diabetes and insulin resistance. Studies of DGAT-1 deficient mice show that DGAT-1 deficiency protects against insulin resistance and obesity, see Chen, H. C. et al., *J Clin Invest.*, 109(8), 1049-1055 (2002). Therefore, inhibitors of DGAT-1 should be useful for the treatment of metabolic disorders, e.g. obesity, Type 2 diabetes, and insulin resistance syndrome (or metabolic syndrome) and other associated or related diseases and conditions.

SUMMARY OF THE INVENTION

This invention relates to compounds of Formula (I):

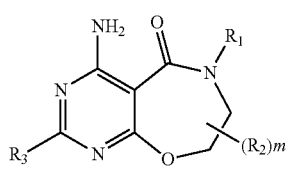

(I)

wherein
$R_1$ is a bicyclic ring system which contains 9 to 11 ring members including 1 to 4 hetero atoms, in which said bicyclic ring system may be substituted by 1 to 3 groups selected from the group consisting of $C_1$-$C_6$alkyl, substituted $C_1$-$C_6$alkyl, $C_3$-$C_7$cycloalkyl, halo, hydroxyl, oxo, amide, carboxylic acid, —C(O)$R_a$, —SO$_2$$R_a$, arylalkyl, —($C_1$-$C_3$alkyl)aryloxy, aryl, heteroaryl and $C_1$-$C_4$alkoxy,
in which each $R_a$ is independently $C_1$-$C_6$alkyl, substituted $C_1$-$C_6$alkyl or unsubstituted $C_3$-$C_7$cycloalkyl;
each $R_2$ and $R_3$ is independently hydrogen, $C_1$-$C_6$alkyl, substituted $C_1$-$C_6$alkyl, halo, hydroxyl, amide, carboxylic acid or $C_1$-$C_4$alkoxy; and
m is 0-2;
or a pharmaceutically acceptable salt thereof.

This invention also relates to a pharmaceutical composition comprising a compound of Formula (I) and a pharmaceutically acceptable carrier.

This invention also relates to a method of treating obesity comprising administering to a human in need thereof an effective amount of a compound of Formula (I) or a pharmaceutically acceptable salt thereof in a pharmaceutical composition.

DETAIL DESCRIPTION OF THE INVENTION

This invention relates to compounds of the Formula (I) as defined above.

This invention also relates to compounds of Formula (I)(A):

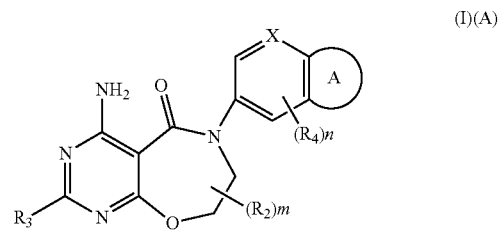

(I)(A)

wherein A is a 5- or 6-membered heterocyclic ring, which may contain 0 to 3 double bonds and may be substituted by 1 to 3 groups selected from the group consisting of $C_1$-$C_6$alkyl, substituted $C_1$-$C_6$alkyl, $C_3$-$C_7$cycloalkyl, halo, hydroxyl, oxo, amide, carboxylic acid, —C(O)$R_a$, —SO$_2$$R_a$, arylalkyl, —($C_1$-$C_3$alkyl)aryloxy, aryl, heteroaryl and $C_1$-$C_4$alkoxy,
in which each $R_a$ is independently $C_1$-$C_6$alkyl, substituted $C_1$-$C_6$alkyl or unsubstituted $C_3$-$C_7$cycloalkyl;
each $R_2$ and $R_3$ is independently hydrogen, $C_1$-$C_6$alkyl, substituted $C_1$-$C_6$alkyl, halo, hydroxyl, amide, carboxylic acid or $C_1$-$C_4$alkoxy;
$R_4$ is halo or alkoxy;
X is N or CH; and
m is 0-2;
n is 0-2;
or a pharmaceutically acceptable salt thereof.

This invention also relates to compounds of Formula (I)(A), wherein A is a 5-membered heterocyclic ring, which may contain 0-2 double bonds and may be substituted by 1 to 3 groups selected from the group consisting of $C_1$-$C_6$alkyl, substituted $C_1$-$C_6$alkyl, $C_3$-$C_7$cycloalkyl, halo, hydroxyl, oxo, amide, carboxylic acid, —C(O)$R_a$, —SO$_2$$R_a$, arylalkyl, —($C_1$-$C_3$alkyl)aryloxy, aryl, heteroaryl and $C_1$-$C_4$alkoxy, in which each $R_a$ is independently $C_1$-$C_6$alkyl, substituted $C_1$-$C_6$alkyl or unsubstituted $C_3$-$C_7$cycloalkyl;

each $R_2$ and $R_3$ is independently hydrogen, $C_1$-$C_6$alkyl, substituted $C_1$-$C_6$alkyl, halo, hydroxyl, amide, carboxylic acid or $C_1$-$C_4$alkoxy;

$R_4$ is halo or alkoxy;

X is N or CH; and m is 0-2;

n is 0-2;

or a pharmaceutically acceptable salt thereof.

This invention also relates to compounds of Formula (I)(A), wherein A is a 6-membered heterocyclic ring, which may contain 0-3 double bonds and may be substituted by 1 to 3 groups selected from the group consisting of $C_1$-$C_6$alkyl, substituted $C_1$-$C_6$alkyl, $C_3$-$C_7$cycloalkyl, halo, hydroxyl, oxo, amide, carboxylic acid, —C(O)$R_a$, —SO$_2$$R_a$, arylalkyl, —($C_1$-$C_3$alkyl)aryloxy, aryl, heteroaryl and $C_1$-$C_4$alkoxy, in which each $R_a$ is independently $C_1$-$C_6$alkyl, substituted $C_1$-$C_6$alkyl or unsubstituted $C_3$-$C_7$cycloalkyl;

each $R_2$ and $R_3$ is independently hydrogen, $C_1$-$C_6$alkyl, substituted $C_1$-$C_6$alkyl, halo, hydroxyl, amide, carboxylic acid or $C_1$-$C_4$alkoxy;

$R_4$ is halo or alkoxy;

X is N or CH; and m is 0-2;

n is 0-2;

or a pharmaceutically acceptable salt thereof.

This invention also relates to any one of the above compounds, wherein m is 0;

n is 0;

$R_3$ is hydrogen; and

X is N or CH;

or a pharmaceutically acceptable salt thereof.

This invention also relates to compounds of Formula (I), wherein m is 0;

$R_3$ is hydrogen;

$R_1$ is a bicyclic ring system selected from the group consisting of tetrahydroisoquinolinyl, tetrahydroquinolinyl, indolyl, dihydroindolyl, indazolyl, dihydroindazolyl, benzothiophenyl, benzodiazolyl, dihydrobenzodiazolyl, benzimidazolyl, indolinyl, benzotriazolyl, pyrrolopyridinyl, benzothiazolyl, benzofuranyl, dihydroquinazolinyl, and pyrrolopyrimidinyl;

wherein said bicyclic ring system may be substituted by 1 to 3 groups selected from the group consisting of $C_1$-$C_6$alkyl, substituted $C_1$-$C_6$alkyl, $C_3$-$C_7$cycloalkyl, halo, hydroxyl, oxo, amide, carboxylic acid, —C(O)$R_a$, —SO$_2$$R_a$, arylalkyl, —($C_1$-$C_3$alkyl)aryloxy, aryl, heteroaryl and $C_1$-$C_4$alkoxy, in which each $R_a$ is independently $C_1$-$C_6$alkyl, substituted $C_1$-$C_6$alkyl or unsubstituted $C_3$-$C_7$cycloalkyl;

or a pharmaceutically acceptable salt thereof.

This invention also relates to compounds of Formula (I), wherein m is 0;

$R_3$ is hydrogen;

$R_1$ is a bicyclic ring system selected from the group consisting of tetrahydroisoquinolinyl, tetrahydroquinolinyl, indolyl, dihydroindolyl, indazolyl, dihydroindazolyl, and pyrrolopyridinyl;

wherein said bicyclic ring system may be substituted by 1 to 3 groups selected from the group consisting of $C_1$-$C_6$alkyl, substituted $C_1$-$C_6$alkyl, $C_3$-$C_7$cycloalkyl, halo, hydroxyl, oxo, amide, carboxylic acid, —C(O)$R_a$, —SO$_2$$R_a$, arylalkyl, —($C_1$-$C_3$alkyl)aryloxy, aryl, heteroaryl and $C_1$-$C_4$alkoxy, in which each $R_a$ is independently $C_1$-$C_6$alkyl, substituted $C_1$-$C_6$alkyl or unsubstituted $C_3$-$C_7$cycloalkyl;

or a pharmaceutically acceptable salt thereof.

This invention also relates to compounds of Formula (I), wherein m is 0;

$R_3$ is hydrogen;

$R_1$ is a bicyclic ring system selected from the group consisting of tetrahydroisoquinolinyl, tetrahydroquinolinyl, indolyl, dihydroindolyl, indazolyl, dihydroindazolyl, benzothiophenyl, benzodiazolyl, dihydrobenzodiazolyl, benzimidazolyl, indolinyl, benzotriazolyl, pyrrolopyridinyl, benzothiazolyl, benzofuranyl, dihydroquinazolinyl, and pyrrolopyrimidinyl;

wherein said bicyclic ring system may be substituted by 1 to 3 groups selected from the group consisting of aryl and heteroaryl;

or a pharmaceutically acceptable salt thereof.

This invention relates to compounds of Formula (I)(B):

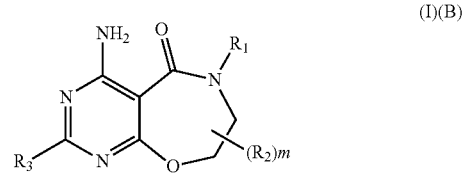

(I)(B)

wherein $R_1$ is a bicyclic ring system which contains 9 to 11 ring members including 1 to 4 hetero atoms, in which said bicyclic ring system may be substituted by 1 to 3 groups selected from the group consisting of $C_1$-$C_6$alkyl, substituted $C_1$-$C_6$alkyl, halo, hydroxyl, oxo, amide, carboxylic acid, and alkoxy;

each $R_2$ and $R_3$ is independently hydrogen, $C_1$-$C_6$alkyl, substituted $C_1$-$C_6$alkyl, halo, hydroxyl, amide, carboxylic acid or alkoxy; and m is 0-2;

or a pharmaceutically acceptable salt thereof.

This invention also relates to compounds of Formula (I)(C):

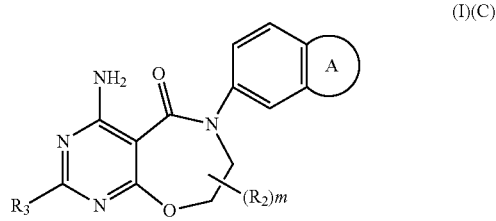

(I)(C)

wherein A is a 5- or 6-membered heterocyclic ring, which may contain 0 to 3 double bonds and may be substituted by 1 to 3 groups selected from the group consisting of $C_1$-$C_6$alkyl, substituted $C_1$-$C_6$alkyl, halo, hydroxyl, oxo, amide, carboxylic acid, and alkoxy; each $R_2$ and $R_3$ is independently hydrogen, $C_1$-$C_6$alkyl, substituted $C_1$-$C_6$alkyl, halo, hydroxyl, amide, carboxylic acid or alkoxy; and m is 0-2;

or a pharmaceutically acceptable salt thereof.

This invention also relates to compounds of Formula (I)(C), wherein A is a 5-membered heterocyclic ring, which may contain 0 to 3 double bonds and may be substituted by 1 to 3 groups selected from the group consisting of $C_1$-$C_6$alkyl, substituted $C_1$-$C_6$alkyl, halo, hydroxyl, oxo, amide, carboxylic acid, and alkoxy;

each $R_2$ and $R_3$ is independently hydrogen, $C_1$-$C_6$alkyl, substituted $C_1$-$C_6$alkyl, halo, hydroxyl, amide, carboxylic acid or alkoxy; and m is 0-2;

or a pharmaceutically acceptable salt thereof.

This invention also relates to compounds of Formula (I), (I)(A), (I)(B) or (I)(C), wherein m is 0, and $R_3$ is hydrogen, or a pharmaceutically acceptable salt thereof.

This invention also relates to compounds that are exemplified in the Experimental section.

Specific compounds of this invention include:

2-(6-{4-amino-5-oxo-5H,6H,7H,8H-pyrimido[5,4-f][1,4]oxazepin-6-yl}-1-oxo-1,2,3,4-tetrahydroisoquinolin-2-yl)acetic acid;

ethyl 2-(6-{4-amino-5-oxo-5H,6H,7H,8H-pyrimido[5,4-f][1,4]oxazepin-6-yl}-2-oxo-1,2,3,4-tetrahydroquinolin-1-yl)acetate;

2-(6-{4-amino-5-oxo-5H,6H,7H,8H-pyrimido[5,4-f][1,4]oxazepin-6-yl}-2-oxo-1,2,3,4-tetrahydroquinolin-1-yl)acetic acid;

ethyl 2-(6-{4-amino-5-oxo-5H,6H,7H,8H-pyrimido[5,4-f][1,4]oxazepin-6-yl}-1-oxo-1,2,3,4-tetrahydroisoquinolin-2-yl)acetate;

6-{4-amino-5-oxo-5H,6H,7H,8H-pyrimido[5,4-f][1,4]oxazepin-6-yl}-1-methyl-1,2,3,4-tetrahydroquinolin-2-one;

6-{4-amino-5-oxo-5H,6H,7H,8H-pyrimido[5,4-f][1,4]oxazepin-6-yl}-2-methyl-1,2,3,4-tetrahydroisoquinolin-1-one;

6-{4-amino-5-oxo-5H,6H,7H,8H-pyrimido[5,4-f][1,4]oxazepin-6-yl}-2-benzyl-1,2,3,4-tetrahydroisoquinolin-1-one;

6-{4-amino-5-oxo-5H,6H,7H,8H-pyrimido[5,4-f][1,4]oxazepin-6-yl}-2-propyl-1,2,3,4-tetrahydroisoquinolin-1-one;

6-{4-amino-5-oxo-5H,6H,7H,8H-pyrimido[5,4-f][1,4]oxazepin-6-yl}-1-propyl-1,2,3,4-tetrahydroquinolin-2-one;

5-{4-amino-5-oxo-5H,6H,7H,8H-pyrimido[5,4-f][1,4]oxazepin-6-yl}-2-benzyl-1-(prop-2-en-1-yl)-2,3-dihydro-1H-indazol-3-one;

5-{4-amino-5-oxo-5H,6H,7H,8H-pyrimido[5,4-f][1,4]oxazepin-6-yl}-1-propyl-2,3-dihydro-1H-indazol-3-one;

4-amino-6-(1-propyl-1H-indol-5-yl)-5H,6H,7H,8H-pyrimido[5,4-f][1,4]oxazepin-5-one;

4-amino-6-(1-propyl-1H-indazol-5-yl)-5H,6H,7H,8H-pyrimido[5,4-f][1,4]oxazepin-5-one;

4-amino-6-(1-benzothiophen-5-yl)-5H,6H,7H,8H-pyrimido[5,4-f][1,4]oxazepin-5-one;

5-{4-amino-5-oxo-5H,6H,7H,8H-pyrimido[5,4-f][1,4]oxazepin-6-yl)}-1,3-dipropyl-2,3-dihydro-1H-1,3-benzodiazol-2-one;

4-amino-6-(2-propyl-2H-indazol-5-yl)-5H,6H,7H, 8H-pyrimido[5,4-f][1,4]oxazepin-5-one;

4-amino-6-(1,3-benzothiazol-6-yl)-5H,6H,7H,8H-pyrimido[5,4-f][1,4]oxazepin-5-one;

5-{4-amino-5-oxo-5H,6H,7H,8H-pyrimido[5,4-f][1,4]oxazepin-6-yl}-1-propyl-2,3-dihydro-1H-indole-2,3-dione;

4-amino-6-(1-benzofuran-5-yl)-5H,6H,7H,8H-pyrimido[5,4-f][1,4]oxazepin-5-one;

4-amino-6-(1-cyclopropyl-1,2,3,4-tetrahydroquinolin-6-yl)-5H,6H,7H,8H-pyrimido[5,4-f][1,4]oxazepin-5-one;

4-amino-6-(2-propyl-1,2,3,4-tetrahydroisoquinolin-6-yl)-5H,6H,7H,8H-pyrimido[5,4-f][1,4]oxazepin-5-one;

4-amino-6-[1-(2,2-difluoroethyl)-1,2,3,4-tetrahydroquinolin-6-yl]-5H,6H,7H,8H-pyrimido[5,4-f][1,4]oxazepin-5-one;

5-{4-amino-5-oxo-5H,6H,7H,8H-oxepino[2,3-d]pyrimidin-6-yl}-1-(propan-2-yl)-2,3-dihydro-1H-indazol-3-one;

5-{4-amino-5-oxo-5H,6H,7H,8H-oxepino[2,3-d]pyrimidin-6-yl}-1-(2-methoxyethyl)-2,3-dihydro-1H-indazol-3-one;

5-{4-amino-5-oxo-5H,6H,7H,8H-pyrimido[5,4-f][1,4]oxazepin-6-yl}-1-(2,2-difluoroethyl)-2,3-dihydro-1H-indazol-3-one;

5-{4-amino-5-oxo-5H,6H,7H,8H-pyrimido[5,4-f][1,4]oxazepin-6-yl}-1-cyclopropyl-2,3-dihydro-1H-indazol-3-one;

6-amino-4-(1-propyl-1H-1,3-benzodiazol-5-yl)-2,3,4,5-tetrahydro-1,4-benzoxazepin-5-one;

4-amino-6-(1-propyl-1H-1,3-benzodiazol-6-yl)-5H,6H,7H,8H-pyrimido[5,4-f][1,4]oxazepin-5-one;

4-amino-6-(2-propyl-2H-1,2,3-benzotriazol-5-yl)-5H,6H,7H,8H-pyrimido[5,4-f][1,4]oxazepin-5-one;

4-amino-6-(1-propyl-1H-1,2,3-benzotriazol-6-yl)-5H,6H,7H,8H-pyrimido[5,4-f][1,4]oxazepin-5-one;

4-amino-6-(2-methyl-1,3-benzothiazol-5-yl)-5H,6H,7H,8H-pyrimido[5,4-f][1,4]oxazepin-5-one;

4-amino-6-[1-(2,2-difluoroethyl)-1H-pyrrolo[2,3-b]pyridin-5-yl]-5H,6H,7H,8H-pyrimido[5,4-f][1,4]oxazepin-5-one;

4-amino-6-{1-cyclopropyl-1H-pyrrolo[2,3-b]pyridin-5-yl}-5H,6H,7H,8H-pyrimido[5,4-f][1,4]oxazepin-5-one;

4-amino-6-[1-(cyclopropylmethyl)-1H-indol-5-yl]-5H,6H,7H,8H-pyrimido[5,4-f][1,4]oxazepin-5-one;

3-(5-{4-amino-5-oxo-5H,6H,7H,8H-pyrimido[5,4-f][1,4]oxazepin-6-yl}-1H-indol-1-yl)propanoic acid;

4-amino-6-[1-(cyclohexylmethyl)-1H-indol-5-yl]-5H,6H,7H,8H-pyrimido[5,4-f][1,4]oxazepin-5-one;

4-amino-6-[1-(pentan-3-yl)-1H-indol-5-yl]-5H,6H,7H,8H-pyrimido[5,4-f][1,4]oxazepin-5-one;

4-amino-6-{1-[(4-methoxyphenyl)methyl]-1H-indol-5-yl}-5H,6H,7H,8H-pyrimido[5,4-f][1,4]oxazepin-5-one;

4-amino-6-{1-[(4-fluorophenyl)methyl]-1H-indol-5-yl}-5H,6H,7H,8H-pyrimido[5,4-f][1,4]oxazepin-5-one;

4-amino-6-{1-[2-(benzyloxy)ethyl]-1H-indol-5-yl}-5H,6H,7H,8H-pyrimido[5,4-f][1,4]oxazepin-5-one;

4-amino-6-(1-benzyl-1H-indol-5-yl)-5H,6H,7H,8H-pyrimido[5,4-f][1,4]oxazepin-5-one;

4-amino-6-[1-(3-methoxypropyl)-1H-indol-5-yl]-5H,6H,7H,8H-pyrimido[5,4-f][1,4]oxazepin-5-one;

4-amino-6-[1-(2,2-difluoroethyl)-1H-indol-5-yl]-5H,6H,7H,8H-pyrimido[5,4-f][1,4]oxazepin-5-one;

4-amino-6-(1-methyl-1H-indol-5-yl)-5H,6H,7H,8H-pyrimido[5,4-f][1,4]oxazepin-5-one;

4-amino-6-[1-(2-methoxyethyl)-1H-indol-5-yl]-5H,6H,7H,8H-pyrimido[5,4-f][1,4]oxazepin-5-one;

4-amino-6-[1-(propan-2-yl)-1H-indol-5-yl]-5H,6H,7H,8H-pyrimido[5,4-f][1,4]oxazepin-5-one;

4-amino-6-(1H-indol-5-yl)-5H,6H,7H,8H-pyrimido[5,4-f][1,4]oxazepin-5-one;

4-amino-6-(1-propyl-2,3-dihydro-1H-indol-5-yl)-5H,6H,7H, 8H-pyrimido[5,4-f][1,4]oxazepin-5-one;

4-amino-6-(2,3-dihydro-1H-indol-5-yl)-5H,6H,7H, 8H-pyrimido[5,4-f][1,4]oxazepin-5-one;

4-amino-6-[1-(2-methoxyethyl)-2,3-dihydro-1H-indol-5-yl]-5H,6H,7H,8H-pyrimido[5,4-f][1,4]oxazepin-5-one;

4-amino-6-(1,2-dimethyl-1H-indol-5-yl)-5H,6H,7H,8H-pyrimido[5,4-f][1,4]oxazepin-5-one;

4-amino-6-[1-(cyclopropylmethyl)-1H-pyrrolo[2,3-b]pyridin-5-yl]-5H,6H,7H,8H-pyrimido[5,4-f][1,4]oxazepin-5-one;

4-amino-6-{1-propyl-1H-pyrrolo[2,3-b]pyridin-5-yl}-5H,6H,7H,8H-pyrimido[5,4-f][1,4]oxazepin-5-one;

4-amino-6-[1-(2-methoxyethyl)-1H-pyrrolo[2,3-b]pyridin-5-yl]-5H,6H,7H,8H-pyrimido[5,4-f][1,4]oxazepin-5-one;

4-amino-6-[1-(cyclohexylmethyl)-1H-pyrrolo[2,3-b]pyridin-5-yl]-5H,6H,7H,8H-pyrimido[5,4-f][1,4]oxazepin-5-one;

4-amino-6-{1-cyclohexyl-1H-pyrrolo[2,3-b]pyridin-5-yl}-5H,6H,7H,8H-pyrimido[5,4-f][1,4]oxazepin-5-one;

4-amino-6-[1-(propan-2-yl)-1H-pyrrolo[2,3-b]pyridin-5-yl]-5H,6H,7H,8H-pyrimido[5,4-f][1,4]oxazepin-5-one;

4-amino-6-[1-(2-hydroxyethyl)-1H-pyrrolo[2,3-b]pyridin-5-yl]-5H,6H,7H,8H-pyrimido[5,4-f][1,4]oxazepin-5-one;

4-amino-6-(1-methanesulfonyl-1H-indol-5-yl)-5H,6H,7H,8H-pyrimido[5,4-f][1,4]oxazepin-5-one;

4-amino-6-(1-cyclopropyl-1H-indol-5-yl)-5H,6H,7H,8H-pyrimido[5,4-f][1,4]oxazepin-5-one;

5-{4-amino-5-oxo-5H,6H,7H,8H-pyrimido[5,4-f][1,4]oxazepin-6-yl}-1-propyl-1H-indole-2-carboxylic acid;

4-amino-6-[1-propyl-3-(trifluoroacetyl)-1H-indol-5-yl]-5H,6H,7H,8H-pyrimido[5,4-f][1,4]oxazepin-5-one;

4-amino-6-[1-propyl-3-(1,1,1-trifluoro-2-methoxypropan-2-yl)-1H-indol-5-yl]-5H,6H,7H,8H-pyrimido[5,4-f][1,4]oxazepin-5-one;

4-amino-6-(1-phenyl-1H-indol-5-yl)-5H,6H,7H,8H-pyrimido[5,4-f][1,4]oxazepin-5-one;

4-amino-6-{1-[4-(trifluoromethyl)phenyl]-1H-pyrrolo[2,3-b]pyridin-5-yl}-5H,6H,7H,8H-pyrimido[5,4-f][1,4]oxazepin-5-one;

4-amino-6-[1-(4-fluorophenyl)-1H-pyrrolo[2,3-b]pyridin-5-yl]-5H,6H,7H,8H-pyrimido[5,4-f][1,4]oxazepin-5-one;

4-amino-6-[1-(3-chlorophenyl)-1H-pyrrolo[2,3-b]pyridin-5-yl]-5H,6H,7H,8H-pyrimido[5,4-f][1,4]oxazepin-5-one;

4-amino-6-[1-(3-chlorophenyl)-1H-indol-5-yl]-5H,6H,7H,8H-pyrimido[5,4-f][1,4]oxazepin-5-one;

4-amino-6-[1-(2-methoxyphenyl)-1H-pyrrolo[2,3-b]pyridin-5-yl]-5H,6H,7H,8H-pyrimido[5,4-f][1,4]oxazepin-5-one;

4-amino-6-[1-(2-methoxyphenyl)-1H-indol-5-yl]-5H,6H,7H,8H-pyrimido[5,4-f][1,4]oxazepin-5-one;

4-amino-6-{1-phenyl-1H-pyrrolo[2,3-b]pyridin-5-yl}-5H,6H,7H,8H-pyrimido[5,4-f][1,4]oxazepin-5-one;

4-amino-6-[1-(2-fluorophenyl)-1H-pyrrolo[2,3-b]pyridin-5-yl]-5H,6H,7H,8H-pyrimido[5,4-f][1,4]oxazepin-5-one;

4-amino-6-[1-(3,4-difluorophenyl)-1H-indol-5-yl]-5H,6H,7H,8H-pyrimido[5,4-f][1,4]oxazepin-5-one;

4-amino-6-[1-(3,4-difluorophenyl)-1H-pyrrolo[2,3-b]pyridin-5-yl]-5H,6H,7H,8H-pyrimido[5,4-f][1,4]oxazepin-5-one;

4-amino-6-[1-(2-fluorophenyl)-1H-indol-5-yl]-5H,6H,7H,8H-pyrimido[5,4-f][1,4]oxazepin-5-one;

4-amino-6-{1-[4-(trifluoromethyl)phenyl]-1H-indol-5-yl}-5H,6H,7H,8H-pyrimido[5,4-f][1,4]oxazepin-5-one;

4-amino-6-[1-(4-chlorophenyl)-1H-pyrrolo[2,3-b]pyridin-5-yl]-5H,6H,7H,8H-pyrimido[5,4-f][1,4]oxazepin-5-one;

4-amino-6-{1-[3-(trifluoromethyl)phenyl]-1H-indol-5-yl}-5H,6H,7H,8H-pyrimido[5,4-f][1,4]oxazepin-5-one;

4-amino-6-{1-[3-(trifluoromethyl)phenyl]-1H-pyrrolo[2,3-b]pyridin-5-yl}-5H,6H,7H,8H-pyrimido[5,4-f][1,4]oxazepin-5-one;

4-amino-6-[1-(1,3-thiazol-2-yl)-1H-indol-5-yl]-5H,6H,7H,8H-pyrimido[5,4-f][1,4]oxazepin-5-one;

4-amino-6-{1-[6-(trifluoromethyl)pyridin-3-yl]-1H-indol-5-yl}-5H,6H,7H,8H-pyrimido[5,4-f][1,4]oxazepin-5-one;

4-amino-6-[1-(pyridin-2-yl)-1H-indol-5-yl]-5H,6H,7H,8H-pyrimido[5,4-f][1,4]oxazepin-5-one;

4-amino-6-[1-(pyridin-2-yl)-1H-pyrrolo[2,3-b]pyridin-5-yl]-5H,6H,7H,8H-pyrimido[5,4-f][1,4]oxazepin-5-one;

4-amino-6-[1-(pyrazin-2-yl)-1H-pyrrolo[2,3-b]pyridin-5-yl]-5H,6H,7H,8H-pyrimido[5,4-f][1,4]oxazepin-5-one;

4-amino-6-[1-(pyrazin-2-yl)-1H-indol-5-yl]-5H,6H,7H,8H-pyrimido[5,4-f][1,4]oxazepin-5-one;

4-amino-6-{1-[5-(trifluoromethyl)pyridin-2-yl]-1H-indol-5-yl}-5H,6H,7H,8H-pyrimido[5,4-f][1,4]oxazepin-5-one;

4-amino-6-{1-[5-(trifluoromethyl)pyridin-2-yl]-1H-pyrrolo[2,3-b]pyridin-5-yl}-5H,6H,7H,8H-pyrimido[5,4-f][1,4]oxazepin-5-one;

4-amino-6-[1-(1,3-thiazol-2-yl)-1H-pyrrolo[2,3-b]pyridin-5-yl]-5H,6H,7H,8H-pyrimido[5,4-f][1,4]oxazepin-5-one;

4-amino-6-{1-[6-(trifluoromethyl)pyridin-3-yl]-1H-pyrrolo[2,3-b]pyridin-5-yl}-5H,6H,7H,8H-pyrimido[5,4-f][1,4]oxazepin-5-one;

4-amino-6-[1-phenyl-3-(propan-2-yl)-1H-indol-5-yl]-5H,6H,7H,8H-pyrimido[5,4-f][1,4]oxazepin-5-one;

4-amino-6-(2-phenyl-1-propyl-1H-indol-5-yl)-5H,6H,7H,8H-pyrimido[5,4-f][1,4]oxazepin-5-one;

4-amino-6-(6-fluoro-1-phenyl-1H-indol-5-yl)-5H,6H,7H,8H-pyrimido[5,4-f][1,4]oxazepin-5-one;

6-{4-amino-5-oxo-5H,6H,7H,8H-pyrimido[5,4-f][1,4]oxazepin-6-yl}-3-benzyl-3,4-dihydroquinazolin-4-one;

6-{4-amino-5-oxo-5H,6H,7H,8H-pyrimido[5,4-f][1,4]oxazepin-6-yl}-3,4-dihydroquinazolin-4-one;

4-amino-6-(1-benzyl-6-fluoro-1H-indol-5-yl)-5H,6H,7H,8H-pyrimido[5,4-f][1,4]oxazepin-5-one;

4-amino-6-{5-propyl-5H-pyrrolo[3,2-d]pyrimidin-2-yl}-5H,6H,7H,8H-pyrimido[5,4-f][1,4]oxazepin-5-one;

4-amino-6-(1-propyl-1H-pyrrolo[3,2-b]pyridin-5-yl)-7,8-dihydropyrimido[5,4-f][1,4]oxazepin-5(6H)-one;

4-amino-6-(1-(6-methylpyridin-3-yl)-1H-indol-5-yl)-7,8-dihydropyrimido[5,4-f][1,4]oxazepin-5(6H)-one;

4-amino-6-(1-(4-(difluoromethyl)phenyl)-1H-indol-5-yl)-7,8-dihydropyrimido[5,4-f][1,4]oxazepin-5(6H)-one;

4-amino-6-(1-(4-(difluoromethyl)phenyl)-1H-pyrrolo[2,3-b]pyridin-5-yl)-7,8-dihydropyrimido[5,4-f][1,4]oxazepin-5(6H)-one;

4-amino-6-(1-(4-(trifluoromethyl)pyridin-2-yl)-1H-pyrrolo[2,3-b]pyridin-5-yl)-7,8-dihydropyrimido[5,4-f][1,4]oxazepin-5(6H)-one;

or a pharmaceutically acceptable salt thereof.

A person of ordinary skills in the art recognizes that compounds of the present invention may have alternative names when different naming software is used.

The following exemplified compounds have alternative chemical names as illustrated in table below.

| Ex | Chemical Name | Alternative Chemical Name |
|---|---|---|
| 1 | 2-(6-{4-amino-5-oxo-5H,6H,7H,8H-pyrimido[5,4-f][1,4]oxazepin-6-yl}-1-oxo-1,2,3,4-tetrahydroisoquinolin-2-yl)acetic acid | 2-(6-(4-amino-5-oxo-5,6,7,8-tetrahydrooxepino(2,3-d)pyrimidin-6-yl)-2-methyl-1-oxo-1,2,3,4-tetrahydronapthalen-2-yl)acetic acid |
| 10 | 5-{4-amino-5-oxo-5H,6H,7H,8H-pyrimido[5,4-f][1,4]oxazepin-6-yl}-2-benzyl- | 6-(1-allyl-2-benzyl-3-oxo-2,3-dihydro-1H-indazol-5-yl)-4-amino-7,8-dihydropyrimido |

-continued

| Ex | Chemical Name | Alternative Chemical Name |
|---|---|---|
|  | 1-(prop-2-en-1-yl)-2,3-dihydro-1H-indazol-3-one | [5,4-f][1,4]oxazepin-5(6H)-one |
| 11 | 5-{4-amino-5-oxo-5H,6H,7H,8H-pyrimido[5,4-f][1,4]oxazepin-6-yl}-1-propyl-2,3-dihydro-1H-indazol-3-one | 4-amino-6-(3-oxo-1-propyl-2,3-dihydro-1H-indazol-5-yl)-7,8-dihydropyrimido[5,4][1,4]oxazepin-5(6H)-one |
| 12 | 4-amino-6-(1-propyl-1H-indol-5-yl)-5H,6H,7H,8H-pyrimido[5,4-f][1,4]oxazepin-5-one | 4-amino-6-(1-propyl-1H-indol-5-yl)-7,8-dihydropyrimido[5,4-f][1,4]oxazepin-5(6H)-one |
| 33 | 4-amino-6-[1-(2,2-difluoroethyl)-1H-pyrrolo[2,3-b]pyridin-5-yl]-5H,6H,7H,8H-pyrimido[5,4-f][1,4]oxazepin-5-one | 4-amino-6-(1-(2,2-difluoroethyl)-1H-pyrrolo[2,3-b]pridinpyridin-5-yl)-7,8-dihydropyrimido[5,4-f][1,4]oxazepin-5(6H)-one |
| 34 | 4-amino-6-{1-cyclopropyl-1H-pyrrolo[2,3-b]pyridin-5-yl}-5H,6H,7H,8H-pyrimido[5,4-f][1,4]oxazepin-5-one | 4-amino-6-(1-cyclopropyl-1H-pyrrolo[2,3-b]pyridinpyridin-5-yl)-7,8-dihydropyrimido[5,4-f][1,4]oxazepin-5(6H)-one |
| 63 | 4-amino-6[1-propyl-3-(trifluoroacetyl)-1H-indol-5-yl]-5H,6H,7H,8H-pyrimido[5,4-f][1,4]oxazepin-5-one | 4-amino-6-(1-propyl-3-(2,2,2-trifluoroacetyl)-1H-indol-5-yl)-7,8-dihydropyrimido[5,4-f][1,4]oxazepin-5(6H)-one |
| 65 | 4-amino-6-(1-phenyl-1H-indol-5-yl)-5H,6H,7H,8H-pyrimido[5,4-f][1,4]oxazepin-5-one | 4-amino-6-(1-phenyl-1H-indol-5-yl)-7,8-dihydropyrimido[5,4-f][1,4]oxazepin-5(6H)-one |
| 66 | 4-amino-6-{1-[4-(trifluoromethyl)phenyl]-1H-pyrrolo[2,3-b]pyridin-5-yl}-5H,6H,7H,8H-pyrimido[5,4-f][1,4]oxazepin-5-one | 4-amino-6-(1-(4-(trifluoromethyl)phenyl)-1H-pyrrolo[2,3-b]pyridinpyridin-5-yl)-7,8-dihydropyrimido[5,4-f][1,4]oxazepin-5(6H)-one |
| 82 | 4-amino-6-[1-(1,3-thiazol-2-yl)-1H-indol-5-yl]-5H,6H,7H,8H-pyrimido[5,4-f][1,4]oxazepin-5-one | 4-amino-6-(1-(thiazol-2-yl)-1H-indol-5-yl)-7,8-dihydropyrimido[5,4-f][1,4]oxazepin-5(6H)-one |
| 83 | 4-amino-6-{1-[6-(trifluoromethyl)pyridin-3-yl]-1H-indol-5-yl}-5H,6H,7H,8H-pyrimido[5,4-f][1,4]oxazepin-5-one | 4-amino-6-(1-(6-(trifluoromethyl)pyridinpyridin-3-yl)-1H-indol-5-yl)-7,8-dihydropyrimido[5,4-f][1,4]oxazepin-5(6H)-one |
| 94 | 4-amino-6[1-phenyl-3-(propan-2-yl)-1H-indol-5-yl]-5H,6H,7H,8H-pyrimido[5,4-f][1,4]oxazepin-5-one | 4-amino-6-(3-isopropyl-1-phenyl-1H-indol-5-yl)-7,8-dihydropyrimido[5,4-f][1,4]oxazepin-5(6H)-one |
| 95 | 4-amino-6-(2-phenyl-1-propyl-1H-indol-5-yl)-5H,6H,7H,8H-pyrimido[5,4-f][1,4]oxazepin-5-one | 4-amino-6-(2-phenyl-1-propyl-1H-indol-5-yl)-7,8-dihydropyrimido[5,4-f][1,4]oxazepin-5(6H)-one |
| 96 | 4-amino-6-(6-fluoro-1-phenyl-1H-indol-5-yl)-5H,6H,7H,8H-pyrimido[5,4-f][1,4]oxazepin-5-one | 4-amino-6-(6-fluoro-1-phenyl-1H-indol-5-yl)-7,8-dihydrooxepino[2,3-d]pyrimidin-5(6H)-one |
| 97 | 6-{4-amino-5-oxo-5H,6H,7H,8H-pyrimido[5,4-f][1,4]oxazepin-6-yl}-3-benzyl-3,4-dihydroquinazolin-4-one | 4-amino-6-(3-benzyl-4-oxo-3,4-dihydroquinazolin-6-yl)-7,8-dihydropyrimido[5,4-f][1,4]oxazepin-5(6H)-one |
| 98 | 6-{4-amino-5-oxo-5H,6H,7H,8H-pyrimido[5,4-f][1,4]oxazepin-6-yl}-3,4-dihydroquinazolin-4-one | 4-amino-6-(4-oxo-3,4-dihydroquinazolin-6-yl)-7,8-dihydropyrimido[5,4-f][1,4]oxazepin-5(6H)-one |
| 100 | 4-amino-6-{5-propyl-5H-pyrrolo[3,2-d]pyrimidin-2-yl}-5H,6H,7H,8H-pyrimido[5,4-f][1,4]oxazepin-5-one | 4-amino-6-(5-propyl-5H-pyrrolo[3,2-d]pyrimidin-2-yl)-7,8-dihydropyrimido[5,4-f][1,4]oxazepin-5(6H)-one |
| 101 | 4-amino-6-(1-propyl-1H-pyrrolo[3,2-b]pyridin-5-yl)-7,8-dihydropyrimido[5,4-f][1,4]oxazepin-5(6H)-one | 4-amino-6-(1-propyl-1H-pyrrolo[3,2-b]pyridinpyridin-5-yl)-7,8-dihydropyrimido[5,4-f][1,4]oxazepin-5(6H)-one |

This invention also relates to compounds of Formula (I), (I)(A), (I)(B), (I)(C), or any of the exemplified compounds, or their pharmaceutically acceptable salts thereof, for use as a medicament.

This invention also relates to compounds of Formula (I), (I)(A), (I)(B), (I)(C), or any of the exemplified compounds, or their pharmaceutically acceptable salts thereof, for use in the treatment of obesity.

This invention also relates to compounds of Formula (I), (I)(A), (I)(B), (I)(C), or any of the exemplified compounds, or their pharmaceutically acceptable salts thereof, in the manufacture of a medicament for the treatment of obesity.

It will be appreciated by those skilled in the art that the compound of the present invention may also be utilized in the form of a pharmaceutically acceptable salt thereof.

Typically, but not absolutely, the salts of the present invention are pharmaceutically acceptable salts. Salts encompassed within the term "pharmaceutically acceptable salts" refer to non-toxic salts of the compounds of this invention. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline or noncrystalline compounds. In crystalline solvates, solvent molecules are incorporated into the crystalline lattice during crystallization. Solvates may involve nonaqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as 2H, 3H, 11C, 13C, 14C, 15N, 17O, 18O, 31P, 32P, 35S, 18F, 36Cl, 123I and 125I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are particularly preferred for their ease of preparation and detectability. 11C and 18F isotopes are particularly useful in PET (positron emission tomography), and 125I isotopes are particularly useful in SPECT (single photon emission computerized tomography), all useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

DEFINITIONS

Terms are used within their accepted meanings. The following definitions are meant to clarify, but not limit, the terms defined.

As used herein, unless otherwise defined, the term "alkyl" (or "alkylene") refers to a straight or branched chain alkyl, preferably having from one to twelve carbon atoms, which may be saturated or unsaturated included within the present invention. Examples of "alkyl" as used herein include methyl, ethyl, propyl, isopropyl, isobutyl, n-butyl, t-butyl, isopentyl, n-pentyl, and the like, as well as substituted versions thereof.

As used herein, unless otherwise defined, the term "substituted alkyl" (or "alkylene") refers to a straight or branched chain alkyl, preferably having from one to twelve carbon atoms, which may be saturated or unsaturated with multiple degrees of substitution included within the present invention, preferably one, two or three. Suitable substituents are selected from the group consisting of unsubstituted $C_3$-$C_7$cycloalkyl, methyl, ethyl, propyl, isopropyl, butyl, t-butyl, difluoromethyl, trifluoromethyl, halo, amino, substituted amino, urea, cyano, hydroxyl, alkoxy, alkylthio, alkylsulfonyl, sulfonamide, carboxylic acid (eg. COOH), carboxylic ester (eg. methyl ester, ethyl ester, and carboxamide.

As used herein, unless otherwise defined, the term "substituted amino" is meant —NR'R" wherein each R' and R" is independently selected from a group including hydrogen, unsubstituted $C_1$-$C_6$alkyl, acyl, unsubstituted $C_3$-$C_7$cycloalkyl, wherein at least one of R' and R" is not hydrogen. Examples of substituted amino includes, but are not limited to alkylamino, dialkylaminio, acylamino, and cycloalkylamino.

As used herein, unless otherwise defined, the term "aryloxy" refers to the group —O—$C_1$-$C_6$alkylaryl. Examples of —O—$C_1$-$C_6$alkylaryl includes, but are not limited to phenylmethoxy, naphthylmethoxy.

As used herein, unless otherwise defined, the term "arylalkyl" refers to the group —$C_1$-$C_6$alkylaryl. Examples of —$C_1$-$C_6$alkylaryl includes, but are not limited to phenylmethyl, naphthylmethyl.

As used herein, unless otherwise defined, the term "cycloalkyl" refers to an unsubstituted or substituted mono- or polycyclic non-aromatic saturated ring, which optionally includes an alkylene linker through which the cycloalkyl may be attached. Suitable substituents are defined in the definition of 'substituted". Exemplary "cycloalkyl" groups include, but are not limited to, cyclopropyl, cyclobutyl, cyclopentyl, cyclohexyl, cycloheptyl, and the like, as well as unsubstituted and substituted versions thereof As used herein, unless otherwise defined, the term "alkoxy" refers to the group —OR$^a$, where R$^a$ is $C_1$-$C_4$alkyl or cycloalkyl as defined above.

As used herein, unless otherwise defined, the term "amide" refers to the group —C(O)NR$^c$R$^d$, wherein R$^c$ and R$^d$ are each independently H, or $C_1$-$C_6$alkyl, or R$^c$ is the remaining portion of a natural or un-natural aminoacid.

As used herein, unless otherwise defined, the term "heterocycle" or "heterocyclyl" or "heterocyclic" refers to unsubstituted and substituted mono- or polycyclic non-aromatic ring system containing one or more heteroatoms. Preferred heteroatoms include N, O, and S, including N-oxides, sulfur oxides, and dioxides. Preferably the ring is three to eight-membered and is either fully saturated or has one or more degrees of unsaturation. Multiple degrees of substitution are included within the present definition. Examples of "heterocyclic" groups include, but are not limited to tetrahydrofuranyl, pyranyl, 1,4-dioxanyl, 1,3-dioxanyl, piperidinyl, pyrrolidinyl, morpholinyl, azetidinyl, piperazinyl, pyrrolidinonyl, piperazinonyl, pyrazolidinyl, and their various tautomers.

As used herein, unless otherwise defined, the term "aryl", unless otherwise defined, is meant aromatic, hydrocarbon, ring system. The ring system may be monocyclic or fused polycyclic (e.g., bicyclic, tricyclic, etc.), substituted or unsubstituted. A C6 ring system, i.e. a phenyl ring, is a suitable aryl group. In various embodiments, the polycyclic ring is a bicyclic aryl group, where suitable bicyclic aryl groups are C8-C12, or C9-C10. A naphthyl ring, which has 10 carbon atoms, is a suitable polycyclic aryl group. Suitable substituents for aryl are described below in the definition of "optionally substituted".

As used herein, unless otherwise defined, the term "heteroaryl", unless otherwise defined, is meant an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include but are not limited to: benzofuran, benzothiophene, furan, imidazole, indole, isothiazole, oxazole, pyrazine, pyrazole, pyridazine, pyridine, pyrimidine, pyrrole, quinoline, quinazoline, quinoxaline, thiazole, and thiophene. Suitable substituents for heteroaryl are described below in the definition of "optionally substituted".

As used herein, unless otherwise defined, the term "cyano" refers to the group —CN.

As used herein, unless otherwise defined, the term "acyl" refers to the group —C(O)R$^b$, where R$^b$ is alkyl, cycloalkyl, or heterocyclyl, as each is defined herein.

As used herein, unless otherwise defined, the term "optionally" means that the subsequently described event(s) may or may not occur, and includes both event(s) that occur and event(s) that do not occur.

As used herein, unless otherwise defined, the phrase "substituted" or variations thereof denote an optional substitution, including multiple degrees of substitution, with one or more substitutent group, preferably one, two or three. The phrase should not be interpreted as duplicative of the substitutions herein described and depicted. Suitable optional substituent groups include acyl, $C_1$-$C_6$alkyl, substituted $C_1$-$C_6$alkyl, unsubstituted $C_3$-$C_7$cycloalkyl, alkyl sulfonyl, alkoxy, alkoxycarbonyl, cyano, halo, urea, amide, hydroxyl, oxo, and nitro.

Pharmaceutical Compositions

The invention further provides a pharmaceutical composition (also referred to as pharmaceutical formulation) comprising a compound of Formula I or pharmaceutically acceptable salt, thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

In accordance with another aspect of the invention there is provided a process for the preparation of a pharmaceutical composition comprising mixing (or admixing) a compound of Formula I or salt thereof with at least one excipient.

Pharmaceutical compositions may be in unit dose form containing a predetermined amount of active ingredient per unit dose. Such a unit may contain a therapeutically effective dose of the compound of Formula I or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

As used herein, the term "treatment" includes prophylaxis and refers to alleviating the specified condition, eliminating or reducing one or more symptoms of the condition, slowing or eliminating the progression of the condition, and preventing or delaying the reoccurrence of the condition in a previously afflicted or diagnosed patient or subject. Prophylaxis (or prevention or delay of disease onset) is typically accomplished by administering a drug in the same or similar manner as one would to a patient with the developed disease or condition.

The present invention provides a method of treatment in a mammal, especially a human, suffering from obesity, diabetes, hypertension, depression, anxiety, drug addiction, substance addiction, or a combination thereof. Such treatment comprises the step of administering a therapeutically effective amount of a compound of Formula I or salt thereof to said mammal, particularly a human. Treatment can also comprise the step of administering a therapeutically effective amount of a pharmaceutical composition containing a compound of Formula I or salt thereof to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula I, as well as salts thereof, may be administered as the raw chemical. Additionally, the active ingredient may be presented as a pharmaceutical composition.

While it is possible that, for use in therapy, a therapeutically effective amount of a compound of Formula I or salt thereof may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formula I or salt thereof will be given for the treatment in the range of about 0.1 to 100 mg/kg body weight of recipient (patient, mammal) per day and more usually in the range of 0.1 to 10 mg/kg body weight per day. Acceptable daily dosages may be from about 1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formula I per se. Similar dosages should be appropriate for treatment (including prophylaxis) of the other conditions referred herein for treatment. In general, determination of appropriate dosing can be readily arrived at by one skilled in medicine or the pharmacy art.

Additionally, the present invention comprises a compound of Formula I or salt thereof or a pharmaceutical composition thereof with at least one other anti-obesity drug and/or at least one anti-diabetes drug. Such anti-obesity drugs can include, for example, Metformin (or glucophage), CB1 receptor antagonists, GLP-1 agonists, opioid antagonists, and neurotransmitter reuptake inhibitors. When a compound of the invention is employed in combination with another anti-obesity drug or anti-diabetes drug, it is to be appreciated by those skilled in the art that the dose of each compound or drug of the combination may differ from that when the drug or compound is used alone. Appropriate doses will be readily appreciated and determined by those skilled in the art. The appropriate dose of the compound of Formula I or salt thereof and the other therapeutically active agent(s) and the relative timings of administration will be selected in order to achieve the desired combined therapeutic effect, and are with the expertise and discretion of the attending doctor or clinician.

Compounds Preparation

Generic Synthesis Schemes

The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) Protecting *Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention.

The synthesis of the compounds of the general Formula (I) and pharmaceutically acceptable derivatives and salts thereof may be accomplished as outlined below in Schemes 1-10 by those skilled in the art. In the following description, the groups are as defined above for compounds of Formula (I) unless otherwise indicated. Starting materials are commercially available or are made from commercially available starting materials using methods known to those skilled in the art.

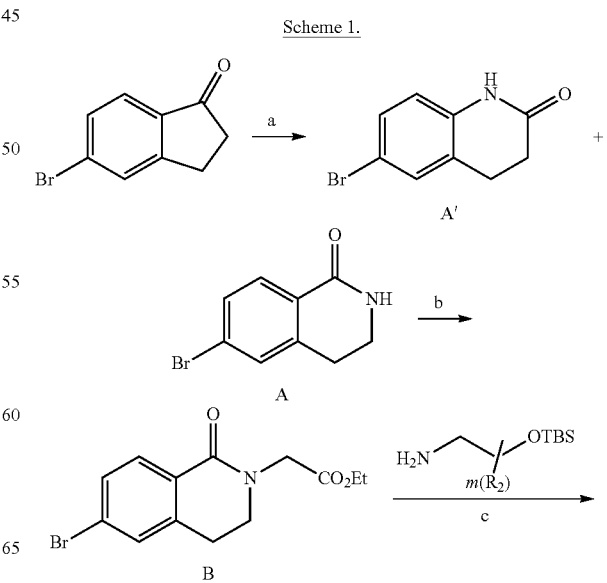

Scheme 1.

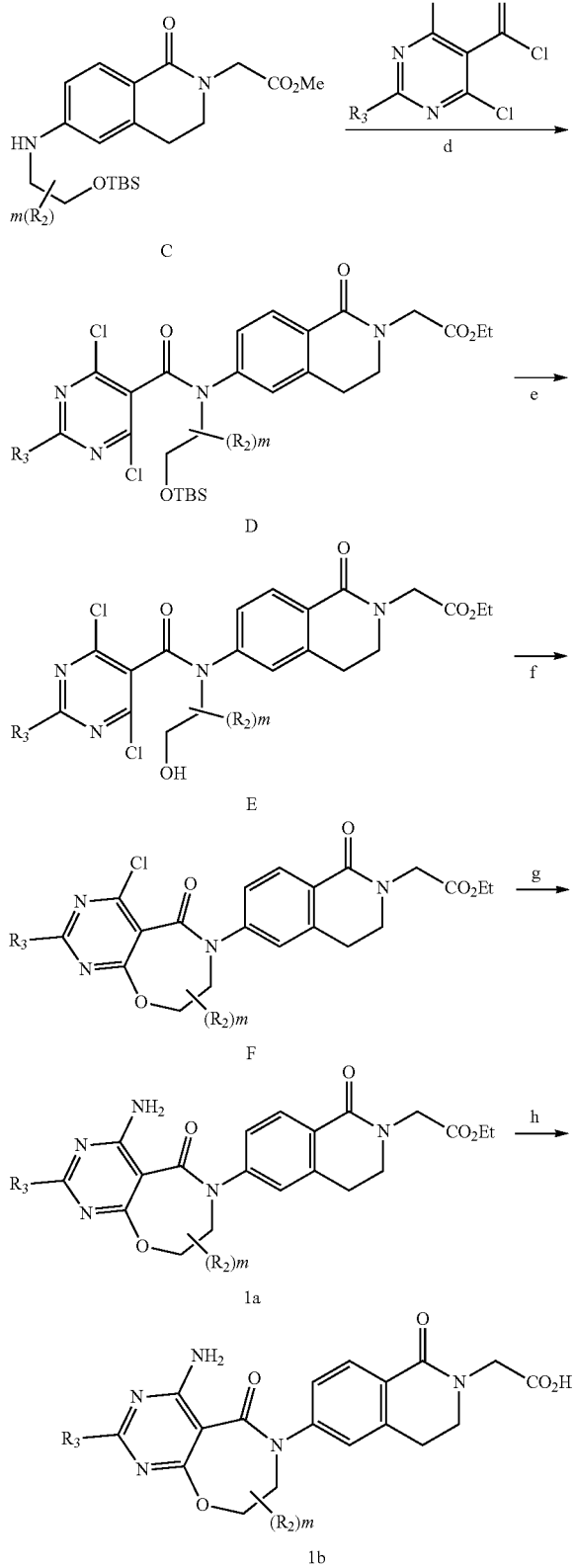

Reagents and conditions: a) NaN₃, MeSO₃H, CH₂Cl₂, RT; b) NaH, BrCH₂CO₂Et, THF, RT; c) Pd(OAc)₂, Cs₂CO₃, X—Phos, Toluene, 120° C.; d) THF, Et₃N, RT; e) 3% HCl—MeOH, RT; f) CH₃CN, Et₃N, 80° C.; g) NH₃, Dioxane, RT; h) LiOH, Dioxane-H₂O, RT Compounds of Formula (I) may be prepared as illustrated in Scheme 1. Intermediate A can be obtained by rearrangement reaction of 5-bromo-1-indanone with NaN₃ in MeSO₃H in solvents such as CH₂Cl₂. Alkylation of intermediate A with an appropriate alkyl halide such as ethyl bromoacetate in the presence of a suitable base such as NaH gives intermediate B. Intermediate A' can also be similarly alkylated and progressed similar to that of intermediate A. Intermediate B can then be subjected to amination under Buchwald conditions using an appropriate amine in the presence of reagents such as palladium acetate, ligand such as X-Phos and a base such as cesium carbonate in toluene at 120° C. Intermediate C thus obtained can then be coupled to the appropriately substituted acid chloride to afford D. Desilylation of intermediate D under standard acidic conditions leads to E which is then subjected to ring closure by heating the reaction mixture in acetonitrile at 80° C. in the presence of a base such as triethylamine to give F. Substitution of the chloro residue in intermediate F with an amino group by treatment with ammonia at room temperature results in compounds of Formula (I) (1a). Hydrolysis of the ester group in compound 1a with base such as LiOH provides another compound of Formula (I) (1b).

Scheme 2.

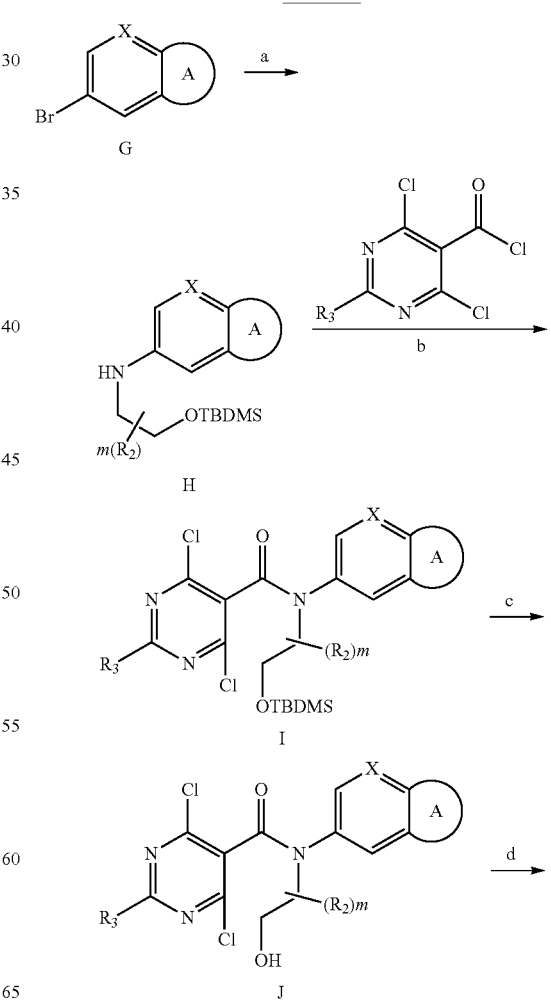

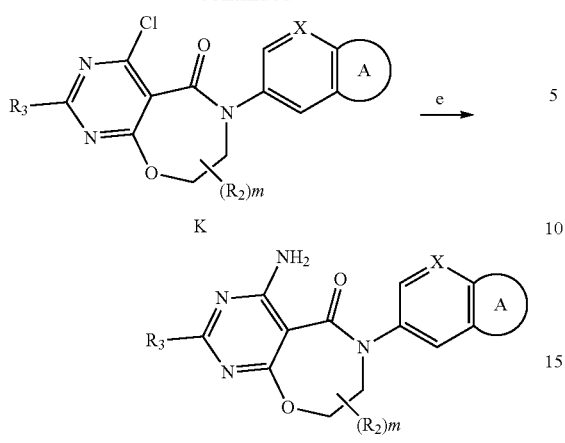

Reagents and conditions: a) NH$_2$(CH$_2$)$_2$OTBDMS, Pd(OAc)$_2$, Cs$_2$CO$_3$, X—PHOS, Toluene, 120° C.; b) THF, Et$_3$N, RT; c) 3% HCl—MeOH, RT; d) CH$_3$CN, Et$_3$N, 80° C.; e) NH$_3$, Dioxane, RT.

Compounds of Formula (I) may be also prepared as illustrated in Scheme 2. Intermediate H can be obtained by the amination of an appropriate bromo substituted heterocyclic compound G with a suitably protected amine under the standard Buchwald conditions. Bromide G is available either commercially or is synthesized according to standard methods of organic synthesis known to those skilled in the art with or without appropriate protecting groups. Amine intermediate H can then be converted to the tertiary amide I with an appropriately substituted acid chloride using triethylamine as a base. Desilylation of intermediate I followed by ring closure of the resulting alcohol J under heating conditions in acetonitrile affords intermediate K. Substitution of the chloro residue in intermediate K with an amino group by treatment with ammonia at room temperature results in compounds of Formula (I) (1c). If necessary, compound 1c can be subjected to a functional group deprotection reaction under standard conditions to remove the group that was introduced during the preparation of bromide G.

Scheme 3.

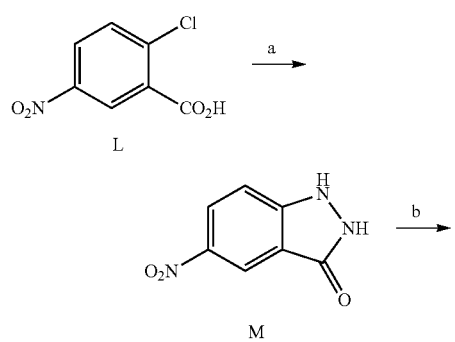

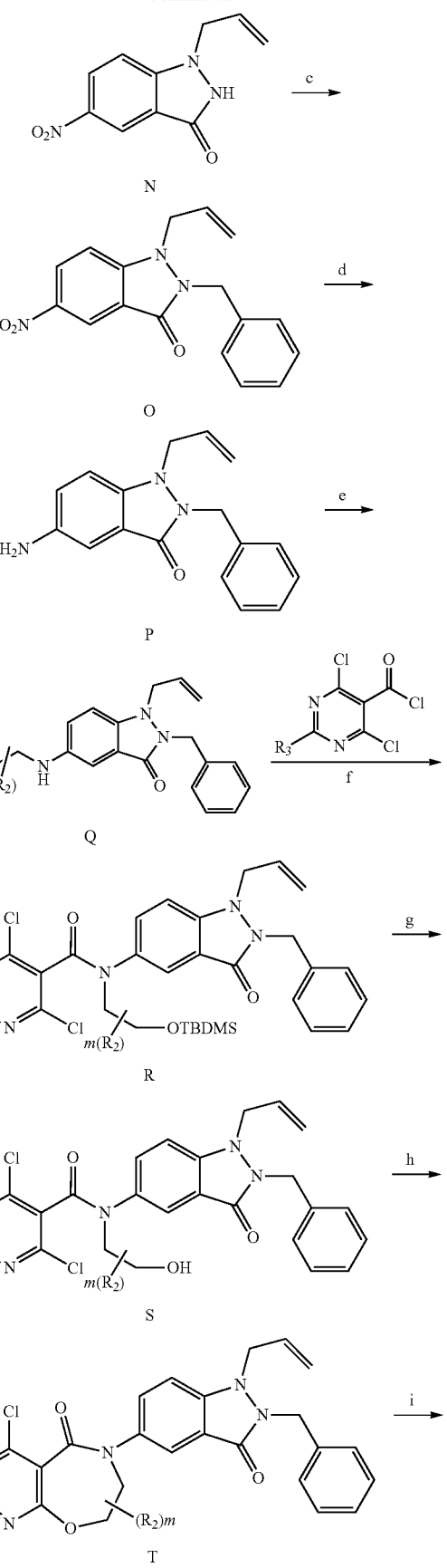

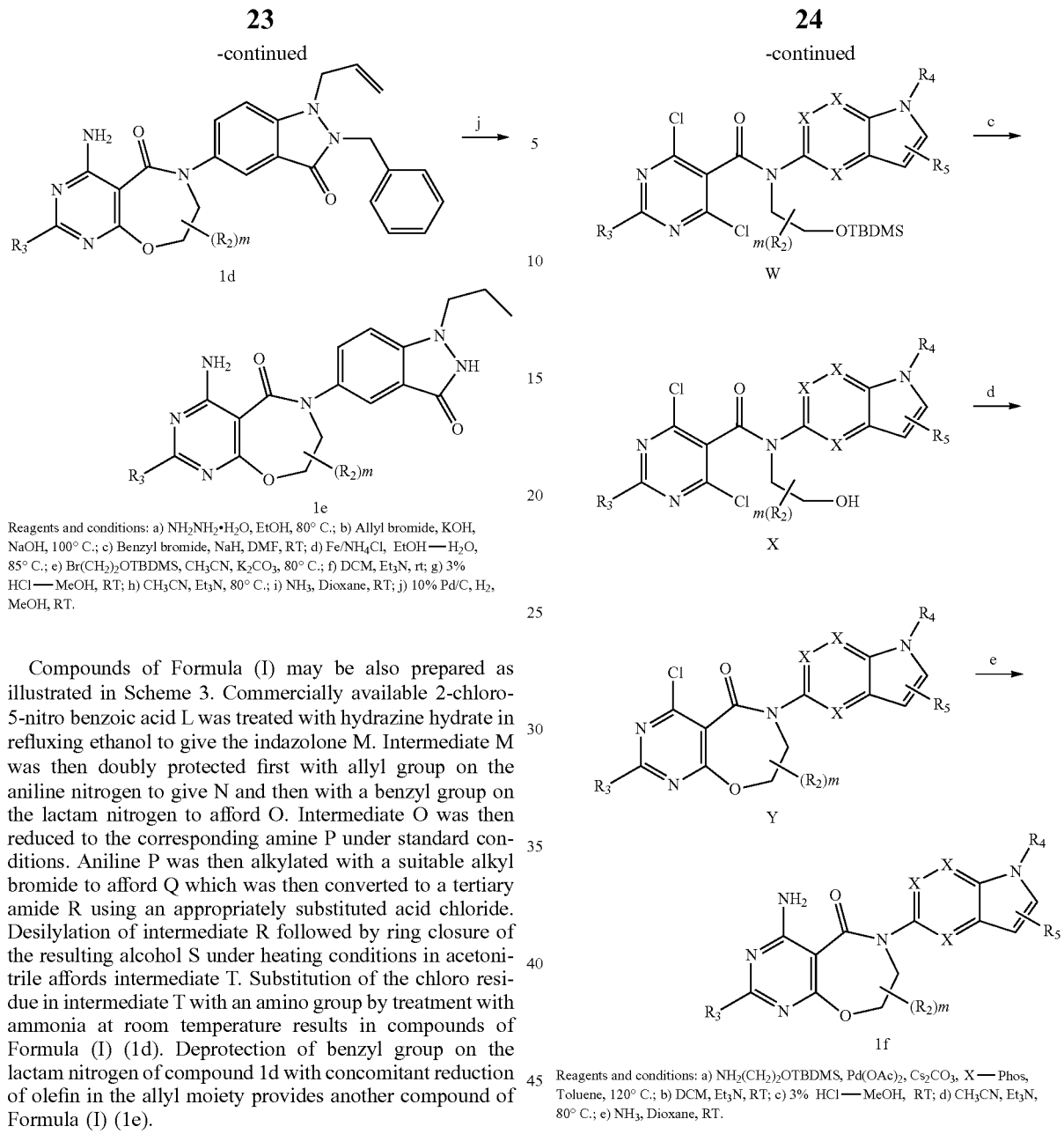

Reagents and conditions: a) NH₂NH₂•H₂O, EtOH, 80° C.; b) Allyl bromide, KOH, NaOH, 100° C.; c) Benzyl bromide, NaH, DMF, RT; d) Fe/NH₄Cl, EtOH—H₂O, 85° C.; e) Br(CH₂)₂OTBDMS, CH₃CN, K₂CO₃, 80° C.; f) DCM, Et₃N, rt; g) 3% HCl—MeOH, RT; h) CH₃CN, Et₃N, 80° C.; i) NH₃, Dioxane, RT; j) 10% Pd/C, H₂, MeOH, RT.

Compounds of Formula (I) may be also prepared as illustrated in Scheme 3. Commercially available 2-chloro-5-nitro benzoic acid L was treated with hydrazine hydrate in refluxing ethanol to give the indazolone M. Intermediate M was then doubly protected first with allyl group on the aniline nitrogen to give N and then with a benzyl group on the lactam nitrogen to afford O. Intermediate O was then reduced to the corresponding amine P under standard conditions. Aniline P was then alkylated with a suitable alkyl bromide to afford Q which was then converted to a tertiary amide R using an appropriately substituted acid chloride. Desilylation of intermediate R followed by ring closure of the resulting alcohol S under heating conditions in acetonitrile affords intermediate T. Substitution of the chloro residue in intermediate T with an amino group by treatment with ammonia at room temperature results in compounds of Formula (I) (1d). Deprotection of benzyl group on the lactam nitrogen of compound 1d with concomitant reduction of olefin in the allyl moiety provides another compound of Formula (I) (1e).

Reagents and conditions: a) NH₂(CH₂)₂OTBDMS, Pd(OAc)₂, Cs₂CO₃, X—Phos, Toluene, 120° C.; b) DCM, Et₃N, RT; c) 3% HCl—MeOH, RT; d) CH₃CN, Et₃N, 80° C.; e) NH₃, Dioxane, RT.

Compounds of Formula (I) may be also prepared as illustrated in Scheme 4. An appropriately substituted indole or a derivative thereof U, can be subjected to amination under Buchwald conditions using an appropriate amine in the presence of reagents such as palladium acetate, ligand such as X-Phos and a base such as cesium carbonate in toluene at 120° C. Intermediate V thus obtained can then be coupled to an appropriately substituted acid chloride to afford W. Desilylation of intermediate W under standard acidic conditions leads to X which is then subjected to ring closure by heating the reaction mixture in acetonitrile at 80° C. in the presence of a base such as triethylamine to give Y. Substitution of the chloro residue in intermediate Y with an amino group by treatment with ammonia at room temperature results in compounds of Formula (I) (1f).

Scheme 4.

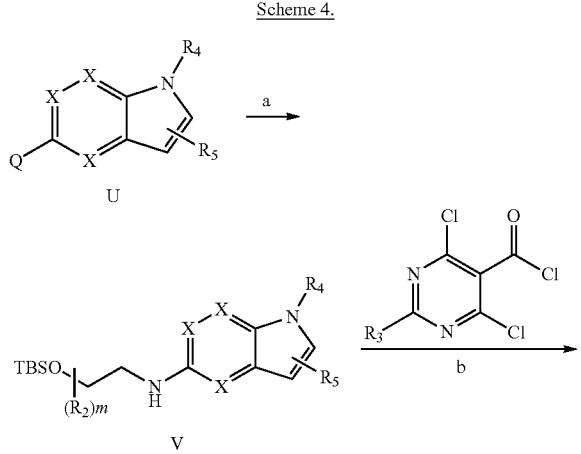

Scheme 5.

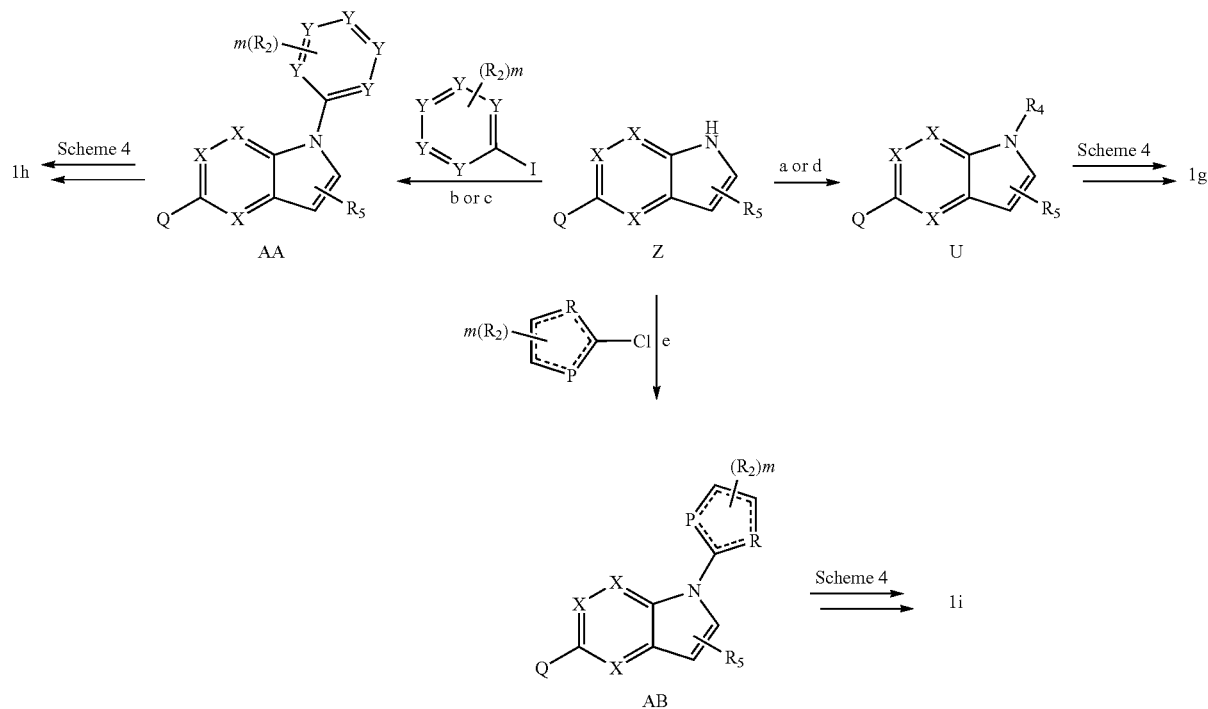

Reagents and conditions: a) R₄—Br/R₄—I, Cs₂CO₃, DMF, 100° C.; b) Cu(I)Br, Cu(OAc)₂, K₂CO₃, NaOH, 140° C.; c) Cu(I)Br, Cu(OAc)₂, K₂CO₃, NaOH, DMF, 110° C.; d) R₄—B(OH)₂, 2,2'-bipyridine, Na₂CO₃, Cu(OAc)₂, DCE, 110° C.; e) Cs₂CO₃, DMF, 100° C.

Compounds of Formula (I) may be also prepared via intermediates U, AA & AB as illustrated in Scheme 5. A suitably substituted indole or a derivative thereof Z is alkylated or arylated using the appropriate alkyl bromide R₄—Br (or iodide R₄—I) or aryl/heteroaryl boronic acid R₄—B(OH)₂ respectively under standard conditions to afford the nitrogen-capped intermediate U. This can be converted to compounds of formula (I) 1g by using this intermediate U via Scheme 4. Similarly Z can also be arylated under copper catalysed conditions with copper (I) bromide and cupric acetate using an appropriately substituted aryl iodide to afford intermediate AA. This intermediate can again be transformed into compounds of formula (I) 1h via Scheme 4. Intermediate Z can be treated with 2-chloro substituted heterocycles under heating conditions in the presence of a mild base such as cesium carbonate. The intermediate AB thus obtained can be transformed into compounds of Formula (I) 1i via Scheme 4.

Scheme 6.

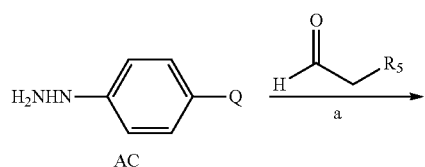

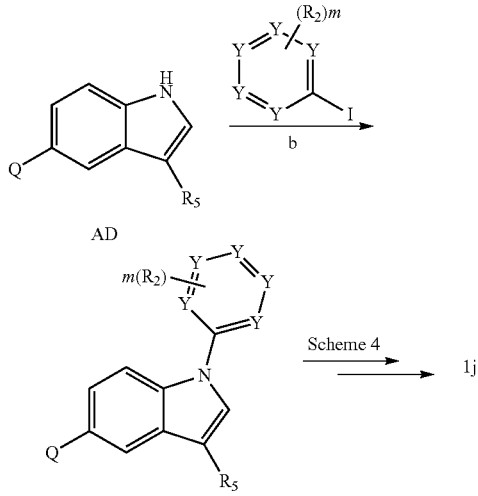

Reagents and conditions: a) AcOH, 120° C.; b) Cu(I)Br, Cu(OAc)₂, K₂CO₃, NaOH, 140° C.

Compounds of Formula (I) may also be synthesized via intermediate AE whose synthesis is shown in Scheme 6. An appropriately substituted phenyl hydrazine AC is heated with a suitably α-substituted aldehyde in acetic acid at 120° C. to afford the 3-substituted indole AD. Intermediate AD then is coupled to an appropriately substituted aryl or heteroaryl iodide under copper catalysed conditions (similar to that described for the synthesis of intermediate AA) to afford intermediate AE. This can then be taken through synthetic sequence similar to that in Scheme 4 to afford compounds of Formula (I)

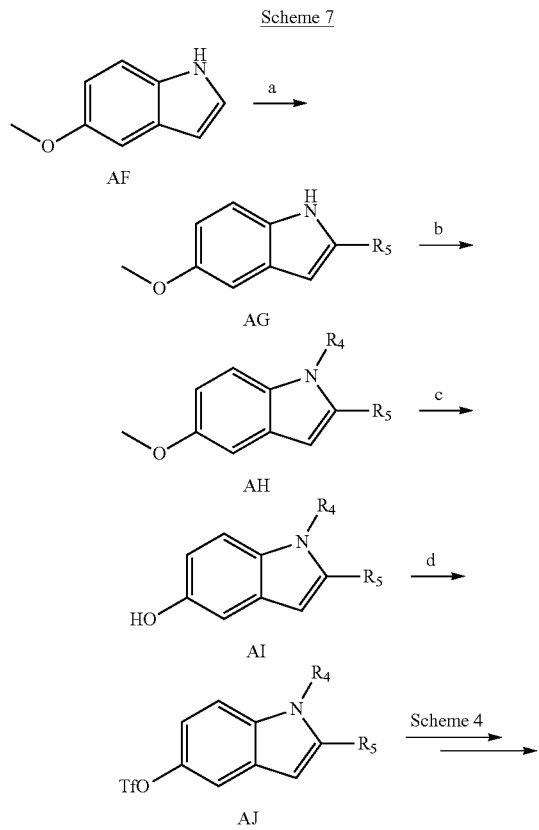

Reagents and conditions: a) R$_5$—B(OH)$_2$, AcOH, Pd(OAc)$_2$, copper(II) acetate, 25° C.; b) R$_4$—Br / R$_4$—I, Cs$_2$CO$_3$, DMF, 25° C.; c) BBr$_3$, DCM, 0° C.; d) Triflic anhydride, Py, DCM, 0° C.

Compounds of Formula (I) may also be synthesized via intermediate AJ whose synthesis is described in Scheme 7. Commercially available 5-methoxy indole AF was substituted suitably with R$_5$ moiety using R$_5$-substituted boronic acid under palladium catalysed conditions to afford 2-substituted indole derivative AG. Intermediate AG in turn is alkylated (or arylated) under standard conditions using a suitable alkylating agent such as R$_4$-bromide (or the corresponding iodide) to afford AH. Demethylation of the methoxy group with boron tribromide and triflation of the resulting intermediate AI gives the appropriately substituted indole derivative AJ. This intermediate can then be taken through the various synthetic steps of Scheme 4 to produce compounds of Formula (I) 1k.

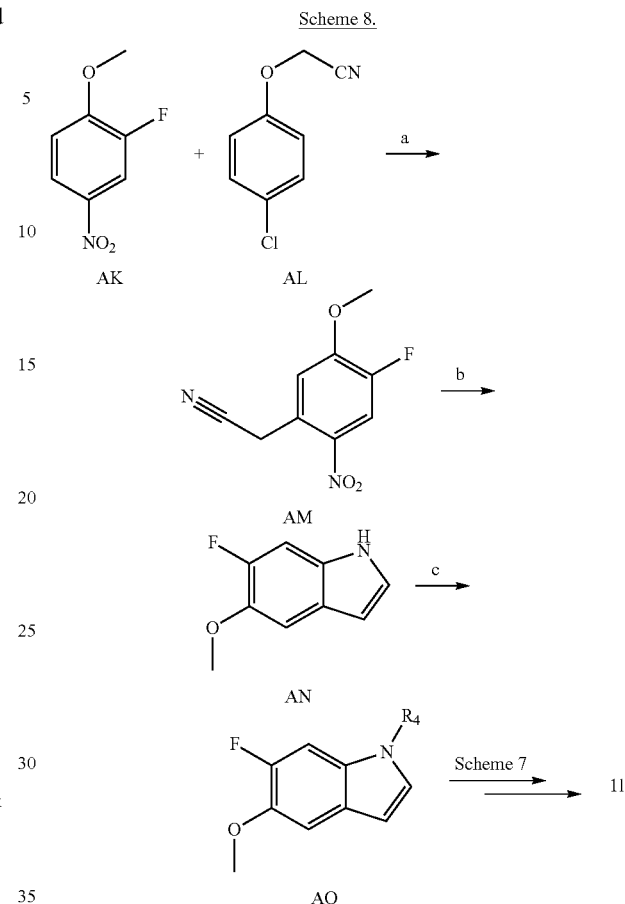

Reagents and conditions: a) K$^t$OBu, DMF, -20° C.; b) 10% Pd/C, Ethanol, 27° C.; c) R$_4$—Br /R$_4$—I, Cu(OAc)$_2$, CuBr, K$_2$CO$_3$, NaOH, DMF, 80° C.

Compounds of Formula (I) may also be synthesized via intermediate AO whose synthesis is described in Scheme 8. Intermediate AM can be prepared by a cyanomethyl transfer reacton using an agent such as AL when treated with the substrate AK in the presence of a strong base such as potassium tert-butoxide. Nitro arene AM can then be subjected to a reduction using palladium on carbon and the resulting transient aniline condenses internally to cyclise to form indole AN thereby losing an equivalent of ammonia. Indole AN can then be suitably alkylated (or arylated) under standard conditions to afford AO. Fluoro indole AO can be taken through steps similar to those described in Scheme 7 for intermediate AH, followed by those in Scheme 4 eventually leading to the synthesis of compounds of Formula (I) 11.

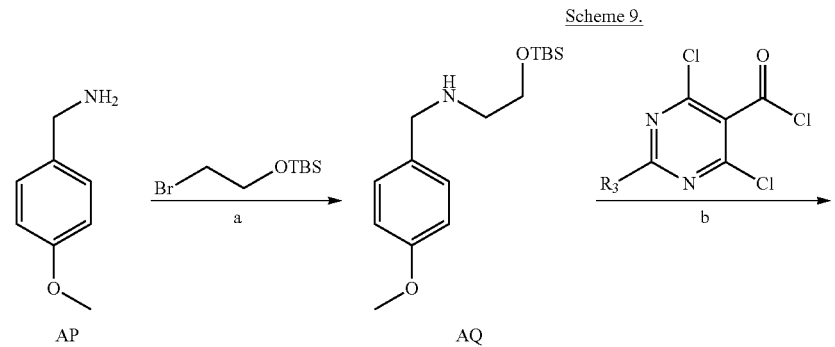

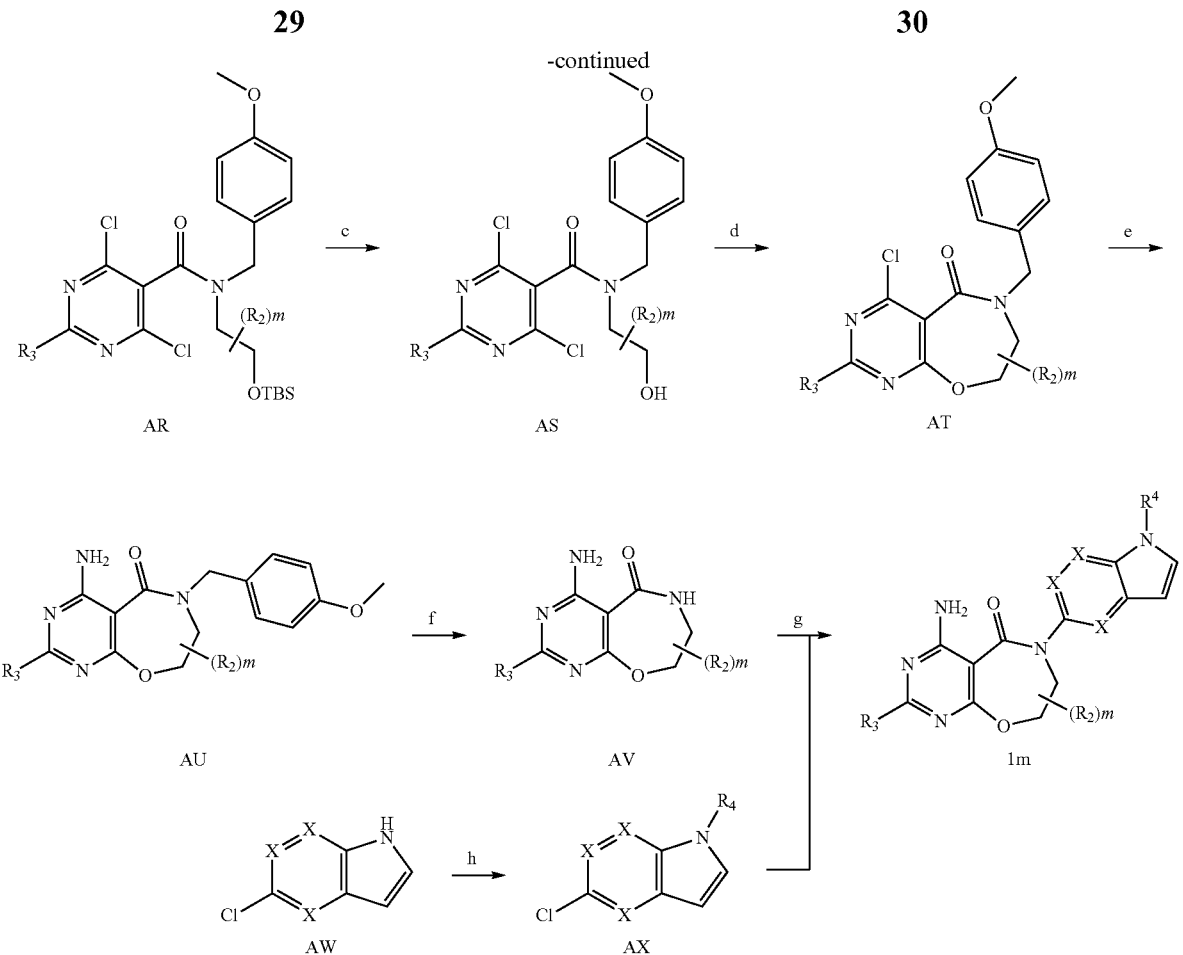

Reagents and conditions: a) Br(CH₂)₂OTBDMS, K₂CO₃, ACN, 80° C.; b) DCM, Et₃N, RT; c) 3% HCl—MeOH, RT; d) CH₃CN, Et₃N, 80° C.; e) NH₃, Dioxane, RT; f) TFA, anisole, 90° C.; g) K₃PO₄, dibasic, CuI, (1S,2S)-cyclohexane-1,2-diamine, 1,4-dioxane, 110° C.; h) R₄—Br, Cs₂CO₃, DMF, 25° C.

An alternative methodology is described in Scheme 9 towards the synthesis of compounds of Formula (I). p-Methoxy benzylamine is alkylated with TBS-protected bromoethanol in acetonitrile using a mild base such as potassium carbonate under heating conditions to afford secondary amine AQ. Intermediate AQ was converted to the tertiary amide AR upon treatment with an appropriately substituted acid chloride under standard conditions. Desilylation of AR under acidic conditions followed by ring closure of the resultant alcohol AS by heating in acetonitrile afforded PMB-substituted oxazepinone AT. Conversion of the chloro group in AT to an amine was effected by treatment with ammonia in dioxane to afford AU. Removal of the PMB group under TFA conditions in the presence of a scavenger anisole at 90° C. afforded the key intermediate AV. Oxazepinone AV was then coupled to appropriately substituted 5-chloro indole AX under copper catalysed conditions to afford compounds of Formula (I) 1m. Intermediate AX can itself be prepared by alkylation of 5-chloro indole AW with a suitable bromide (or iodide) under standard conditions.

Scheme 10.

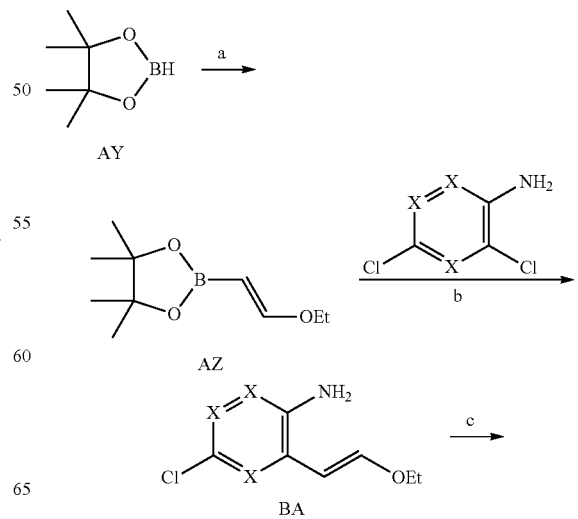

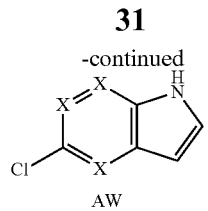

AW

Reagents and conditions: a) di(cyclopenta-2,4-dien-1-yl)zirconium(IV) chloride, ethoxyethyne, DCM, RT, b) K₃PO₄ dibasic, Pd(OAc)₂, dicyclohexyl(2',6'-dimethoxy-[1,1'-biphenyl]-2-yl)phosphine, ACN, water, 80° C.; c) AcOH, 140° C.

Compounds of Formula (I) can also be synthesized via intermediates such as AW as described in Scheme 10. Various substituted indoles represented by AW can be synthesized starting from ethoxy vinyl boronate AZ which itself is prepared by treatment of pinacolate borane AY with ethoxyethyne in the presence of a zirconium catalyst at room temperature. Intermediate AZ is then treated with 2, 4-dichloro substituted aniline under palladium catalysed conditions using a suitable ligand and base such as potassium phosphate dibasic to afford aniline BA. Intermediate BA is then heated in acetic acid at 140° C. to give indole AW. Intermediate AW can then be carried over through appropriate synthetic steps described in Scheme 9 to finally afford compounds of Formula (I) 1n.

EXPERIMENTALS

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention. Unless otherwise noted, reagents are commercially available or are prepared according to procedures in the literature. The symbols and conventions used in the descriptions of processes, schemes, and examples are consistent with those used in the contemporary scientific literature, for example, the Journal of the American Chemical Society or the Journal of Biological Chemistry.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Flash column chromatography was performed on silica gel.

The naming programs used are ACDLABs 11.0 Namebatch, ACD IUPAC or Chem Draw.

Abbreviations:
Ac acetyl
ACN acetonitrile
AcOH acetic acid
BBr₃ boron tribromide
CH₂Cl₂ dichloromethane
CH₃CN acetonitrile
Cs₂CO₃ cesium carbonate
Cu(I)Br copper (I) bromide
Cu(OAc)₂ copper (II) acetate
DCE dichloroethane
DCM dichloromethane
DMF dimethylformamide
DMSO dimethylsulfoxide
Et₃N triethylamine
g grams
h hours
LiOH lithium hydroxide
K₂CO₃ potassium carbonate
K'OBu potassium tert-butoxide
KOH potassium hydroxide
m/z mass to charge ratio
MeOH methanol
MeSO₃H methyl sulfonic acid
mmol millimoles
Na₂CO₃ sodium carbonate
NaH sodium hydride
NaN₃ sodium azide
NaOH sodium hydroxide
NMR nuclear magnetic resonance
Pd palladium
Pd/C palladium on carbon
Pd(OAc)₂ palladium (II) acetate
Py pyridine
rt room temperature
TBAF tetrabutyl ammonium fluoride
TBDMS (TBS) tert-butyl dimethylsilyl
Tf₂O triflic anhydride
TFA trifluoroacetic acid
TFAA trifluoroacetic anhydride
THF tetrahydrofuran
X-Phos 2-dicyclohexylphosphino-2',4',6'-triisopropylbiphenyl Example 1

2-(6-(4-Amino-5-oxo-5,6,7,8-tetrahydrooxepino(2,3-d)pyrimidin-6-yl)-2-methyl-1-oxo-1,2,3,4-tetrahydronapthalen-2-yl) acetic acid

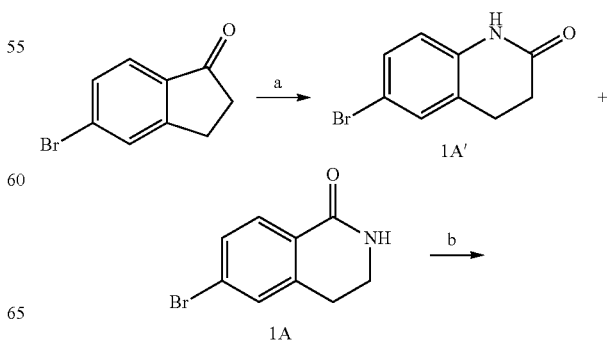

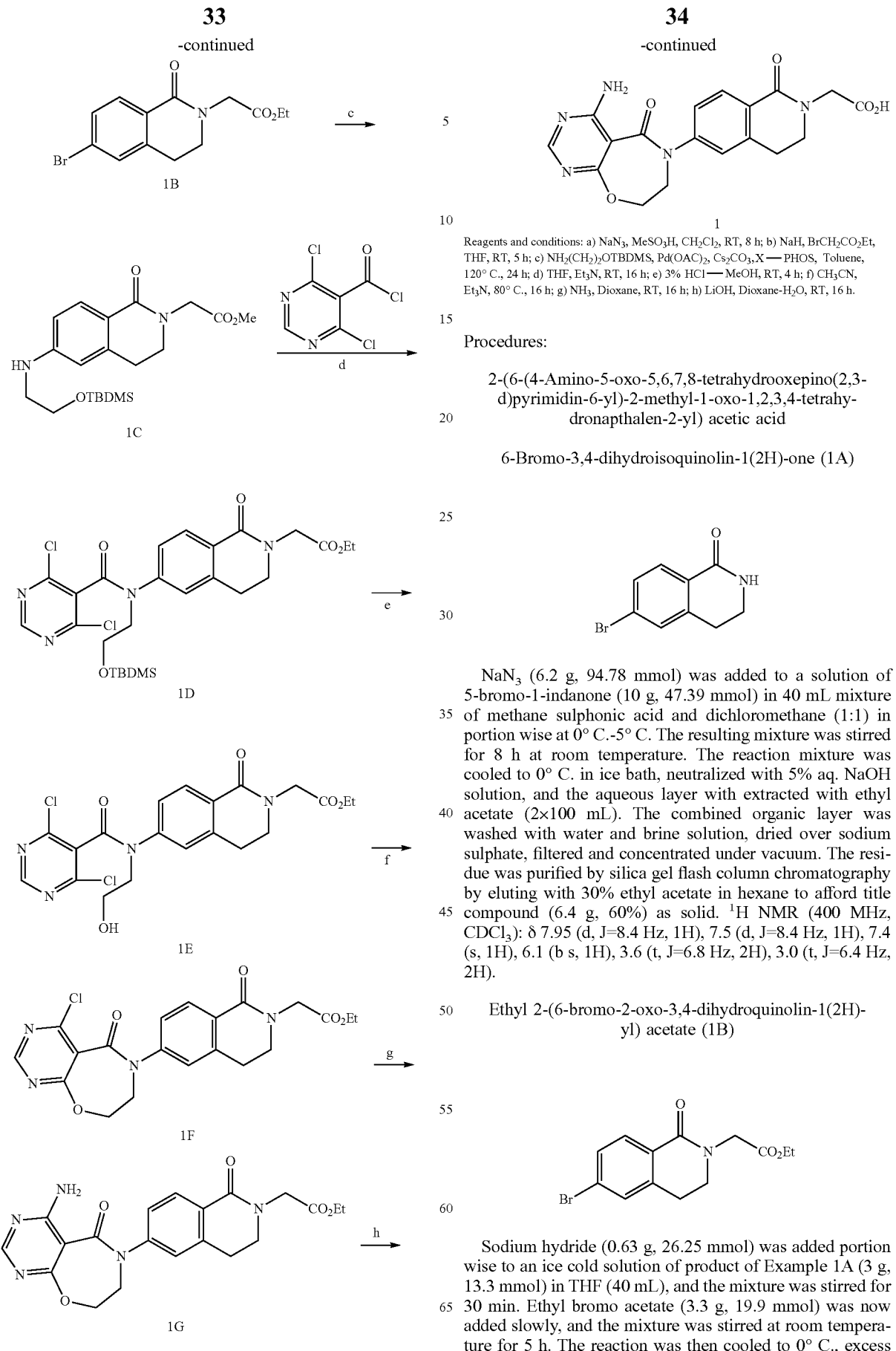

Reagents and conditions: a) NaN₃, MeSO₃H, CH₂Cl₂, RT, 8 h; b) NaH, BrCH₂CO₂Et, THF, RT, 5 h; c) NH₂(CH₂)₂OTBDMS, Pd(OAc)₂, Cs₂CO₃, X—PHOS, Toluene, 120° C., 24 h; d) THF, Et₃N, RT, 16 h; e) 3% HCl—MeOH, RT, 4 h; f) CH₃CN, Et₃N, 80° C., 16 h; g) NH₃, Dioxane, RT, 16 h; h) LiOH, Dioxane-H₂O, RT, 16 h.

Procedures:

2-(6-(4-Amino-5-oxo-5,6,7,8-tetrahydrooxepino(2,3-d)pyrimidin-6-yl)-2-methyl-1-oxo-1,2,3,4-tetrahydronapthalen-2-yl) acetic acid 6-Bromo-3,4-dihydroisoquinolin-1(2H)-one (1A)

NaN₃ (6.2 g, 94.78 mmol) was added to a solution of 5-bromo-1-indanone (10 g, 47.39 mmol) in 40 mL mixture of methane sulphonic acid and dichloromethane (1:1) in portion wise at 0° C.-5° C. The resulting mixture was stirred for 8 h at room temperature. The reaction mixture was cooled to 0° C. in ice bath, neutralized with 5% aq. NaOH solution, and the aqueous layer with extracted with ethyl acetate (2×100 mL). The combined organic layer was washed with water and brine solution, dried over sodium sulphate, filtered and concentrated under vacuum. The residue was purified by silica gel flash column chromatography by eluting with 30% ethyl acetate in hexane to afford title compound (6.4 g, 60%) as solid. ¹H NMR (400 MHz, CDCl₃): δ 7.95 (d, J=8.4 Hz, 1H), 7.5 (d, J=8.4 Hz, 1H), 7.4 (s, 1H), 6.1 (b s, 1H), 3.6 (t, J=6.8 Hz, 2H), 3.0 (t, J=6.4 Hz, 2H).

Ethyl 2-(6-bromo-2-oxo-3,4-dihydroquinolin-1(2H)-yl) acetate (1B)

Sodium hydride (0.63 g, 26.25 mmol) was added portion wise to an ice cold solution of product of Example 1A (3 g, 13.3 mmol) in THF (40 mL), and the mixture was stirred for 30 min. Ethyl bromo acetate (3.3 g, 19.9 mmol) was now added slowly, and the mixture was stirred at room temperature for 5 h. The reaction was then cooled to 0° C., excess NaH quenched with ice water, and the aqueous layer was extracted twice with ethyl acetate (2×50 mL). The combined organic layers were washed with water followed by brine solution, dried over sodium sulphate, filtered and concentrated under vacuum. The residue was purified using flash column chromatography by eluting with 15% ethyl acetate in hexane to afford title compound (2 g, 48%) as solid. $^1$H NMR (300 MHz, CDCl$_3$): δ 7.4 (m, 2H), 6.6 (m, 1H), 4.6 (s, 2H), 4.2 (q, J=6.9 Hz, 2H), 2.9 (m, 2H), 2.7 (m, 2H), 1.2 (t, J=6.9 Hz, 3H).

Ethyl 2-(6-(2-(tert-butyldimethylsilyloxy)ethylamino)-1-oxo-3,4-dihydroisoquinolin-2(1H)-yl)acetate (1C)

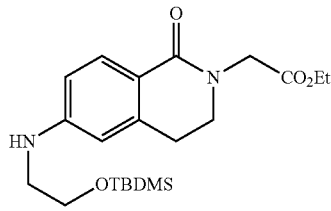 [SMILES: CCOC(=O)CN1CCc2cc(NCCO[Si](C)(C)C(C)(C)C)ccc2C1=O]

A mixture of product of Example 1B (1.5 g, 4.8 mmol), 2-(tert-butyldimethylsilyloxy)ethanamine (1.0 g, 5.71 mmol), cesium carbonate (1.87 g, 5.73 mmol), palladium acetate (0.11 g, 0.47 mmol) and X-PHOS (0.23 g, 0.47 mmol) in toluene (15 mL) under argon was refluxed at 120° C. for 24 h. The reaction was cooled, the mixture was diluted into ethyl acetate and washed with water (2×10 mL) and saturated aqueous brine. The organic layer was dried over sodium sulfate, filtered and concentrated to obtain dark oil. The residue was purified by flash chromatography using 10% ethyl acetate in hexane to afford title compound (0.95 g, 48%) as solid. $^1$H NMR (300 MHz, CDCl$_3$): δ 7.89 (d, J=8.4 Hz, 1H), 6.51 (m, 1H), 6.32 (s, 1H), 4.4 (m, 1H), 4.29 (s, 2H), 4.2 (q, J=6.9 Hz, 2H), 3.81 (t, J=5.1 Hz, 2H), 3.59 (t, J=6.3 Hz, 2H), 3.25 (q, J=5.7 Hz, 2H), 2.94 (t, J=6.9 Hz, 2H), 1.27 (t, J=6.9 Hz, 3H), 0.9 (s, 9H), 0.06 (s, 6H); ESI-MS m/z=407 (M+H)$^+$.

Ethyl 2-(6-(N-(2-(tert-butyldimethylsilyloxy)ethyl)-4,6-dichloropyrimidine-5-carboxamido)-1-oxo-3,4-dihydroisoquinolin-2(1H)-yl)acetate (1D)

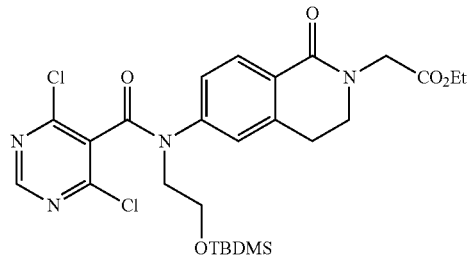 [SMILES: CCOC(=O)CN1CCc2cc(N(CCO[Si](C)(C)C(C)(C)C)C(=O)c3c(Cl)ncnc3Cl)ccc2C1=O]

To a stirred, cooled (0° C.) solution of product of Example 1C (0.95 g, 2.33 mmol) and TEA (1.18 g, 11.67 mmol) in THF (15 mL) was added drop wise a solution of 4,6-dichloropyrimidine-5-carbonyl chloride (0.74 g, 3.5 mmol) in THF (5 mL). After 16 h, the reaction was concentrated in vacuo, diluted with ethyl acetate, and washed with water (2×10 mL) and saturated aqueous brine. The organic layer was dried over sodium sulphate, filtered and concentrated in vacuo to afford oil. The residue was purified by flash chromatography using 12% ethyl acetate in hexane as eluent to afford title compound (0.75 g, 55%) as an solid. $^1$H NMR (300 MHz, CDCl$_3$): δ 8.6 (s, 1H), 7.95 (d, J=8.4 Hz, 1H), 7.34 (dd, J$_1$=1.2 Hz, J$_2$=7.5 Hz, 1H), 7.29 (s, 1H), 4.34 (s, 2H), 4.21 (q, J=6.9 Hz, 2H), 4.03 (t, J=5.7 Hz, 2H), 3.93 (t, J=4.8 Hz, 2H), 3.6 (t, J=6.3 Hz, 2H), 2.94 (t, J=7.2 Hz, 2H), 1.27 (t, J=7.8 Hz, 3H), 0.86 (s, 9H), 0.05 (s, 6H); ESI-MS m/z=581 (M+H)$^+$.

Ethyl 2-(6-(4,6-dichloro-N-(2-hydroxyethyl)pyrimidine-5-carboxamido)-1-oxo-3,4-dihydroisoquinolin-2(1H)-yl)acetate (1E)

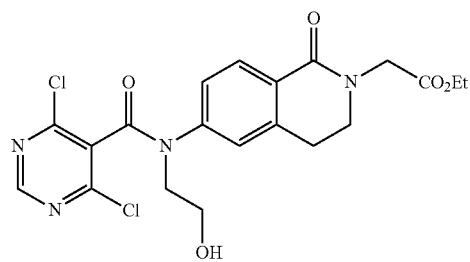 [SMILES: CCOC(=O)CN1CCc2cc(N(CCO)C(=O)c3c(Cl)ncnc3Cl)ccc2C1=O]

A solution of product of Example 1D (0.75 g, 1.29 mmol), in a methanolic solution of HCl (3 mL concentrated aqueous HCl in 97 mL of methanol) was stirred at room temperature for 4 h. Methanol was removed in vacuo. The residue was dissolved in ethyl acetate, and washed with saturated aqueous sodium bicarbonate and saturated aqueous brine. The organic layer was dried over sodium sulfate, filtered and concentrated in vacuo to afford title compound (0.45 g, 75%) as solid, which was carried on to the next step without further purification. $^1$H NMR (400 MHz, CDCl$_3$): δ 8.62 (s, 1H), 7.99 (d, J=8.0 Hz, 1H), 7.36 (m, 1H), 7.31 (s, 1H), 4.28 (s, 2H), 4.2 (q, J=7.2 Hz, 2H), 4.1 (m, 2H), 3.96 (m, 2H), 3.62 (t, J=6.4 Hz, 2H), 3.0 (t, J=6.4 Hz, 2H), 2.1 (t, J=5.6 Hz, 1H), 1.28 (t, J=7.2 Hz, 3H); ESI-MS m/z=467 (M+H)$^+$.

Ethyl 2-(6-(4-chloro-5-oxo-7,8-dihydropyrimido[5,4-f][1,4]oxazepin-6(5H)-yl)-1-oxo-3,4-dihydroisoquinolin-2(1H)-yl)acetate (1F)

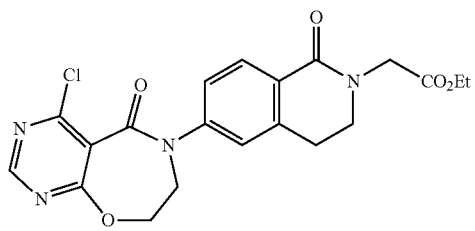 [SMILES: CCOC(=O)CN1CCc2cc(N3CCOc4ncnc(Cl)c4C3=O)ccc2C1=O]

A slurry of product of Example 1E (0.4 g, 0.85 mmol) and TEA (0.43 g, 4.28 mmol) in acetonitrile (10 mL) was stirred at 80° C. for 16 h. The reaction was cooled, concentrated in vacuo, and diluted with ethyl acetate. The mixture was washed with water and saturated aqueous brine. The organic layer was dried over sodium sulfate, filtered and concentrated in vacuo to afford title compound (0.35 g, 95%) as a white solid. $^1$H NMR (400 MHz, CDCl$_3$): δ 8.78 (s, 1H), 8.19 (d, J=8.4 Hz, 1H), 7.35 (s, 1H), 7.29 (dd, J$_1$=2.8 Hz, J$_2$=8.8 Hz, 1H), 4.78 (t, J=4.8 Hz, 2H), 4.34 (s, 2H), 4.23 (q, J=7.6 Hz, 2H), 4.1 (t, J=4.8 Hz, 2H), 3.7 (t, J=6.8 Hz, 2H), 3.1 (m, 2H), 1.29 (t, J=7.2 Hz, 3H); ESI-MS m/z=431 (M+H)$^+$.

Ethyl 2-(6-(4-amino-5-oxo-7,8-dihydropyrimido[5,4-f][1,4]oxazepin-6(5H)-yl)-1-oxo-3,4-dihydroisoquinolin-2(1H)-yl)acetate (1G)

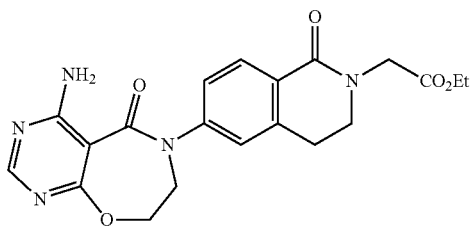 [SMILES: CCOC(=O)CN1CCc2cc(N3CCOc4ncnc(N)c4C3=O)ccc2C1=O]

A solution of product of Example 1F (0.3 g, 0.697 mmol) in 0.5M ammonia in p-dioxane (10 mL) was stirred at room temperature for 16 h. The reaction mixture was concentrated in vacuo and diluted with ethyl acetate. The organic layer was washed with water, saturated aqueous brine, dried over sodium sulfate, filtered and concentrated in vacuo to afford title compound (0.22 g, 70%) as an white solid. $^1$H NMR (300 MHz, CDCl$_3$): δ 8.3 (s, 1H), 8.18 (d, J=7.8 Hz, 1H), 7.2 (m, 2H), 4.71 (t, J=4.2 Hz, 2H), 4.34 (s, 2H), 4.23 (q, J=6.9 Hz, 2H), 4.04 (t, J=4.8 Hz, 2H), 3.69 (m, 2H), 3.1 (t, J=6.3 Hz, 2H), 1.29 (t, J=6.9 Hz, 3H); LC-MS: 91% pure, m/z=412 (M+H)$^+$.

2-(6-(4-Amino-5-oxo-5,6,7,8-tetrahydrooxepino(2,3-d)pyrimidin-6-yl)-2-methyl-1-oxo-1,2,3,4-tetrahydronapthalen-2-yl) acetic acid (1)

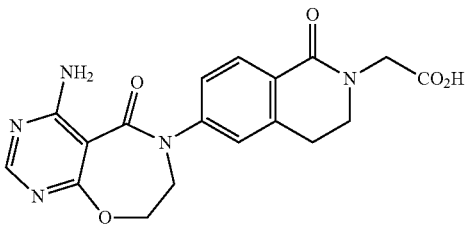 [SMILES: Nc1ncnc2c1C(=O)N(c1ccc3c(c1)CCN(CC(=O)O)C3=O)CCO2]

A solution of product of Example 1G (0.18 g, 0.43 mmol) and lithium hydroxide (0.055 g, 1.309 mmol) in 5 mL of p-dioxane-water (4:1) mixture was stirred at room temperature for 16 h. After the solvent was removed in vacuo, the residue was dissolved in water and washed with ethyl acetate. The aqueous layer was acidified using 2N aqueous solution of HCl until pH 2 was attained. The resulting solution was cooled to 0° C., and resulting solids were filtered off and dried in vacuo to afford title compound (0.12 g, 72%) as a white solid. $^1$H NMR (300 MHz, DMSO-d$_6$): δ 12.8 (bs, 1H), 8.45 (bs, 2H), 8.36 (s, 1H), 7.9 (d, J=9.0 Hz, 1H), 7.4 (m, 2H), 4.7 (m, 2H), 4.21 (m, 2H), 4.13 (m, 2H), 3.64 (t, J=6.3 Hz, 2H), 3.03 (t, J=5.7 Hz, 2H); HPLC purity: 99%, m/z=384 (M+H)$^+$.

Examples 2-9 were prepared by the method described above for Example 1 or routine variations thereof starting from the requisite halo-quinolinone.

| Ex | Structure | Analytical Data | Mass/Purity |
|---|---|---|---|
| 2 | ![structure] | $^1$H NMR (300 MHz, DMSO-d$_6$): δ 8.17 (s, 1H), 7.61 (bs, 2H), 7.29 (m, 1H), 7.23 (dd, J$_1$ = 2.1 Hz, J$_2$ = 8.1 Hz, 1H), 7.0 (d, J = 9.0 Hz, 1H), 4.67 (s, 2H), 4.6 (t, J = 4.2 Hz, 2H), 4.15 (q, J = 7.8 Hz, 2H), 3.96 (t, J = 4.2 Hz, 2H), 2.91 (t, J = 6.9 Hz, 2H), 2.6 (t, J = 7.8 Hz, 2H), 1.21 (t, J = 7.5 Hz, 3H). | ESI-MS m/z = 412 (M + H)$^+$; LC-MS purity: 97%. |
| 3 | ![structure] | $^1$H NMR (400 MHz, DMSO-d$_6$): δ 13.0 (bs, 1H), 8.17 (s, 1H), 7.61 (bs, 2H), 7.28 (s, 1H), 7.23 (d, J = 8.4 Hz, 1H), 6.98 (d, J = 8.4 Hz, 1H), 4.6 (m, 4H), 3.96 (m, 2H), 2.9 (t, J = 6.8 Hz, 2H), 2.59 (t, J = 7.2 Hz, 2H). | ESI-MS m/z = 384 (M + H)$^+$; LC-MS purity: 99%. |

-continued

| Ex | Structure | Analytical Data | Mass/Purity |
|---|---|---|---|
| 4 | 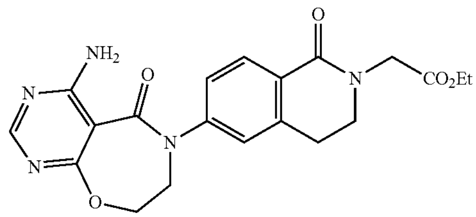 [SMILES: CCOC(=O)CN1CCc2cc(N3CCOc4ncnc(N)c4C3=O)ccc2C1=O] | $^1$H NMR (300 MHz, CDCl$_3$): δ 8.3 (s, 1H), 8.18 (d, J = 7.8 Hz, 1H), 7.2 (m, 2H), 4.71 (t, J = 4.2 Hz, 2H), 4.34 (s, 2H), 4.23 (q, J = 6.9 Hz, 2H), 4.04 (t, J = 4.8 Hz, 2H), 3.69 (m, 2H), 3.1 (t, J = 6.3 Hz, 2H), 1.29 (t, J = 6.9 Hz, 3H). | ESI-MS m/z = 412 (M + H)$^+$; LC-MS purity: 91%. |
| 5 | 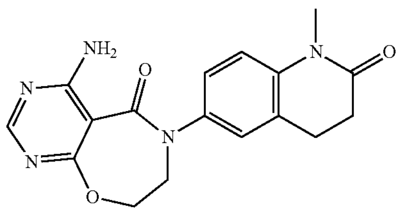 [SMILES: CN1C(=O)CCc2cc(N3CCOc4ncnc(N)c4C3=O)ccc21] | $^1$H NMR (400 MHz, DMSO-d$_6$): δ 8.17 (s, 1H), 7.62 (bs, 2H), 7.25 (m, 1H), 7.12 (m, 1H), 4.6 (t, J = 4.0 Hz, 2H), 3.95 (t, J = 4.4 Hz, 2H), 3.27 (s, 3H), 2.88 (t, J = 7.2 Hz, 2H), 2.55 (t, J = 8.4 Hz, 2H). | ESI-MS m/z = 340 (M + H)$^+$; HPLC purity: 96%. |
| 6 | 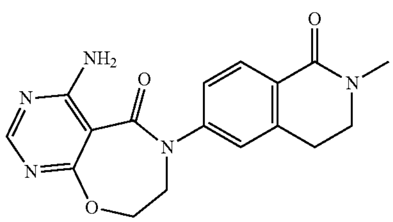 [SMILES: CN1CCc2cc(N3CCOc4ncnc(N)c4C3=O)ccc2C1=O] | $^1$H NMR (300 MHz, DMSO-d$_6$): δ 8.18 (s, 1H), 7.9 (d, J = 9.0 Hz, 1H), 7.62 (bs, 2H), 7.35 (m, 2H), 4.6 (t, J = 4.2 Hz, 2H), 4.02 (t, J = 4.8 Hz, 2H), 3.56 (t, J = 6.3 Hz, 2H), 2.99 (m, 5H). | ESI-MS m/z = 340 (M + H)$^+$; LC-MS purity: 96.6%. |
| 7 | 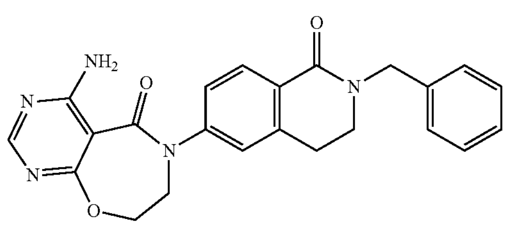 [SMILES: Nc1ncnc2c1C(=O)N(c1ccc3c(c1)CCN(Cc1ccccc1)C3=O)CCO2] | $^1$H NMR (400 MHz, DMSO-d$_6$): δ 8.18 (s, 1H), 7.97 (d, J = 8.4 Hz, 1H), 7.62 (bs, 2H), 7.41-7.27 (m, 6H), 7.15 (s, 1H), 4.72 (s, 2H), 4.61 (t, J = 4.4 Hz, 2H), 4.02 (t, J = 4.4 Hz, 2H), 3.5 (t, J = 6.4 Hz, 2H), 2.98 (t, J = 6.8 Hz, 2H). | ESI-MS m/z = 416 (M + H)$^+$; HPLC purity: 97%. |
| 8 | 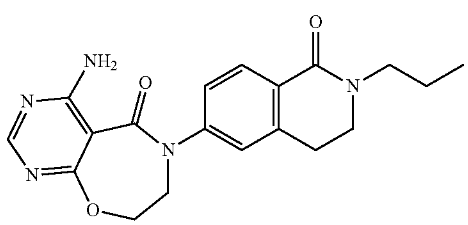 [SMILES: CCCN1CCc2cc(N3CCOc4ncnc(N)c4C3=O)ccc2C1=O] | $^1$H NMR (400 MHz, DMSO-d$_6$): δ 8.18 (s, 1H), 7.9 (d, J = 9.2 Hz, 1H), 7.62 (bs, 2H), 7.35 (m, 2H), 4.6 (t, J = 4.0 Hz, 2H), 4.02 (t, J = 4.4 Hz, 2H), 3.55 (m, 2H), 3.44 (t, J = 6.8 Hz, 2H), 2.97 (t, J = 6.4 Hz, 2H), 1.58 (m, 2H), 0.87 (t, J = 7.6 Hz, 3H). | ESI-MS m/z = 368 (M + H)$^+$; HPLC purity: 97%. |
| 9 | 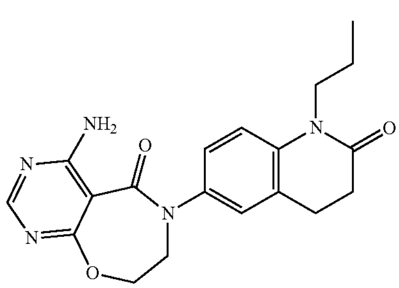 [SMILES: CCCN1C(=O)CCc2cc(N3CCOc4ncnc(N)c4C3=O)ccc21] | $^1$H NMR (400 MHz, DMSO-d$_6$): δ 8.17 (s, 1H), 7.61 (bs, 2H), 7.21 (m, 3H), 4.6 (t, J = 4.4 Hz, 2H), 3.96 (t, J = 4.4 Hz, 2H), 3.8 (t, J = 7.6 Hz, 2H), 2.86 (t, J = 6.8 Hz, 2H), 2.55 (t, J = 7.6 Hz, 2H), 1.55 (m, 2H), 0.88 (t, J = 7.2 Hz, 3H). | ESI-MS m/z = 368 (M + H)$^+$; HPLC purity: 99%. |

Example 10

6-(1-Allyl-2-benzyl-3-oxo-2,3-dihydro-1H-indazol-5-yl)-4-amino-7,8-dihydropyrimido[5,4-f][1,4]oxazepin-5(6H)-one and

Example 11

4-Amino-6-(3-oxo-1-propyl-2,3-dihydro-1H-indazol-5-yl)-7,8-dihydropyrimido[5,4-f][1,4]oxazepin-5(6H)-one

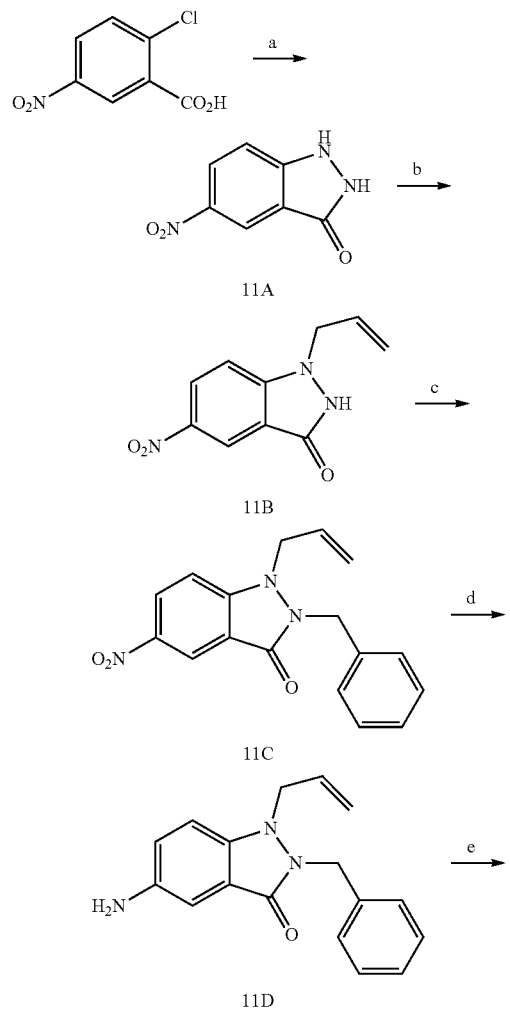

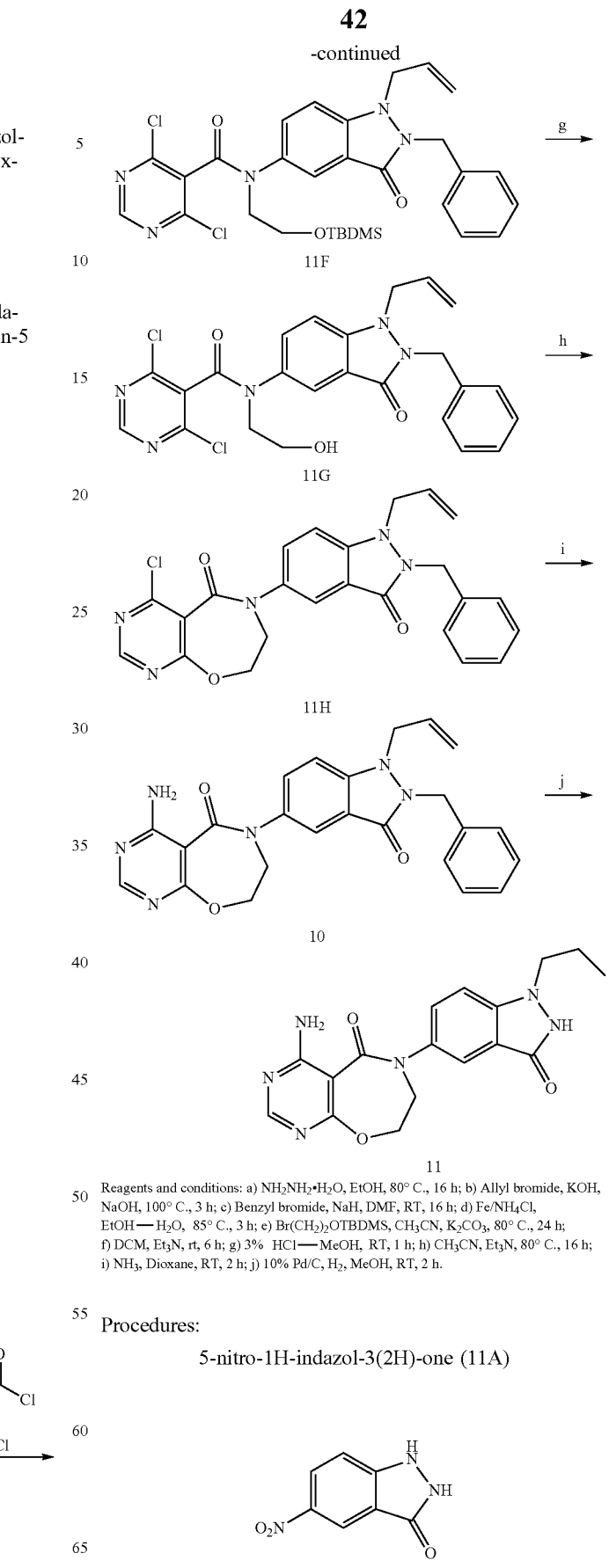

Reagents and conditions: a) NH₂NH₂·H₂O, EtOH, 80° C., 16 h; b) Allyl bromide, KOH, NaOH, 100° C., 3 h; c) Benzyl bromide, NaH, DMF, RT, 16 h; d) Fe/NH₄Cl, EtOH—H₂O, 85° C., 3 h; e) Br(CH₂)₂OTBDMS, CH₃CN, K₂CO₃, 80° C., 24 h; f) DCM, Et₃N, rt, 6 h; g) 3% HCl—MeOH, RT, 1 h; h) CH₃CN, Et₃N, 80° C., 16 h; i) NH₃, Dioxane, RT, 2 h; j) 10% Pd/C, H₂, MeOH, RT, 2 h.

Procedures:

5-nitro-1H-indazol-3(2H)-one (11A)

Hydrazine hydrate (4 mL, 124 mmol) was added to a solution of 2-chloro-5-nitro benzoic acid (5 g, 24.8 mmol) in absolute ethanol (30 mL), and the resulting mixture was refluxed for 16 h. The reaction mixture was concentrated under reduced pressure. Residue was triturated with methanol to give 6.5 g of crude intermediate. 2N aq. HCl (40 mL) was added to the crude product, and the mixture was refluxed for 8 h. Reaction mixture was cooled to 0° C., solids were collected via filtration, washed with cold water and dried under vacuum. Residue was purified by flash chromatography using 1% methanol in chloroform as eluent to afford title compound (2 g, 27%) as a solid. $^1$H NMR (400 MHz, DMSO-d$_6$): δ 12.4 (bs, 1H), 11.3 (bs, 1H), 8.67 (s, 1H), 8.12 (dd, J$_1$=2.1 Hz, J$_2$=9.0 Hz, 1H), 7.5 (d, J=9.0 Hz, 1H); ESI-MS m/z: 179 (M+H)$^+$.

1-Allyl-5-nitro-1H-indazol-3(2H)-one (11B)

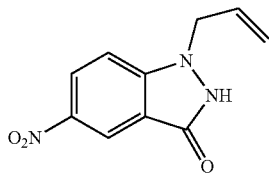 [SMILES: C=CCn1[nH]c(=O)c2cc([N+](=O)[O-])ccc21]

Allyl bromide (2.7 g, 22.34 mmol) was added to a mixture of product of Example 11A (4 g, 22.34 mmol) and 1N aqueous KOH solution (25 mL), and the mixture was refluxed for 2 h. 15% NaOH (2 mL) and allyl bromide (0.54 mg, 0.04 mmol) were added, and again the mixture was refluxed for 1 h. The reaction mixture was cooled to room temperature and neutralized using 3N aqueous HCl solution. Resulting solids were collected via filtration, washed with water and dried under vacuum to afford title product (4.5 g, 92%) as solid. $^1$H NMR (300 MHz, DMSO-d$_6$): δ 11.5 (bs, 1H), 8.67 (s, 1H), 8.15 (dd, J$_1$=2.1 Hz, J$_2$=9.9 Hz, 1H), 7.62 (d, J=9.0 Hz, 1H), 5.96 (m, 1H), 5.13 (m, 2H), 4.93 (d, J=5.7 Hz, 2H).

1-Allyl-2-benzyl-5-nitro-1H-indazol-3(2H)-one (11C)

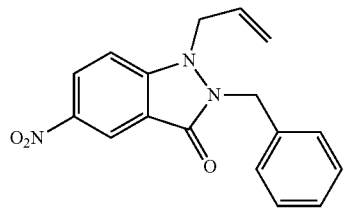

Sodium hydride (0.55 g, 13.68 mmol) was added portion wise to an ice cold solution of product of Example 11B (2.5 g, 11.4 mmol) in DMF (20 mL), and the mixture was stirred for 30 min. Benzyl bromide (3.9 g, 22.8 mmol) was now added slowly, and the mixture was stirred at room temperature for 16 h. The reaction was then cooled to 0° C. and quenched with ice water. The aqueous layer was extracted twice with ethyl acetate (2×50 mL). The combined organic layers were washed with water followed by brine solution, dried over sodium sulphate, filtered and concentrated in vacuo. The residue was purified by flash column chromatography using 5% ethyl acetate in hexane as eluent to afford title compound (2.2 g, 62%) as solid. $^1$H NMR (400 MHz, DMSO-d$_6$): δ 8.57 (d, J=2.0 Hz, 1H), 8.23 (dd, J$_1$=2.0 Hz, J$_2$=9.2 Hz, 1H), 7.7 (d, J=9.2 Hz, 1H), 7.5 (d, J=5.7 Hz, 2H), 7.4 (m, 3H), 5.98 (m, 1H), 5.44 (s, 2H), 5.2-5.07 (m, 2H), 4.98 (d, J=5.2 Hz, 2H).

1-Allyl-5-amino-2-benzyl-1H-indazol-3(2H)-one (11D)

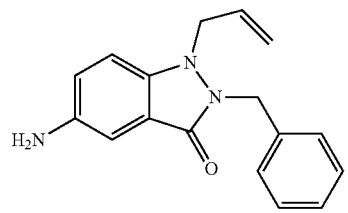 [SMILES: C=CCn1c2ccc([N+](=O)[O-])cc2c(=O)n1Cc1ccccc1]

Iron powder (0.77 g, 14.22 mmol) was added to a solution of product of Example 11C (2.2 g, 7.11 mmol) in 80 mL of ethanol-water mixture (4:1) followed by NH$_4$Cl (0.19 g, 3.55 mmol), and the mixture was refluxed for 4 h. The solvent was removed under reduced pressure, and residue was partitioned between ethyl acetate and water. The organic layer was dried over sodium sulphate, filtered and removed in vacuo. Residue was purified by flash chromatography using 20% ethyl acetated in hexane as eluent to afford title compound as solid (1.6 g, 66%). $^1$H NMR (300 MHz, DMSO-d$_6$): δ 7.5 (m, 2H), 7.39 (m, 3H), 7.19 (d, J=8.4 Hz, 1H), 6.81 (dd, J$_1$=2.1 Hz, J$_2$=9.3 Hz, 1H), 6.64 (m, 1H), 5.9 (m, 1H), 5.3 (s, 2H), 5.06 (m, 2H), 4.73 (m, 2H); ESI-MS m/z=280 (M+H)$^+$.

1-Allyl-2-benzyl-5-(2-(tert-butyldimethylsilyloxy)ethylamino)-1H-indazol-3(2H)-one (11E)

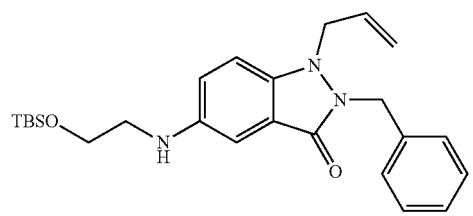 [SMILES: C=CCn1c2ccc(NCCO[Si](C)(C)C(C)(C)C)cc2c(=O)n1Cc1ccccc1]

Potassium carbonate (2.6 g, 19.32 mmol) was added to a mixture of (2-bromoethoxy)(tert-butyl)dimethylsilane (0.92 g, 3.87 mmol) and product of Example 11D (0.9 g, 3.22 mmol) in acetonitrile (70 mL), and the mixture was refluxed for 24 h. Reaction mixture was cooled to room temperature and partitioned between ethyl acetate and water. Separated organic layer was washed with brine solution, dried over sodium sulfate, filtered and concentrated under vacuum. Residue was purified by flash chromatography using 15% ethyl acetate in hexane as eluent to afford title compound (0.35 g, 25%) as solid. $^1$H NMR (400 MHz, DMSO-$d_6$): δ 7.48 (m, 2H), 7.34 (m, 3H), 7.21 (d, J=8.8 Hz, 1H), 6.84 (dd, $J_1$=2.0 Hz, $J_2$=9.6 Hz, 1H), 6.49 (d, J=1.6 Hz, 1H), 5.86 (m, 1H), 5.28 (s, 2H), 5.21 (t, J=6.0 Hz, 1H), 5.05 (m, 2H), 4.72 (d, J=5.2 Hz, 2H), 3.69 (t, J=6.4 Hz, 2H), 3.11 (q, J=5.6 Hz, 2H), 0.82 (s, 9H), 0.03 (s, 6H).

N-(1-Allyl-2-benzyl-3-oxo-2,3-dihydro-1H-indazol-5-yl)-N-(2-(tert-butyldimethylsilyloxy)ethyl)-4,6-dichloropyrimidine-5-carboxamide (11F)

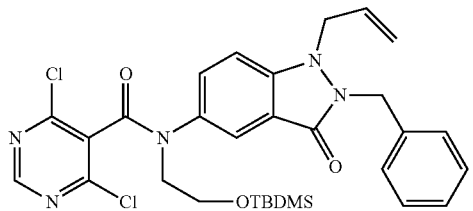 [SMILES: C=CCn1c2ccc(N(CCO[Si](C)(C)C(C)(C)C)C(=O)c3c(Cl)ncnc3Cl)cc2c(=O)n1Cc1ccccc1]

To a stirred, cooled (0° C.) solution of product of 11E (0.55 g, 1.23 mmol) and TEA (0.5 g, 5.0 mmol) in DCM (12 mL) was added drop wise a solution of 4,6-dichloropyrimidine-5-carbonyl chloride (0.26 g, 1.23 mmol) in DCM (5 mL). After 6 h, the reaction was concentrated in vacuo, diluted with ethyl acetate, and washed with water (2×10 mL) and saturated aqueous brine. The organic layer was dried over sodium sulphate, filtered and concentrated in vacuo to afford oil. The residue was purified by flash chromatography using 12% ethyl acetate in hexane as eluent to afford title compound (0.35 g, 46%) as an oil. $^1$H NMR (400 MHz, DMSO-$d_6$): δ 8.75 (s, 1H), 7.75 (s, 1H), 7.46 (m, 3H), 7.36 (m, 4H), 5.94 (m, 1H), 5.34 (s, 2H), 5.08 (m, 1H), 4.96 (m, 1H), 4.82 (m, 2H), 4.0 (m, 2H), 3.77 (t, J=4.8 Hz, 2H), 0.8 (s, 9H), 0.01 (s, 6H); ESI-MS m/z=611 (M+H)$^+$.

N-(1-Allyl-2-benzyl-3-oxo-2,3-dihydro-1H-indazol-5-yl)-4,6-dichloro-N-(2-hydroxyethyl)pyrimidine-5-carboxamide (11G)

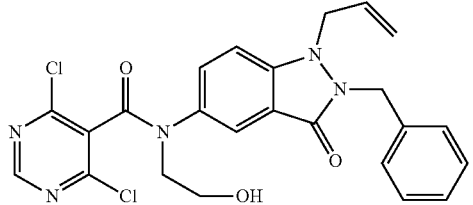 [SMILES: C=CCn1c2ccc(N(CCO)C(=O)c3c(Cl)ncnc3Cl)cc2c(=O)n1Cc1ccccc1]

A solution of product of Example 11F (0.35 g, 0.57 mmol) in a methanolic solution of HCl (3 mL concentrated aqueous HCl in 97 mL of methanol) was stirred at room temperature for 1 h. Methanol was removed in vacuo. The residue was dissolved in ethyl acetate, washed with saturated aqueous sodium bicarbonate and saturated aqueous brine. The organic layer was dried over sodium sulfate, filtered and concentrated in vacuo to afford title compound (0.25 g, 88%) as an oil, which was carried on to the next step without further purification. $^1$H NMR (400 MHz, DMSO-$d_6$): δ 8.75 (s, 1H), 7.75 (s, 1H), 7.46 (m, 3H), 7.36 (m, 4H), 5.94 (m, 1H), 5.34 (s, 2H), 5.12 (m, 1H), 5.03 (m, 1H), 4.86 (m, 2H), 3.9 (t, J=6.0 Hz, 2H), 3.77 (t, J=4.8 Hz, 2H); ESI-MS m/z=498 (M+H)$^+$.

6-(1-Allyl-2-benzyl-3-oxo-2,3-dihydro-1H-indazol-5-yl)-4-chloro-7,8-dihydropyrimido[5,4-f][1,4]oxazepin-5(6H)-one (11H)

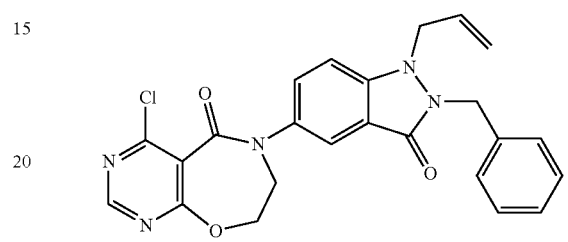

A slurry of product of Example 11G (0.25 g, 0.5 mmol) and TEA (0.22 g, 2.2 mmol) in acetonitrile (20 mL) was stirred at 80° C. for 16 h. The reaction was cooled, concentrated in vacuo, and diluted with ethyl acetate. The organic layer was washed with water and saturated aqueous brine. The organic layer was dried over sodium sulfate, filtered and concentrated in vacuo to afford title compound (0.22 g, 94%) as a white solid. $^1$H NMR (300 MHz, DMSO-$d_6$): δ 8.8 (s, 1H), 7.68 (s, 1H), 7.55 (m, 3H), 7.38 (m, 4H), 5.94 (m, 1H), 5.4 (s, 2H), 5.17 (m, 1H), 5.05 (m, 1H), 4.93 (d, J=4.8 Hz, 2H), 4.76 (t, J=4.0 Hz, 2H), 4.15 (t, J=4.8 Hz, 2H); ESI-MS m/z=462 (M+H)$^+$.

6-(1-Allyl-2-benzyl-3-oxo-2,3-dihydro-1H-indazol-5-yl)-4-amino-7,8-dihydropyrimido[5,4-f][1,4]oxazepin-5(6H)-one (10)

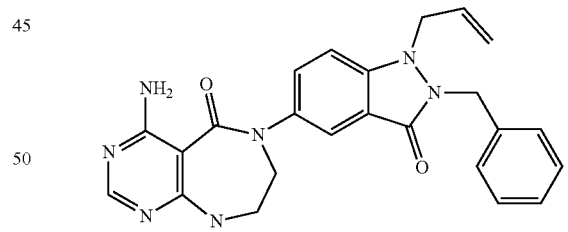

A solution of product of Example 11H (0.22 g, 0.46 mmol) in 0.5M ammonia in p-dioxane (40 mL) was stirred at room temperature for 4 h. The reaction mixture was concentrated in vacuo and diluted with ethyl acetate. The organic layer was washed with water and saturated aqueous brine. The organic layer was dried over sodium sulfate, filtered and concentrated in vacuo to afford title compound (0.17 g, 82%) as an white solid. $^1$H NMR (400 MHz, DMSO-$d_6$): δ 8.16 (s, 1H), 7.62 (s, 1H), 7.55 (m, 3H), 7.38 (m, 4H), 7.19 (bs, 2H), 5.97 (m, 1H), 5.39 (s, 2H), 5.16 (m, 1H), 5.09 (m, 1H), 4.91 (d, J=5.6 Hz, 2H), 4.65 (t, J=4.4 Hz, 2H), 3.98 (t, J=4.4 Hz, 2H); LC-MS purity: 94%, m/z=443 (M+H)$^+$.

4-Amino-6-(3-oxo-1-propyl-2,3-dihydro-1H-indazol-5-yl)-7,8-dihydropyrimido[5,4-f][1,4]oxazepin-5(6H)-one (11)

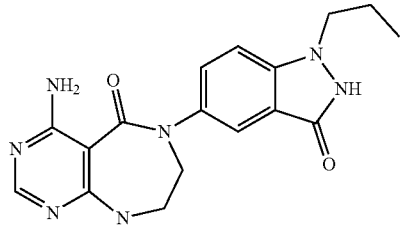 [SMILES: CCCn1[nH]c(=O)c2cc(N3CCNc4ncnc(N)c4C3=O)ccc21]

Excess 10% Pd/C (0.15 g) was added to a solution of product of Example 10 (0.15 g, 0.226 mmol) in 120 mL of methanol, and the mixture was stirred at room temperature for 2 h. The reaction mixture was filtered over celite bed, filtrate was concentrated under reduced pressure, and the residue partitioned between ethyl acetate and water. The organic layer was dried over sodium sulphate, filtered and concentrated in vacuo. The crude product was triturated with ethyl acetate to afford title compound (0.09 g, 75%) as brown solid. $^1$H NMR (300 MHz, DMSO-$d_6$): δ 10.5 (bs, 1H), 8.17 (s, 1H), 7.63 (bs, 2H), 7.56 (m, 1H), 7.51 (d, J=9.3 Hz, 1H), 7.3 (dd, $J_1$=1.2 Hz, $J_2$=9.0 Hz, 1H), 4.63 (t, J=4.2 Hz, 2H), 4.1 (t, J=7.2 Hz, 2H), 3.98 (t, J=4.2 Hz, 2H), 1.76 (m, 2H), 0.81 (t, J=7.2 Hz, 3H); HPLC purity: 95%, ESI-MS m/z=355 (M+H)$^+$.

Example 12

4-Amino-6-(1-propyl-1H-indol-5-yl)-7,8-dihydropyrimido[5,4-f][1,4]oxazepin-5(6H)-one

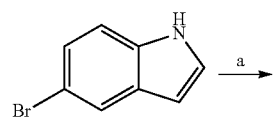

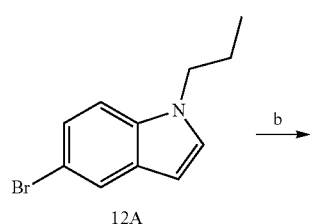

12A

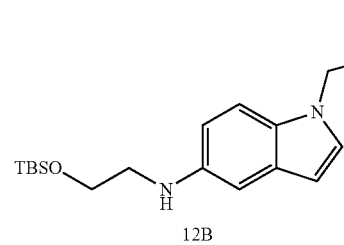 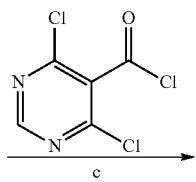

12B

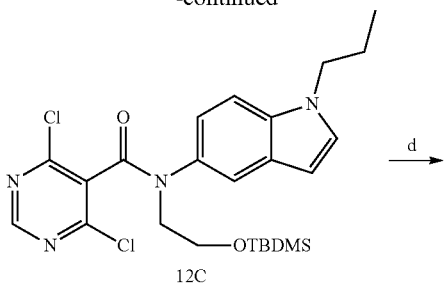

12C

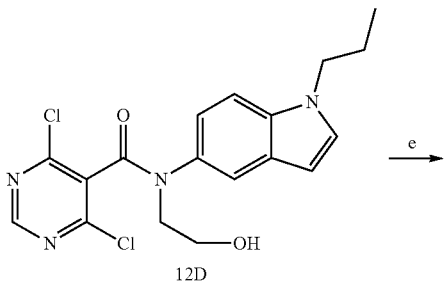

12D

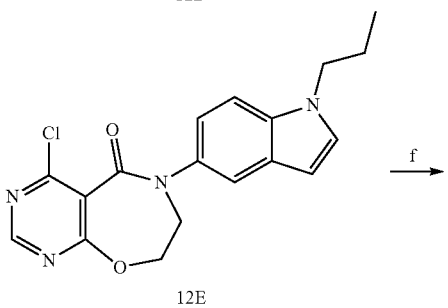

12E

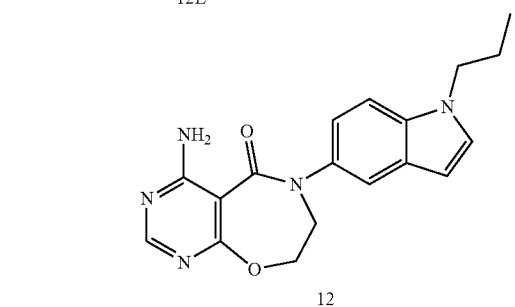

12

Reagents and conditions: a) n-propyl bromide, Cs$_2$Co$_3$, DMF, 100° C, 2 h; b) NH$_2$(CH$_2$)OTBDMS, Pd(OAc)$_2$, CS$_2$CO$_3$, X-PHOS, Toluene, 120° C., 2.5 h; c) DCM, Et$_3$N, RT, 1 h; d) 3% HCl-MeOH, RT, 1 h; e) CH$_3$CN, Et$_3$N, 80° C., 16 h; f) NH$_3$, Dioxane, RT, 2 h.

Procedures:

4-Amino-6-(1-propyl-1H-indol-5-yl)-7,8-dihydropyrimido[5,4-f][1,4]oxazepin-5(6H)-one 5-bromo-1-propyl-1H-indole (12A)

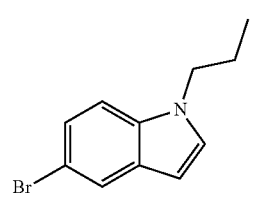

1-Bromopropane (1.25 g, 10.2 mmol) was added to a solution of 5-bromo indole (2 g, 10.2 mmol) in DMF (30 mL) followed by cesium carbonate (6.63 g, 20.4 mmol), and the mixture was stirred at 100° C. for 2 h. Insoluble solids were filtered off, and filtrate was concentrated. Residue was partitioned between ethyl acetate and water. Organic layer was separated, washed with brine, dried over sodium sulphate, filtered and concentrated in vacuo. The crude product was purified by flash chromatography using 5% ethyl acetate in hexane as eluent to afford title compound (1.8 g, 74%) as oil. $^1$H NMR (400 MHz, CDCl$_3$): δ 7.74 (d, J=1.6 Hz, 1H), 7.28 (m, 1H), 7.20 (m, 1H), 7.09 (d, J=3.2 Hz, 1H), 6.41 (d, J=2.4 Hz, 1H), 4.05 (t, J=7.2 Hz, 2H), 1.87 (m, 2H), 0.9 (t, J=7.2 Hz, 3H); ESI-MS m/z=238 (M+H)$^+$.

N-(2-(tert-Butyldimethylsilyloxy)ethyl)-1-propyl-1H-indol-5-amine (12B)

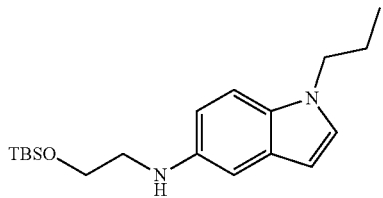 [SMILES: CCCn1ccc2cc(NCCO[Si](C)(C)C(C)(C)C)ccc21]

A mixture of product of Example 12A (2 g, 8.4 mmol), 2-(tert-butyldimethylsilyloxy)ethanamine (1.5 g, 8.4 mmol), cesium carbonate (4.09 g, 12.6 mmol), palladium acetate (0.18 g, 0.84 mmol) and X-PHOS (0.4 g, 0.84 mmol) in Toluene (25 mL) under Argon was refluxed at 120° C. for 2.5 h. The reaction was cooled, diluted with ethyl acetate, and washed with water (2×10 mL) and saturated aqueous brine. The organic layer was dried over sodium sulfate, filtered and concentrated to obtain dark oil. The residue was purified by flash chromatography using 10% ethyl acetate in hexane to afford title compound (1.5 g, 53%) as oil. $^1$H NMR (400 MHz, CDCl$_3$): δ 7.16 (d, J=8.8 Hz, 1H), 7.0 (d, J=2.8 Hz, 1H), 6.86 (d, J=2.08 Hz, 1H), 6.68-6.65 (dd, J$_1$=2.0 Hz, J$_2$=8.4 Hz, 1H), 6.30 (d, J=3.2 Hz, 1H), 4.01 (t, J=7.2 Hz, 2H), 3.85 (t, J=5.6 Hz, 2H), 3.25 (t, J=5.2 Hz, 2H), 1.86-1.81 (m, 2H), 0.93 (t, J=5.6 Hz, 3H), 0.91 (s, 9H), 0.07 (s, 6H); ESI-MS m/z=333 (M+H)$^+$.

N-(2-(tert-Butyldimethylsilyloxy)ethyl)-4,6-dichloro-N-(1-propyl-1H-indol-5-yl)pyrimidine-5-carboxamide (12C)

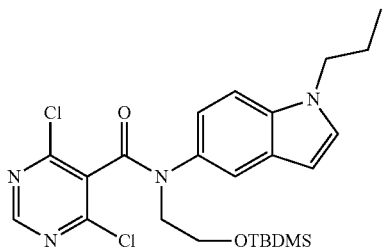 [SMILES: CCCn1ccc2cc(N(CCO[Si](C)(C)C(C)(C)C)C(=O)c3c(Cl)ncnc3Cl)ccc21]

To a stirred, cooled (0° C.) solution of product of Example 12B (1.5 g, 4.51 mmol) and TEA (1.82 g, 18 mmol) in DCM (30 mL) was added drop wise a solution of 4,6-dichloropyrimidine-5-carbonyl chloride (0.95 g, 4.5 mmol) in DCM (5 mL). After 1 h, the reaction was concentrated in vacuo, diluted into ethyl acetate, and washed with water (2×10 mL) and saturated aqueous brine. The organic layer was dried over sodium sulphate, filtered and concentrated in vacuo to afford oil. The residue was purified by flash chromatography using 12% ethyl acetate in hexane as eluent to afford title compound (1 g, 43%) as a syrup. $^1$H NMR (400 MHz, CDCl$_3$): δ 8.46 (s, 1H), 7.66 (m, 1H), 7.21-7.13 (m, 2H), 7.09 (d, J=3.6 Hz, 1H), 6.39 (d, J=3.2 Hz, 1H), 4.06 (t, J=6.4 Hz, 2H), 4.01 (t, J=7.2 Hz, 2H), 3.91 (t, J=5.6 Hz, 2H), 1.84-1.78 (m, 2H), 0.94 (t, J=8.0 Hz, 3H), 0.88 (s, 9H), 0.06 (s, 6H); ESI-MS m/z=507 (M+H)$^+$.

4,6-Dichloro-N-(2-hydroxyethyl)-N-(1-propyl-1H-indol-5-yl)pyrimidine-5-carboxamide (12D)

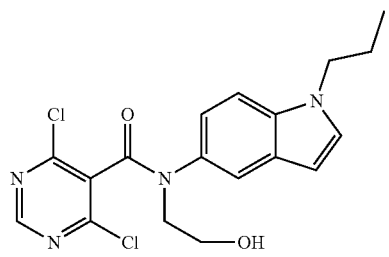 [SMILES: CCCn1ccc2cc(N(CCO)C(=O)c3c(Cl)ncnc3Cl)ccc21]

A solution of product of Example 12C (1 g, 1.97 mmol), in 15 mL of methanolic solution of HCl (3 mL concentrated aqueous HCl in 97 mL of methanol) was stirred at room temperature for 1 h. Methanol was removed in vacuo, the residue dissolved in ethyl acetate, washed with saturated aqueous sodium bicarbonate solution and saturated aqueous brine. The organic layer was dried over sodium sulfate, filtered and concentrated in vacuo to afford title compound (0.6 g, 77%) as solid, which was carried on to the next step without further purification $^1$H NMR (400 MHz, DMSO-d$_6$): δ 8.49 (s, 1H), 7.65 (s, 1H), 7.17 (m, 2H), 7.11 (d, J=2.8 Hz, 1H), 6.42 (d, J=2.8 Hz, 1H), 4.15 (t, J=5.2 Hz, 2H), 4.02 (t, J=6.8 Hz, 2H), 3.93 (q, J=4.8 Hz, 2H), 1.84-1.77 (m, 2H), 0.90 (t, J=7.6 Hz, 3H); ESI-MS m/z=393 (M+H)$^+$.

4-Chloro-6-(1-propyl-1H-indol-5-yl)-7,8-dihydropyrimido[5,4-f][1,4]oxazepin-5(6H)-one (12E)

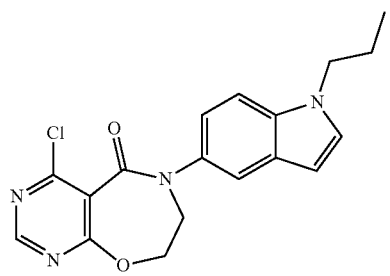 [SMILES: CCCn1ccc2cc(N3CCOc4ncnc(Cl)c4C3=O)ccc21]

A slurry of product of Example 12D (0.6 g, 1.68 mmol) and TEA (1.36 g, 13.44 mmol) in acetonitrile (25 mL) was stirred at 80° C. for 16 h. The reaction was cooled, concentrated in vacuo, diluted with ethyl acetate and washed with water and saturated aqueous brine. The organic layer was dried over sodium sulfate, filtered and concentrated in vacuo to afford title compound (0.3 g, 55%) as a white solid. $^1$H NMR (300 MHz, DMSO-d$_6$): δ 8.82 (s, 1H), 7.57 (m, 2H), 7.46 (d, J=3.0 Hz, 1H), 7.13 (dd, J$_1$=2.1 Hz, J$_2$=8.7 Hz, 1H), 6.48 (d, J=3.0 Hz, 1H), 4.75 (t, J=4.5 Hz, 2H), 4.16 (m, 4H), 1.82 (m, 2H), 0.84 (t, J=7.5 Hz, 3H); ESI-MS m/z=357 (M+H)$^+$.

4-Amino-6-(1-propyl-1H-indol-5-yl)-7,8-dihydropy-rimido[5,4-f][1,4]oxazepin-5(6H)-one (12)

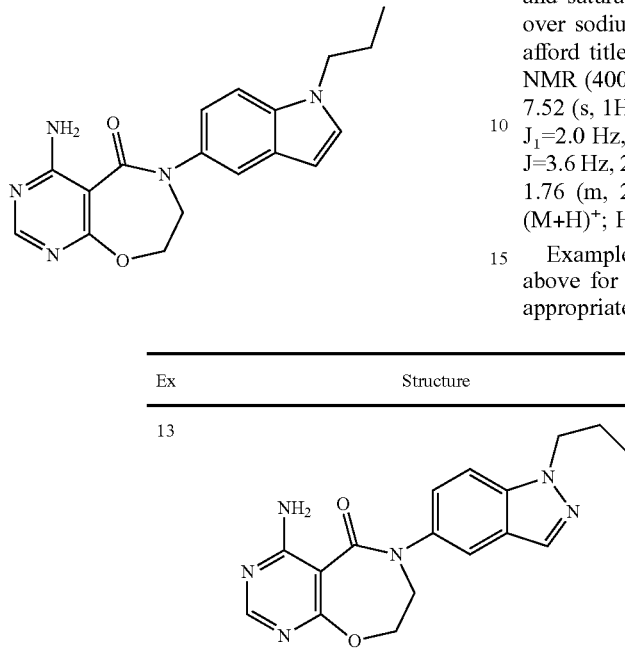

A solution of product of Example 12E (0.3 g, 0.84 mmol) in 0.5M ammonia in p-dioxane (15 mL) was stirred at room temperature for 2 h. The reaction mixture was concentrated in vacuo, diluted with ethyl acetate, and washed with water and saturated aqueous brine. The organic layer was dried over sodium sulfate, filtered and concentrated in vacuo to afford title compound (0.2 g, 71%) as an white solid. $^1$H NMR (400 MHz, DMSO-$d_6$): δ 8.17 (s, 1H), 7.61 (bs, 2H), 7.52 (s, 1H), 7.5 (m, 1H), 7.42 (d, J=3.2 Hz, 1H), 7.09 (dd, $J_1$=2.0 Hz, $J_2$=8.8 Hz, 1H), 6.45 (d, J=2.8 Hz, 1H), 4.63 (t, J=3.6 Hz, 2H), 4.15 (t, J=6.8 Hz, 2H), 3.98 (t, J=4.4 Hz, 2H), 1.76 (m, 2H), 0.83 (t, J=7.2 Hz, 3H); ESI-MS m/z=338 (M+H)$^+$; HPLC purity: 92.5%.

Examples 13-31 were prepared by the method described above for Example 12 or routine variations thereof using appropriately substituted starting materials.

| Ex | Structure | Analytical Data | Mass/Purity |
|---|---|---|---|
| 13 | 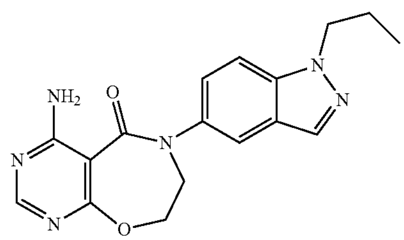 [SMILES: CCCn1ncc2cc(N3CCOc4ncnc(N)c4C3=O)ccc21] | $^1$H NMR (300 MHz, DMSO-$d_6$): δ 8.18 (s, 1H), 8.08 (s, 1H), 7.74 (m, 2H), 7.6 (bs, 2H), 7.38 (d, J = 1.8 Hz, 1H), 4.65 (t, J = 4.2 Hz, 2H), 4.39 (t, J = 6.9 Hz, 2H), 4.01 (t, J = 4.5 Hz, 2H), 1.9-1.83 (m, 2H), 0.82 (t, J = 7.5 Hz, 3H). | ESI-MS m/z = 339 (M + H)$^+$; HPLC purity: 99%. |
| 14 | 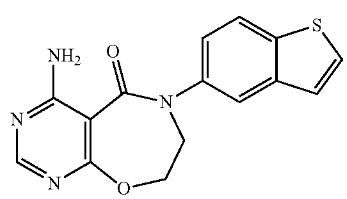 [SMILES: Nc1ncnc2c1C(=O)N(c1ccc3sccc3c1)CCO2] | $^1$H NMR (300 MHz, DMSO-$d_6$): δ 8.18 (s, 1H), 8.05 (d, J = 8.7 Hz, 1H), 7.9 (m, 1H), 7.84 (d, J = 5.7 Hz, 1H), 7.64 (bs, 2H), 7.47 (d, J = 5.4 Hz, 1H), 7.38 (dd, $J_1$ = 2.1 Hz, $J_2$ = 8.7 Hz, 1H), 4.65 (t, J = 4.2 Hz, 2H), 4.04 (t, J = 4.5 Hz, 2H). | ESI-MS m/z = 313 (M + H)$^+$. HPLC purity: 94%, |
| 15 | 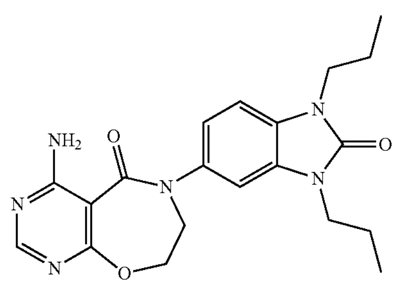 [SMILES: CCCn1c(=O)n(CCC)c2cc(N3CCOc4ncnc(N)c4C3=O)ccc21] | $^1$H NMR (400 MHz, DMSO-$d_6$): δ 8.17 (s, 1H), 7.62 (bs, 2H), 7.24 (m, 2H), 7.02 (d, J = 7.6 Hz, 1H), 4.63 (m, 2H), 3.97 (m, 2H), 3.83-3.56 (q, J = 7.2 Hz, 4H), 1.68-1.65 (m, 4H), 0.86 (t, J = 6.8 Hz, 6H). | ESI-MS m/z = 397 (M + H)$^+$; LCMS purity: 98%. |
| 16 | 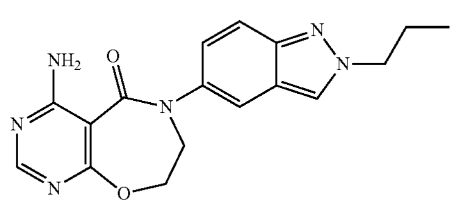 [SMILES: CCCn1cc2cc(N3CCOc4ncnc(N)c4C3=O)ccc2n1] | $^1$H NMR (300 MHz, DMSO-$d_6$): δ 8.4 (s, 1H), 8.17 (s, 1H), 7.67 (d, J = 2.1 Hz, 1H), 7.63 (d, J = 9.0 Hz, 1H), 7.19 (dd, $J_1$ = 2.1 Hz, $J_2$ = 9.0 Hz, 1H), 7.15 (bs, 2H), 4.64 (t, J = 4.2 Hz, 2H), 4.39 (t, J = 7.2 Hz, 2H), 4.0 (t, J = 4.2 Hz, 2H), 2.0 (m, 2H), 0.83 (t, J = 7.5 Hz, 3H). | ESI-MS m/z = 339 (M + H)$^+$; HPLC purity: 96%. |
| 17 | 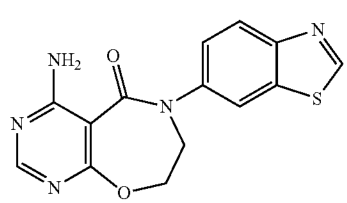 [SMILES: Nc1ncnc2c1C(=O)N(c1ccc3ncsc3c1)CCO2] | $^1$H NMR (300 MHz, DMSO-$d_6$): δ 9.43 (s, 1H), 8.23 (d, J = 1.5 Hz, 1H), 8.19 (s, 1H), 8.12 (d, J = 8.7 Hz, 1H), 7.9 (bs, 2H), 7.57 (dd, $J_1$ = 1.8 Hz, $J_2$ = 8.7 Hz, 1H), 4.66 (t, J = 4.5 Hz, 2H), 4.07 (t, J = 4.5 Hz, 2H). | ESI-MS m/z = 314 (M + H)$^+$; HPLC purity: 96%. |

| Ex | Structure | Analytical Data | Mass/Purity |
|---|---|---|---|
| 18 | 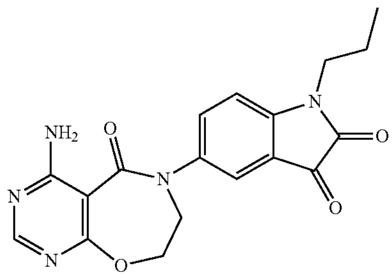 [SMILES: CCCN1C(=O)C(=O)c2cc(N3CCOc4ncnc(N)c4C3=O)ccc21] | $^1$H NMR (300 MHz, DMSO-d$_6$): δ 8.16 (s, 1H), 7.66 (bs, 2H), 7.63 (m, 2H), 7.26 (d, J = 8.1 Hz, 1H), 4.64 (t, J = 4.5 Hz, 2H), 3.97 (t, J = 4.5 Hz, 2H), 3.65 (t, J = 7.2 Hz, 2H), 1.64 (m, 2H), 0.92 (t, J = 7.2 Hz, 2H). | ESI-MS m/z = 368 (M + H)$^+$; HPLC purity: 93%. |
| 19 | 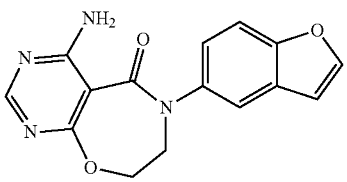 [SMILES: Nc1ncnc2c1C(=O)N(c1ccc3occc3c1)CCO2] | $^1$H NMR (400 MHz, DMSO-d$_6$): δ 8.18 (s, 1H), 8.05 (d, J = 2.0 Hz, 1H), 7.66-7.63 (m, 3H), 7.30 (dd, J$_1$ = 2.0 Hz, J$_2$ = 8.4 Hz, 1H), 7.1 (bs, 2H), 4.65 (t, J = 4.4 Hz, 2H), 4.01 (t, J = 4.8 Hz, 2H). | ESI-MS m/z: 297 (M + H)$^+$; HPLC purity: 97%. |
| 20 | 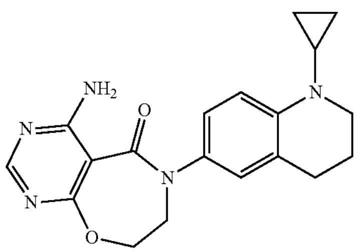 [SMILES: Nc1ncnc2c1C(=O)N(c1ccc3c(c1)CCCN3C1CC1)CCO2] | $^1$H NMR (300 MHz, DMSO-d$_6$): δ 8.15 (s, 1H), 7.57 (bs, 2H), 7.04 (d, J = 8.7 Hz, 1H), 7.0 (dd, J$_1$ = 2.4 Hz, J$_2$ = 8.7 Hz, 1H), 6.89 (d, J = 2.7 Hz, 1H), 4.57 (t, J = 4.8 Hz, 2H), 3.88 (t, J = 4.5 Hz, 2H), 3.20 (t, J = 5.4 Hz, 2H), 2.67 (t, J = 6.3 Hz, 2H), 2.28 (m, 1H), 1.84 (m, 2H), 0.80 (m, 2H), 0.53 (m, 2H). | ESI-MS m/z = 352 (M + H)$^+$; HPLC purity: 99.2%. |
| 21 | 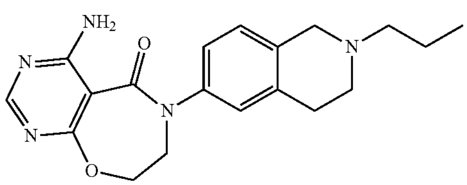 [SMILES: CCCN1CCc2cc(N3CCOc4ncnc(N)c4C3=O)ccc2C1] | $^1$H NMR (400 MHz, DMSO-d$_6$): δ 8.17 (s, 1H), 7.61 (bs, 2H), 7.24 (m, 3H), 4.60 (m, 2H), 4.12 (s, 2H), 3.97 (m, 2H), 3.31-3.25 (m, 2H), 3.0 (m, 2H), 2.82 (m, 2H), 1.73 (m, 2H), 0.84 (t, J = 6.8 Hz, 3H). | ESI-MS m/z = 354 (M + H)$^+$; HPLC purity: 95%. |
| 22 | 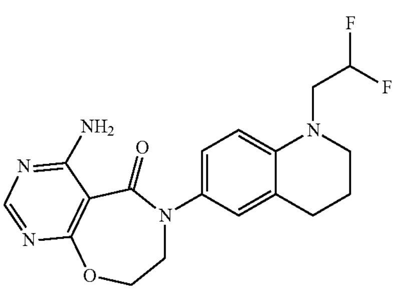 [SMILES: Nc1ncnc2c1C(=O)N(c1ccc3c(c1)CCCN3CC(F)F)CCO2] | $^1$H NMR (400 MHz, DMSO-d$_6$): δ 8.15 (s, 1H), 7.58 (bs, 2H), 6.94 (dd, J$_1$ = 2.4 Hz, J$_2$ = 8.4 Hz, 1H), 6.89 (d, J = 2.0 Hz, 1H), 6.71 (d, J = 8.0 Hz, 1H), 6.21 (tt, J$_1$ = 4.0 Hz, J$_2$ = 55.2 Hz, 1H), 4.56 (t, J = 4.8 Hz, 2H), 3.87 (t, J = 4.4 Hz, 2H), 3.70 (dt, J$_1$ = 3.6 Hz, J$_2$ = 15.6 Hz, 2H), 3.37 (m, 2H), 2.70 (t, J = 6.0 Hz, 2H), 1.85 (m, 2H). | ESI-MS m/z = 376 (M + H)$^+$; HPLC purity: 98.24%. |
| 23 | 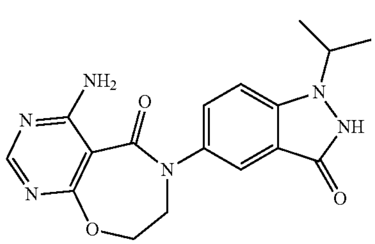 [SMILES: CC(C)n1[nH]c(=O)c2cc(N3CCOc4ncnc(N)c4C3=O)ccc21] | $^1$H NMR (400 MHz, DMSO-D$_2$O): δ 8.18 (s, 1H), 7.56 (d, J = 1.2 Hz, 1H), 7.52 (d, J = 8.8 Hz, 1H), 7.28 (dd, J$_1$ = 1.6 Hz, J$_2$ = 8.8 Hz, 1H), 4.76 (m, 1H), 4.64 (t, J = 4.8 Hz, 2H), 3.99 (t, J = 4.4 Hz, 2H), 1.38 (d, J = 6.8 Hz, 6H). | ESI-MS m/z = 354 (M + H)$^+$; HPLC purity: 96.4%. |

-continued

| Ex | Structure | Analytical Data | Mass/Purity |
|---|---|---|---|
| 24 | 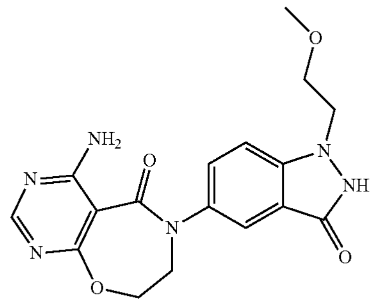 [SMILES: COCCn1[nH]c(=O)c2cc(N3CCOc4ncnc(N)c4C3=O)ccc21] | $^1$H NMR (300 MHz, DMSO-$d_6$): δ 10.65 (bs, 1H), 8.17 (s, 1H), 7.64 (bs, 2H), 7.55 (s, 1H), 7.49 (d, J = 9.3 Hz, 1H), 7.29 (m, 1H), 4.63 (m, 2H), 4.30 (m, 2H), 3.99 (m, 2H), 3.66 (m, 2H), 3.19 (s, 3H). | ESI-MS m/z = 370 (M + H)$^+$; HPLC purity: 95.2%. |
| 25 | 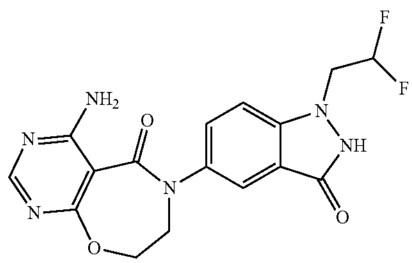 [SMILES: Nc1ncnc2c1C(=O)N(c1ccc3c(c1)c(=O)[nH]n3CC(F)F)CCO2] | $^1$H NMR (300 MHz, DMSO-$d_6$): δ 10.85 (bs, 1H), 8.17 (s, 1H), 7.64 (bs, 2H), 7.6-7.56 (m, 2H), 7.37 (dd, $J_1$ = 1.8 Hz, $J_2$ = 8.7 Hz, 1H), 6.50 (tt, $J_1$ = 3.3 Hz, $J_2$ = 54.9 Hz, 1H), 4.74-4.58 (m, 4H), 4.0 (t, J = 4.5 Hz, 2H). | ESI-MS m/z = 377 (M + H)$^+$; HPLC purity: 97%. |
| 26 | 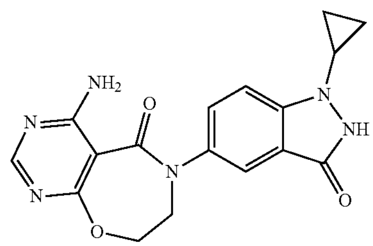 [SMILES: Nc1ncnc2c1C(=O)N(c1ccc3c(c1)c(=O)[nH]n3C1CC1)CCO2] | $^1$H NMR (300 MHz, DMSO-$d_6$): δ 10.85 (bs, 1H), 8.17 (s, 1H), 7.63 (bs, 2H), 7.58 (d, J = 1.5 Hz, 1H), 7.46 (d, J = 9.0 Hz, 1H), 7.32 (dd, $J_1$ = 2.1 Hz, $J_2$ = 9.0 Hz, 1H), 4.61 (t, J = 3.9 Hz, 2H), 3.96 (t, J = 4.2 Hz, 2H), 3.38 (m, 1H), 0.99 (d, J = 5.4 Hz, 4H). | ESI-MS m/z = 353 (M + H)$^+$, HPLC purity: 93%. |
| 27 | 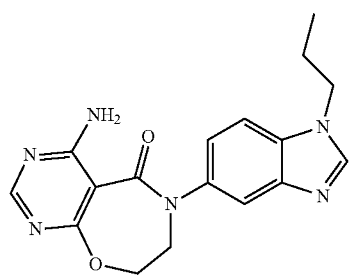 [SMILES: CCCn1cnc2cc(N3CCOc4ncnc(N)c4C3=O)ccc21] | $^1$H NMR (400 MHz, DMSO-$d_6$): δ 8.29 (s, 1H), 8.18 (s, 1H), 7.7-7.6 (m, 4H), 7.23 (dd, $J_1$ = 1.6 Hz, $J_2$ = 8.4 Hz, 1H), 4.66 (t, J = 4.4 Hz, 2H), 4.20 (t, J = 6.8 Hz, 2H), 4.02 (t, J = 4.4 Hz, 2H), 1.81 (m, 2H), 0.86 (t, J = 7.2 Hz, 3H). | ESI-MS m/z = 337 (M + H)$^+$; LCMS purity: 95%. |
| 28 | 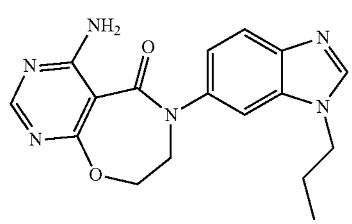 [SMILES: CCCn1cnc2ccc(N3CCOc4ncnc(N)c4C3=O)cc21] | $^1$H NMR (400 MHz, DMSO-$d_6$): δ 8.28 (s, 1H), 8.18 (s, 1H), 7.7-7.6 (m, 4H), 7.18 (dd, $J_1$ = 1.6 Hz, $J_2$ = 8.4 Hz, 1H), 4.66 (t, J = 4.4 Hz, 2H), 4.2 (t, J = 6.8 Hz, 2H), 4.02 (t, J = 4.4 Hz, 2H), 1.81 (m, 2H), 0.85 (t, J = 7.2 Hz, 3H). | ESI-MS m/z = 339 (M + H)$^+$; LCMS purity: 99%. |
| 29 | 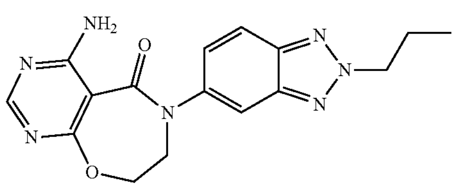 [SMILES: CCCn1nc2ccc(N3CCOc4ncnc(N)c4C3=O)cc2n1] | $^1$H NMR (300 MHz, DMSO-$d_6$): δ 8.18 (s, 1H), 7.97-7.93 (m, 2H), 7.67 (bs, 2H), 7.44 (dd, $J_1$ = 1.8 Hz, $J_2$ = 9.3 Hz, 1H), 4.72 (t, J = 6.9 Hz, 2H), 4.66 (t, J = 4.2 Hz, 2H), 4.06 (t, J = 4.5 Hz, 2H), 2.04 (m, 2H), 0.86 (t, J = 7.5 Hz, 3H). | ESI-MS m/z = 340 (M + H)$^{+-}$; HPLC Purity: 98%. |

| Ex | Structure | Analytical Data | Mass/Purity |
|---|---|---|---|
| 30 | 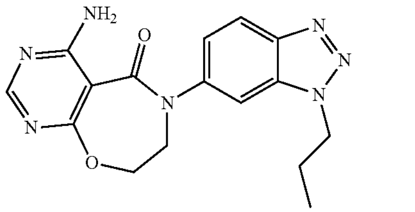 [SMILES: CCCn1nnc2ccc(N3CCOc4ncnc(N)c4C3=O)cc21] | $^1$H NMR (400 MHz, DMSO-$d_6$): δ 8.19 (s, 1H), 8.06 (d, J = 8.8 Hz, 1H), 7.99 (d, J = 1.6 Hz, 1H), 7.66 (bs, 2H), 7.43 (dd, J$_1$ = 1.6 Hz, J$_2$ = 8.8 Hz, 1H), 4.67 (m, 4H), 4.09 (t, J = 4.4 Hz, 2H), 1.95 (m, 2H), 0.88 (t, J = 7.6 Hz, 3H). | ESI-MS m/z = 340 (M + H)$^{+-}$; HPLC Purity: 97%. |
| 31 | 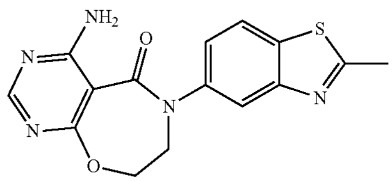 [SMILES: Cc1nc2cc(N3CCOc4ncnc(N)c4C3=O)ccc2s1] | $^1$H NMR (400 MHz, DMSO-$d_6$): δ 8.18 (s, 1H), 8.07 (d, J = 8.8 Hz, 1H), 7.94 (d, J = 2.0 Hz, 1H), 7.65 (bs, 2H), 7.42 (dd, J$_1$ = 1.2 Hz, J$_2$ = 8.0 Hz, 1H), 4.66 (t, J = 4.4 Hz, 2H), 4.05 (t, J = 4.4 Hz, 2H), 2.82 (s, 3H). | ESI-MS m/z = 328 (M + H)$^+$; HPLC purity: 92%. |
Example 33
4-Amino-6-(1-(2,2-difluoroethyl)-1H-pyrrolo[2,3-b]pyridin-5-yl)-7,8-dihydropyrimido[5,4-f][1,4]oxazepin-5(6H)-one
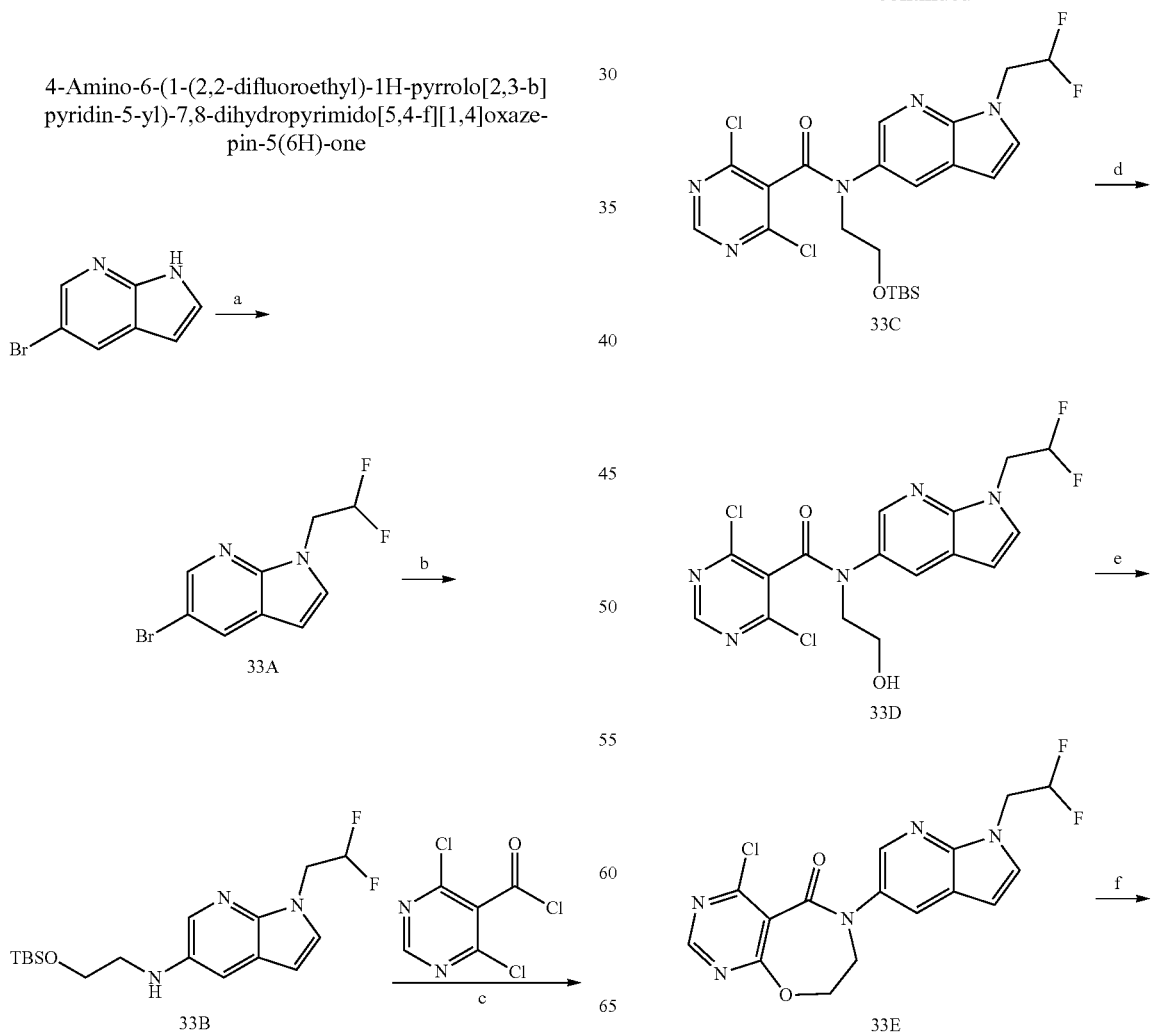

-continued

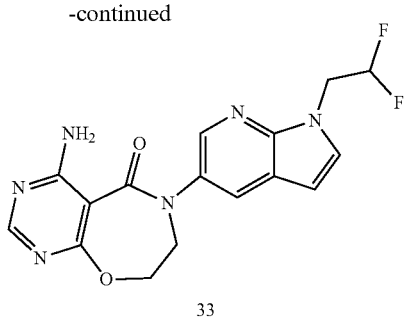

33

Reagents and conditions: a) 1,1-Difluoro-2-iodoethane, Cs₂CO₃, DMF, 70° C., 1 h; b) NH₂(CH₂)₂OTBDMS, Pd(OAc)₂, Cs₂CO₃, X-PHOS, Toluene, 110° C., 3 h; c) DCM, Et₃N, RT, 1 h; d) 3% HCl-MeOH, RT, 1 h; e) CH₃CN, Et₃N, 70° C., 4 h: f) NH₃, Dioxane, RT, 2 h.

Procedures:

4-Amino-6-(1-(2,2-difluoroethyl)-1H-pyrrolo[2,3-b]pyridin-5-yl)-7,8-dihydropyrimido[5,4-f][1,4]oxazepin-5(6H)-one 5-Bromo-1-(2,2-difluoroethyl)-1H-pyrrolo[2,3-b]pyridine (33A)

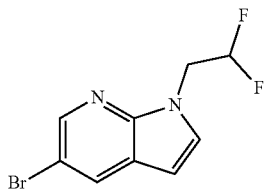

33A 1,1-Difluoro-2-iodoethane (2.19 g, 11.42 mmol) was added to a solution of 5-bromo,7-azaindole (1.5 g, 7.61 mmol) in DMF (30 mL) followed by cesium carbonate (4.96 g, 15.2 mmol), and the mixture was stirred at 70° C. for 1 h. Insoluble solids were filtered off, and filtrate was concentrated. Residue was partitioned between ethyl acetate and water. Organic layer was separated, washed with brine, dried over Na₂SO₄ and filtered. The filtrate was concentrated in reduced pressure and purified by flash chromatography using 5% ethyl acetate in hexane to afford title compound (1.3 g, 65%) as oil. ¹H NMR (300 MHz, CDCl₃): δ 8.33 (d, J=2.1 Hz, 1H), 8.04 (d, J=2.4 Hz, 1H), 7.26 (d, J=2.1 Hz, 1H), 6.46 (d, J=3.6 Hz, 1H), 6.28-5.88 (tt, J₁=3.9 Hz, J₂=55.8 Hz, 1H), 4.60 (dt, J₁=4.2 Hz, J₂=14.1 Hz, 2H).

N-(2-(tert-Butyldimethylsilyloxy)ethyl)-1-(2,2-difluoroethyl)-1H-pyrrolo[2,3-b]pyridin-5-amine (33B)

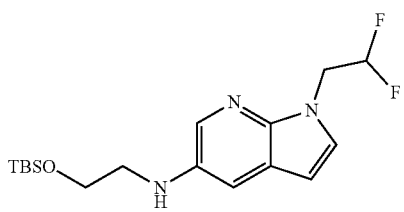

33B

A mixture of product of Example 33A (1.3 g, 8.4 mmol), 2-(tert-butyldimethylsilyloxy)ethanamine (1.0 g, 5.98 mmol), cesium carbonate (3.24 g, 9.96 mmol), palladium acetate (0.11 g, 0.49 mmol) and X-PHOS (0.23 g, 0.49 mmol) in toluene (25 mL) under Argon was refluxed at 110° C. for 3 h. The reaction was cooled, diluted with ethyl acetate, and washed with water (2×15 mL) and saturated aqueous brine. The organic layer was dried over sodium sulfate, filtered and concentrated to obtain dark oil. The residue was purified by flash chromatography using 10% ethyl acetate in hexane to afford title compound (0.61 g, 34.5%) as oil. ¹H NMR (400 MHz, CDCl₃): δ 7.87 (d, J=2.4 Hz, 1H), 7.18 (d, J=2.4 Hz, 1H), 7.14 (d, J=3.2 Hz, 1H), 6.34 (d, J=3.6 Hz, 1H), 6.23-5.92 (tt, =4.4 Hz, J₂=55.6 Hz, 1H), 4.54 (dt, J₁=4.0 Hz, J₂=14.0 Hz, 2H), 3.94 (bs, 1H), 3.85 (t, J=5.6 Hz, 2H), 3.25 (t, J=4.8 Hz, 1H), 0.91 (s, 9H), 0.08 (s, 6H).

N-(2-(tert-Butyldimethylsilyloxy)ethyl)-4,6-dichloro-N-(1-(2,2-difluoroethyl)-1H-pyrrolo[2,3-b]pyridin-5-yl)pyrimidine-5-carboxamide (33C)

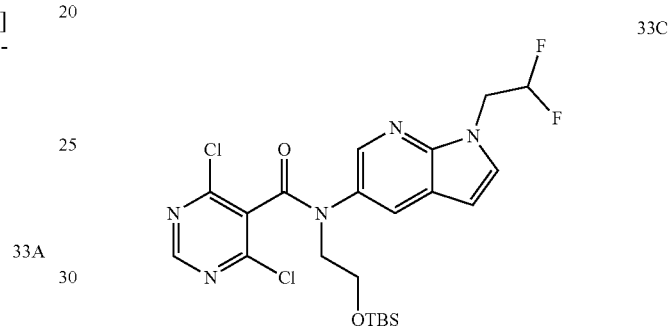

33C

To a stirred, cooled (0° C.) solution of product of Example 33B (0.61 g, 1.71 mmol) and TEA (0.52 g, 5.15 mmol) in DCM (25 mL) was added drop wise a solution of 4,6-dichloropyrimidine-5-carbonyl chloride (0.43 g, 2.05 mmol) in DCM (5 mL). After 1 h, the reaction was concentrated in vacuo, diluted with ethyl acetate, and washed with water (2×10 mL) and saturated aqueous brine. The organic layer was dried over sodium sulphate, filtered and concentrated in vacuo to afford oil. The residue was purified by flash chromatography using 12% ethyl acetate in hexane as eluent to afford title compound (0.67 g, 73%) as a syrup. ¹H NMR (300 MHz, CDCl₃): δ 8.53 (s, 1H), 8.35 (d, J=2.4 Hz, 1H), 8.05 (d, J=2.1 Hz, 1H), 7.27 (d, J=3.6 Hz, 1H), 6.45 (d, J=3.9 Hz, 1H), 6.24-5.84 (tt, J₁=4.2 Hz, J₂=55.5 Hz, 1H), 4.55 (dt, J₁=4.2 Hz, J₂=14.1 Hz, 2H), 4.06 (t, J=5.1 Hz, 2H), 3.94 (t, J=4.8 Hz, 2H), 0.86 (s, 9H), 0.058 (s, 6H).

4,6-Dichloro-N-(1-(2,2-difluoroethyl)-1H-pyrrolo[2,3-b]pyridin-5-yl)-N-(2-hydroxyethyl)pyrimidine-5-carboxamide (33D)

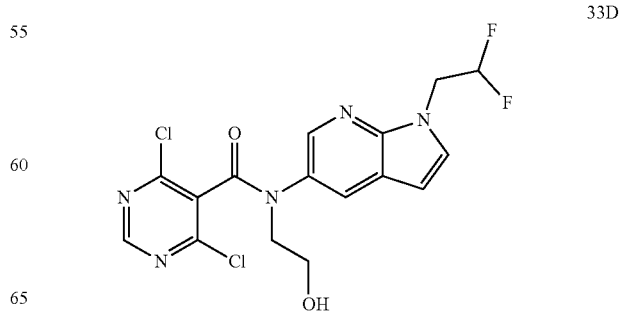

33D

A solution of product of Example 33C (0.67 g, 1.26 mmol), in 20 mL of methanolic solution of HCl (3 mL concentrated aqueous HCl in 97 mL of methanol) was stirred at room temperature for 1 h. Methanol was removed in vacuo, the residue was dissolved in ethyl acetate, and washed with saturated aqueous sodium bicarbonate solution and saturated aqueous brine. The organic layer was dried over $Na_2SO_4$ and filtered. The filtrate was concentrated in reduced pressure to afford title compound (0.4 g, 76%) as solid, which was carried to the next step without further purification. $^1$H NMR (300 MHz, CDCl$_3$): δ 8.55 (s, 1H), 8.39 (d, J=2.4 Hz, 1H), 8.03 (d, J=2.4 Hz, 1H), 7.30 (d, J=3.6 Hz, 1H), 6.49 (d, J=3.6 Hz, 1H), 6.25-5.85 (tt, $J_1$=4.2 Hz, $J_2$=55.5 Hz, 1H), 4.56 (dt, =4.2 Hz, $J_2$=14.1 Hz, 2H), 4.14 (t, J=4.8 Hz, 2H), 3.96 (t, J=4.8 Hz, 2H).

4-Chloro-6-(1-(2,2-difluoroethyl)-1H-pyrrolo[2,3-b]pyridin-5-yl)-7,8-dihydropyrimido[5,4-f][1,4]oxazepin-5(6H)-one (33E)

A slurry of product of Example 33D (0.4 g, 0.96 mmol) and TEA (0.19 g, 1.92 mmol) in acetonitrile (20 mL) was stirred at 70° C. for 4 h. The reaction was cooled, concentrated in vacuo, diluted with ethyl acetate, and washed with water and saturated aqueous brine. The organic layer was dried over $Na_2SO_4$ and filtered. The filtrate was concentrated in reduced pressure to afford title compound (0.3 g, 82%) as a white solid. $^1$H NMR (300 MHz, CDCl$_3$): δ 8.79 (s, 1H), 8.33 (d, J=2.4 Hz, 1H), 7.96 (d, J=2.4 Hz, 1H), 7.35 (d, J=3.9 Hz, 1H), 6.57 (d, J=3.6 Hz, 1H), 6.31-5.91 (tt, $J_1$=3.9 Hz, $J_2$=56.1 Hz, 1H), 4.81 (t, J=4.5 Hz, 2H), 4.66 (dt, $J_1$=3.9 Hz, $J_2$=13.8 Hz, 2H), 4.10 (t, J=4.8 Hz, 2H).

4-Amino-6-(1-(2,2-difluoroethyl)-1H-pyrrolo[2,3-b]pyridin-5-yl)-7,8-dihydropyrimido[5,4-f][1,4]oxazepin-5(6H)-one (33)

A solution of product of Example 33E (0.3 g, 0.79 mmol) in 0.5M ammonia in p-dioxane (15 mL) was stirred at room temperature for 2 h. The reaction mixture was concentrated in vacuo, diluted with ethyl acetate, and washed with water and saturated aqueous brine. The organic layer was dried over $Na_2SO_4$ and filtered. The filtrate was concentrated in reduced pressure to afford title compound (0.25 g, 86%) as an off-white solid. $^1$H NMR (300 MHz, CDCl$_3$): δ 8.30 (s, 1H), 8.24 (d, J=2.4 Hz, 1H), 8.20 (bs, 1H), 7.84 (d, J=2.4 Hz, 1H), 7.33 (d, J=3.3 Hz, 1H), 6.55 (d, J=3.6 Hz, 1H), 6.31-5.91 (tt, $J_1$=4.5 Hz, =55.8 Hz, 1H), 5.67 (bs, 1H), 4.75 (t, J=4.5 Hz, 2H), 4.65 (dt, $J_1$=3.9 Hz, $J_2$=13.8 Hz, 2H), 4.07 (t, J=4.5 Hz, 2H); ESI-MS m/z=361 (M+H)$^+$. HPLC purity: 98.14%.

Example 34

4-Amino-6-(1-cyclopropyl-1H-pyrrolo[2,3-b]pyridin-5-yl)-7,8-dihydropyrimido[5,4-f][1,4]oxazepin-5(6H)-one

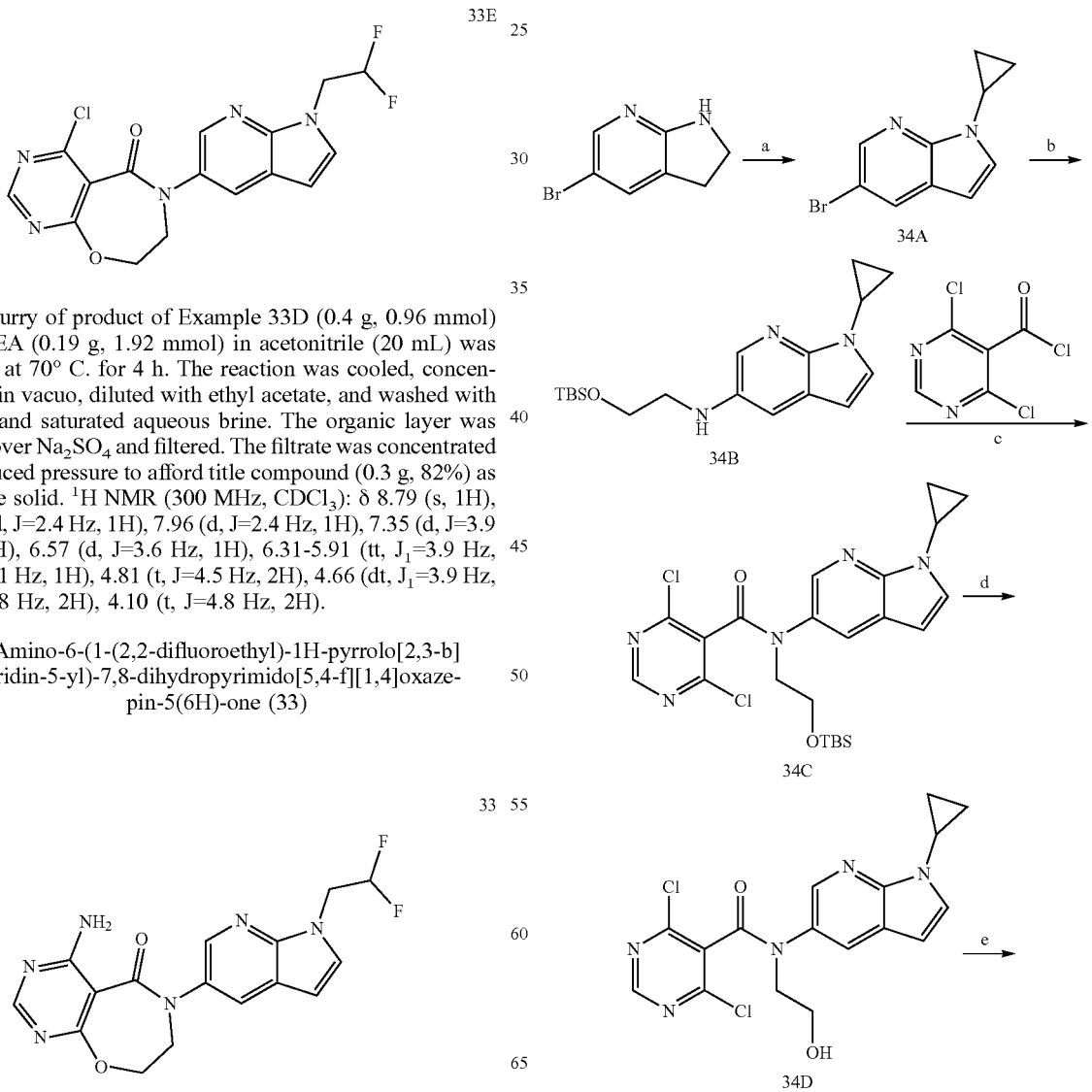

-continued

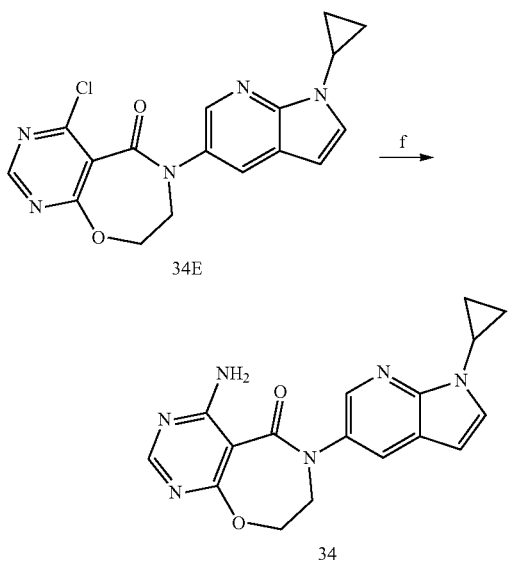

Reagents and conditions: a) Cyclopropyl boronic acid, 2,2'-bipyridine, Na₂CO₃, Cu(OAc)₂, DCE, 110° C., 8 h; b) NH₂(CH₂)₂OTBDMS, Pd(OAc)₂, Cs₂CO₃, X-PHOS, Toluene, 120° C., 2.5 h; c) DCM, ET₃N, RT, 1 h; d) TBAF, THF, RT, 1h; e) CH₃CN, Et₃N, 80° C., 16 h; f) NH₃, Dioxane, RT, 2 h.

Procedures:

4-Amino-6-(1-cyclopropyl-1H-pyrrolo[2,3-b]pyridin-5-yl)-7,8-dihydropyrimido[5,4-f][1,4]oxazepin-5(6H)-one

5-Bromo-1-cyclopropyl-1H-pyrrolo[2,3-b]pyridine (34A)

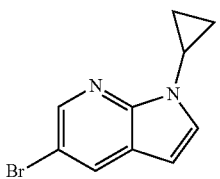

Cyclopropylboronic acid (0.872 g, 10.15 mmol) was added to a solution of 5-bromo-1H-pyrrolo[2,3-b]pyridine (1 g, 5.08 mmol), Na₂CO₃ (1.076 g, 10.15 mmol), copper (II)acetate (0.922 g, 5.08 mmol) and 2,2'-bipyridine (0.793 g, 5.08 mmol) in dichloroethane (20 mL), and the mixture was stirred at 110° C. for 8 h. The reaction mixture was concentrated, and then diluted with ethyl acetate and water. Organic layer was separated, washed with brine, dried over Na₂SO₄ and filtered. The filtrate was concentrated in reduced pressure and purified by flash chromatography using 10% ethyl acetate in pet ether to afford title compound (0.38 g, 31.3%) as oil. ¹H NMR (300 MHz, CDCl₃): δ 8.38 (d, J=2.1 Hz, 1H), 7.99 (d, J=2.1 Hz, 1H), 7.20 (d, J=3.3 Hz, 1H), 6.34 (d, J=3.6 Hz, 1H), 3.5 (m, 1H), 1.15 (m, 2H), 1.03 (m, 2H).

N-(2-(tert-Butyldimethylsilyloxy)ethyl)-1-cyclopropyl-1H-pyrrolo[2,3-b]pyridin-5-amine (34B)

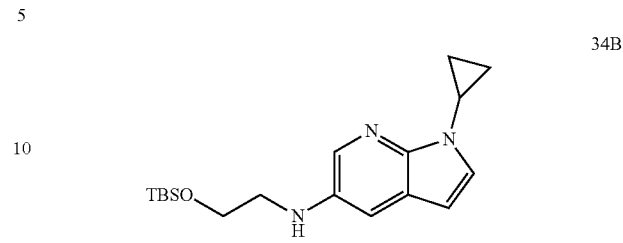

A mixture of product of Example 34A (0.38 mg, 1.603 mmol), 2-(tert-butyldimethylsilyloxy)ethanamine (0.337 g, 1.923 mmol), cesium carbonate (0.783 g, 2404 mmol), palladium acetate (0.036 g, 0.160 mmol) and X-PHOS (0.076 g, 0.160 mmol) in Toluene (15 mL) under Argon was refluxed at 120° C. for 12 h. The reaction was cooled, diluted with ethyl acetate, and washed with water (2×5 mL) and saturated aqueous brine. The organic layer was dried over Na₂SO₄ and filtered. The filtrate was concentrated in reduced pressure and purified by flash chromatography using 10% ethyl acetate in hexane to afford title compound (0.25 g, 40.5%) as oil. ¹H NMR (400 MHz, CDCl₃): δ 7.94 (d, J=2.4 Hz, 1H), 7.16 (d, J=2.8 Hz, 1H), 7.10 (d, J=3.6 Hz, 1H), 6.22 (d, J=3.2 Hz, 1H), 3.84 (t, J=5.2 Hz, 2H), 3.46 (m, 1H), 3.24 (t, J=5.2 Hz, 2H), 1.1 (m, 2H), 1.01 (m, 2H), 0.91 (s, 9H), 0.07 (s, 6H).

N-(2-(tert-Butyldimethylsilyloxy)ethyl)-4,6-dichloro-N-(1-cyclopropyl-1H-pyrrolo[2,3-b]pyridin-5-yl)pyrimidine-5-carboxamide (34C)

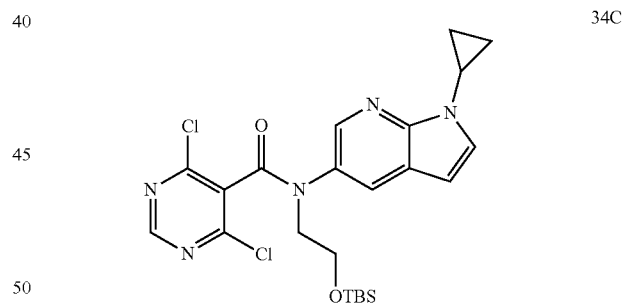

To a stirred, cooled (0° C.) solution of product of Example 34B (0.25 g, 0.754 mmol) and TEA (0.315 mL, 2.262 mmol) in DCM (10 mL) was added drop wise a solution of 4,6-dichloropyrimidine-5-carbonyl chloride (0.191 g, 0.905 mmol) in DCM (5 mL). After 1 h, the reaction was concentrated in vacuo, diluted with ethyl acetate, and washed with water (2×5 mL) and saturated aqueous brine. The organic layer was dried over sodium sulphate, filtered and concentrated in vacuo to afford oil. The residue was purified by flash chromatography using 12% ethyl acetate in pet ether to afford title compound (0.25 g, 60.2%) as a syrup. ¹H NMR (400 MHz, CDCl₃): δ 8.53 (s, 1H), 8.37 (s, 1H), 8.0 (s, 1H), 7.22 (d, J=3.6 Hz, 1H), 6.33 (d, J=3.2 Hz, 1H), 4.05 (t, J=5.6 Hz, 2H), 3.92 (t, J=5.2 Hz, 2H), 3.45 (m, 1H), 1.13 (m, 2H), 1.0 (m, 2H), 0.86 (s, 9H), 0.05 (s, 6H).

4,6-Dichloro-N-(1-cyclopropyl-1H-pyrrolo[2,3-b]pyridin-5-yl)-N-(2-hydroxyethyl)pyrimidine-5-carboxamide (34D)

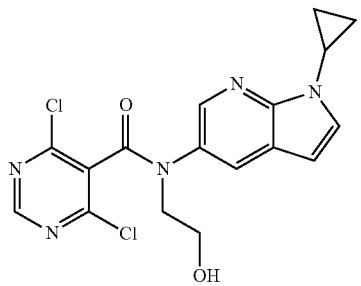

TBAF (0.387 g, 1.481 mmol) was added to a solution of Example 34C (0.25 g, 0.494 mmol) in THF (10 mL), and the mixture was stirred at room temperature for 1 h. THF was removed in vacuo, the residue dissolved in ethyl acetate, and washed with saturated aqueous sodium bicarbonate solution and saturated aqueous brine. The organic layer was dried over sodium sulfate, filtered and concentrated in vacuo to afford title compound (0.19 g, 91%) as solid, which was carried on to the next step without further purification. $^1$H NMR (400 MHz, CDCl$_3$): δ 8.55 (s, 1H), 8.42 (s, 1H), 7.97 (s, 1H), 7.24 (d, J=3.2 Hz, 1H), 6.36 (d, J=2.4 Hz, 1H), 4.15 (m, 2H), 3.97 (q, J=4.8 Hz, 2H), 3.45 (m, 1H), 2.11 (t, J=5.2 Hz, 1H), 1.12 (m, 2H), 1.01 (m, 2H).

4-Chloro-6-(1-cyclopropyl-1H-pyrrolo[2,3-b]pyridin-5-yl)-7,8-dihydropyrimido[5,4-f][1,4]oxazepin-5(6H)-one (34E)

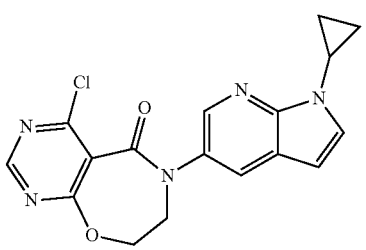

A slurry of product of Example 34D (0.19 g, 0.484 mmol) and TEA (0.203 mL, 1.453 mmol) in acetonitrile (15 mL) was stirred at 80° C. for 6 h. The reaction was cooled, concentrated in vacuo, diluted with ethyl acetate, and washed with water and saturated aqueous brine. The organic layer was dried over sodium sulfate, filtered and concentrated in vacuo to afford title compound (0.17 g, 98%) as a white solid. $^1$H NMR (300 MHz, CDCl$_3$): δ 8.78 (s, 1H), 8.36 (d, J=2.4 Hz, 1H), 7.91 (d, J=2.4 Hz, 1H), 7.30 (d, J=3.9 Hz, 1H), 6.45 (d, J=3.3 Hz, 1H), 4.8 (t, J=4.8 Hz, 2H), 4.09 (t, J=4.5 Hz, 2H), 3.56 (m, 1H), 1.16 (m, 2H), 1.08 (m, 2H).

4-Amino-6-(1-cyclopropyl-1H-pyrrolo[2,3-b]pyridin-5-yl)-7,8-dihydropyrimido[5,4-f][1,4]oxazepin-5(6H)-one (34)

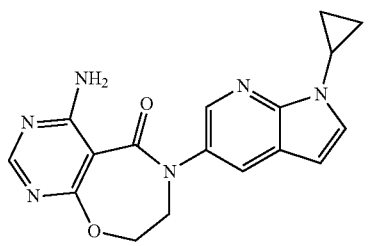

A solution of product of Example 34E (0.17 g, 0.478 mmol) in 0.5M ammonia in p-dioxane (15 mL) was stirred at room temperature for 2 h. The reaction mixture was concentrated in vacuo, diluted with ethyl acetate, and washed with water and saturated aqueous brine. The organic layer was dried over sodium sulfate, filtered and concentrated in vacuo to afford title compound (0.1 g, 60.4%) as an white solid. $^1$H NMR (300 MHz, DMSO-d$_6$): δ 8.26 (d, J=2.1 Hz, 1H), 8.18 (s, 1H), 7.96 (d, J=2.4 Hz, 1H), 7.65 (bs, 2H), 7.54 (d, J=3.6 Hz, 1H), 6.46 (d, J=3.3 Hz, 1H), 4.67 (t, J=3.6 Hz, 2H), 4.02 (t, J=4.2 Hz, 2H), 3.62 (m, 1H), 1.1-1.0 (m, 4H); ESI-MS m/z=337 (M+H)$^+$; HPLC purity: 97%.

Examples 35-62 were prepared by the procedures analogous to those described in Example 33 or Example 34 using appropriately substituted starting materials.

| Ex | Structure | Analytical Data | Mass/Purity |
|---|---|---|---|
| 35 | 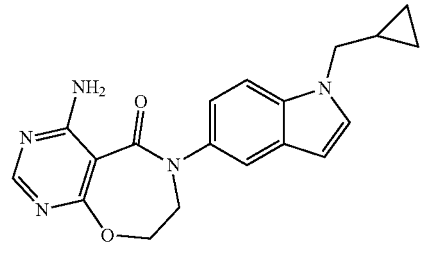 [SMILES: Nc1ncnc2c1C(=O)N(c1ccc3c(ccn3CC3CC3)c1)CCO2] | $^1$H NMR (400 MHz, DMSO-d$_6$): δ 8.17 (s, 1H), 7.61 (bs, 2H), 7.55 (d, J = 8.0 Hz, 1H), 7.49 (m, 2H), 7.08 (dd, J$_1$ = 2.0 Hz, J$_2$ = 8.4 Hz, 2H), 6.52 (d, J = 3.2 Hz, 1H), 4.64 (t, J = 4.4 Hz, 2H), 4.06 (d, J = 6.8 Hz, 2H), 3.98 (t, J = 4.8 Hz, 2H), 1.25 (m, 1H), 0.52 (m, 2H), 0.38 (m, 2H). | ESI-MS m/z = 350 (M + H)$^+$; HPLC purity: 98.7%. |

-continued

| Ex | Structure | Analytical Data | Mass/Purity |
|---|---|---|---|
| 36 | (structure) | ¹H NMR (400 MHz, DMSO-d₆): δ 12.4 (bs, 1H), 8.17 (s, 1H), 7.61 (bs, 2H), 7.54 (d, J = 8.8 Hz, 1H), 7.49 (d, J = 1.6 Hz, 1H), 7.41 (d, J = 3.6 Hz, 1H), 7.09 (dd, J₁ = 1.6 Hz, J₂ = 10.8 Hz, 1H), 6.44 (d, J = 3.6 Hz, 1H), 4.63 (t, J = 4.4 Hz, 2H), 4.41 (t, J = 6.8 Hz, 2H), 3.98 (t, J = 4.4 Hz, 2H), 2.75 (t, J = 6.4 Hz, 2H) | ESI-MS m/z = 366 (M − H)⁻; HPLC purity: 97.7%. |
| 37 | (structure) | ¹H NMR (400 MHz, DMSO-d₆): δ 8.17 (s, 1H), 7.61 (bs, 2H), 7.52 (m, 2H), 7.38 (d, J = 3.3 Hz, 1H), 7.06 (dd, J₁ = 2.1 Hz, J₂ = 10.8 Hz, 1H), 6.44 (d, J = 2.7 Hz, 1H), 4.63 (t, J = 3.9 Hz, 2H), 4.04 (m, 4H), 1.79 (m, 1H), 1.7-1.45 (m, 5H), 1.2-0.9 (m, 5H). | ESI-MS m/z = 392 (M + H)⁺; HPLC purity: 97%. |
| 38 | (structure) | ¹H NMR (400 MHz, DMSO-d₆): δ 8.17 (s, 1H), 7.60 (bs, 2H), 7.57 (d, J = 8.8 Hz, 1H), 7.49 (m, 2H), 7.05 (dd, J₁ = 1.6 Hz, J₂ = 7.2 Hz, 1H), 6.52 (d, J = 2.4 Hz, 1H), 4.63 (t, J = 4.0 Hz, 2H), 4.27 (m, 1H), 4.0 (t, J = 3.6 Hz, 2H), 1.86 (m, 4H), 0.66 (t, J = 7.2 Hz, 6H). | ESI-MS m/z = 366 (M + H)⁺; HPLC purity: 96%. |
| 39 | (structure) | ¹H NMR (300 MHz, DMSO-d₆): δ 8.17 (s, 1H), 7.60 (bs, 2H), 7.55 (d, J = 3.3 Hz, 1H), 7.49 (m, 2H), 7.2 (d, J = 8.4 Hz, 2H), 7.04 (dd, J₁ = 1.8 Hz, J₂ = 8.7 Hz, 1H), 6.88 (d, J = 8.4 Hz, 2H), 6.48 (d, J = 3.0 Hz, 1H), 5.35 (s, 2H), 4.61 (t, J = 3.9 Hz, 2H), 3.96 (t, J = 4.5 Hz, 2H), 3.69 (s, 3H). | ESI-MS m/z = 416 (M + H)⁺; HPLC purity: 96%. |
| 40 | (structure) | ¹H NMR (300 MHz, DMSO-d₆): δ 8.16 (s, 1H), 7.58 (m, 3H), 7.52 (m, 2H), 7.28-7.25 (m, 2H), 7.22-7.0 (m, 3H), 6.51 (d, J = 3.3 Hz, 1H), 5.43 (s, 2H), 4.62 (t, J = 4.5 Hz, 2H), 3.97 (t, J = 4.5 Hz, 2H). | ESI-MS m/z = 404 (M + H)⁺; HPLC purity: 97%. |

-continued

| Ex | Structure | Analytical Data | Mass/Purity |
|---|---|---|---|
| 41 | 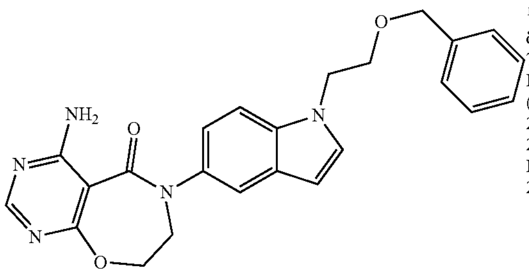 [SMILES: Nc1ncnc2c1C(=O)N(c1ccc3c(ccn3CCOCc3ccccc3)c1)CCO2] | $^1$H NMR (400 MHz, DMSO-d$_6$): δ 8.17 (s, 1H), 7.61 (bs, 2H), 7.56-7.5 (m, 2H), 7.44 (d, J = 2.8 Hz, 1H), 7.32-7.16 (m, 4H), 7.09 (d, J = 8.8 Hz, 1H), 6.46 (d, J = 2.8 Hz, 1H), 4.64 (t, J = 4.0 Hz, 2H), 4.45 (s, 2H), 4.41 (t, J = 4.8 Hz, 2H), 3.98 (t, J = 4.4 Hz, 2H), 3.75 (t, J = 4.8 Hz, 2H). | ESI-MS m/z = 430 (M + H)+; HPLC purity: 99%. |
| 42 | 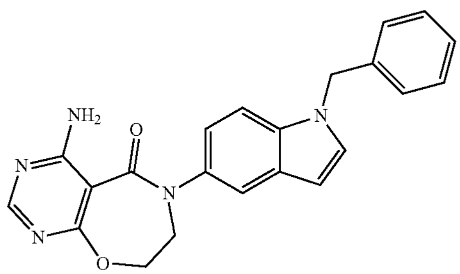 [SMILES: Nc1ncnc2c1C(=O)N(c1ccc3c(ccn3Cc3ccccc3)c1)CCO2] | $^1$H NMR (400 MHz, DMSO-d$_6$): δ 8.16 (s, 1H), 7.60 (bs, 2H), 7.58 (d, J = 2.8 Hz, 1H), 7.51 (d, J = 1.6 Hz, 1H), 7.48 (d, J = 8.8 Hz, 1H), 7.33-7.29 (m, 1H), 7.26-7.20 (m, 4H), 7.06 (dd, J$_1$ = 2.0 Hz, J$_2$ = 8.8 Hz, 1H), 6.51 (d, J = 3.2 Hz, 1H), 5.44 (s, 2H), 4.61 (t, J = 4.4 Hz, 2H), 3.97 (t, J = 4.4 Hz, 2H). | ESI-MS m/z = 386 (M + H)$^+$; HPLC purity: 98%. |
| 43 | 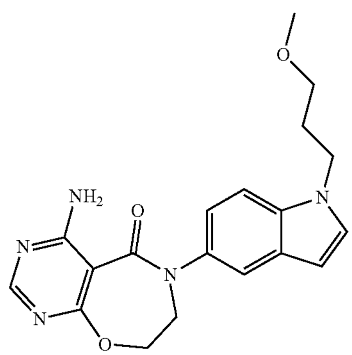 [SMILES: COCCCn1ccc2cc(N3CCOc4ncnc(N)c4C3=O)ccc21] | $^1$H NMR (400 MHz, DMSO-d$_6$): δ 8.17 (s, 1H), 7.61 (bs, 2H), 7.50 (m, 2H), 7.40 (d, J = 2.8 Hz, 1H), 7.1 (d, J = 8.8 Hz, 1H), 6.46 (d, J = 2.4 Hz, 1H), 4.63 (m, 2H), 4.24 (t, J = 6.8 Hz, 2H), 3.98 (m, 2H), 3.24 (m, 5H), 1.97 (m, 2H). | ESI-MS m/z = 368 (M + H)$^+$; HPLC purity: 99%. |
| 44 | 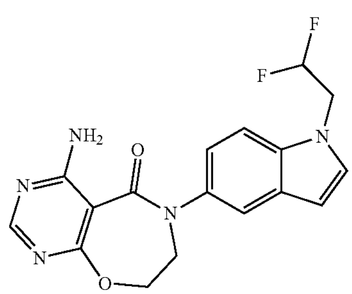 [SMILES: Nc1ncnc2c1C(=O)N(c1ccc3c(ccn3CC(F)F)c1)CCO2] | $^1$H NMR (400 MHz, DMSO-d$_6$): δ 8.17 (s, 1H), 7.60 (bs, 2H), 7.58-7.53 (m, 2H), 7.43 (d, J = 2.8 Hz, 1H), 7.13 (d, J = 8.0 Hz, 1H), 6.52 (d, J = 3.2 Hz, 1H), 6.5-6.2 (m, 1H), 4.76-4.6 (m, 4H), 4.0 (t, J = 4.4 Hz, 2H). | ESI-MS m/z = 360 (M + H)$^+$; HPLC purity: 95%. |
| 45 | 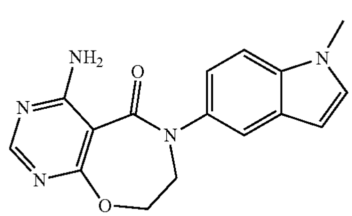 [SMILES: Cn1ccc2cc(N3CCOc4ncnc(N)c4C3=O)ccc21] | $^1$H NMR (400 MHz, DMSO-d$_6$): δ 8.17 (s, 1H), 7.61 (bs, 2H), 7.51 (d, J = 1.8 Hz, 1H), 7.46 (d, J = 9.0 Hz, 1H), 7.38 (d, J = 3.0 Hz, 1H), 7.12 (dd, J$_1$ = 1.8 Hz, J$_2$ = 8.4 Hz, 1H), 6.44 (d, J = 3.0 Hz, 1H), 4.64 (t, J = 4.2 Hz, 2H), 3.98 (t, J = 4.5 Hz, 2H), 3.8 (s, 3H). | ESI-MS m/z = 310 (M + H)$^+$; HPLC purity: 92%. |

| Ex | Structure | Analytical Data | Mass/Purity |
|---|---|---|---|
| 46 | 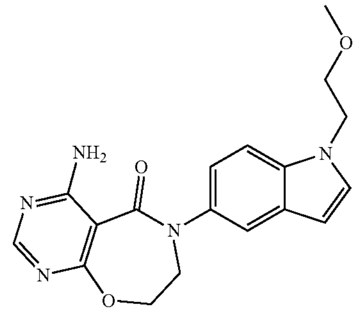 [SMILES: COCCn1ccc2cc(N3CCOc4ncnc(N)c4C3=O)ccc21] | $^1$H NMR (400 MHz, DMSO-d$_6$): δ 8.17 (s, 1H), 7.61 (bs, 2H), 7.50 (m, 2H), 7.41 (d, J = 2.8 Hz, 1H), 7.08 (dd, J$_1$ = 2.0 Hz, J$_2$ = 8.8 Hz, 1H), 6.44 (d, J =2.8 Hz, 1H), 4.64 (t, J = 4.4 Hz, 2H), 4.35 (t, J = 5.2 Hz, 2H), 3.98 (t, J = 4.4 Hz, 2H), 3.65 (t, J = 5.2 Hz, 2H), 3.22 (s, 3H) | ESI-MS m/z = 354 (M + H)$^+$; HPLC purity: 99%. |
| 47 | 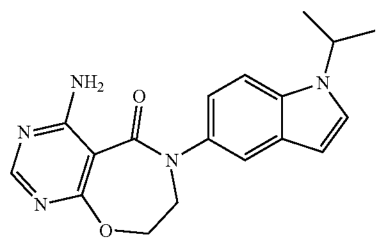 [SMILES: CC(C)n1ccc2cc(N3CCOc4ncnc(N)c4C3=O)ccc21] | $^1$H NMR (300 MHz, DMSO-d$_6$): δ 8.17 (s, 1H), 7.61 (bs, 2H), 7.56-7.49 (m, 2H), 7.5 (d, J = 1.8 Hz, 1H), 7.08 (dd, J$_1$ = 1.8 Hz, J$_2$ = 8.7 Hz, 1H), 6.48 (d, J = 3.0 Hz, 1H), 4.77 (m, 1H), 4.63 (t, J = 4.2 Hz, 2H), 3.98 (t, J = 4.5 Hz, 2H), 1.46 (d, J = 6.9 Hz, 6H). | ESI-MS m/z = 338 (M + H)$^+$; HPLC purity: 96%. |
| 48 | 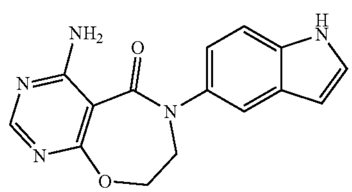 [SMILES: Nc1ncnc2c1C(=O)N(c1ccc3[nH]ccc3c1)CCO2] | $^1$H NMR (400 MHz, DMSO-d$_6$): δ 11.2 (bs, 1H), 8.17 (s, 1H), 7.60 (bs, 2H), 7.49 (d, J = 1.6 Hz, 1H), 7.40 (m, 2H), 7.04 (dd, J$_1$ = 2.0 Hz, J$_2$ = 8.8 Hz, 1H), 6.44 (m, 1H), 4.63 (t, J = 4.4 Hz, 2H), 3.97 (t, J = 4.8 Hz, 2H). | ESI-MS m/z = 296 (M + H)$^+$; HPLC purity: 93%. |
| 49 | 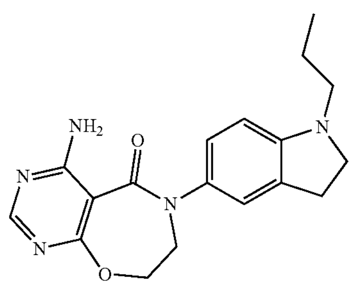 [SMILES: CCCN1CCc2cc(N3CCOc4ncnc(N)c4C3=O)ccc21] | $^1$H NMR (400 MHz, DMSO-d$_6$): δ 8.15 (s, 1H), 7.57 (bs, 2H), 6.98 (s, 1H), 6.92 (dd, J$_1$ = 2.0 Hz, J$_2$ = 8.4 Hz, 1H), 6.47 (d, J = 8.4 Hz, 1H), 4.57 (t, J = 4.4 Hz, 2H), 3.86 (t, J = 4.8 Hz, 2H), 3.33 (t, J = 8.0 Hz, 2H), 3.0 (t, J = 7.6 Hz, 2H), 2.89 (t, J = 8.4 Hz, 2H), 1.55 (m, 2H), 0.93 (t, J = 7.6 Hz, 3H). | ESI-MS m/z = 340 (M + H)$^{+-}$; LCMS Purity: 99%. |
| 50 | 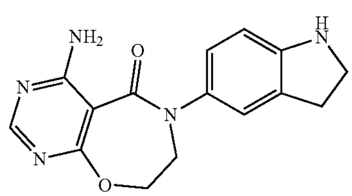 [SMILES: Nc1ncnc2c1C(=O)N(c1ccc3c(c1)CCN3)CCO2] | $^1$H NMR (400 MHz, DMSO-d$_6$): δ 8.15 (s, 1H), 7.57 (bs, 2H), 6.98 (s, 1H), 6.84 (dd, J$_1$ = 1.6 Hz, J$_2$ = 8.0 Hz, 1H), 6.49 (d, J = 8.4 Hz, 1H), 5.58 (bs, 1H), 4.57 (t, J = 4.4 Hz, 2H), 3.86 (t, J = 4.4 Hz, 2H), 3.44 (t, J = 8.4 Hz, 2H), 2.91 (t, J = 8.0 Hz, 2H). | ESI-MS m/z = 298 (M + H)$^{+-}$; HPLC Purity: 94%. |
| 51 | 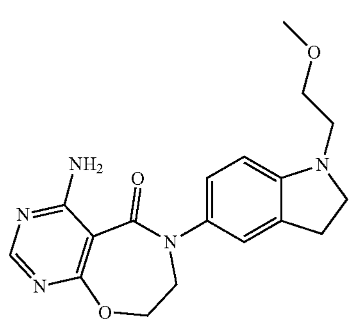 [SMILES: COCCN1CCc2cc(N3CCOc4ncnc(N)c4C3=O)ccc21] | $^1$H NMR (400 MHz, DMSO-d$_6$): δ 8.15 (s, 1H), 7.58 (bs, 2H), 6.98 (s, 1H), 6.92 (dd, J$_1$ = 2.4 Hz, J$_2$ = 8.4 Hz, 1H), 6.50 (d, J = 8.4 Hz, 1H), 4.57 (t, J = 4.4 Hz, 2H), 3.87 (t, J = 4.4 Hz, 2H), 3.53 (t, J = 6.0 Hz, 2H), 3.41 (t, J = 8.0 Hz, 2H), 3.28 (s, 3H), 3.23 (t, J = 5.6 Hz, 2H), 2.89 (t, J = 8.4 Hz, 2H). | ESI-MS m/z = 356 (M + H)$^{+-}$; HPLC Purity: 97%. |

-continued

| Ex | Structure | Analytical Data | Mass/Purity |
|----|-----------|-----------------|-------------|
| 52 | 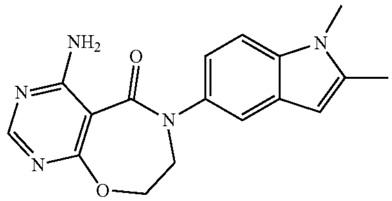 [SMILES: Cc1cc2cc(N3CCOc4ncnc(N)c4C3=O)ccc2n1C] | $^1$H NMR (400 MHz, DMSO-d$_6$): δ 8.17 (s, 1H), 7.61 (bs, 2H), 7.02-6.98 (m, 2H), 7.01 (dd, J$_1$ = 2.0 Hz, J$_2$ = 8.8 Hz, 1H), 6.23 (s, 1H), 4.63 (t, J = 4.0 Hz, 2H), 3.96 (t, J = 4.4 Hz, 2H), 3.67 (s, 3H), 2.87 (s, 3H). | ESI-MS m/z = 324 (M + H)$^+$; HPLC purity: 96%. |
| 53 | 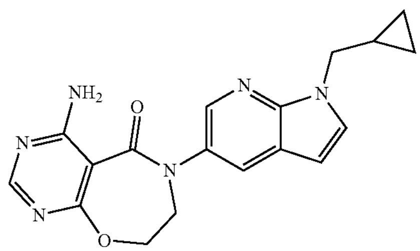 [SMILES: Nc1ncnc2c1C(=O)N(c1cnc3c(ccn3CC3CC3)c1)CCO2] | $^1$H NMR (400 MHz, CDCl$_3$): δ 8.30 (s, 1H), 8.22 (d, J = 2.0 Hz, 1H), 7.81 (d, J = 1.6 Hz, 1H), 7.41 (d, J = 3.2 Hz, 1H), 6.50 (d, J = 3.6 Hz, 1H), 5.64 (bs, 1H), 4.75 (t, J = 4.0 Hz, 2H), 4.17 (d, J = 6.8 Hz, 2H), 4.07 (t, J = 4.4 Hz, 2H), 1.29 (m, 1H), 0.61 (q, J = 6.0 Hz, 2H), 0.42 (q, J = 4.8 Hz, 2H). | ESI-MS m/z = 351 (M + H)$^+$; HPLC purity: 96%. |
| 54 | 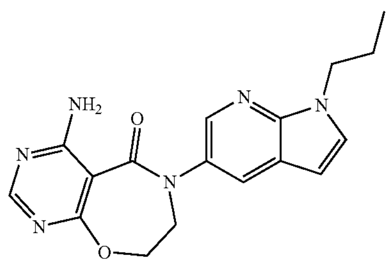 [SMILES: CCCn1ccc2cc(N3CCOc4ncnc(N)c4C3=O)cnc21] | $^1$H NMR (400 MHz, CDCl3): δ 8.30 (s, 1H), 8.22 (d, J = 2.4 Hz, 1H), 7.81 (d, J = 2.4 Hz, 1H), 7.29 (d, J = 3.6 Hz, 1H), 6.48 (d, J = 3.6 Hz, 1H), 5.64 (bs, 1H), 4.75 (t, J = 4.4 Hz, 2H), 4.26 (t, J = 6.8 Hz, 2H), 4.07 (t, J = 4.4 Hz, 2H), 1.91 (m, 2H), 0.95 (t, J = 7.6 Hz, 3H); | ESI-MS m/z = 339 (M + H)$^+$; HPLC purity: 93.5%. |
| 55 | 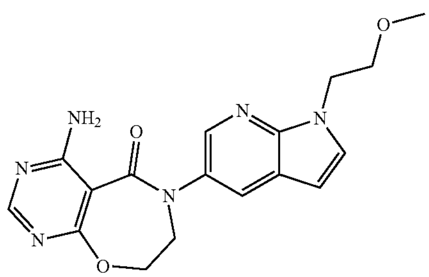 [SMILES: COCCn1ccc2cc(N3CCOc4ncnc(N)c4C3=O)cnc21] | $^1$H NMR (400 MHz, CDCl$_3$): δ 8.30 (s, 1H), 8.22 (d, J = 2.0 Hz, 1H), 7.81 (d, J = 2.0 Hz, 1H), 7.40 (d, J = 3.6 Hz, 1H), 6.48 (d, J = 3.6 Hz, 1H), 5.71 (bs, 1H), 4.75 (t, J = 4.4 Hz, 2H), 4.48 (t, J = 5.2 Hz, 2H), 4.06 (t, J = 4.4 Hz, 2H), 3.74 (t, J = 4.8 Hz, 2H), 3.33 (s, 3H); | ESI-MS m/z = 355 (M + H)$^+$; HPLC purity: 91.63%. |
| 56 | 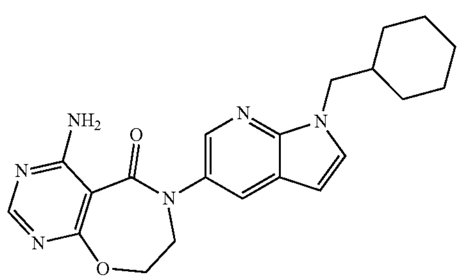 [SMILES: Nc1ncnc2c1C(=O)N(c1cnc3c(ccn3CC3CCCCC3)c1)CCO2] | $^1$H NMR (400 MHz, CDCl$_3$): δ 8.30 (s, 1H), 8.22 (d, J = 2.0 Hz, 1H), 7.80 (d, J = 2.0 Hz, 1H), 7.25 (d, J = 3.6 Hz, 1H), 6.46 (d, J = 3.2 Hz, 1H), 5.65 (bs, 1H), 4.75 (t, J = 4.4 Hz, 2H), 4.12 (d, J = 7.2 Hz, 2H) 4.07 (t, J = 4.4 Hz, 2H), 1.93 (m, 1H), 1.7-1.6 (m, 4H), 1.25-1.14 (m, 3H), 1.03 (m, 2H). | ESI-MS m/z = 393 (M + H)$^+$; HPLC purity: 98.7%. |
| 57 | 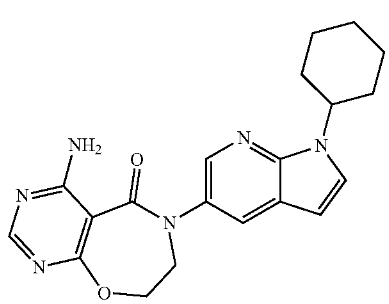 [SMILES: Nc1ncnc2c1C(=O)N(c1cnc3c(ccn3C3CCCCC3)c1)CCO2] | $^1$H NMR (300 MHz, CDCl$_3$): δ 8.30 (s, 1H), 8.21 (d, J = 2.1 Hz, 1H), 7.8 (d, J = 2.1 Hz, 1H), 7.39 (d, J = 3.3 Hz, 1H), 6.48 (d, J = 3.3 Hz, 1H), 5.65 (bs, 1H), 4.84-4.7 (m, 3H), 4.06 (t, J = 4.5 Hz, 2H), 2.18-2.04 (m, 2H), 1.95-1.88 (m, 2H), 1.8-1.6 (m, 4H), 1.4-1.2 (m, 2H). | ESI-MS m/z = 379 (M + H)$^+$; HPLC purity: 92.8%. |

-continued

| Ex | Structure | Analytical Data | Mass/Purity |
|---|---|---|---|
| 58 | 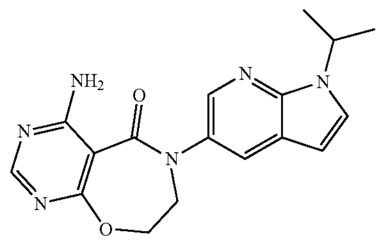 [SMILES: CC(C)n1ccc2cc(N3CCOc4ncnc(N)c4C3=O)cnc21] | ¹H NMR (300MHz, DMSO d₆): δ 8.23 (d, J = 2.1 Hz, 1H), 8.18 (s, 1H), 7.96 (d, J = 1.8 Hz, 1H), 7.73 (d, J = 3.6 Hz, 1H), 7.65 (bs, 2H), 6.52 (d, J = 3.3 Hz, 1H), 5.07 (m, 1H), 4.67 (t, J = 4.2 Hz, 2H), 4.02 (t, J = 4.5 Hz, 2H), 1.48 (d, J = 6.3 Hz, 6H). | ESI-MS m/z = 339 (M + H)⁺; HPLC purity: 97%. |
| 59 | 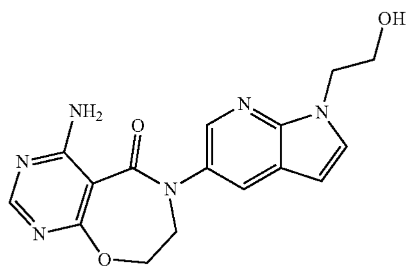 [SMILES: Nc1ncnc2c1C(=O)N(c1cnc3c(ccn3CCO)c1)CCO2] | ¹H NMR (300 MHz, DMSO-d₆): δ 8.22 (d, J = 2.4 Hz, 1H), 8.18 (s, 1H), 7.97 (d, J = 2.1 Hz, 1H), 7.64 (bs, 2H), 7.61 (d, J = 3.3 Hz, 1H), 6.48 (d, J = 3.3 Hz, 1H), 4.92 (t, J = 5.4 Hz, 1H), 4.67 (t, J = 5.1 Hz, 2H), 4.32 (t, J = 5.7 Hz, 2H), 4.02 (t, J = 4.5 Hz, 2H), 3.75 (q, J = 5.7 Hz, 2H). | ESI-MS m/z = 341 (M + H)⁺. HPLC purity: 95%. |
| 60 | 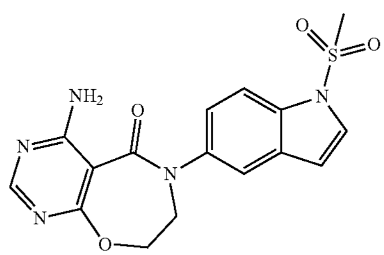 [SMILES: CS(=O)(=O)n1ccc2cc(N3CCOc4ncnc(N)c4C3=O)ccc21] | ¹H NMR (300 MHz, DMSO-d₆-D₂O): δ 8.19 (s, 1H), 7.88 (d, J = 8.7 Hz, 1H), 7.7 (d, J = 2.1 Hz, 1H), 7.65 (d, J = 3.6 Hz, 1H), 7.38 (dd, J₁ = 2.1 Hz, J₂ = 8.7 Hz, 1H), 6.87 (d, J = 3.6 Hz, 1H), 4.66 (t, J = 4.2 Hz, 2H), 4.02 (t, J = 4.5 Hz, 2H), 3.46 (s, 3H). | ESI-MS m/z = 374 (M + H)⁺; HPLC purity: 98%. |
| 61 | 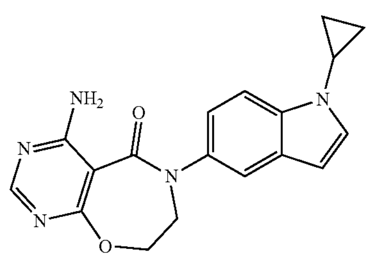 [SMILES: Nc1ncnc2c1C(=O)N(c1ccc3c(ccn3C3CC3)c1)CCO2] | ¹H NMR (300 MHz, DMSO-d₆): δ 8.17 (s, 1H), 7.61 (bs, 2H), 7.58 (d, J = 8.4 Hz, 1H), 7.50 (d, J = 1.8 Hz, 1H), 7.38 (d, J = 3.3 Hz, 1H), 7.13 (dd, J₁ = 1.8 Hz, J₂ = 10.8 Hz, 1H), 6.42 (d, J = 3.0 Hz, 1H), 4.63 (t, J = 3.9 Hz, 2H), 3.98 (t, J = 4.8 Hz, 2H), 3.45 (m, 1H), 1.08 (m, 2H), 0.95 (m, 2H). | ESI-MS m/z = 336 (M + H)⁺; HPLC purity: 94%. |
| 62 | 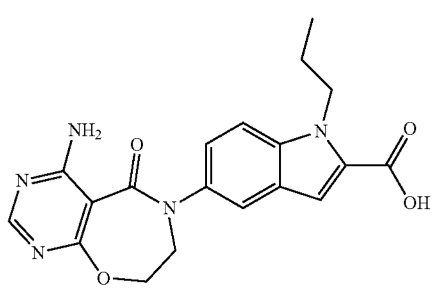 [SMILES: CCCn1c(C(=O)O)cc2cc(N3CCOc4ncnc(N)c4C3=O)ccc21] | ¹H NMR (400 MHz, DMSO-d₆): δ 13.1 (bs, 1H), 8.18 (s, 1H), 7.68-7.6 (m, 4H), 7.29 (d, J = 10.4 Hz, 1H), 7.23 (s, 1H), 4.64 (t, J = 4.4 Hz, 2H), 4.56 (t, J = 7.6 Hz, 2H), 4.0 (t, J = 4.4 Hz, 2H), 1.72 (m, 2H), 0.83 (t, J = 7.6 Hz, 3H). | ESI-MS m/z = 382 (M + H)⁺. HPLC purity: 98%. |

Example 63

4-Amino-6-(1-propyl-3-(2,2,2-trifluoroacetyl)-1H-indol-5-yl)-7,8-dihydropyrimido[5,4-f][1,4]oxazepin-5(6H)-one

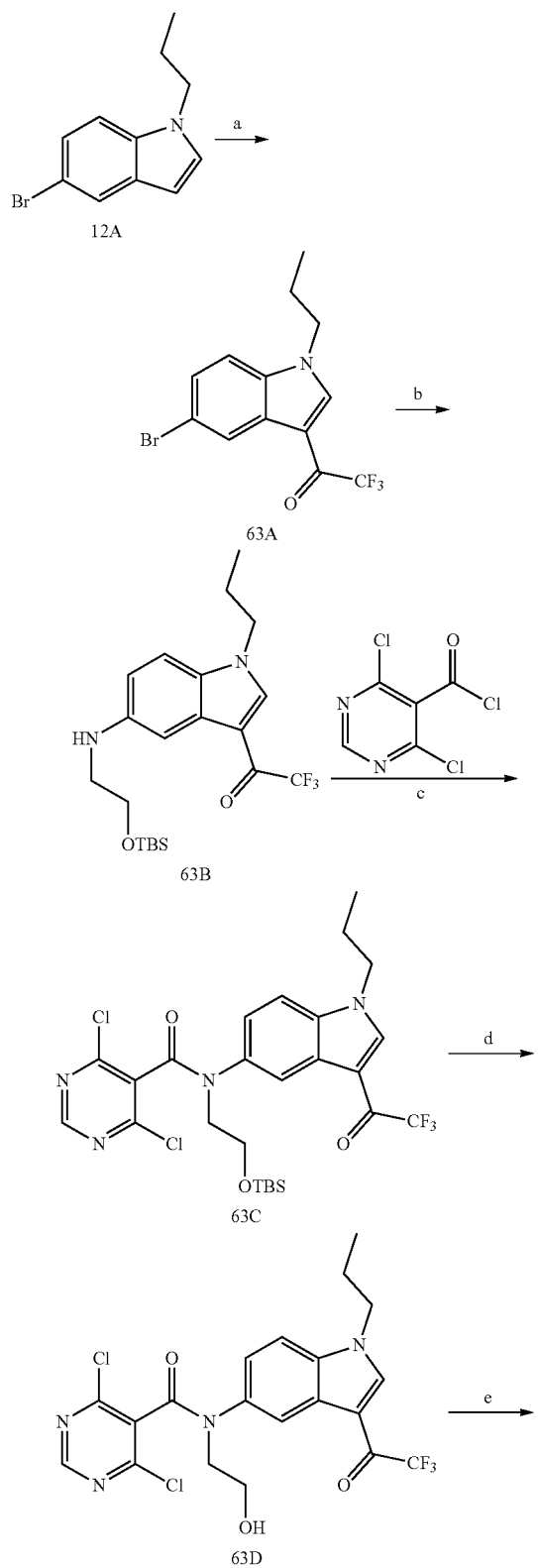

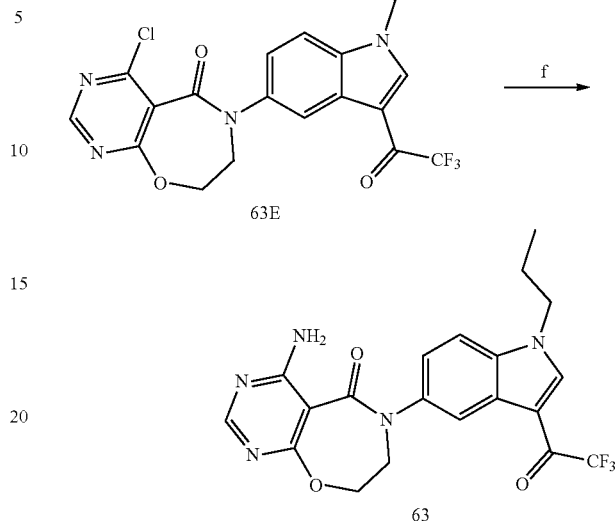

Reagents and conditions: a) TFAA, Et₃N, DCM, RT, 1 h; b) NH₂(CH₂)₂OTBDMS, Pd(Oac)₂, Cs₂CO₃, X-PHOS, Toluence, 120° C., 2.5 h; c) DCM, Et₃N, RT, 1 h; d) 3% HCl-MeOH, RT, 1 h; e) CH₃CN, Et₃N, 80° C., 16 h; f) NH₃, Dioxane, RT, 2 h.

Procedures:

4-Amino-6-(1-propyl-3-(2,2,2-trifluoroacetyl)-1H-indol-5-yl)-7,8-dihydropyrimido[5,4-f][1,4]oxazepin-5(6H)-one

1-(5-Bromo-1-propyl-1H-indol-3-yl)-2,2,2-trifluoroethanone (63A)

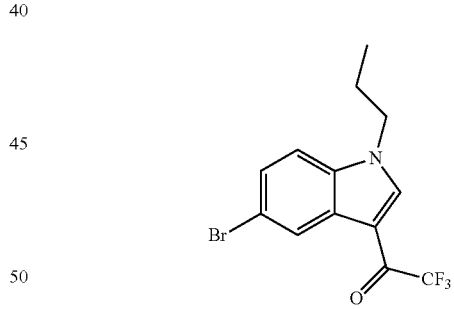

TFAA (5.0 mL, 35.4 mmol) was added to a solution of product of Example 12A (2.5 g, 10.5 mmol) in DCM (10 mL) followed by TEA (2.5 mL, 17.94 mmol) at 0° C., and the mixture was stirred at 25° C. for 1 h. The reaction mixture was diluted with DCM and quenched with water. Organic layer was separated, washed with brine, dried over sodium sulphate, filtered and concentrated in vacuo. The crude product was purified by flash chromatography using 5% ethyl acetate in hexane to afford title compound (2.0 g, 57%) as a yellow solid. $^1$H NMR (300 MHz, CDCl₃): δ 8.57 (d, J=1.5 Hz, 1H), 7.90 (d, J=1.5 Hz, 1H), 7.49-7.45 (dd, $J_1$=1.8 Hz, $J_2$=9.0 Hz, 1H), 7.09 (m, 1H), 4.16 (t, J=6.9 Hz, 2H), 1.98-1.91 (m, 2H), 0.98 (t, J=7.5 Hz, 3H); ESI-MS m/z=238 (M+H)⁺.

1-(5-(2-(tert-Butyldimethylsilyloxy)ethylamino)-1-propyl-1H-indol-3-yl)-2,2,2-trifluoroethanone (63B)

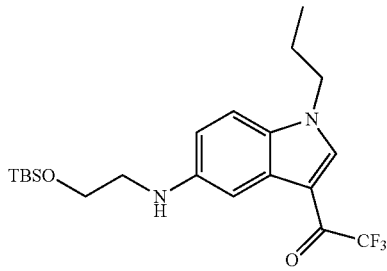 [SMILES: CCCn1cc(C(=O)C(F)(F)F)c2cc(NCCO[Si](C)(C)C(C)(C)C)ccc21]

A mixture of product of Example 63A (1.25 g, 3.74 mmol), 2-(tert-butyldimethylsilyloxy)ethanamine (0.656 g, 3.74 mmol), cesium carbonate (1.463 g, 4.49 mmol), palladium acetate (0.084 g, 0.374 mmol) and X-PHOS (0.178 g, 0.374 mmol) in toluene (20 mL) under Argon was refluxed at 110° C. for 2 h. The reaction mixture was cooled, diluted with ethyl acetate, and washed with water (2×15 mL) and saturated aqueous brine. The organic layer was dried over sodium sulfate, filtered and concentrated to obtain dark oil. The residue was purified by flash chromatography using 10% ethyl acetate in hexane to afford title compound (0.7 g, 43.7%) as an oil. $^1$H NMR (300 MHz, CDCl$_3$): δ 7.78 (d, J=1.5 Hz, 1H), 7.63 (d, J=2.4 Hz, 1H), 7.20 (d, J=0.9.0 Hz, 1H), 6.75-6.72 (dd, J$_1$=2.4 Hz, J$_2$=8.7 Hz, 1H), 4.17 (bs, 1H), 4.09 (t, J=7.5 Hz, 2H), 3.87 (t, J=5.1 Hz, 2H), 3.30 (t, J=7.5 Hz, 1H), 1.96-1.89 (m, 2H), 0.97 (t, J=7.2 Hz, 3H), 0.91 (s, 9H), 0.07 (s, 6H); ESI-MS m/z=429 (M+H)$^+$.

N-(2-(tert-Butyldimethylsilyloxy)ethyl)-4,6-dichloro-N-(1-propyl-3-(2,2,2-trifluoroacetyl)-1H-indol-5-yl)pyrimidine-5-carboxamide (63C)

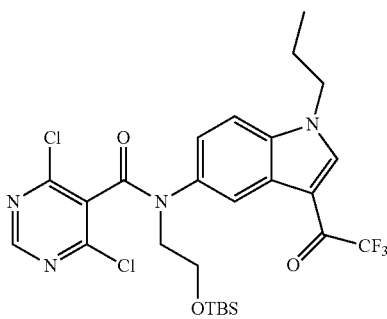 [SMILES: CCCn1cc(C(=O)C(F)(F)F)c2cc(N(CCO[Si](C)(C)C(C)(C)C)C(=O)c3c(Cl)ncnc3Cl)ccc21]

To a stirred, cooled (0° C.) solution of product of Example 63B (0.7 g, 1.633 mmol) and TEA (1.138 g, 8.17 mmol) in DCM (20 mL) was added drop wise a solution of 4,6-dichloropyrimidine-5-carbonyl chloride (0.345 g, 1.633 mmol) in DCM (5 mL). After 1 h, the reaction mixture was concentrated in vacuo, diluted with ethyl acetate, and washed with water (2×15 mL) and saturated aqueous brine. The organic layer was dried over sodium sulphate, filtered and concentrated in vacuo to afford oil. The residue was purified by flash chromatography using 12% ethyl acetate in hexane as eluent to afford title compound (0.6 g, 60.9%) as a syrup. $^1$H NMR (400 MHz, CDCl$_3$): δ 8.49 (s, 1H), 8.46 (d, J=1.6 Hz, 1H), 7.91 (d, J=1.2 Hz, 1H), 7.45-7.43 (dd, J$_1$=2.0 Hz J$_2$=8.8 Hz, 1H), 7.26 (m, 1H), 4.13-4.10 (m, 4H), 3.92 (t, J=5.6 Hz, 2H), 1.93-1.88 (q, J=7.6 Hz, 2H), 0.98 (t, J=7.2 Hz, 3H), 0.83 (s, 9H), 0.045 (s, 6H); ESI-MS m/z=605 (M+H)$^+$.

4,6-Dichloro-N-(2-hydroxyethyl)-N-(1-propyl-3-(2,2,2-trifluoroacetyl)-1H-indol-5-yl)pyrimidine-5-carboxamide (63D)

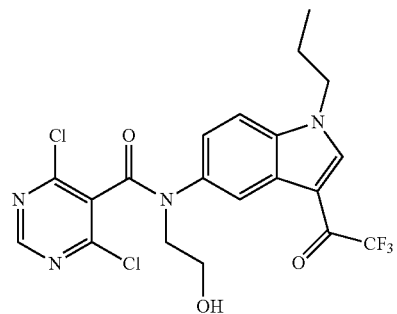 [SMILES: CCCn1cc(C(=O)C(F)(F)F)c2cc(N(CCO)C(=O)c3c(Cl)ncnc3Cl)ccc21]

A solution of product of Example 63C (0.6 g, 0.994 mmol), in 10 mL of methanolic solution of HCl (3 mL concentrated aqueous HCl in 97 mL of methanol) was stirred at room temperature for 1 h. Methanol was removed in vacuo, the residue was dissolved in ethyl acetate, and washed with saturated aqueous sodium bicarbonate and saturated aqueous brine. The organic layer was dried over sodium sulfate, filtered and concentrated in vacuo to afford title compound (0.4 g, 82%) as a solid, which was carried on to the next step without further purification. $^1$H NMR (400 MHz, CDCl$_3$): δ 8.51 (s, 1H), 8.50 (d, J=1.6 Hz, 1H), 7.93 (d, J=1.6 Hz, 1H), 7.45-7.42 (dd, J$_1$=2.4 Hz, J$_2$=8.8 Hz, 1H), 7.29 (m, 1H), 4.18 (t, J=5.2 Hz, 2H), 4.11 (t, J=7.2 Hz, 2H), 3.95 (t, 2H), 1.92 (q, J=7.6 Hz, 2H), 0.98 (t, J=8.0 Hz, 3H); ESI-MS m/z=490 (M+H)$^+$. 4-Chloro-6-(1-propyl-3-(2,2,2-trifluoroacetyl)-1H-indol-5-yl)-7,8-dihydropyrimido[5,4-f][1,4]oxazepin-5(6H)-one (63E):

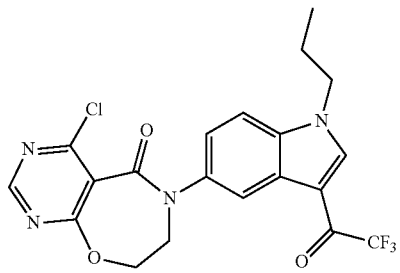 [SMILES: CCCn1cc(C(=O)C(F)(F)F)c2cc(N3CCOc4ncnc(Cl)c4C3=O)ccc21]

A slurry of product of Example 63D (0.4 g, 0.818 mmol) and TEA (0.57 mL, 4.09 mmol) in acetonitrile (15 mL) was stirred at 80° C. for 16 h. The reaction mixture was cooled and concentrated in vacuo. The residue was diluted with ethyl acetate, and washed with water and saturated aqueous brine. The organic layer was dried over sodium sulfate, filtered and concentrated in vacuo to afford title compound (0.25 g, 67.5%) as a white solid. $^1$H NMR (300 MHz, DMSO-d$_6$): δ 8.78 (s, 1H), 8.35 (s, 1H), 7.99 (d, J=0.9 Hz, 1H), 7.50-7.48 (m, 2H), 4.82 (t, J=7.8 Hz, 2H), 4.21 (t, J=7.2 Hz, 2H), 4.15 (t, J=4.8 Hz, 2H), 2.04-1.96 (m, 2H), 1.00 (t, J=7.2 Hz, 3H); ESI-MS m/z=453 (M+H)$^+$.

4-Amino-6-(1-propyl-3-(2,2,2-trifluoroacetyl)-1H-indol-5-yl)-7,8-dihydropyrimido[5,4-f][1,4]oxazepin-5(6H)-one (63)

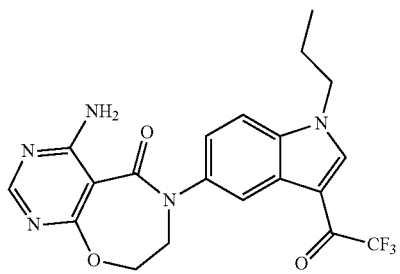 [SMILES: CCCn1cc(C(=O)C(F)(F)F)c2cc(N3CCOc4ncnc(N)c4C3=O)ccc21]

A solution of product of Example 63E (0.25 g, 0.552 mmol) in 0.5M ammonia in p-dioxane (10 mL) was stirred at room temperature for 2 h. The reaction mixture was concentrated in vacuo, diluted water ethyl acetate, and washed with water and saturated aqueous brine. The organic layer was dried over sodium sulfate, filtered and concentrated in vacuo to afford title compound (70 mg, 27.2%) as a white solid. $^1$H NMR (400 MHz, DMSO-$d_6$): δ 8.65 (d, J=1.6 Hz, 1H), 8.18 (s, 1H), 8.11 (d, J=1.2 Hz, 1H), 7.82 (d, J=8.8 Hz, 1H), 7.65 (bs, 2H), 7.40-7.38 (dd, $J_1$=2.0 Hz, $J_2$=8.4 Hz, 1H), 4.63 (t, J=3.6 Hz, 2H), 4.37 (t, J=6.8 Hz, 2H), 4.04 (t, J=4.8 Hz, 2H), 1.87-1.82 (m, 2H), 0.870 (t, J=7.2 Hz, 3H); ESI-MS m/z=434 (M+H)$^+$; LCMS purity: 92%.

Example 64 was prepared by the procedures analogous to those described in Example 63 using appropriately substituted starting materials.

| Ex | Structure | Analytical Data | Mass/Purity |
|---|---|---|---|
| 64 | 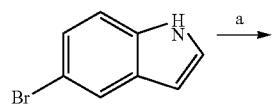 | $^1$H NMR (300 MHz, DMSO-$d_6$): δ 8.18 (s, 1H), 7.64-7.54 (m, 3H), 7.15 (dd, $J_1$ = 2.1 Hz, $J_2$ = 9.0 Hz, 1H), 7.03 (bs, 2H), 4.59 (t, J = 4.2 Hz, 2H), 4.17 (t, J = 6.9 Hz, 2H), 4.0 (t, J = 4.5 Hz, 2H), 3.12 (s, 3H), 1.83-1.7 (m, 5H), 0.83 (t, J = 7.2 Hz, 3H). | ESI-MS m/z = 464 (M + H)$^+$; HPLC purity: 90%. |

Example 65

4-Amino-6-(1-phenyl-1H-indol-5-yl)-7,8-dihydropyrimido[5,4-f][1,4]oxazepin-5(6H)-one

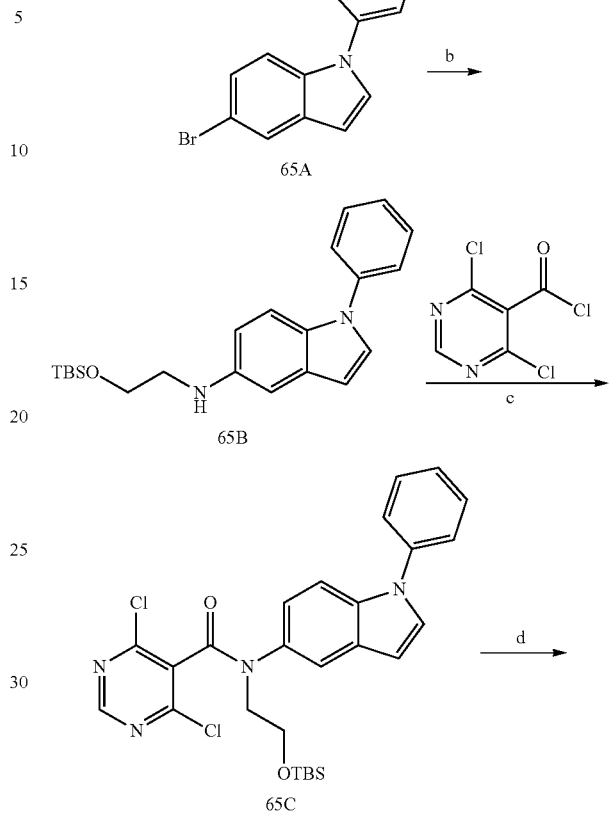

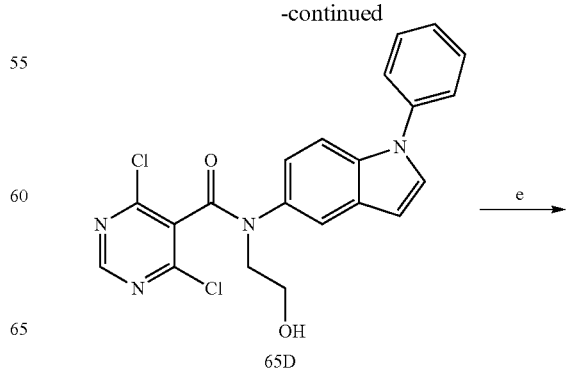

83
-continued

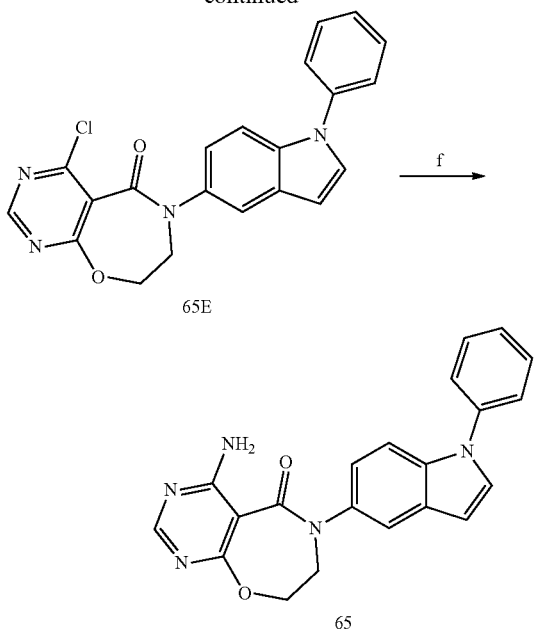

Reagents and conditions: a) Iodo benzene, CuBr, Cu(OAc)₂, K₂CO₃, NaOH, 140° C., 9 h; b) NH₂(CH₂)₂OTBDMS, Pd(OAc)₂, Cs₂CO₃, X-PHOS, Toluene, 120° C., 2.5 h; c) DCM, Et₃N, RT, 1 h; d) 3% HCl-MeOH, RT, 1 h: e) CH₃CN, Et₃N, 80° C, 16 h; f) NH₃, Dioxane, RT, 2 h.

Procedures:

4-Amino-6-(1-phenyl-1H-indol-5-yl)-7,8-dihydropyrimido[5,4-f][1,4]oxazepin-5(6H)-one 5-bromo-1-phenyl-1H-indole (65A)

65A

Copper(I) bromide (0.073 g, 0.509 mmol) was added to a solution of 5-bromo indole (1 g, 10.2 mmol) in iodo benzene (13.5 g, 66.2 mmol) followed by potassium carbonate (2.7 g, 19.54 mmol), and the mixture was stirred at 100° C. for 10 min. NaOH (150 mg, 3.75 mmol) and copper(II) acetate (0.01 g, 0.055 mmol) was added at 140° C., and the mixture was stirred for 9 h. Insoluble solids were filtered off, filtrate was concentrated and partitioned between ethyl acetate and water. Organic layer was separated, washed with brine, dried over sodium sulphate and filtered. The filtrate was concentrated under reduced pressure and purified by flash chromatography using 8% ethyl acetate in pet ether to afford title compound (0.5 g, 36%) as an oil. $^1$H NMR (300 MHz, CDCl$_3$): δ 7.80 (m, 1H), 7.60-7.45 (m, 4H), 7.42-7.38 (m, 2H), 7.35-7.25 (m, 2H), 6.62 (d, J=3.3 Hz, 1H).

84
N-(2-(tert-Butyldimethylsilyloxy)ethyl)-1-phenyl-1H-indol-5-amine (65B)

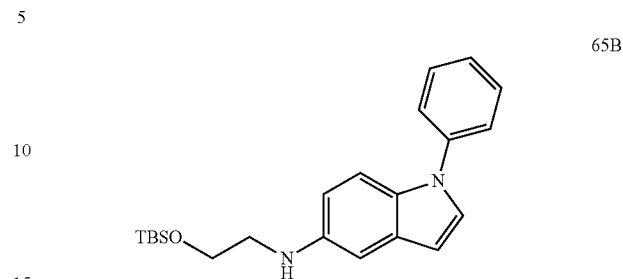

A mixture of product of Example 65A (1.7 g, 6.25 mmol), 2-(tert-butyldimethylsilyloxy)ethanamine (1.095 g, 6.25 mmol), cesium carbonate (3.05 g, 9.37 mmol), palladium acetate (0.14 g, 0.625 mmol) and X-PHOS (0.298 g, 0.625 mmol) in toluene (30 mL) under argon was refluxed at 120° C. for 16 h. The reaction was cooled, diluted with ethyl acetate, and washed with water (2×10 mL) and saturated aqueous brine. The organic layer was dried over sodium sulfate, filtered and concentrated to obtain dark oil. The residue was purified by flash chromatography using 10% ethyl acetate in hexane to afford title compound (0.8 g, 34.9%) as an oil. $^1$H NMR (400 MHz, CDCl$_3$): δ 7.55-7.48 (m, 4H), 7.45-7.39 (m, 2H), 7.3 (m, 1H), 6.89 (d, J=2.0 Hz, 1H), 6.66 (dd, J$_1$=2.0 Hz, J$_2$=8.8 Hz, 1H), 6.52 (d, J=2.8 Hz, 1H), 3.94 (bs, 1H), 3.86 (t, J=5.2 Hz, 2H), 3.27 (t, J=5.2 Hz, 2H), 0.92 (s, 9H), 0.08 (s, 6H).

N-(2-(tert-Butyldimethylsilyloxy)ethyl)-4,6-dichloro-N-(1-phenyl-1H-indol-5-yl)pyrimidine-5-carboxamide (65C)

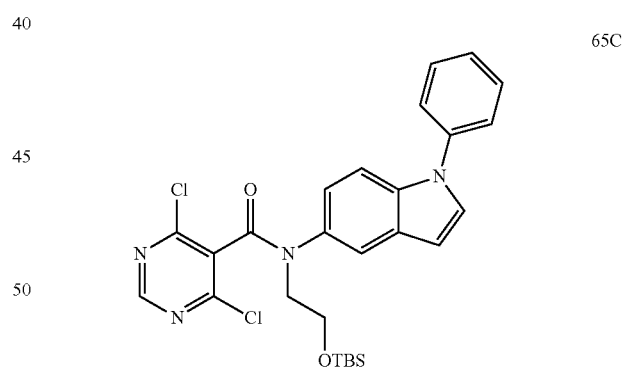

To a stirred, cooled (0° C.) solution of product of Example 65B (0.8 g, 2.182 mmol) and TEA (1.521 mL, 10.91 mmol) in DCM (30 mL) was added drop wise a solution of 4,6-dichloropyrimidine-5-carbonyl chloride (0.461 g, 2.182 mmol) in DCM (5 mL). After 1 h, the reaction was concentrated in vacuo, diluted with ethyl acetate, and washed with water (2×10 mL) and saturated aqueous brine. The organic layer was dried over sodium sulphate, filtered and concentrated in vacuo to afford oil. The residue was purified by flash chromatography using 12% ethyl acetate in hexane as eluent to afford title compound (0.65 g, 5%) as a syrup. $^1$H NMR (400 MHz, CDCl$_3$): δ 8.5 (s, 1H), 7.74 (d, J=2.0 Hz, 1H), 7.51 (t, J=8.0 Hz, 2H), 7.41-7.33 (m, 5H), 7.22 (dd, $J_1$=2.0 Hz, $J_2$=8.8 Hz, 1H), 6.59 (d, J=3.2 Hz, 1H), 4.16 (t, J=4.8 Hz, 2H), 3.95 (t, J=5.2 Hz, 2H), 0.92 (s, 9H), 0.08 (s, 6H).

4,6-Dichloro-N-(2-hydroxyethyl)-N-(1-phenyl-1H-indol-5-yl)pyrimidine-5-carboxamide (65D)

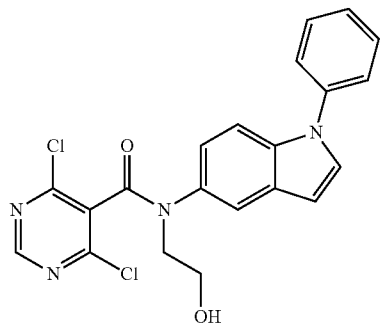

A solution of product of Example 65C (0.65 g, 1.2 mmol), in 20.5 mL of methanolic solution of HCl (3 mL concentrated aqueous HCl in 97 mL of methanol) was stirred at room temperature for 1 h. Methanol was removed in vacuo, the residue was dissolved in ethyl acetate, and washed with saturated aqueous sodium bicarbonate and saturated aqueous brine. The organic layer was dried over sodium sulfate, filtered and concentrated in vacuo to afford title compound (0.45 g, 72.8%) as a solid, which was carried on to the next step without further purification. $^1$H NMR (400 MHz, CDCl$_3$): δ 8.52 (s, 1H), 7.73 (d, J=2.0 Hz, 1H), 7.49 (t, J=8.0 Hz, 2H), 7.40-7.38 (m, 4H), 7.36 (d, J=3.6 Hz, 1H), 7.23 (dd, $J_1$=2.4 Hz, $J_2$=8.8 Hz, 1H), 6.62 (d, J=2.8 Hz, 1H), 4.16 (t, J=4.8 Hz, 2H), 3.95 (t, J=5.2 Hz, 2H).

4-Chloro-6-(1-phenyl-1H-indol-5-yl)-7,8-dihydropyrimido[5,4-f][1,4]oxazepin-5(6H) one 65E

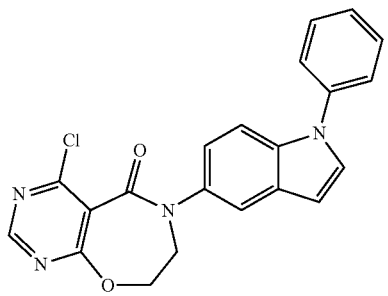

A slurry of product of Example 65D (0.45 g, 1.053 mmol) and TEA (0.734 mL, 5.27 mmol) in acetonitrile (20 mL) was stirred at 80° C. for 16 h. The reaction was cooled, concentrated in vacuo, diluted with ethyl acetate, and washed with water and saturated aqueous brine. The organic layer was dried over sodium sulfate, filtered and concentrated in vacuo to afford title compound (0.3 g, 67.1%) as a white solid. $^1$H NMR (400 MHz, CDCl$_3$): δ 8.77 (s, 1H), 7.67 (d, J=2.0 Hz, 1H), 7.6 (d, J=8.8 Hz, 1H), 7.56-7.47 (m, 4H), 7.41-7.38 (m, 2H), 7.20 (dd, $J_1$=2.0 Hz, $J_2$=8.8 Hz, 1H), 6.71 (d, J=3.6 Hz, 1H), 4.18 (t, J=4.4 Hz, 2H), 4.10 (t, J=4.8 Hz, 2H).

4-Amino-6-(1-phenyl-1H-indol-5-yl)-7,8-dihydropyrimido[5,4-f][1,4]oxazepin-5(6H)-one (65)

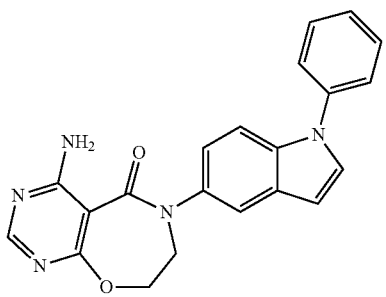

A solution of product of Example 65E (0.3 g, 0.768 mmol), in 0.5M ammonia in p-dioxane (15 mL) was stirred at room temperature for 2 h. The reaction mixture was concentrated in vacuo, diluted with ethyl acetate, and washed with water and saturated aqueous brine. The organic layer was dried over sodium sulfate, filtered and concentrated in vacuo to afford title compound (0.22 g, 73.3%) as a white solid. $^1$H NMR (400 MHz, DMSO-d$_6$): δ 8.18 (s, 1H), 7.73 (d, J=3.6 Hz, 1H), 7.64-7.56 (m, 5H), 7.45 (m, 1H), 7.18-7.15 (m, 4H), 6.73 (d, J=3.2 Hz, 1H), 4.65 (t, J=4.4 Hz, 2H), 4.01 (t, J=4.4 Hz, 2H); ESI-MS m/z=372 (M+H)$^+$; HPLC purity: 95%.

Example 66

4-Amino-6-(1-(4-(trifluoromethyl)phenyl)-1H-pyrrolo[2,3-b]pyridin-5-yl)-7,8-dihydropyrimido[5,4-f][1,4]oxazepin-5(6H)-one

87
-continued

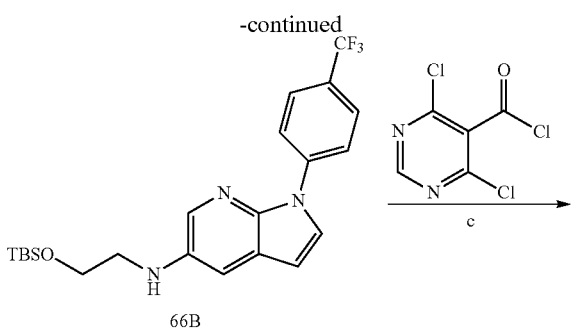

66B

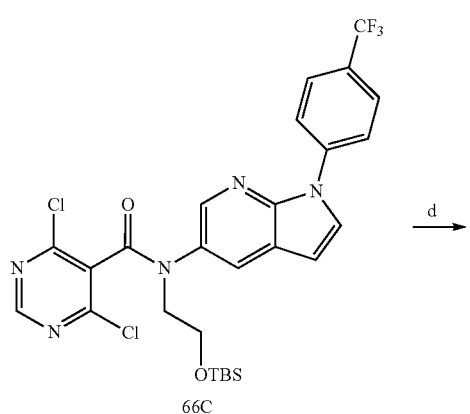

66C

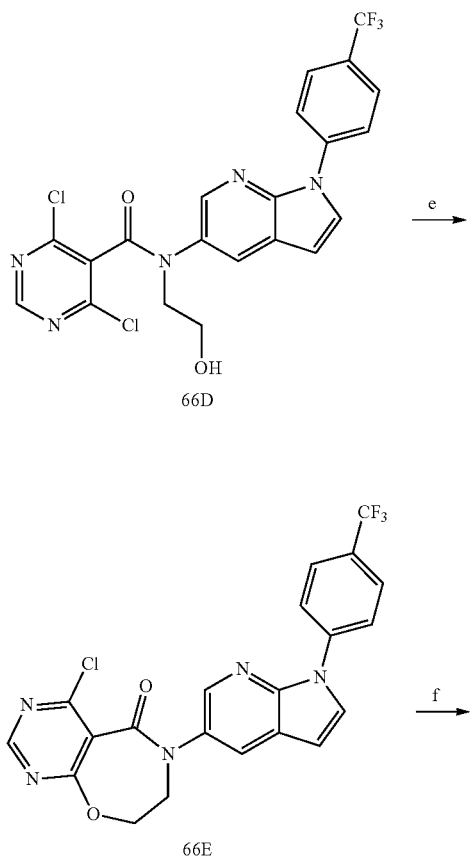

88
-continued

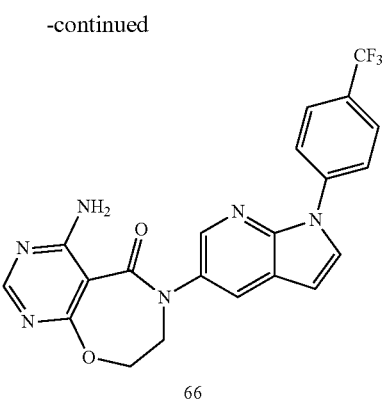

66

Reagents and conditions: a) 1-Iodo-4-(trifluoromethyl)benzene, CuBr, Cu(OAc)$_2$, K$_2$CO$_3$, NaOH, DMF, 110° C., 16 h; b) NH$_2$(CH$_2$)$_2$OTBDMS, Pd(OAc)$_2$, Cs$_2$CO$_3$, X—PHOS, Toluene, 120° C., 12 h; c) DCM, Et$_3$N, RT, 1 h; d) TBAF, THF, RT, 1 h; e) CH$_3$CN, Et$_3$N, 80° C., 16 h; f) NH$_3$, Dioxane, RT, 2 h.

Procedures:

4-Amino-6-(1-(4-(trifluoromethyl)phenyl)-1H-pyrrolo[2,3-b]pyridin-5-yl)-7,8-dihydropyrimido[5,4-f][1,4]oxazepin-5(6H)-one 5-Bromo-1-(4-(trifluoromethyl)phenyl)-1H-pyrrolo[2,3-b]pyridine (66A)

1-Iodo-4-(trifluoromethyl)benzene (1.657 g, 6.09 mmol) was added to a solution of 5-bromo-1H-pyrrolo[2,3-b]pyridine (1 g, 5.08 mmol) and Copper(I) bromide (0.073 g, 0.508 mmol) in DMF (10 mL) followed by potassium carbonate (1.75 g, 12.69 mmol), and the mixture was stirred at 100° C. for 10 min. NaOH (150 mg, 3.75 mmol) and copper(II) acetate (4.61 mg, 0.025 mmol) were added to the reaction mixture at 110° C., and the mixture was stirred for 16 h. Insoluble solids were filtered off, and the filtrate was concentrated. Residue was partitioned between ethyl acetate and water. Organic layer was separated, washed with brine, dried over sodium sulphate, filtered and concentrated in vacuo. The crude product was purified by flash chromatography using 10% ethyl acetate in pet ether to afford title compound (0.4 g, 22%) as a off-white solid. $^1$H NMR (400 MHz, CDCl$_3$): δ 8.4 (d, J=2.0 Hz, 1H), 8.11 (d, J=2.4 Hz, 1H), 7.93 (d, J=8.0 Hz, 2H), 7.78 (d, J=8.8 Hz, 2H), 7.56 (d, J=4.0 Hz, 1H), 6.63 (d, J=3.6 Hz, 1H).

89

N-(2-(tert-Butyldimethylsilyloxy)ethyl)-1-(4-(trifluoromethyl)phenyl)-1H-pyrrolo[2,3-b]pyridin-5-amine (66B)

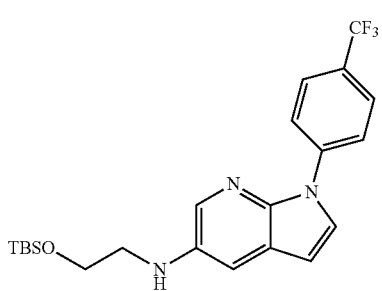

A mixture of product of Example 66A (0.4 g, 1.173 mmol), 2-(tert-butyldimethylsilyloxy)ethanamine (0.247 g, 1.407 mmol), cesium carbonate (0.573 g, 1.759 mmol), palladium acetate (26.3 mg, 0.117 mmol) and X-PHOS (0.0559 g, 0.117 mmol) in Toluene (15 mL) under Argon was refluxed at 120° C. for 2.5 h. The reaction was cooled, diluted with ethyl acetate, and washed with water (2×5 mL) and saturated aqueous brine. The organic layer was dried over sodium sulfate, filtered and concentrated to obtain dark oil. The residue was purified by flash chromatography using 10% ethyl acetate in hexane to afford title compound (0.3 g, 50.5%) as an oil. $^1$H NMR (400 MHz, CDCl$_3$): δ 7.98 (d, J=8.0 Hz, 2H), 7.93 (d, J=2.8 Hz, 1H), 7.76 (d, J=8.8 Hz, 1H), 7.47 (d, J=4.0 Hz, 1H), 7.21 (d, J=2.8 Hz, 1H), 6.52 (d, J=4.0 Hz, 1H), 3.88 (t, J=5.2 Hz, 2H), 3.27 (t, J=5.6 Hz, 2H), 0.92 (s, 9H), 0.07 (s, 6H).

N-(2-(tert-Butyldimethylsilyloxy)ethyl)-4,6-dichloro-N-(1-(4-(trifluoromethyl)phenyl)-1H-pyrrolo[2,3-b]pyridin-5-yl)pyrimidine-5-carboxamide (66C)

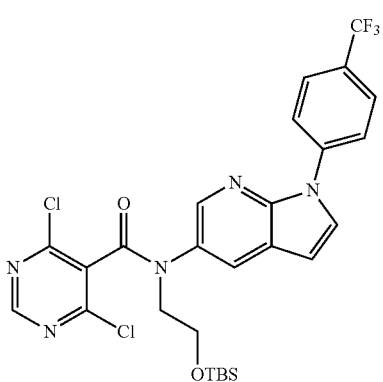

To a stirred, cooled (0° C.) solution of product of Example 66B (0.3 g, 0.689 mmol) and TEA (0.288 mL, 2.06 mmol) in DCM (10 mL) was added drop wise a solution of 4,6-dichloropyrimidine-5-carbonyl chloride (0.175 g, 0.827 mmol) in DCM (2 mL). After 1 h, the reaction mixture was concentrated in vacuo, diluted with ethyl acetate, and washed with water (2×5 mL) and saturated aqueous brine. The organic layer was dried over sodium sulphate, filtered and concentrated in vacuo to afford an oil. The residue was purified by flash chromatography using 12% ethyl acetate in pet ether to afford title compound (0.28 g, 62.6%) as a syrup. $^1$H NMR (400 MHz, CDCl$_3$): δ 8.54 (s, 1H), 8.40 (d, J=2.4 Hz, 1H), 8.13 (d, J=2.0 Hz, 1H), 7.87 (d, J=8.8 Hz, 2H), 7.78 (d, J=8.8 Hz, 2H), 7.58 (d, J=4.0 Hz, 1H), 6.63 (d, J=4.0 Hz, 1H), 4.09 (t, J=5.2 Hz, 2H), 3.97 (t, J=5.2 Hz, 2H), 0.87 (s, 9H), 0.06 (s, 6H).

90

4,6-Dichloro-N-(2-hydroxyethyl)-N-(1-(4-(trifluoromethyl)phenyl)-1H-pyrrolo[2,3-b]pyridin-5-yl)pyrimidine-5-carboxamide (66D)

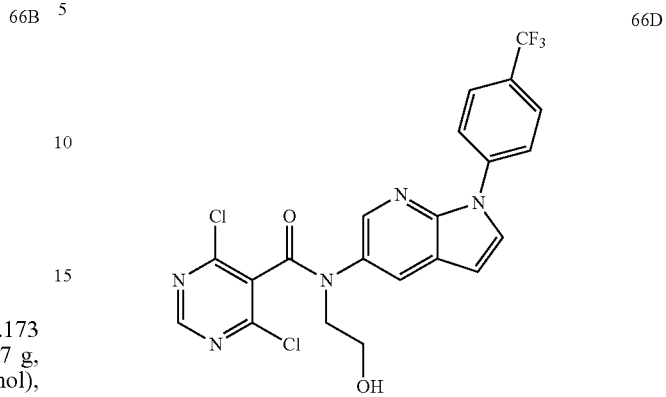

TBAF (0.3 g, 1.147 mmol) was added to a solution of Example 66C (0.28 g, 0.459 mmol) in THF (10 mL), and the mixture was stirred at room temperature for 1 h. THF was removed in vacuo. The residue was dissolved in ethyl acetate, washed with saturated aqueous sodium bicarbonate solution and saturated aqueous brine. The organic layer was dried over sodium sulfate, filtered and concentrated in vacuo to afford title compound (0.2 g, 86%) as a solid, which was carried on to the next step without further purification. $^1$H NMR (400 MHz, CDCl$_3$): δ 8.56 (s, 1H), 8.45 (d, J=2.4 Hz, 1H), 8.11 (d, J=2.4 Hz, 1H), 7.88 (d, J=8.8 Hz, 2H), 7.78 (d, J=8.8 Hz, 2H), 7.6 (d, J=4.0 Hz, 1H), 6.66 (d, J=3.2 Hz, 1H), 4.16 (t, J=4.8 Hz, 2H), 3.98 (q, J=4.8 Hz, 2H).

4-Chloro-6-(1-(4-(trifluoromethyl)phenyl)-1H-pyrrolo[2,3-b]pyridin-5-yl)-7,8-dihydropyrimido[5,4-f][1,4]oxazepin-5(6H)-one (66E)

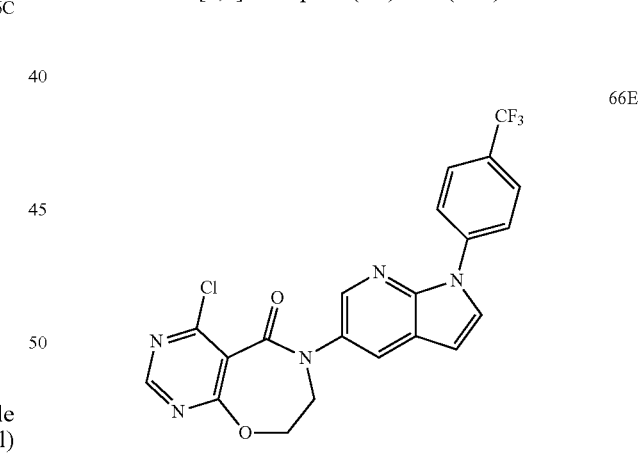

A slurry of product of Example 66D (0.2 g, 0.403 mmol) and TEA (0.169 mL, 1.209 mmol) in acetonitrile (15 mL) was stirred at 80° C. for 6 h. The reaction was cooled, concentrated in vacuo, diluted with ethyl acetate, and washed with water and saturated aqueous brine. The organic layer was dried over sodium sulfate, filtered and concentrated in vacuo to afford title compound (0.16 g, 83%) as a white solid. $^1$H NMR (400 MHz, CDCl$_3$): δ 8.80 (s, 1H), 8.39 (d, J=2.4 Hz, 1H), 8.04 (d, J=2.8 Hz, 1H), 7.96 (d, J=8.8 Hz, 2H), 7.8 (d, J=8.8 Hz, 2H), 7.65 (d, J=3.6 Hz, 1H), 6.74 (d, J=3.6 Hz, 1H), 4.81 (t, J=5.2 Hz, 2H), 4.12 (t, J=4.8 Hz, 2H).

4-Amino-6-(1-(4-(trifluoromethyl)phenyl)-1H-pyrrolo[2,3-b]pyridin-5-yl)-7,8-dihydropyrimido[5,4-f][1,4]oxazepin-5(6H)-one (66)

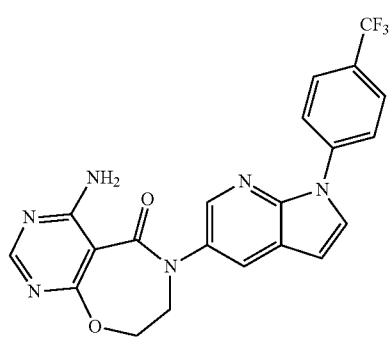

A solution of product of Example 66E (0.16 g, 0.348 mmol) in 0.5M ammonia in p-dioxane (12 mL) was stirred at room temperature for 2 h. The reaction mixture was concentrated in vacuo, diluted with ethyl acetate, and washed with water and saturated aqueous brine. The organic layer was dried over sodium sulfate, filtered and concentrated in vacuo to afford title compound (0.1 g, 64.6%) as a white solid. $^1$H NMR (300 MHz, DMSO-d$_6$): δ 8.37 (d, J=2.4 Hz, 1H), 8.23 (d, J=8.0 Hz, 2H), 8.19 (s, 1H), 8.16 (d, J=2.0 Hz, 1H), 8.13 (d, J=4.0 Hz, 1H), 7.95 (d, J=8.4 Hz, 2H), 7.66 (bs, 2H), 6.87 (d, J=4.0 Hz, 1H), 4.71 (t, J=4.0 Hz, 2H), 4.07 (t, J=3.6 Hz, 2H); ESI-MS m/z=441 (M+H)$^+$; HPLC purity: 99%.

Examples 67-81 were prepared by the procedures analogous to those described in Example 65 or Example 66 using appropriately substituted starting materials.

| Ex | Structure | Analytical Data | Mass/Purity |
|---|---|---|---|
| 67 | 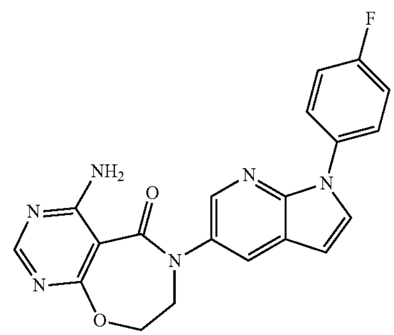 [SMILES: Nc1ncnc2c1C(=O)N(c1cnc3c(ccn3-c3ccc(F)cc3)c1)CCO2] | $^1$H NMR (400 MHz, DMSO-d$_6$): δ 8.32 (d, J = 2.0 Hz, 1H), 8.19 (s, 1H), 8.11 (d, J = 2.0 Hz, 1H), 8.0 (d, J = 4.0 Hz, 1H), 7.94-7.91 (m, 2H), 7.66 (bs, 2H), 7.41 (t, J = 8.8 Hz, 2H), 6.76 (d, J = 4.0 Hz, 1H), 4.69 (t, J = 4.4 Hz, 2H), 4.06 (t, J = 4.4 Hz, 2H). | ESI-MS m/z = 391 (M + H)$^+$; HPLC purity: 97%. |
| 68 | 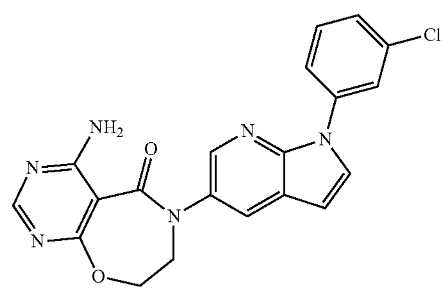 [SMILES: Nc1ncnc2c1C(=O)N(c1cnc3c(ccn3-c3cccc(Cl)c3)c1)CCO2] | $^1$H NMR (400 MHz, DMSO-d$_6$): δ 8.37 (d, J = 2.4 Hz, 1H), 8.19 (s, 1H), 8.16-8.10 (m, 3H), 7.95 (dd, J$_1$ = 1.6 Hz, J$_2$ = 8.4 Hz, 1H), 7.67 (bs, 2H), 7.59 (t, J = 8.4 Hz, 1H), 7.43 (d, J = 8.0 Hz, 1H), 6.8 (d, J = 3.6 Hz, 1H), 4.69 (t, J = 4.0 Hz, 2H), 4.06 (t, J = 4.4 Hz, 2H). | ESI-MS m/z = 407 (M + H)$^+$; HPLC purity: 97%. |
| 69 | 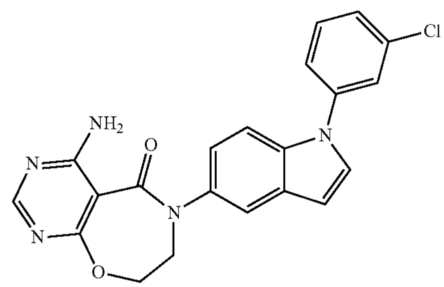 [SMILES: Nc1ncnc2c1C(=O)N(c1ccc3c(ccn3-c3cccc(Cl)c3)c1)CCO2] | $^1$H NMR (300 MHz, DMSO-d$_6$): δ 8.18 (s, 1H), 7.78 (d, J = 3.3 Hz, 1H), 7.7 (bs, 2H), 7.66-7.58 (m, 5H), 7.48 (m, 1H), 7.22 (dd, J$_1$ = 2.1 Hz, J$_2$ = 9.0 Hz, 1H), 6.76 (d, J = 3.3 Hz, 1H), 4.65 (t, J = 3.6 Hz, 2H), 4.01 (t, J = 4.5 Hz, 2H). | ESI-MS m/z = 406 (M + H)$^+$; HPLC purity: 95%. |

| Ex | Structure | Analytical Data | Mass/Purity |
|---|---|---|---|
| 70 | 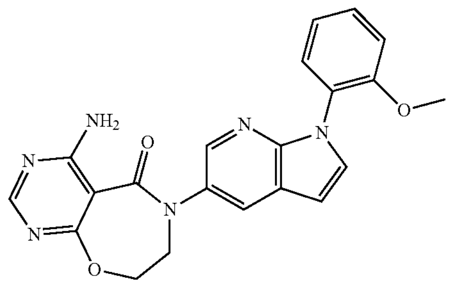 [SMILES: COc1ccccc1-n1ccc2cc(N3CCOc4ncnc(N)c4C3=O)cnc21] | $^1$H NMR (300 MHz, DMSO-d$_6$): δ 8.18 (m, 2H), 8.05 (d, J = 2.1 Hz, 1H), 7.66 (bs, 2H), 7.46 (d, J = 7.8 Hz, 2H), 7.27 (d, J = 8.1 Hz, 1H), 7.12 (t, J = 6.3 Hz, 2H), 6.66 (d, J = 3.9 Hz, 1H), 4.67 (t, J = 4.5 Hz, 2H), 4.04 (t, J = 4.5 Hz, 2H), 3.74 (s, 3H). | ESI-MS m/z = 403 (M + H)$^+$; HPLC purity: 92%. |
| 71 | 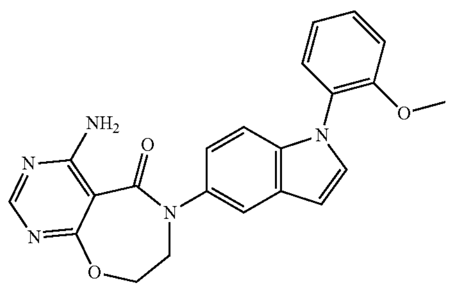 [SMILES: COc1ccccc1-n1ccc2cc(N3CCOc4ncnc(N)c4C3=O)ccc21] | $^1$H NMR (300 MHz, DMSO-d$_6$): δ 8.18 (s, 1H), 7.62 (bs, 2H), 7.59 (s, 1H), 7.54-7.46 (m, 2H), 7.39 (d, J = 6.9 Hz, 1H), 7.30 (d, J = 8.1 Hz, 1H), 7.2-7.05 (m, 3H), 6.66 (d, J = 3.0 Hz, 1H), 4.64 (t, J = 4.5 Hz, 2H), 4.0 (t, J = 4.5 Hz, 2H), 3.77 (s, 3H). | ESI-MS m/z = 402 (M + H)$^+$; HPLC purity: 92%. |
| 72 | 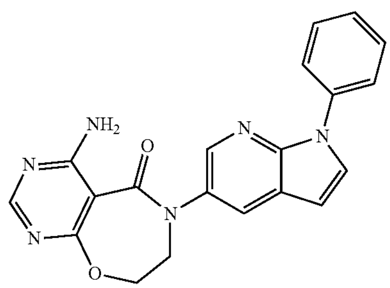 [SMILES: Nc1ncnc2c1C(=O)N(c1cnc3c(ccn3-c3ccccc3)c1)CCO2] | $^1$H NMR (300 MHz, CDCl$_3$): δ 8.3 (s, 1H), 8.28 (d, J = 2.4 Hz, 1H), 8.20 (bs, 1H), 7.90 (d, J = 2.4 Hz, 1H), 7.74 (m, 2H), 7.6 (d, J = 3.6 Hz, 1H), 7.54 (t, J = 7.8 Hz, 2H), 7.37 (t, J = 7.5 Hz, 1H), 6.66 (d, J = 3.3 Hz, 1H), 5.70 (bs, 1H), 4.76 (t, J = 4.2 Hz, 2H), 4.08 (t, J = 4.5 Hz, 2H). | ESI-MS m/z = 373 (M + H)$^+$; HPLC purity: 99%. |
| 73 | 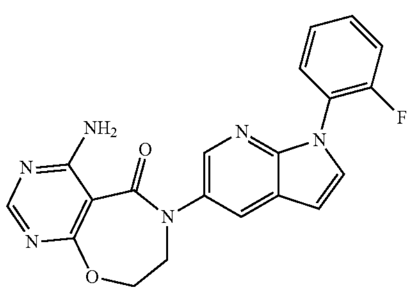 [SMILES: Nc1ncnc2c1C(=O)N(c1cnc3c(ccn3-c3ccccc3F)c1)CCO2] | $^1$H NMR (300 MHz, CDCl$_3$): δ 8.30 (s, 1H), 8.25 (d, J = 2.4 Hz, 1H), 8.20 (bs, 1H), 7.90 (d, J = 2.4 Hz, 1H), 7.69 (dt, J$_1$ = 1.5 Hz, J$_2$ = 7.5 Hz, 1H), 7.49 (m, 1H), 7.46-7.38 (m, 1H), 7.34-7.27 (m, 2H), 6.68 (d, J = 3.3 Hz, 1H), 5.75 (bs, 1H), 4.75 (t, J = 4.5 Hz, 2H), 4.08 (t, J = 4.5 Hz, 2H). | ESI-MS m/z = 391 (M + H)$^+$; HPLC purity: 96%. |
| 74 | 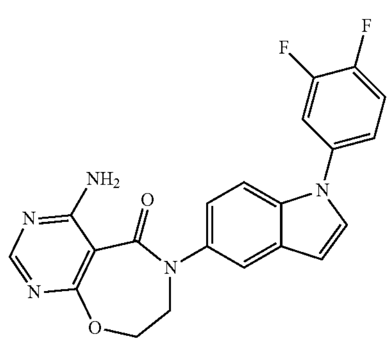 [SMILES: Nc1ncnc2c1C(=O)N(c1ccc3c(ccn3-c3ccc(F)c(F)c3)c1)CCO2] | $^1$H NMR (400 MHz, DMSO-d$_6$): δ 8.18 (s, 1H), 7.80 (m, 1H), 7.73 (d, J = 3.2 Hz, 1H), 7.70-7.58 (m, 5H), 7.50 (m, 1H), 7.20 (dd, J$_1$ = 2.0 Hz, J$_2$ = 8.8 Hz, 2H), 6.75 (d, J = 3.2 Hz, 1H), 4.65 (t, J = 4.4 Hz, 2H), 4.0 (t, J = 4.4 Hz, 2H). | ESI-MS m/z = 408 M + H)$^+$; HPLC purity: 96%. |

-continued

| Ex | Structure | Analytical Data | Mass/Purity |
|----|-----------|-----------------|-------------|
| 75 | 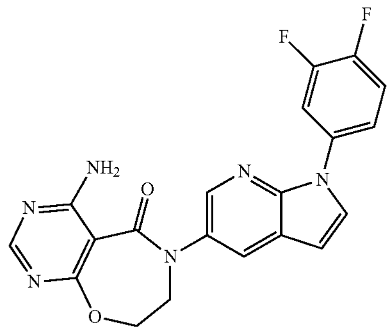 [SMILES: Nc1ncnc2c1C(=O)N(c1cnc3c(ccn3-c3ccc(F)c(F)c3)c1)CCO2] | ¹H NMR (300 MHz, DMSO-d$_6$): δ 8.36 (d, J = 2.1 Hz, 1H), 8.18 (s, 1H), 8.13 (m, 2H), 8.08 (d, J = 3.9 Hz, 1H), 7.85 (m, 1H), 7.70-7.60 (m, 3H), 6.80 (d, J = 3.3 Hz, 1H), 4.69 (t, J = 3.9 Hz, 2H), 4.06 (t, J = 4.2 Hz, 2H). | ESI-MS m/z = 409 (M + H)⁺; HPLC purity: 90%. |
| 76 | 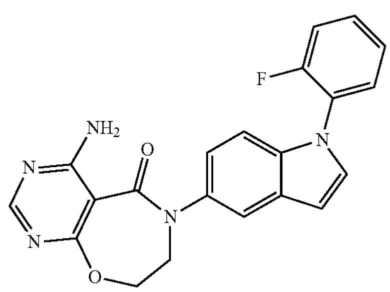 [SMILES: Nc1ncnc2c1C(=O)N(c1ccc3c(ccn3-c3ccccc3F)c1)CCO2] | ¹H NMR (400 MHz, DMSO-d$_6$): δ 8.18 (s, 1H), 7.68-7.60 (m, 5H), 7.55 (m, 2H), 7.43 (m, 1H), 7.24 (d, J = 8.4, 1H), 7.16 (d, J = 8.8 Hz, 1H), 6.76 (d, J = 2.8 Hz, 1H), 4.65 (t, J = 4.4 Hz, 2H), 4.01 (t, J = 4.4 Hz, 2H). | ESI-MS m/z = 390 (M + H)⁺; LCMS purity: 98%. |
| 78 | 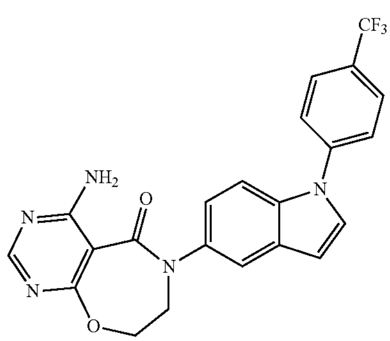 [SMILES: Nc1ncnc2c1C(=O)N(c1ccc3c(ccn3-c3ccc(C(F)(F)F)cc3)c1)CCO2] | ¹H NMR (400 MHz, DMSO-d$_6$): δ 8.18 (s, 1H), 7.95 (d, J = 8.0 Hz, 2H), 7.87 (d, J = 8.8 Hz, 2H), 7.84 (d, J = 2.8 Hz, 1H), 7.71-7.6 (m, 4H), 7.22 (d, J = 8.8 Hz, 1H), 6.81 (d, J = 3.2 Hz, 1H), 4.65 (t, J = 4.0 Hz, 2H), 4.02 (t, J = 4.4 Hz, 2H). | ESI-MS m/z = 440 (M + H)⁺; HPLC purity: 99%. |
| 79 | 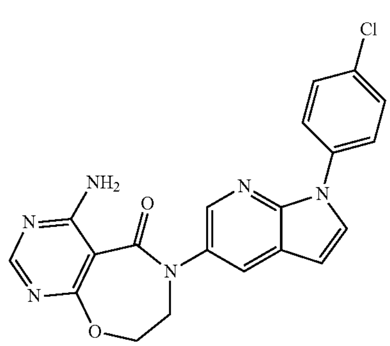 [SMILES: Nc1ncnc2c1C(=O)N(c1cnc3c(ccn3-c3ccc(Cl)cc3)c1)CCO2] | ¹H NMR (300 MHz, DMSO-d$_6$): δ 8.34 (d, J = 2.1 Hz, 1H), 8.19 (s, 1H), 8.13 (d, J = 1.8 Hz, 1H), 8.05 (d, J = 3.6 Hz, 1H), 7.99 (d, J = 8.4 Hz, 2H), 7.7-7.6 (m, 4H), 6.79 (d, J = 3.3 Hz, 1H), 4.68 (t, J = 4.2 Hz, 2H), 4.06 (t, J = 4.5 Hz, 2H). | ESI-MS m/z = 407 (M + H); HPLC purity: 94%. |

| Ex | Structure | Analytical Data | Mass/Purity |
|---|---|---|---|
| 80 | 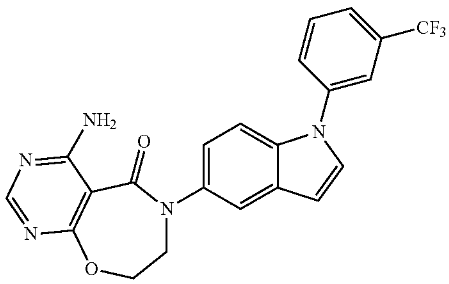 [SMILES: Nc1ncnc2c1C(=O)N(c1ccc3c(ccn3-c3cccc(C(F)(F)F)c3)c1)CCO2] | $^1$H NMR (400 MHz, DMSO-d$_6$): δ 8.10 (s, 1H), 7.91-7.84 (m, 2H), 7.8-7.68 (m, 3H), 7.59 (d, J = 2.0 Hz, 1H), 7.55 (bs, 2H), 7.52 (d, J = 8.8 Hz, 1H), 7.14 (dd, J$_1$ = 2.0 Hz, J$_2$ = 8.8 Hz, 1H), 6.71 (d, J = 3.6 Hz, 1H), 4.58 (t, J = 4.8 Hz, 2H), 3.94 (t, J = 4.4 Hz, 2H). | ESI-MS m/z = 440 (M + H)$^+$; HPLC purity: 93%. |
| 81 | 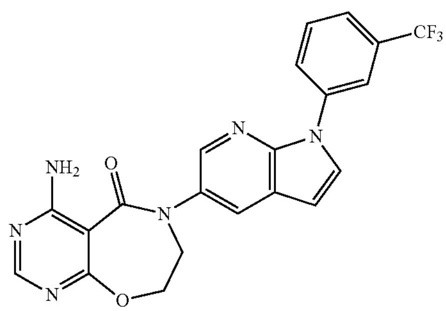 [SMILES: Nc1ncnc2c1C(=O)N(c1cnc3c(ccn3-c3cccc(C(F)(F)F)c3)c1)CCO2] | $^1$H NMR (400 MHz, DMSO-d$_6$): δ 8.43 (s, 1H), 8.39 (d, J = 2.4 Hz, 1H), 8.27 (d, J = 8.0 Hz, 1H), 8.19 (m, 2H), 8.15 (d, J = 2.0 Hz, 1H), 7.81 (t, J = 7.6 Hz, 1H), 7.72 (d, J = 8.0 Hz, 1H), 7.67 (bs, 2H), 6.83 (d, J = 3.6 Hz, 1H), 4.70 (t, J = 4.0 Hz, 2H), 4.07 (t, J = 4.4 Hz, 2H). | ESI-MS m/z = 441 (M + H)$^+$; HPLC purity: 97%. |
Example 82
4-Amino-6-(1-(thiazol-2-yl)-1H-indol-5-yl)-7,8-dihydropyrimido[5,4-f][1,4]oxazepin-5(6H)-one
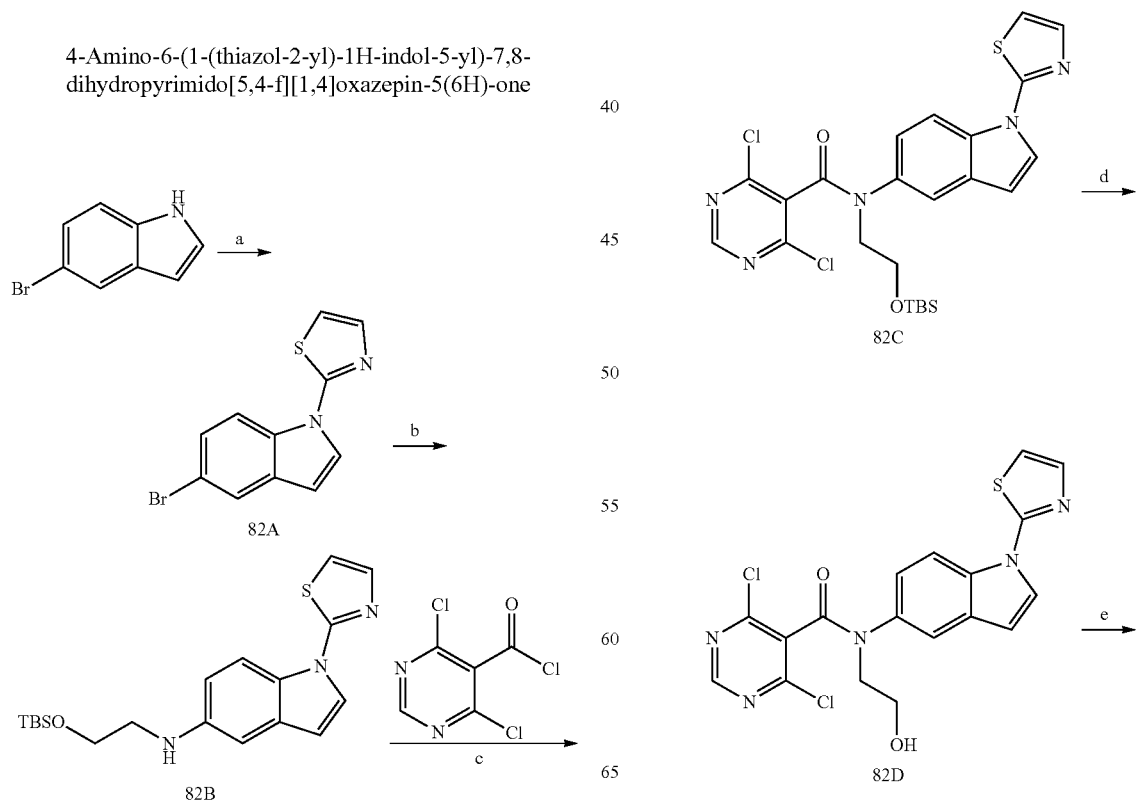

-continued

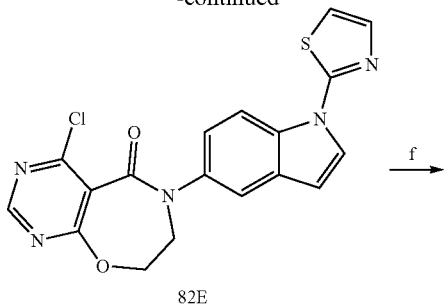

82E

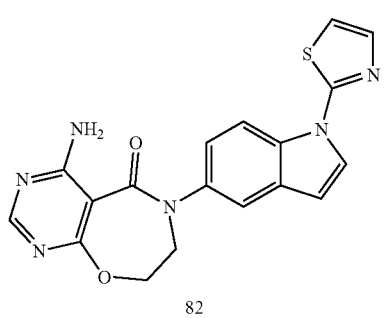

82

Reagents and conditions: a) 2-Bromo thiazole, Cs₂CO₃, DMF, 100° C., 2 h; b) NH₂(CH₂)₂OTBDMS, Pd(OAc)₂, Cs₂CO₃, X-PHOS, Toluene, 120° C., 2.5 h; c) DCM, Et₃N, RT, 1 h; d) 3% HCl-MeOH, RT, 1 h; e) CH₃CN, Et₃N, 80° C., 16 h; f) NH₃, Dioxane, RT, 2 h.

Procedures:

4-Amino-6-(1-(thiazol-2-yl)-1H-indol-5-yl)-7,8-dihydropyrimido[5,4-f][1,4]oxazepin-5(6H)-one 2-(5-Bromo-1H-indol-1-yl)thiazole (82A)

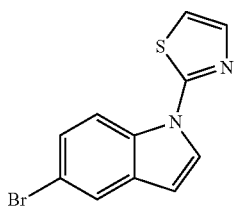

82A

2-Bromo thiazole (0.837 g, 5.10 mmol) was added to a solution of 5-bromo indole (1 g, 5.10 mmol) in DMF (15 mL) followed by cesium carbonate (3.32 g, 10.20 mmol), and the mixture was stirred at 90° C. for 12 h. Insoluble solids were filtered off, the filtrate was concentrated and partitioned between ethyl acetate and water. Organic layer was separated, washed with brine, dried over sodium sulphate, and filtered. The filtrate was concentrated under reduced pressure and purified by flash chromatography using 5% ethyl acetate in pet ether to afford title compound (0.75 g, 52.7%) as a white solid. ¹H NMR (400 MHz, CDCl₃): δ 8.24 (d, J=8.8 Hz, 1H), 7.77 (d, J=2.0 Hz, 1H), 7.62 (dd, J₁=3.2 Hz, J₂=10.4 Hz, 2H), 7.45 (dd, J₁=2.0 Hz, J₂=8.8 Hz, 1H), 7.08 (d, J=3.6 Hz, 1H), 6.66 (d, J=4.0 Hz, 1H).

N-(2-(tert-Butyldimethylsilyloxy)ethyl)-1-(thiazol-2-yl)-1H-indol-5-amine (82B)

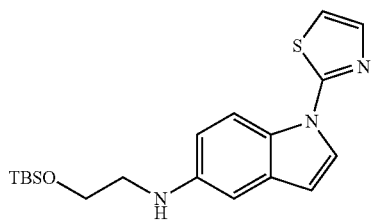

82B

A mixture of product of Example 82A (0.75 g, 2.69 mmol), 2-(tert-butyldimethylsilyloxy)ethanamine (0.471 g, 2.69 mmol), cesium carbonate (1.751 g, 5.37 mmol), palladium acetate (0.060 g, 0.269 mmol) and X-PHOS (0.128 g, 0.269 mmol) in Toluene (15 mL) under Argon was refluxed at 120° C. for 4 h. The reaction was cooled, diluted with ethyl acetate, and washed with water (2×15 mL) and saturated aqueous brine. The organic layer was dried over sodium sulfate, filtered and concentrated to obtain dark oil. The residue was purified by flash chromatography using 10% ethyl acetate in hexane to afford title compound (0.4 g, 40%) as an oil. ¹H NMR (300 MHz, CDCl₃): δ 8.11 (d, J=9.0 Hz, 1H), 7.56 (dd, J₁=3.6 Hz, J₂=9.9 Hz, 2H), 6.99 (d, J=2.4 Hz, 1H), 6.84 (d, J=2.1 Hz, 1H), 6.76 (dd, J₁=2.1 Hz, J₂=8.7 Hz, 1H), 6.56 (d, J=3.6 Hz, 1H), 4.03 (bs, 1H), 3.86 (t, J=4.8 Hz, 2H), 3.27 (t, J=5.4 Hz, 2H), 0.92 (s, 9H), 0.07 (s, 6H).

N-(2-(tert-Butyldimethylsilyloxy)ethyl)-4,6-dichloro-N-(1-(thiazol-2-yl)-1H-indol-5-yl)pyrimidine-5-carboxamide (82C)

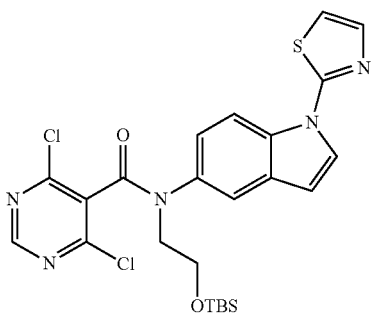

82C

To a stirred, cooled (0° C.) solution of product of Example 82B (0.4 g, 1.071 mmol) and TEA (0.746 mL, 5.35 mmol) in DCM (15 mL) was added drop wise a solution of 4,6-dichloropyrimidine-5-carbonyl chloride (0.226 g, 1.071 mmol) in DCM (5 mL). After 1 h, the reaction was concentrated in vacuo, diluted into ethyl acetate, and washed with water (2×15 mL) and saturated aqueous brine. The organic layer was dried over sodium sulphate, filtered and concentrated in vacuo to afford oil. The residue was purified by flash chromatography using 12% ethyl acetate in hexane to afford title compound (0.35 g, 59.6%) as a syrup. $^1$H NMR (300 MHz, CDCl$_3$): δ 8.49 (s, 1H), 8.23 (d, J=9.0 Hz, 1H), 7.73 (d, J=2.1 Hz, 1H), 7.62 (d, J=3.3 Hz, 1H), 7.59 (d, J=3.9 Hz, 1H), 7.38 (dd, J$_1$=2.4 Hz, J$_2$=9.0 Hz, 1H), 7.08 (d, J=2.4 Hz, 1H), 6.63 (d, J=3.6 Hz, 1H), 4.07 (t, J=5.4 Hz, 2H), 3.93 (t, J=5.4 Hz, 2H), 0.89 (s, 9H), 0.07 (s, 6H).

4,6-Dichloro-N-(2-hydroxyethyl)-N-(1-(thiazol-2-yl)-1H-indol-5-yl)pyrimidine-5-carboxamide (82D)

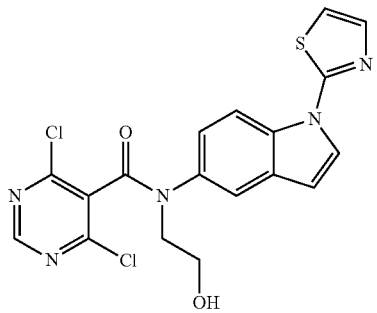

TBAF (1.276 mL, 1.276 mmol) was added to a solution of Example 82C (0.35 g, 0.638 mmol) in THF (10 mL), and the mixture was stirred at room temperature for 1 h. THF was removed in vacuo, the residue was dissolved in ethyl acetate, and washed with saturated aqueous sodium bicarbonate solution and saturated aqueous brine. The organic layer was dried over sodium sulfate, filtered and concentrated in vacuo to afford title compound (0.25 g, 90%) as a solid, which was carried on to the next step without further purification. ESI-MS m/z=434 (M+H)$^+$; LCMS purity: 88%.

4-Chloro-6-(1-(thiazol-2-yl)-1H-indol-5-yl)-7,8-dihydropyrimido[5,4-f][1,4]oxazepin-5(6H)-one (82E)

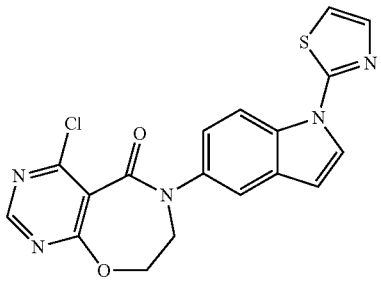

A slurry of product of Example 82D (0.25 g, 0.576 mmol) and TEA (0.080 mL, 0.576 mmol) in acetonitrile (12 mL) was stirred at 90° C. for 16 h. The reaction was cooled, concentrated in vacuo, diluted with ethyl acetate, and washed with water and saturated aqueous brine. The organic layer was dried over sodium sulfate and concentrated in vacuo to afford title compound (0.377 g, 65.5%) as a white solid. $^1$H NMR (300 MHz, DMSO-d$_6$): δ 8.78 (s, 1H), 8.45 (d, J=9.0 Hz, 1H), 7.73 (d, J=3.6 Hz, 1H), 7.67 (d, J=1.8 Hz, 1H), 7.64 (d, J=3.9 Hz, 1H), 7.34 (dd, J$_1$=1.8 Hz, J$_2$=8.7 Hz, 1H), 7.11 (d, J=3.6 Hz, 1H), 6.75 (d, J=3.6 Hz, 1H), 4.81 (t, J=4.5 Hz, 2H), 4.11 (t, J=5.1 Hz, 2H).

4-Amino-6-(1-(thiazol-2-yl)-1H-indol-5-yl)-7,8-dihydropyrimido[5,4-f][1,4]oxazepin-5(6H)-one (82)

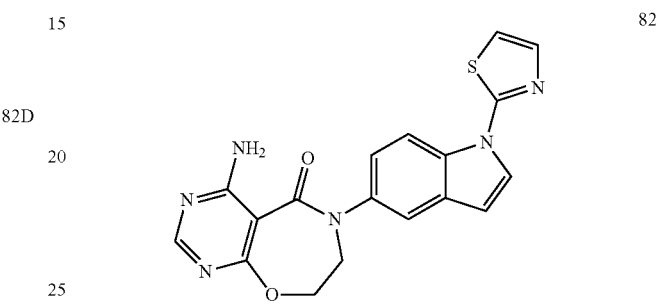

A solution of product of Example 82E (0.15 g, 0.377 mmol) in 0.5M ammonia in p-dioxane (10 mL) was stirred at room temperature for 2 h. The reaction mixture was concentrated in vacuo, diluted with ethyl acetate, and washed with water and saturated aqueous brine. The organic layer was dried over sodium sulfate, filtered and concentrated in vacuo to afford title compound (0.09 g, 58%) as a white solid. $^1$H NMR (400 MHz, DMSO-d$_6$): δ 8.35 (d, J=8.8 Hz, 1H), 8.18 (s, 1H), 7.98 (d, J=3.2 Hz, 1H), 7.72 (d, J=3.6 Hz, 1H), 7.69 (d, J=2.0 Hz, 1H), 7.63 (bs, 2H), 7.57 (d, J=3.2 Hz, 1H), 7.35 (dd, J$_1$=2.0 Hz, J$_2$=8.8 Hz, 1H), 6.86 (d, J=3.6 Hz, 1H), 4.82 (t, J=4.4 Hz, 2H), 4.11 (t, J=4.8 Hz, 2H); ESI-MS m/z=379 (M+H)$^+$; HPLC purity: 92%.

Example 83

4-Amino-6-(1-(6-(trifluoromethyl)pyridin-3-yl)-1H-indol-5-yl)-7,8-dihydropyrimido[5,4-f][1,4]oxazepin-5(6H)-one

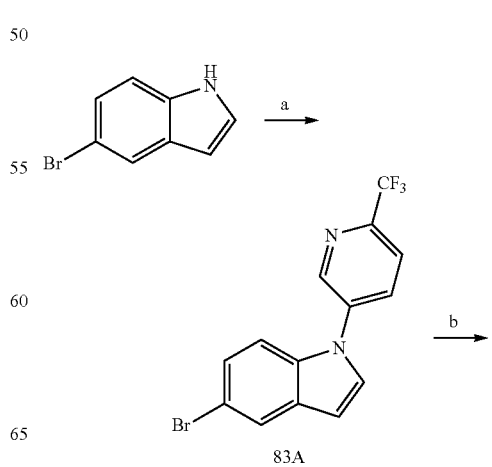

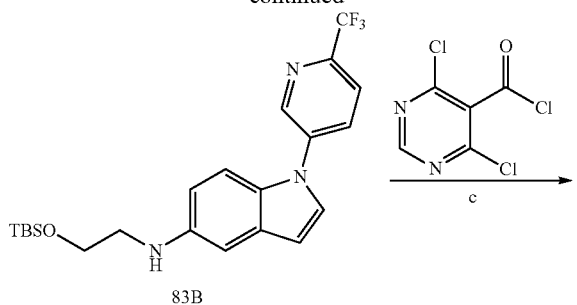

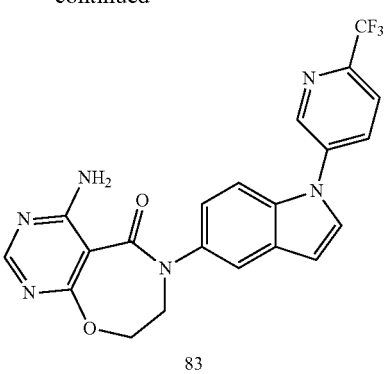

Reagents and conditions: a) 5-Bromo-2-(trifluoromethyl)pyridine, Cs$_2$CO$_3$, DMF, 90° C., 15 h; b) NH$_2$(CH$_2$)$_2$OTBDMS, Pd(OAc)$_2$, Cs$_2$CO$_3$, X—PHOS, Toluene, 120° C., 12 h; c) DCM, Et$_3$N, RT, 1 h; d) TBAF, THF, RT, 1 h; e) CH$_3$CN, Et$_3$N, 80° C., 16 h; f) NH$_3$, Dioxane, RT, 2 h.

Procedures:

4-Amino-6-(1-(6-(trifluoromethyl)pyridin-3-yl)-1H-indol-5-yl)-7,8-dihydropyrimido[5,4-f][1,4]oxazepin-5(6H)-one 5-Bromo-1-(6-(trifluoromethyl)pyridin-3-yl)-1H-indole (83A)

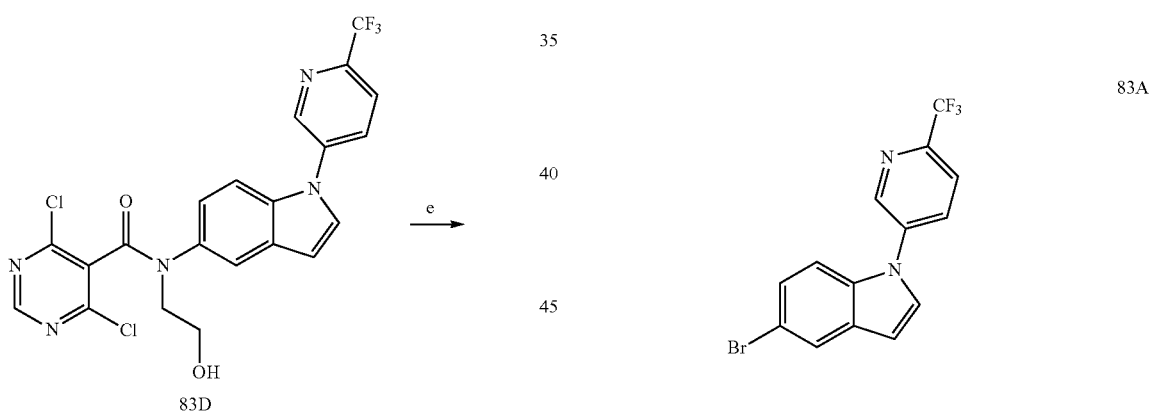

5-Bromo-2-(trifluoromethyl)pyridine (2.075 g, 9.18 mmol) was added to a solution of 5-bromo-1H-indole (1.5 g, 7.65 mmol) and in DMF (20 mL) followed by cesium carbonate (7.48 g, 22.95 mmol), and the mixture was stirred at 90° C. for 15 min. Insoluble solids were filtered, filtrate was concentrated and partitioned between ethyl acetate and water. Organic layer was separated, washed with brine, dried over sodium sulphate and filtered. The filtrate was concentrated in vacuo and purified by flash chromatography using 5% ethyl acetate in pet ether to afford title compound (1.1 g, 42.1%) as an off-white solid. $^1$H NMR (300 MHz, DMSO-d$_6$): δ 9.09 (d, J=2.4 Hz, 1H), 8.37 (dd, J$_1$=2.4 Hz, J$_2$=8.4 Hz, 1H), 8.11 (d, J=8.4 Hz, 1H), 7.91 (m, 2H), 7.68 (d, J=9.0 Hz, 1H), 7.37 (dd, J$_1$=1.8 Hz, =8.4 Hz, 1H), 6.82 (d, J=3.0 Hz, 1H).

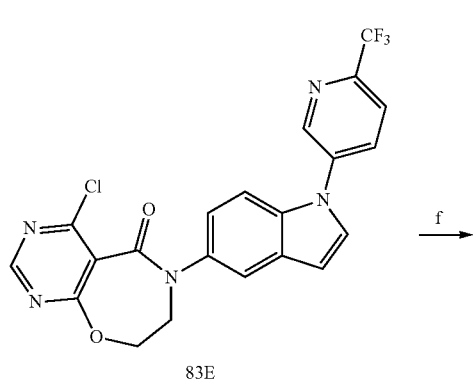

N-(2-(tert-Butyldimethylsilyloxy)ethyl)-1-(6-(trifluoromethyl)pyridin-3-yl)-1H-indol-5-amine (83B)

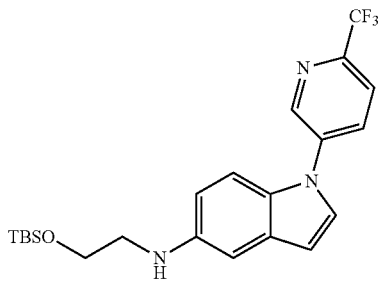

A mixture of product of Example 83A (0.3 g, 0.879 mmol), 2-(tert-butyldimethylsilyloxy)ethanamine (0.231 g, 1.319 mmol), cesium carbonate (0.86 g, 2.64 mmol), palladium acetate (19 mg, 0.088 mmol) and X-PHOS (0.042 g, 0.088 mmol) in Toluene (25 mL) under Argon was refluxed at 110° C. for 12 h. The reaction was cooled, diluted with ethyl acetate, and washed with water (2×15 mL) and saturated aqueous brine. The organic layer was dried over sodium sulfate, filtered and concentrated to obtain dark oil. The residue was purified by flash chromatography using 7% ethyl acetate in hexane to afford title compound (0.15 g, 39.2%) as a pale yellow solid. $^1$H NMR (400 MHz, DMSO-$d_6$): δ 9.04 (d, J=2.4 Hz, 1H), 8.29 (dd, $J_1$=2.4 Hz, $J_2$=8.8 Hz, 1H), 8.03 (d, J=8.8 Hz, 1H), 7.70 (d, J=3.2 Hz, 1H), 7.50 (d, J=8.8 Hz, 1H), 6.78 (d, J=2.0 Hz, 1H), 6.68 (dd, $J_1$=2.0 Hz, $J_2$=8.8 Hz, 1H), 6.59 (d, J=3.2 Hz, 1H), 5.22 (t, J=6.0 Hz, 1H) 3.76 (t, J=6.0 Hz, 2H), 3.18 (q, J=6.0, 2H), 0.88 (s, 9H), 0.05 (s, 6H).

N-(2-(tert-Butyldimethylsilyloxy)ethyl)-4,6-dichloro-N-(1-(6-(trifluoromethyl)pyridin-3-yl)-1H-indol-5-yl)pyrimidine-5-carboxamide (83C)

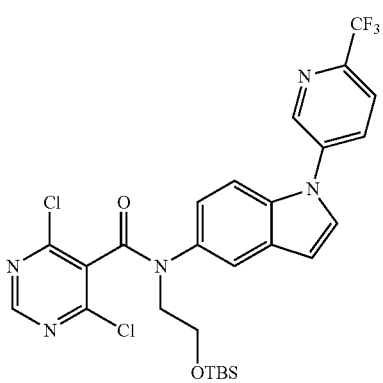

To a stirred, cooled (0° C.) solution of product of Example 83B (0.5 g, 1.148 mmol) and TEA (0.8 mL, 5.74 mmol) in DCM (10 mL) was added drop wise a solution of 4,6-dichloropyrimidine-5-carbonyl chloride (0.362 g, 1.72 mmol) in DCM (3 mL). After 1 h, the reaction was concentrated in vacuo, diluted with ethyl acetate, and washed with water (2×5 mL) and saturated aqueous brine. The organic layer was dried over sodium sulphate, filtered and concentrated in vacuo to afford oil. The residue was purified by flash chromatography using 10% ethyl acetate in hexane as eluent to afford title compound (0.5 g, 57.5%) as pale yellow solid. $^1$H NMR (400 MHz, DMSO-$d_6$): δ 9.02 (d, J=2.0 Hz, 1H), 8.75 (s, 1H), 8.31 (dd, $J_1$=2.0 Hz, $J_2$=8.4 Hz, 1H), 8.06 (d, J=8.4 Hz, 1H), 7.90 (d, J=3.6 Hz, 1H), 7.79 (d, J=2.0 Hz, 1H), 7.65 (d, J=8.8 Hz, 1H), 7.28 (dd, $J_1$=1.2 Hz, $J_2$=8.8 Hz, 1H), 6.80 (d, J=3.2 Hz, 1H), 4.01 (t, J=4.4 Hz, 2H) 3.79 (t, J=5.6 Hz, 2H), 0.8 (s, 9H), 0.04 (s, 6H).

4,6-Dichloro-N-(2-hydroxyethyl)-N-(1-(6-(trifluoromethyl)pyridin-3-yl)-1H-indol-5-yl)pyrimidine-5-carboxamide (83D)

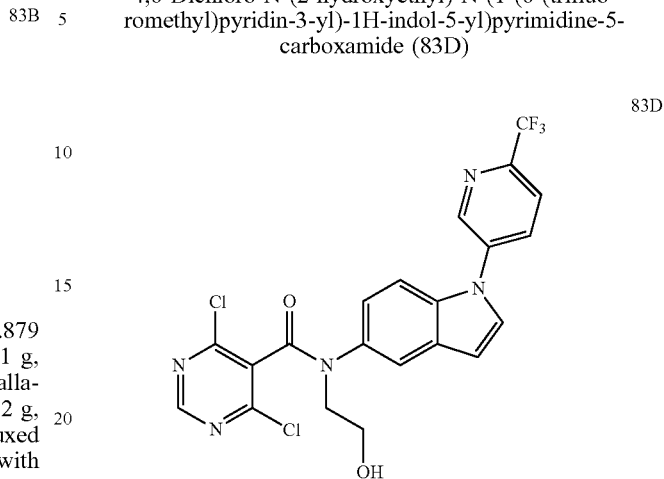

A solution of product of Example 83C (0.5 g, 0.819 mmol), in 15 mL of methanolic solution of HCl (3 mL concentrated aqueous HCl in 97 mL of methanol) was stirred at room temperature for 3 h. Methanol was removed in vacuo, the residue was dissolved in ethyl acetate, and washed with saturated aqueous sodium bicarbonate and saturated aqueous brine. The organic layer was dried over sodium sulfate, filtered and concentrated in vacuo to afford title compound (0.3 g, 67.5%) as a white solid, which was carried on to the next step without further purification. $^1$H NMR (400 MHz, DMSO-$d_6$): δ 9.03 (d, J=1.6 Hz, 1H), 8.74 (s, 1H), 8.33 (dd, $J_1$=2.0 Hz, $J_2$=8.4 Hz, 1H), 8.07 (d, J=8.4 Hz, 1H), 7.90 (d, J=3.2 Hz, 1H), 7.80 (d, J=2.0 Hz, 1H), 7.65 (d, J=8.8 Hz, 1H), 7.30 (dd, $J_1$=2.0 Hz, $J_2$=8.8 Hz, 1H), 6.83 (d, J=2.8 Hz, 1H), 4.87 (m, 1H) 3.95 (t, J=6.4 Hz, 2H), 3.63 (m, 2H).

4-Chloro-6-(1-(6-(trifluoromethyl)pyridin-3-yl)-1H-indol-5-yl)-7,8-dihydropyrimido[5,4-f][1,4]oxazepin-5(6H)-one (83E)

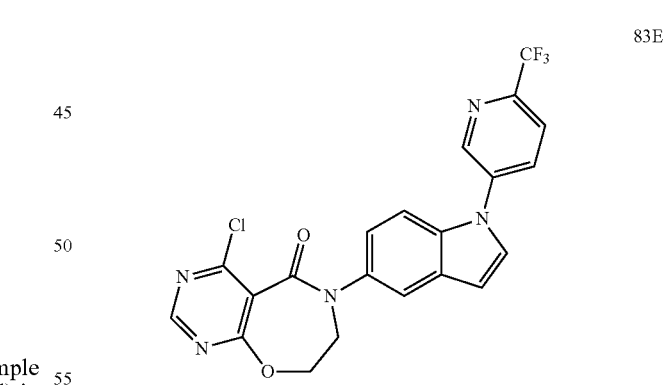

A slurry of product of Example 83D (0.3 g, 0.605 mmol) and TEA (0.42 mL, 3.02 mmol) in acetonitrile (25 mL) was stirred at 80° C. for 12 h. The reaction was cooled, concentrated in vacuo, diluted with ethyl acetate, and washed with water and saturated aqueous brine. The organic layer was dried over sodium sulfate, filtered and concentrated in vacuo to afford title compound (0.2 g, 69.4%) as a white solid. $^1$H NMR (400 MHz, DMSO-$d_6$): δ 9.12 (d, J=2.4 Hz, 1H), 8.84 (s, 1H), 8.40 (dd, $J_1$=2.4 Hz, $J_2$=8.8 Hz, 1H), 8.13 (d, J=8.4 Hz, 2H), 7.95 (d, J=3.6 Hz, 1H), 7.80 (s, 1H), 7.77 (d, J=2.4 Hz, 2H), 7.30 (dd, $J_1$=2.0 Hz, $J_2$=8.8 Hz, 1H), 6.89 (d, J=2.8 Hz, 1H), 4.78 (t, J=5.2 Hz, 2H), 4.19 (t, J=4.8 Hz, 2H).

4-Amino-6-(1-(6-(trifluoromethyl)pyridin-3-yl)-1H-indol-5-yl)-7,8-dihydropyrimido[5,4-f][1,4]oxazepin-5(6H)-one (83)

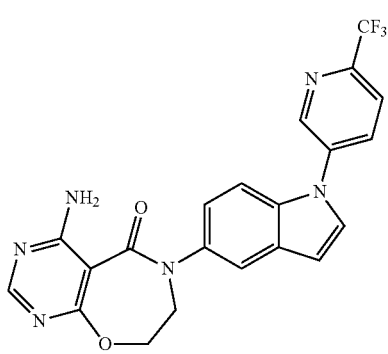

A solution of product of Example 83E (0.21 g, 0.457 mmol) in 0.5M ammonia in p-dioxane (10 mL) was stirred at room temperature for 4 h. The reaction mixture was concentrated in vacuo, diluted with ethyl acetate, and washed with water and saturated aqueous brine. The organic layer was dried over sodium sulfate, filtered and concentrated in vacuo to afford title compound (0.135 g, 65.6%) as a white solid $^1$H NMR (400 MHz, DMSO-$d_6$): δ 9.12 (d, J=2.4 Hz, 1H), 8.40 (dd, $J_1$=2.4 Hz, $J_2$=8.8 Hz, 1H), 8.18 (s, 1H), 8.12 (d, J=8.4 Hz, 1H), 7.93 (d, J=3.6 Hz, 1H), 7.75 (d, J=8.8 Hz, 1H), 7.69 (d, J=2.0 Hz, 1H), 7.64 (bs, 2H), 7.25 (dd, $J_1$=1.6 Hz, $J_2$=8.8 Hz, 1H), 6.86 (d, J=2.8 Hz, 1H), 4.66 (t, J=4.0 Hz, 2H), 4.02 (t, J=5.2 Hz, 2H). ESI-MS m/z: 441 (M+H)$^+$; HPLC purity: 97%.

Examples 84-93 were prepared by the procedures analogous to those described in Example 82 or Example 83 using appropriately substituted starting materials.

| Ex | Structure | Analytical Data | Mass/Purity |
|---|---|---|---|
| 84 | 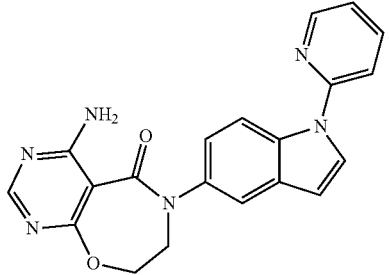 [SMILES: Nc1ncnc2c1C(=O)N(c1ccc3c(ccn3-c3ccccn3)c1)CCO2] | $^1$H NMR (400 MHz, DMSO-$d_6$): δ 8.59 (d, J = 3.2 Hz, 1H), 8.44 (d, J = 8.8 Hz, 1H), 8.19 (s, 1H), 8.11 (d, J = 3.2 Hz, 1H), 8.01 (dt, $J_1$ = 1.6 Hz, $J_2$ = 8.4 Hz, 1H), 7.80 (d, J = 8.0 Hz, 1H), 7.64 (m, 3H), 7.33 (m, 1H), 7.26 (dd, $J_1$ = 2.0 Hz, $J_2$ = 8.8 Hz, 1H), 6.79 (d, J = 3.6 Hz, 1H), 4.66 (t, J = 3.6 Hz, 2H), 4.03 (t, J = 4.4 Hz, 2H). | ESI-MS m/z = 373 (M + H)$^+$; HPLC purity: 98%. |
| 85 | 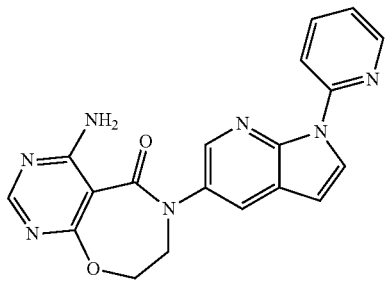 [SMILES: Nc1ncnc2c1C(=O)N(c1cnc3c(ccn3-c3ccccn3)c1)CCO2] | $^1$H NMR (400 MHz, CDCl$_3$): δ 8.86 (d, J = 8.4 Hz, 1H), 8.50 (d, J = 3.6 Hz, 1H), 8.45 (d, J = 4.0 Hz, 1H), 8.32 (m, 2H), 8.20 (bs, 1H), 7.88 (dt, $J_1$ = 2.0 Hz, $J_2$ = 8.8 Hz, 2H), 7.20 (m, 1H), 6.67 (d, J = 4.0 Hz, 1H), 5.70 (bs, 1H), 4.77 (t, J = 4.4 Hz, 2H), 4.10 (t, J = 4.4 Hz, 2H). | ESI-MS m/z = 374 (M + H)$^+$; HPLC purity: 98%. |
| 86 | 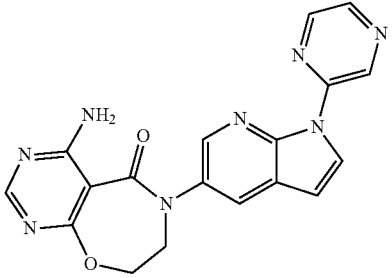 [SMILES: Nc1ncnc2c1C(=O)N(c1cnc3c(ccn3-c3cnccn3)c1)CCO2] | $^1$H NMR (300 MHz, DMSO-$d_6$): δ 10.1 (d, J = 1.2 Hz, 1H), 8.64-8.6 (m, 2H), 8.49 (d, J = 2.4 Hz, 1H), 8.40 (d, J = 3.9 Hz, 1H), 8.20 (m, 2H), 7.68 (bs, 2H), 6.91 (d, J = 4.2 Hz, 1H), 4.71 (t, J = 3.6 Hz, 2H), 4.09 (t, J = 4.5 Hz, 2H). | ESI-MS m/z = 375 (M + H)$^+$; HPLC purity: 98%. |

-continued

| Ex | Structure | Analytical Data | Mass/Purity |
|---|---|---|---|
| 87 | 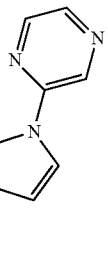 | $^1$H NMR (400 MHz, DMSO-d$_6$): δ 9.21 (s, 1H), 8.63 (s, 1H), 8.55 (d, J = 2.4 Hz, 1H), 8.48 (d, J = 8.8 Hz, 1H), 8.26 (d, J = 3.6 Hz, 1H), 8.19 (s, 1H), 7.67 (d, J = 1.6 Hz, 1H), 7.63 (bs, 2H), 7.30 (dd, J$_1$ = 2.0 Hz, J$_2$ = 8.8 Hz, 1H), 6.87 (d, J = 3.6 Hz, 1H), 4.66 (t, J = 4.4 Hz, 2H), 4.03 (t, J = 5.2 Hz, 2H). | ESI-MS m/z = 374 (M + H)$^+$; HPLC purity: 98%. |
| 88 | 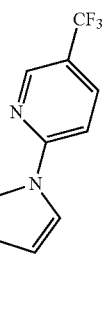 | $^1$H NMR (300 MHz, DMSO-d$_6$): δ 8.9 (s, 1H), 8.59 (d, J = 9.0 Hz, 1H), 8.39 (dd, J$_1$ = 2.4 Hz, J$_2$ = 9.0 Hz, 1H), 8.24 (d, J = 3.3 Hz, 1H), 8.19 (s, 1H), 8.05 (d, J = 8.4 Hz, 1H), 7.67 (d, J = 1.8 Hz, 1H), 7.63 (bs, 2H), 7.32 (dd, J = 1.8 Hz, J$_2$ = 8.7 Hz, 1H), 6.88 (d, J = 3.3 Hz, 1H), 4.66 (t, J = 4.2 Hz, 2H), 4.04 (t, J = 4.2 Hz, 2H). | ESI-MS m/z = 441 (M + H)$^+$; HPLC purity: 94%. |
| 89 | 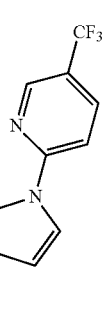 | $^1$H NMR (400 MHz, DMSO-d$_6$): δ 9.18 (d, J = 8.8 Hz, 1H), 8.94 (s, 1H), 8.85 (s, 1H), 8.53 (m, 2H), 8.49 (dd, J$_1$ = 2.0 Hz, J$_2$ = 8.8 Hz, 1H), 8.28 (d, J = 2.4 Hz, 1H), 6.93 (d, J = 4.0 Hz, 1H), 4.82 (t, J = 4.4 Hz, 2H), 4.27 (t, J = 4.8 Hz, 2H). | ESI-MS m/z = 442 (M + H)$^+$; HPLC purity: 98%. |
| 90 | 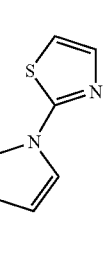 | $^1$H NMR (300 MHz, DMSO-d$_6$): δ 8.52 (d, J = 2.1 Hz, 1H), 8.37 (d, J = 3.9 Hz, 1H), 8.22 (d, J = 2.4 Hz, 1H) 8.19 (s, 1H), 7.69 (m, 3H), 7.58 (d, J = 3.6 Hz, 1H), 6.90 (d, J = 3.6 Hz, 1H), 4.71 (t, J = 4.2 Hz, 2H), 4.09 (t, J = 4.2 Hz, 2H). | ESI-MS m/z = 380 (M + H)$^+$; HPLC purity: 95%. |
| 93 | 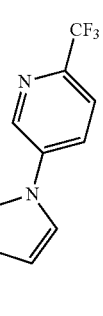 | $^1$H NMR (300 MHz, DMSO-d$_6$): δ 9.46 (d, J = 1.8 Hz, 1H), 8.8 (dd, J$_1$ = 2.1 Hz, J$_2$ = 8.4 Hz, 1H), 8.42 (d, J = 2.1 Hz, 1H), 8.28 (d, J = 3.6 Hz, 1H), 8.19 (m, 2H), 8.14 (d, J = 8.4 Hz, 2H), 7.68 (bs, 2H), 6.91 (d, J = 3.9 Hz, 1H), 4.71 (t, J = 4.2 Hz, 2H), 4.07 (t, J = 4.2 Hz, 2H). | ESI-MS m/z: 442 (M + H)$^+$; HPLC purity: 96%. |

Example 94

4-Amino-6-(3-isopropyl-1-phenyl-1H-indol-5-yl)-7,8-dihydropyrimido[5,4-f][1,4]oxazepin-5(6H)-one

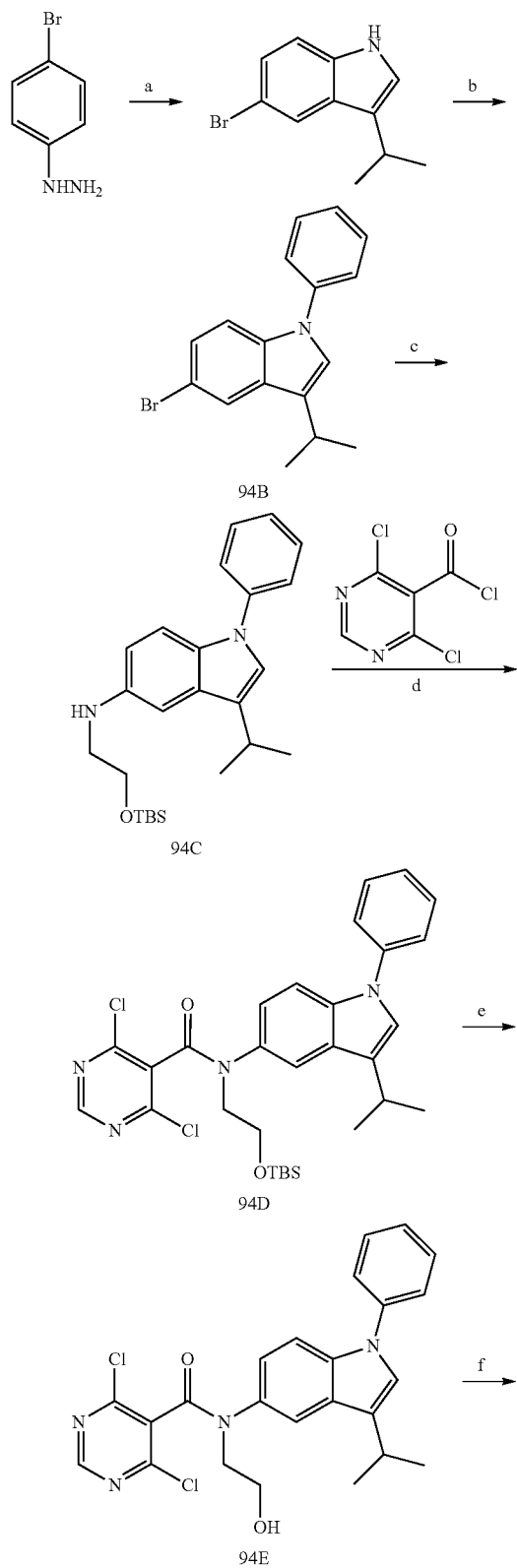

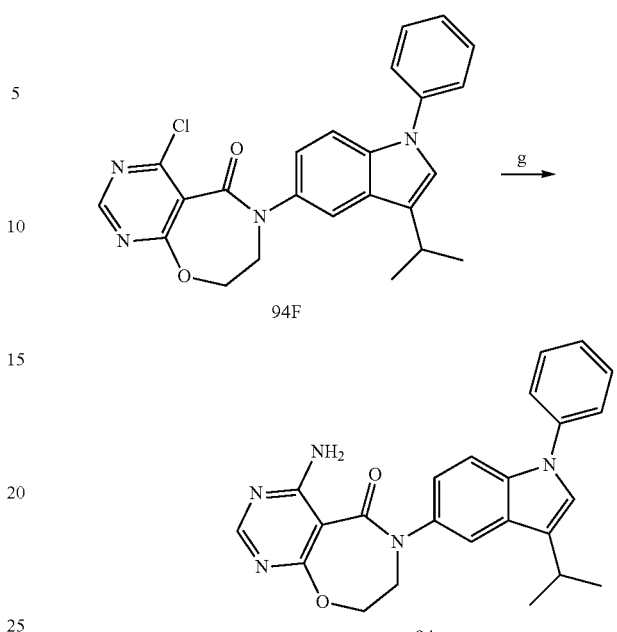

Reagents and conditions: a) Iso-valeraldehyde, AcOH, 120° C., 3 h  b) Iodobenzene, CuBr, Cu(OAc)$_2$, K$_2$CO$_3$, NaOH, 140° C., 9 h; c) NH$_2$(CH$_2$)$_2$OTBDMS, Pd(OAc)$_2$, Cs$_2$CO$_3$, X—PHOS, Toluene, 120° C., 2.5 h; d) DCM, Et$_3$N, RT, 1 h; e) 3% HCl—MeOH, RT, 1 h; f) CH$_3$CN, Et$_3$N, 80° C., 16 h; g) NH$_3$, Dioxane, RT, 2 h.

Procedures:

4-Amino-6-(3-isopropyl-1-phenyl-1H-indol-5-yl)-7,8-dihydropyrimido[5,4-f][1,4]oxazepin-5(6H)-one

5-Bromo-3-isopropyl-1H-indole (94A)

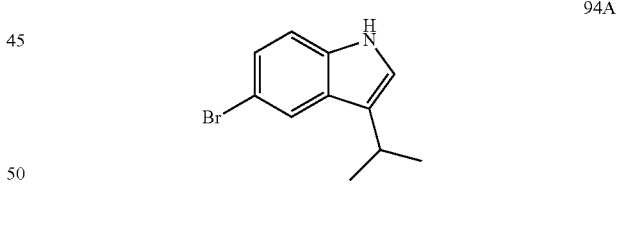

3-Methylbutanal (0.921 g, 10.69 mmol) was added to a solution of (4-bromophenyl)hydrazine (2 g, 10.69 mmol) in acetic acid (100 mL) at 80° C., and the mixture was stirred for 3 h at 120° C. The reaction mixture was concentrated to get the residue, and the residue was partitioned between ethyl acetate and water. Organic layer was separated, washed with saturated bicarbonate solution and brine, dried over sodium sulphate and filtered. The filtrate was concentrated in vacuo and purified by flash chromatography using 2% ethyl acetate in pet ether to afford title compound (1.1 g, 38.4%) as an oil. $^1$H NMR (400 MHz, CDCl$_3$): δ 7.91 (bs, 1H), 7.76 (m, 1H), 7.25-7.20 (m, 2H), 6.95 (d, J=2.4 Hz, 1H), 3.18-3.11 (m, 1H), 1.35 (d, J=6.8 Hz, 6H).

5-Bromo-3-isopropyl-1-phenyl-1H-indole (94B)

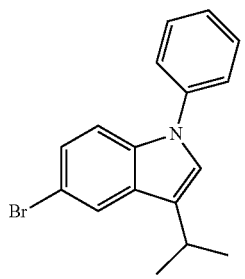

94B

Copper(I) bromide (66 mg, 0.462 mmol) was added to a solution of 94A (1.1 g, 4.62 mmol) in iodo benzene (3.77 g, 18.48 mmol) followed by potassium carbonate (2.55 g, 18.48 mmol), and the mixture was stirred at 100° C. for 10 min. NaOH (150 mg, 3.75 mmol) and copper(II) acetate (10 mg, 0.055 mmol) was added at 140° C., and the mixture was stirred for 9 h. Insoluble solids were filtered, the filtrate was concentrated and partitioned between ethyl acetate and water. Organic layer was separated, washed with brine, dried over sodium sulphate and filtered. The filtrate was concentrated in vacuo and purified by flash chromatography using 8% ethyl acetate in hexane to afford title compound (1.0 g, 68.9%) as an oil. $^1$H NMR (300 MHz, CDCl$_3$): δ 7.80 (d, J=2.1 Hz, 1H), 7.54-7.42 (m, 5H), 7.4-7.28 (m, 2H), 7.21-7.08 (m, 2H), 3.19 (m, 1H), 1.38 (d, J=6.9 Hz, 6H).

N-(2-(tert-Butyldimethylsilyloxy)ethyl)-3-isopropyl-1-phenyl-1H-indol-5-amine (94C)

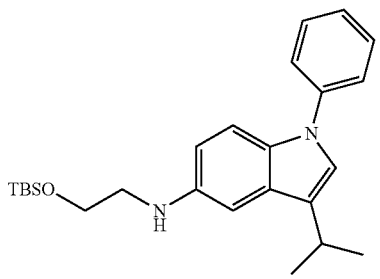

94C

A mixture of product of Example 94B (1 g, 3.18 mmol), 2-(tert-butyldimethylsilyloxy)ethanamine (0.558 g, 3.18 mmol), cesium carbonate (2.074 g, 6.36 mmol), palladium acetate (0.071 g, 0.318 mmol) and X-PHOS (0.152 g, 0.318 mmol) in Toluene (20 mL) under Argon was refluxed at 120° C. for 2.5 h. The reaction was cooled, diluted with ethyl acetate, and washed with water (2×15 mL) and saturated aqueous brine. The organic layer was dried over sodium sulfate, filtered and concentrated to obtain dark oil. The residue was purified by flash chromatography using 10% ethyl acetate in hexane to afford title compound (0.6 g, 46.1%) as an oil. $^1$H NMR (400 MHz, CDCl$_3$): δ 7.47-7.46 (m, 4H), 7.28 (m, 1H), 7.18 (m, 1H), 7.05 (s, 1H), 6.94 (m, 1H), 6.70 (dd, J$_1$=2.0 Hz, J$_2$=8.0 Hz, 1H), 3.87 (t, J=5.6 Hz, 2H), 3.31 (t, J=5.6 Hz, 2H), 3.18 (m, 1H), 1.38 (d, J=7.2 Hz, 6H), 0.92 (s, 9H), 0.09 (s, 6H).

N-(2-(tert-Butyldimethylsilyloxy)ethyl)-4,6-dichloro-N-(3-isopropyl-1-phenyl-1H-indol-5-yl)pyrimidine-5-carboxamide (94D)

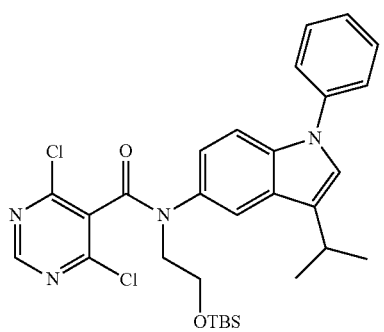

94D

To a stirred, cooled (0° C.) solution of product of Example 94C (0.6 g, 1.468 mmol) and TEA (1.023 mL, 7.34 mmol) in DCM (15 mL) was added drop wise a solution of 4,6-dichloropyrimidine-5-carbonyl chloride (0.31 g, 1.468 mmol) in DCM (5 mL). After 1 h, the reaction mixture was concentrated in vacuo, diluted with ethyl acetate, and washed with water (2×10 mL) and saturated aqueous brine. The organic layer was dried over sodium sulphate, filtered and concentrated in vacuo to afford an oil. The residue was purified by flash chromatography using 12% ethyl acetate in hexane to afford title compound (0.4 g, 46.7%) as a syrup.

4,6-Dichloro-N-(2-hydroxyethyl)-N-(3-isopropyl-1-phenyl-1H-indol-5-yl)pyrimidine-5-carboxamide (94E)

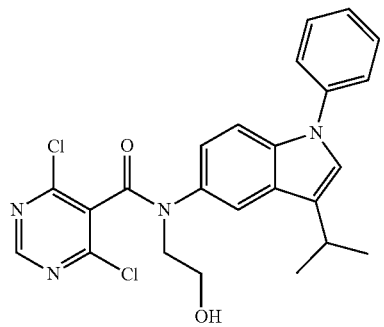

94E

TBAF (0.358 g, 1.371 mmol) was added to a solution of Example 94D (0.4 g, 0.685 mmol) in THF (15 mL), and the mixture was stirred at room temperature for 1 h. THF was removed in vacuo, the residue was dissolved in ethyl acetate, and washed with saturated aqueous sodium bicarbonate and saturated aqueous brine. The organic layer was dried over sodium sulfate, filtered and concentrated in vacuo to afford title compound (0.2 g, 62.2%) as a solid, which was carried on to the next step without further purification.

115

4-Chloro-6-(3-isopropyl-1-phenyl-1H-indol-5-yl)-7,8-dihydropyrimido[5,4-f][1,4]oxazepin-5(6H)-one
(94F)

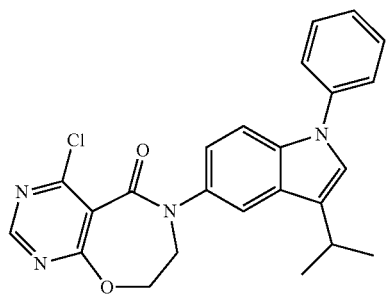

94F

A slurry of product of Example 94E (0.2 g, 0.426 mmol) and TEA (0.297 mL, 2.131 mmol) in acetonitrile (15 mL) was stirred at 80° C. for 16 h. The reaction was cooled, concentrated in vacuo, diluted with ethyl acetate, and washed with water and saturated aqueous brine. The organic layer was dried over sodium sulfate, filtered and concentrated in vacuo to afford title compound (0.1 g, 54.2%) as a white solid. $^1$H NMR (300 MHz, CDCl$_3$): δ 8.77 (s, 1H), 7.65 (d, J=2.1 Hz, 1H), 7.60-7.48 (m, 5H), 7.4-7.3 (m, 1H), 7.19-7.12 (m, 2H), 4.95 (t, J=3.9 Hz, 1H), 4.02 (t, J=4.5 Hz, 2H), 3.25-3.21 (m, 1H), 1.36 (d, J=7.2 Hz, 6H).

4-Amino-6-(3-isopropyl-1-phenyl-1H-indol-5-yl)-7,8-dihydropyrimido[5,4-f][1,4]oxazepin-5(6H)-one
(94)

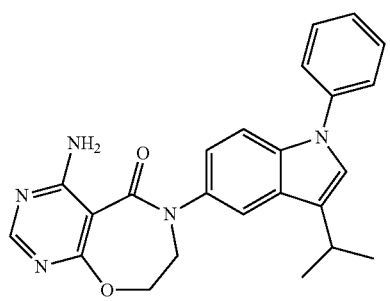

94

A solution of product of Example 94F (0.1 g, 0.231 mmol) in 0.5M ammonia in p-dioxane (10 mL) was stirred at room temperature for 2 h. The reaction mixture was concentrated in vacuo, diluted with ethyl acetate, and washed with water and saturated aqueous brine. The organic layer was dried over sodium sulfate, filtered and concentrated in vacuo to afford title compound (0.06 g, 61.6%) as a white solid. $^1$H NMR (300 MHz, DMSO-d$_6$): δ 8.18 (s, 1H), 7.64 (d, J=1.5 Hz, 1H), 7.66-7.54 (m, 6H), 7.47 (m, 1H), 7.38 (m, 1H), 7.14 (bs, 2H), 4.65 (t, J=3.9 Hz, 2H), 4.02 (t, J=4.5 Hz, 2H), 3.20 (m, 1H), 1.36 (d, J=7.2 Hz, 6H); ESI-LC MS m/z=414 (M+H)$^+$; HPLC purity: 98.30%.

116

Example 95

4-Amino-6-(2-phenyl-1-propyl-1H-indol-5-yl)-7,8-dihydropyrimido[5,4-f][1,4]oxazepin-5(6H)-one

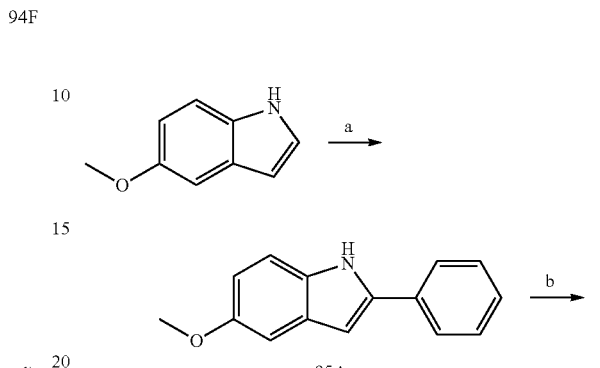

117
-continued

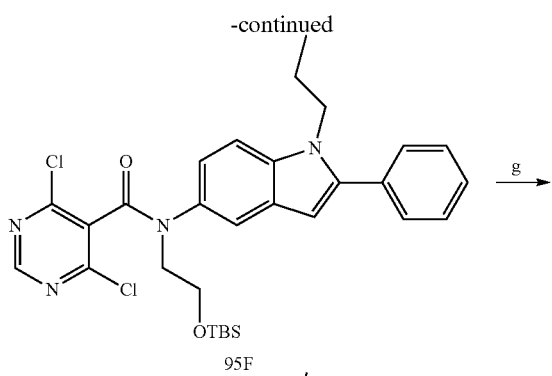
95F

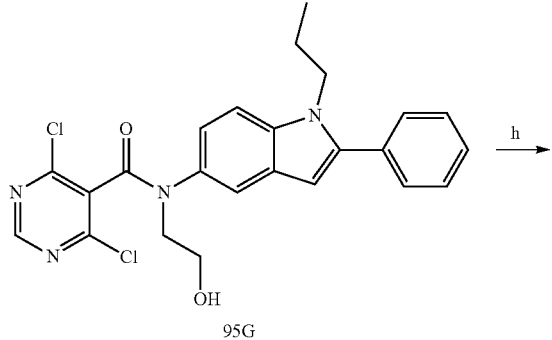
95G

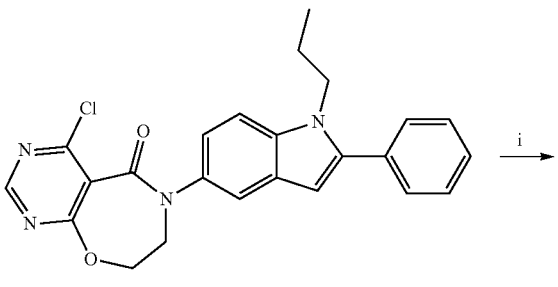
95H

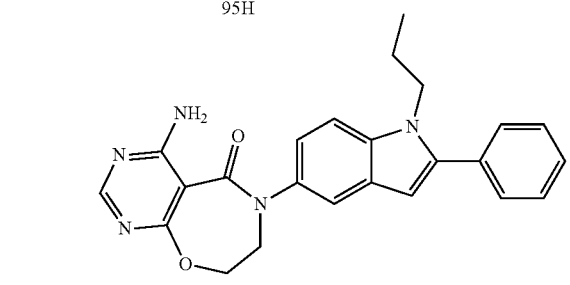
95

Reagents and conditions: a) Phenyl boronic acid, AcOH, Pd(OAc)₂, copper(II) acetate, 25° C. 12 h; b) Cs₂CO₃, DMF, 25° C., 12 h; c) BBr₃, DCM, 0° C., 1 h; d) Triflic anhydride, Py, DCM, 0° C., 1 h; e) NH₂(CH₂)₂OTBDMS, Pd(OAc)₂, Cs₂CO₃, X—PHOS, Toluene, 110° C., 4 h; f) Et₃N, DCM, 0° C., 1 h; g) MeOH/HCl, 25° C., 2 h; h) Et₃N, ACN, 70° C., 24 h; i) NH₃ gas, Dioxane, 25° C., 3 h.

Procedures:

4-Amino-6-(2-phenyl-1-propyl-1H-indol-5-yl)-7,8-dihydropyrimido[5,4-f][1,4]oxazepin-5(6H)-one 5-methoxy-2-phenyl-1H-indole (95A)

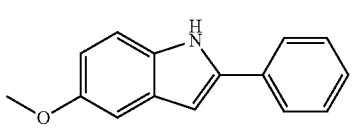
95A

118

Pd(OAc)₂ (0.031 g, 0.136 mmol) was added to a solution of 5-methoxy-1H-indole (0.2 g, 1.359 m mol) and phenylboronic acid (0.249 g, 2.038 mmol) in acetic acid (2 mL) followed by copper (II) acetate (0.025 g, 0.138 mmol), and the mixture was stirred at 25° C. for 2 h under oxygen atmosphere. Insoluble solids were filtered off, and filtrate was concentrated. Residue was partitioned between ethyl acetate and water. Organic layer was separated, washed with brine, dried over sodium sulphate, filtered and concentrated in vacuo. The crude product was purified by flash chromatography using 10% ethyl acetate in hexane to afford title compound (0.08 g, 24%) as a solid. ¹H NMR (400 MHz, DMSO-d₆): δ 11.3 (s, 1H), 7.82 (d, J=7.2 Hz, 2H), 7.44 (t, J=7.2 Hz, 2H), 7.32-7.26 (m, 2H), 7.02 (d, J=2.4 Hz 1H), 6.81 (d, J=1.2 Hz, 1H), 6.74 (dd, J₁=2.4 Hz, J₂=8.8 Hz, 1H) 3.78 (s, 3H).

5-Methoxy-2-phenyl-1-propyl-1H-indole (95B)

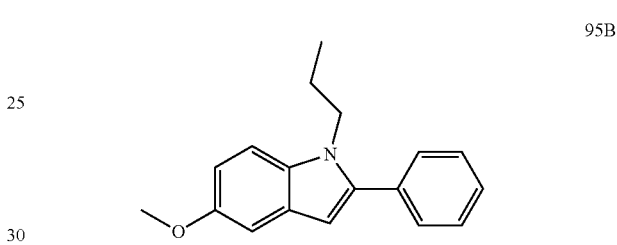
95B

1-Bromopropane (0.248 g, 2.015 mmol) was added to a solution of 95A (0.15 g, 0.672 mmol) in DMF (5 mL) followed by cesium carbonate (0.657 g, 2.015 mmol), and the mixture was stirred at 25° C. for 12 h. Insoluble solids were filtered off, and filtrate was concentrated. Residue was partitioned between ethyl acetate and water. Organic layer was separated, washed with brine, dried over sodium sulphate, filtered and concentrated in vacuo. The crude product was purified by flash chromatography using 3% ethyl acetate in hexane as eluent to afford title compound (0.1 g, 56.1%) as a solid. ¹H NMR (400 MHz, DMSO-d₆): δ 7.54-7.5 (m, 4H), 7.46-7.39 (m, 2H), 7.06 (d, J=2.0 Hz, 1H), 6.8 (dd, J₁=2.4 Hz, J₂=8.8 Hz, 1H), 6.42 (s, 1H), 4.12 (t, J=7.2 Hz, 2H), 3.76 (s, 3H), 1.54 (m, 2H), 0.63 (t, J=7.2 Hz).

2-Phenyl-1-propyl-1H-indol-5-ol (95C)

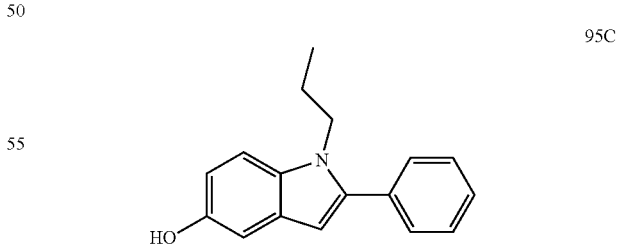
95C

BBr₃ (0.107 mL, 1.131 mmol) was added to a solution of Example 95B (0.1 g, 0.398 mmol) in DCM (20 mL) at 0° C., and the mixture was stirred for 1 h. The reaction mixture was quenched with saturated bicarbonate solution and extracted with DCM (2×30 mL). Organic layer was separated, washed with water and brine. The organic layer was dried over sodium sulphate, filtered and concentrated in vacuo. The crude product was triturated with diethyl ether to afford title compound (0.05 g, 52.8%) as white solid. $^1$H NMR (400 MHz, DMSO-$d_6$): δ 8.72 (s, 1H), 7.5 (m, 4H), 7.42 (m, 1H), 7.30 (d, J=8.8 Hz, 1H), 6.86 (d, J=2.4 Hz, 1H), 6.67 (dd, $J_1$=2.4 Hz, $J_2$=8.8 Hz, 1H), 6.32 (s, 1H), 4.07 (t, J=7.2 Hz, 2H), 1.53 (m, 2H), 0.64 (t, J=7.2 Hz, 3H).

2-Phenyl-1-propyl-1H-indol-5-yl trifluoromethanesulfonate (95D)

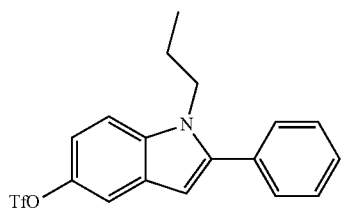

95D

Triflic anhydride (0.112 g, 0.398 mmol) was added to an ice cold solution of product of Example 95C (0.1 g, 0.398 mmol) and pyridine (0.048 mL, 0.597 mmol) in dichloromethane (20 mL), and the mixture was stirred at 0° C. for 1 h. The reaction mixture was diluted with dichloromethane (10 mL) and extracted with saturated aqueous solution of NaCl (45 mL). The organic layer was dried over sodium sulphate, filtered and evaporated under reduced pressure. The crude product was purified by flash chromatography using 6% ethyl acetate in hexanes to give the title compound (0.08 g, 52.4%) as a solid. $^1$H NMR (300 MHz, DMSO-$d_6$): δ 7.73 (d, J=9.0 Hz, 1H), 7.68 (d, J=2.7 Hz, 1H), 7.58-7.46 (m, 5H), 7.22 (dd, $J_1$=2.7 Hz, $J_2$=8.7 Hz, 1H), 6.65 (s, 1H), 4.20 (t, J=6.9 Hz, 2H), 1.56 (m, 2H), 0.65 (t, J=7.8 Hz, 3H).

N-(2-(tert-Butyldimethylsilyloxy)ethyl)-2-phenyl-1-propyl-1H-indol-5-amine (95E)

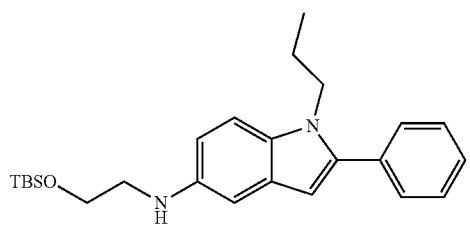

95E

A mixture of product of Example 95D (0.2 g, 0.522 mmol), 2-(tert-butyldimethylsilyloxy)ethanamine (0.183 g, 1.043 mmol), cesium carbonate (0.510 g, 1.565 mmol), palladium acetate (0.012 g, 0.052 mmol) and X-PHOS (0.0025 g, 0.052 mmol) in Toluene (20 mL) under Argon was refluxed at 111° C. for 4 h. The reaction was cooled, diluted with ethyl acetate, and washed with water (2×10 mL) and saturated aqueous brine The organic layer was dried over sodium sulfate, filtered and concentrated to obtain dark oil. The residue was purified by flash chromatography using 15% ethyl acetate in hexane to afford title compound (1.5 g, 53%) as a solid. $^1$H NMR (400 MHz, DMSO-$d_6$): δ 7.50 (m, 4H), 7.4 (m, 1H), 7.25 (d, J=8.4 Hz, 1H), 6.66 (d, J=1.6 Hz, 1H), 6.61 (dd, $J_1$=2.4 Hz, $J_2$=8.8 Hz, 1H), 6.27 (s, 1H), 4.91 (t, J=6.0 Hz, 1H), 4.05 (t, J=6.8 Hz, 2H), 3.76 (t, J=6.4 Hz, 2H), 3.16 (q, J=6.0 Hz, 2H), 1.52 (m, 2H), 0.87 (s, 9H), 0.63 (t, J=7.2 Hz, 3H), 0.059 (s, 6H).

N-(2-(tert-Butyldimethylsilyloxy)ethyl)-4,6-dichloro-N-(2-phenyl-1-propyl-1H-indol-5-yl)pyrimidine-5-carboxamide (95F)

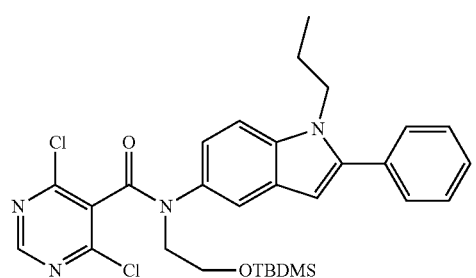

95F

To a stirred, cooled (0° C.) solution of product of Example 95E (0.04 g, 0.98 mmol) and TEA (0.041 mL, 0.294 mmol) in DCM (10 mL) was added drop wise a solution of 4,6-dichloropyrimidine-5-carbonyl chloride (0.030 g, 0.14 mmol) in DCM (3 mL). After 1 h, the reaction was concentrated in vacuo, diluted with ethyl acetate, and washed with water (2×10 mL) and saturated aqueous brine. The organic layer was dried over sodium sulphate, filtered and concentrated in vacuo to afford oil. The residue was purified by flash chromatography using 20% ethyl acetate in hexane as eluent to afford title compound (0.031 g, 32.1%) as a solid. $^1$H NMR (400 MHz, DMSO-$d_6$): δ 8.74 (s, 1H), 7.66 (d, J=2.0 Hz, 1H), 7.54-7.44 (m, 6H), 7.18 (dd, $J_1$=2.0, $J_2$=8.8 Hz, 1H), 6.48 (s, 1H), 4.09 (t, J=7.2 Hz, 2H), 3.99 (t, J=6.0 Hz, 2H), 3.8 (t, J=5.6 Hz, 2H), 1.46 (m, 2H), 0.85 (s, 9H), 0.59 (t, J=7.2 Hz, 3H), 0.04 (s, 6H).

4,6-Dichloro-N-(2-hydroxyethyl)-N-(2-phenyl-1-propyl-1H-indol-5-yl)pyrimidine-5-carboxamide (95G)

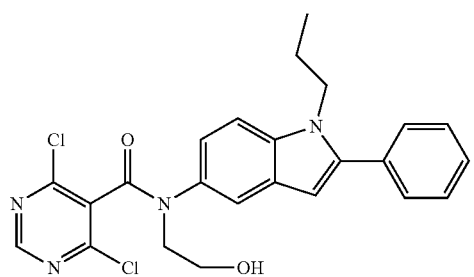

95G

A solution of product of Example 95F (0.35 g, 0.6 mmol), in 20 mL of methanolic solution of HCl (3 mL concentrated aqueous HCl in 97 mL of methanol) was stirred at room temperature for 2 h. Methanol was removed in vacuo, the residue was dissolved in ethyl acetate, and washed with saturated aqueous sodium bicarbonate solution and saturated aqueous brine. The organic layer was dried over sodium sulfate, filtered and concentrated in vacuo to afford title compound (0.225 g, 76%) as a solid, which was carried on to the next step without further purification. $^1$H NMR (400 MHz, DMSO-$d_6$): δ 8.73 (s, 1H), 7.66 (d, J=2.0 Hz, 1H), 7.53-7.43 (m, 6H), 7.20 (dd, $J_1$=2.0 Hz, $J_2$=8.4 Hz, 1H), 6.51 (s, 1H), 4.84 (t, J=5.2 Hz, 1H), 4.09 (t, J=7.6 Hz, 2H), 3.93 (t, J=6.4 Hz, 2H), 3.63 (q, J=6.0 Hz, 2H), 1.49 (m, 2H), 0.6 (t, J=7.2 Hz, 3H).

4-Chloro-6-(2-phenyl-1-propyl-1H-indol-5-yl)-7,8-dihydropyrimido[5,4-f][1,4]oxazepin-5(6H)-one (95H)

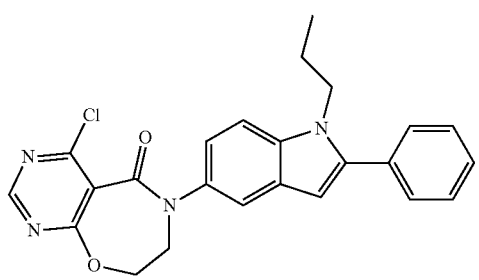

A slurry of product of Example 95G (0.225 g, 0.479 mmol) and TEA (0.334 mL, 2.397 mmol) in acetonitrile (15 mL) was stirred at 80° C. for 16 h. The reaction was cooled, concentrated in vacuo, diluted with ethyl acetate, and washed with water and saturated aqueous brine. The organic layer was dried over sodium sulfate, filtered and concentrated in vacuo to afford title compound (0.15 g, 72.3%) as a white solid. $^1$H NMR (400 MHz, DMSO-$d_6$): δ 8.83 (s, 1H), 7.64 (d, J=8.8 Hz, 1H), 7.61 (d, J=2.0 Hz, 1H), 7.58-7.44 (m, 5H), 7.19 (dd, $J_1$=2.0 Hz, $J_2$=8.4 Hz, 1H), 6.58 (s, 1H), 4.77 (t, J=5.2 Hz, 2H), 4.22-4.15 (m, 4H), 1.58 (m, 2H), 0.66 (t, J=7.6 Hz, 3H).

4-Amino-6-(2-phenyl-1-propyl-1H-indol-5-yl)-7,8-dihydropyrimido[5,4-f][1,4]oxazepin-5(6H)-one (95)

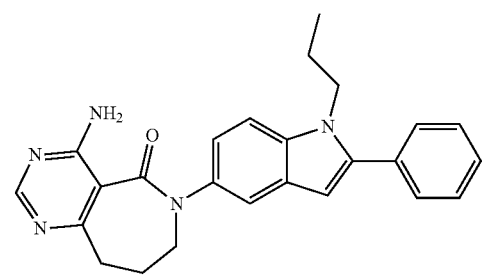

A solution of product of Example 95H (0.15 g, 0.346 mmol) in 0.5M ammonia in p-dioxane (20 mL) was stirred at room temperature for 2 h. The reaction mixture was concentrated in vacuo, diluted with ethyl acetate, and washed with water and saturated aqueous brine. The organic layer was dried over sodium sulfate, filtered and concentrated in vacuo to afford title compound (0.105 g, 71.1%) as a white solid. $^1$H NMR (400 MHz, DMSO-$d_6$): δ 8.18 (s, 1H), 7.68-7.44 (m, 9H), 7.15 (d, J=8.0 Hz, 1H), 6.55 (s, 1H), 4.65 (m, 2H), 4.19 (t, J=6.8 Hz, 2H), 4.01 (m, 2H), 1.58 (m, 2H), 0.68 (t, J=7.6 Hz, 3H); ESI-MS m/z=414.0 (M+H)$^+$; HPLC purity: 97%.

Example 96

4-Amino-6-(6-fluoro-1-phenyl-1H-indol-5-yl)-7,8-dihydrooxepino[2,3-d]pyrimidin-5(6H)-one

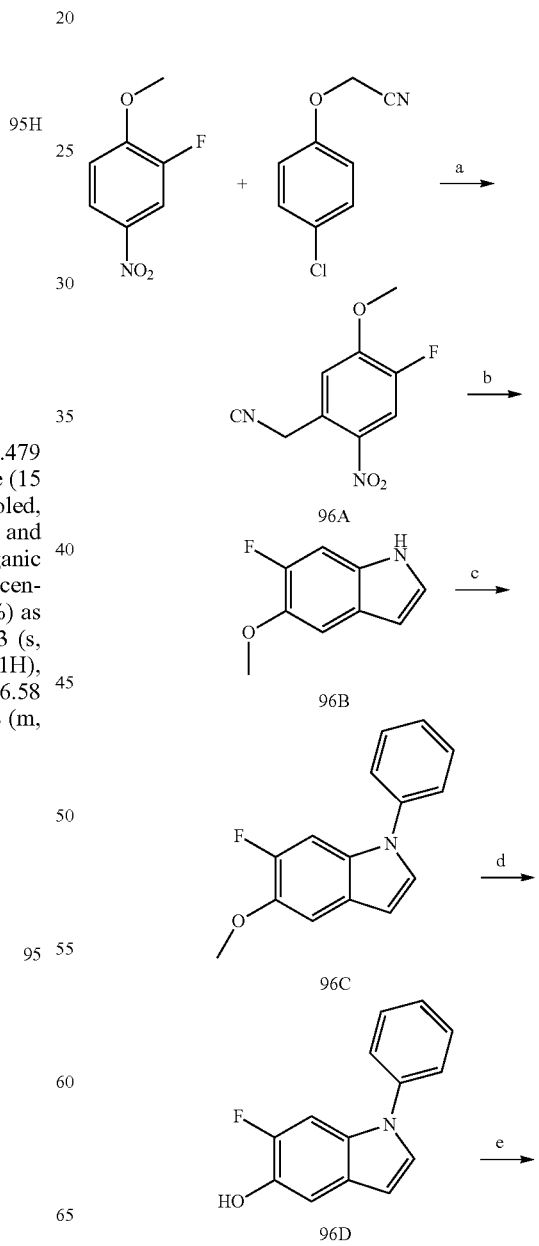

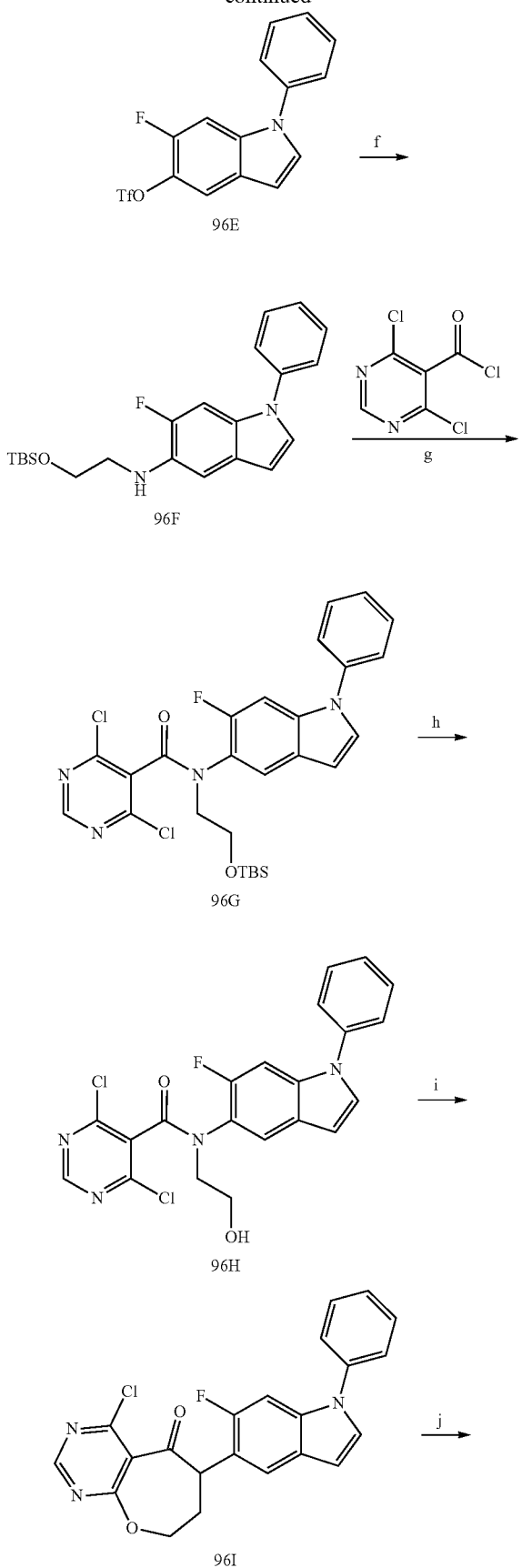

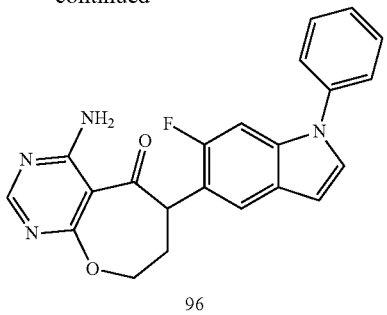

Reagents and conditions: a) K'Obu, DMF, -20° C., 1 h; b) 10% Pd/C, Ethanol, 27° C., 3 h; c) Cu(OAc)₂, CuBr, K₂CO₃, NaOH, DMF, 80° C., 16 h; d) Py/HCl, 180° C., 4 h; e) Tf₂O, Pyridine, DCM, 0° C., 0.5 h; f) Pd(OAc)₂, NH₂(CH₂)₂OTBDMS, Cs₂CO₃, X—PHOS, Toluene, 100° C., 4 h; g) DCM, Et₃N, RT, 3 h; h) 3% HCl—EtOH, RT, 1 h; i) CH₃CN, Et₃N, 80° C., 16 h; j) NH₃, Dioxane, RT, 6 h.

Procedures:

4-Amino-6-(6-fluoro-1-phenyl-1H-indol-5-yl)-7,8-dihydrooxepino[2,3-d]pyrimidin-5(6H)-one 1-Fluoro-4-(isocyanomethyl)-2-methoxy-5-nitrobenzene (96A)

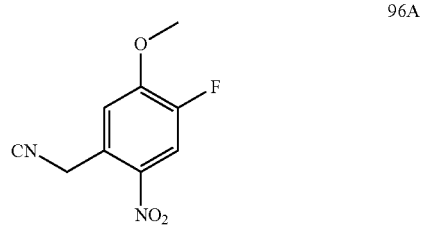

Potassium t-butoxide (15.74 g, 140 mmol) in DMF (50 mL) was added to a solution of 2-fluoro-1-methoxy-4-nitrobenzene (12 g, 70.1 mmol) and 2-(4-chlorophenoxy)acetonitrile (11.75 g, 70.1 mmol) in DMF (100 mL) at −20° C. The reaction mixture was stirred for 1 h and then quenched with water. The aqueous layer was extracted with ethyl acetate. Organic layer was separated, washed with brine, dried over sodium sulphate, filtered and concentrated in vacuo. The crude product was purified by flash chromatography using 3% ethyl acetate in hexane to afford title compound (3.6 g, 23.21%) as a solid. ¹H NMR (400 MHz, CDCl₃): δ 8.05 (d, J=10.84 Hz, 1H), 7.27-7.23 (m, 1H), 4.28 (s, 2H), 4.05 (s, 3H); ESI-MS m/z=209 (M−H)⁻; LCMS Purity: 95%

6-Fluoro-5-methoxy-1H-indole (96B)

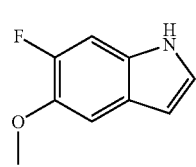

Palladium on carbon (1 g, 0.940 mmol) was added to a solution of product of Example 96A (3.5 g, 16.65 mmol) in ethanol (40 mL) under hydrogen atmosphere, and the mixture was stirred for 4 h. Insoluble solids were filtered off, and filtrate was concentrated to afford title compound (2.2 g, 78%) as a solid. $^1$H NMR (400 MHz, CDCl$_3$): δ 8.05 (bs, 1H), 7.20-7.11 (m, 3H), 6.48 (d, J=2.4 Hz, 1H), 3.95 (s, 3H).

6-Fluoro-5-methoxy-1-phenyl-1H-indole (96C)

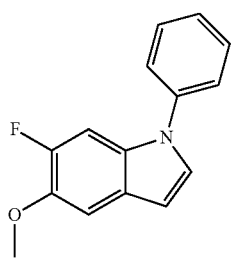

Iodo benzene (1.729 g, 8.48 mmol) was added to a solution of product of Example 96B (1.4 g, 8.48 mmol) and Copper(I) bromide (10.46 mg, 0.073 mmol) in DMF (10 mL) followed by potassium carbonate (3.51 g, 25.4 mmol), and the mixture was stirred at 100° C. for 10 min. NaOH (210 mg, 5.25 mmol) and copper(II) acetate (14 mg, 0.077 mmol) was added, and the mixture was stirred at 110° C. for 16 h. Insoluble solids were filtered off, and filtrate was concentrated. Residue was partitioned between diethyl ether and water. Organic layer was separated, washed with brine, dried over sodium sulphate, filtered and concentrated in vacuo. The crude product was purified by flash chromatography using 10% ethyl acetate in hexane as eluent to afford title compound (1.45 g, 67.4%) as off-white solid. $^1$H NMR (300 MHz, CDCl$_3$): δ 7.55-7.44 (m, 4H), 7.38-7.26 (m, 3H), 7.19 (d, J=8.1 Hz, 1H), 6.59 (d, J=2.7 Hz, 1H), 3.95 (s, 3H).

6-Fluoro-1-phenyl-1H-indol-5-ol (96D)

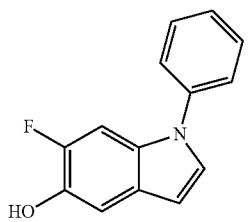

A mixture of product of Example 96C (1.1 g, 4.56 mmol) and pyridine-hydrochloride (0.527 g, 4.56 mmol) was stirred at 160° C. in seal tube for 6 h. The mixture was dissolved in ethyl acetate, washed with water and saturated aqueous brine, dried over sodium sulfate and filtered. The filtrate was concentrated in vacuo and purified by flash chromatography using 12% ethyl acetate in hexane to afford title compound (0.37 g, 32.5%) as a pale brown solid. $^1$H NMR (400 MHz, CDCl$_3$): δ 7.6 (d, J=6.8 Hz, 1H), 7.58-7.53 (m, 2H), 7.48-7.34 (m, 5H), 6.7 (d, J=3.6 Hz, 1H).

6-Fluoro-1-phenyl-1H-indol-5-yl trifluoromethanesulfonate (96E)

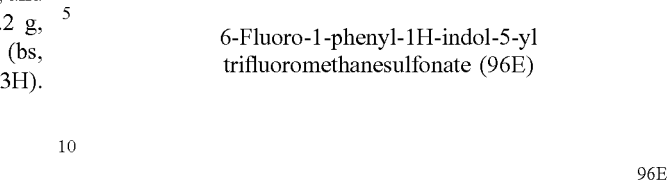

Triflic anhydride (0.372 g, 2.2 mmol) was added to an ice cold solution of product of Example 96D (0.5 g, 2.2 mmol) and pyridine (0.087 mg, 1.1 mmol) in dichloromethane (10 mL), and the mixture was stirred at room temperature for 1 h. The reaction mixture was diluted with dichloromethane (20 mL) and extracted with saturated aqueous solution of NaCl (15 mL). The organic layer dried over sodium sulphate, filtered and the filtrate was concentrated under reduced pressure to afford title compound (0.7 g, 89%) as an oil. ESI-MS m/z=360 (M+H)$^+$; LCMS Purity: 85%.

N-(2-(tert-Butyldimethylsilyloxy)ethyl)-6-fluoro-1-phenyl-1H-indol-5-amine (96F)

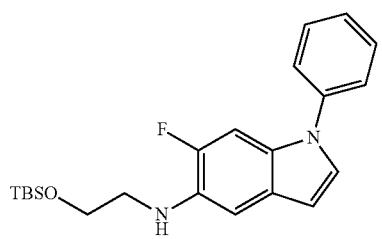

A mixture of product of Example 96E (0.1 g, 0.278 mmol), 2-(t-butyldimethylsilyloxy)ethanamine (0.048 g, 0.278 mmol), cesium carbonate (0.136 g, 0.417 mmol), palladium acetate (6.25 mg, 0.028 mmol) and X-PHOS (13.27 mg, 0.028 mmol) in toluene (10 mL) under Argon was refluxed at 120° C. for 2.5 h. The reaction was cooled, diluted with ethyl acetate, and washed with water (2×5 mL) and saturated aqueous brine. The organic layer was dried over sodium sulfate, filtered and concentrated to obtain dark oil. The residue was purified by flash chromatography using 10% ethyl acetate in hexane to afford title compound (0.03 g, 25%) as an off-white solid. $^1$H NMR (300 MHz, CDCl$_3$): δ 7.6-7.5 (m, 5H), 7.4-7.25 (m, 2H), 6.94 (d, J=8.4 Hz, 1H), 6.52 (d, J=3.0 Hz, 1H), 4.75 (m, 1H), 3.81 (t, J=5.7 Hz, 2H), 3.25 (q, J=5.7 Hz, 2H), 0.88 (s, 9H), 0.05 (s, 6H).

127

N-(2-(tert-Butyldimethylsilyloxy)ethyl)-4,6-dichloro-N-(6-fluoro-1-phenyl-1H-indol-5-yl)pyrimidine-5-carboxamide (96G)

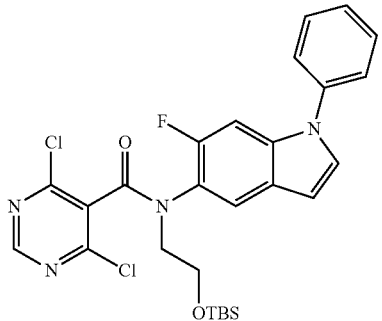

To a stirred, cooled (0° C.) solution of product of Example 96F (0.18 g, 0.468 mmol) and TEA (0.065 mL, 0.468 mmol) in DCM (8 mL) was added drop wise a solution of 4,6-dichloropyrimidine-5-carbonyl chloride (0.098 g, 0.468 mmol) in DCM (2 mL). After 1 h, the reaction was concentrated in vacuo, diluted with ethyl acetate, and washed with water (2×5 mL) and saturated aqueous brine. The organic layer was dried over sodium sulphate, filtered and concentrated in vacuo to afford oil. The residue was purified by flash chromatography using 20% ethyl acetate in hexane to afford title compound (100 mg, 38%) as a pale yellow oil.

4,6-Dichloro-N-(6-fluoro-1-phenyl-1H-indol-5-yl)-N-(2-hydroxyethyl)pyrimidine-5-carboxamide (96H)

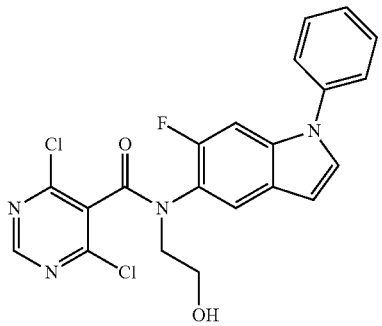

A solution of product of Example 96G (100 mg, 0.179 mmol), in 10 mL of ethanolic solution of HCl (3 mL concentrated aqueous HCl in 97 mL of ethanol) was stirred at room temperature for 1 h. Ethanol was removed in vacuo, the residue was dissolved in ethyl acetate, and washed with saturated aqueous sodium bicarbonate and saturated aqueous brine. The organic layer was dried over sodium sulfate, filtered and concentrated in vacuo to afford title compound (0.07 g, 77%) as an oil, which was carried on to the next step without further purification.

128

4-Chloro-6-(6-fluoro-1-phenyl-1H-indol-5-yl)-7,8-dihydrooxepino[2,3-d]pyrimidin-5(6H)-one (96I)

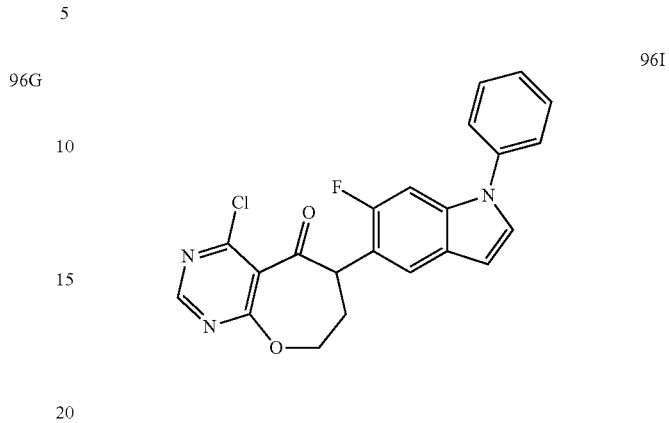

A slurry of product of Example 96H (0.07 g, 0.157 mmol) and TEA (0.022 mL, 0.157 mmol) in acetonitrile (8 mL) was stirred at 80° C. for 16 h. The reaction mixture was cooled, concentrated in vacuo, diluted with ethyl acetate, and washed with water and saturated aqueous brine. The organic layer was dried over sodium sulfate, filtered and concentrated in vacuo to afford title compound (0.067 g, 87%) as a pale yellow solid. $^1$H NMR (400 MHz, CDCl$_3$): δ 8.76 (s, 1H), 7.66 (d, J=7.2 Hz, 1H), 7.6-7.3 (m, 7H), 6.7 (d, J=2.8 Hz, 1H), 4.84 (t, J=4.4 Hz, 2H), 4.04 (t, J=4.4 Hz, 2H).

4-Amino-6-(6-fluoro-1-phenyl-1H-indol-5-yl)-7,8-dihydrooxepino[2,3-d]pyrimidin-5(6H)-one (96)

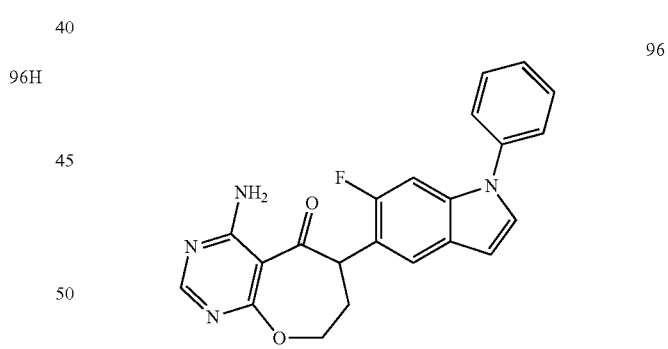

A solution of product of Example 96I (0.06 g, 0.147 mmol), in 0.5M ammonia in p-dioxane (8 mL) was stirred at room temperature for 1 h. The reaction mixture was concentrated in vacuo, diluted with ethyl acetate, and washed with water and saturated aqueous brine. The organic layer was dried over sodium sulfate, filtered and concentrated in vacuo to afford title compound (0.03 g, 48.8%) as a pale yellow solid. $^1$H NMR (400 MHz, DMSO-d$_6$): $^1$H NMR (400 MHz, DMSO-d$_6$): δ 8.19 (s, 1H), 7.76-7.56 (m, 7H), 7.5-7.4 (m, 3H), 6.76 (d, J=2.8 Hz, 1H), 4.64 (t, J=4.0 Hz, 2H), 4.0 (t, J=4.0 Hz, 2H); ESI-MS m/z=390 (M+H)$^+$; HPLC purity: 93%.

Example 97

4-Amino-6-(3-benzyl-4-oxo-3,4-dihydroquinazolin-6-yl)-7,8-dihydropyrimido[5,4-f][1,4]oxazepin-5(6H)-one

Example 98

4-Amino-6-(4-oxo-3,4-dihydroquinazolin-6-yl)-7,8-dihydropyrimido[5,4-f][1,4]oxazepin-5(6H)-one

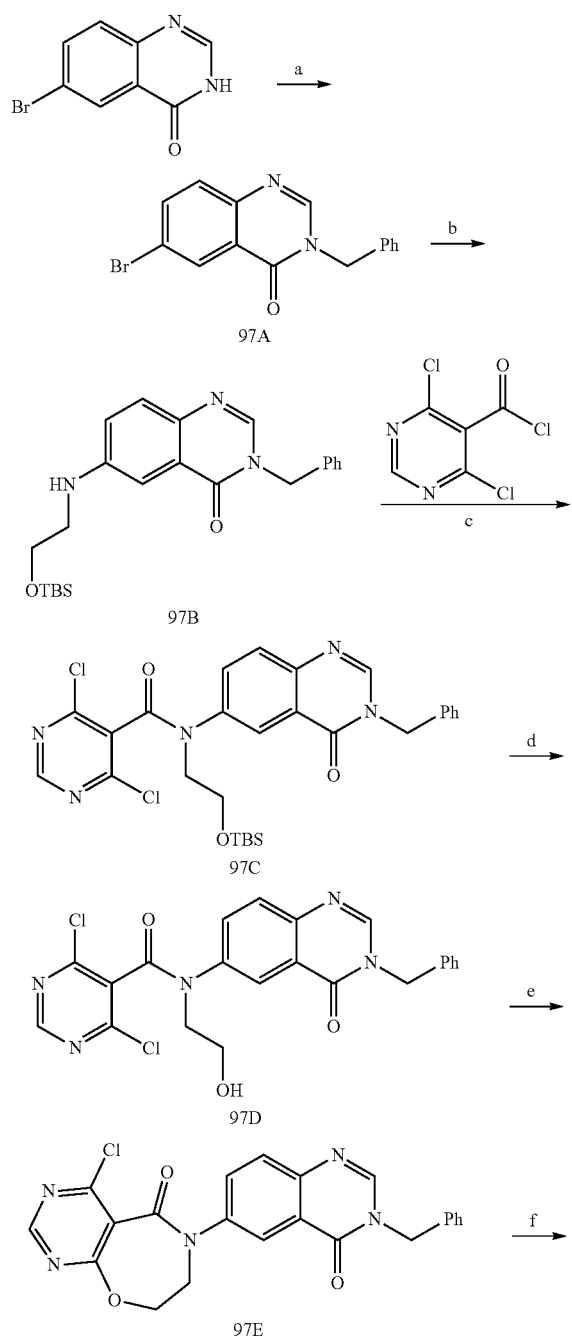

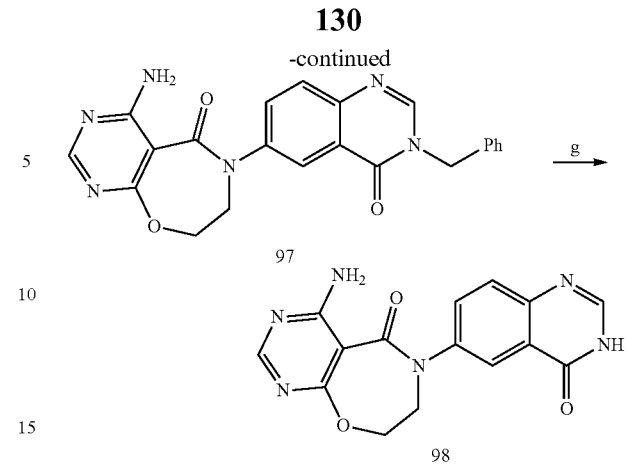

Reagents and conditions: a) benzyl bromide, NaH, DMF, 80° C., 4 h; b) NH$_2$(CH$_2$)$_2$OTBDMS, Pd(OAc)$_2$, Cs$_2$CO$_3$, X—PHOS, Toluene, 110° C., 16 h; c) DCM, Et$_3$N, RT, 1 h; d) 3% HCl—MeOH, RT, 1 h; e) CH$_3$CN, Et$_3$N, 80° C.,16 h; f) NH$_3$, Dioxane, RT, 2 h.

Procedures:

3-Benzyl-6-bromoquinazolin-4(3H)-one (97A)

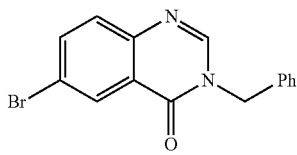

Benzyl bromide (0.264 mL, 2.22 mmol) was added to a solution of 6-bromoquinazolin-4(3H)-one (0.5 g, 2.22 mmol) and NaH (0.08 g, 3.33 mmol) in DMF (5 mL) at 0° C. The reaction mixture was heated to 80° C. for 4 h. The reaction mixture was partitioned between ethyl acetate and water. Organic layer was separated, washed with brine, dried over sodium sulphate, filtered and concentrated in vacuo to afford title compound (0.4 g, 48.1%) as pale yellow solid. $^1$H NMR (400 MHz, CDCl$_3$): δ 8.46 (d, J=1.6 Hz, 1H), 8.09 (s, 1H), 7.83 (dd, J$_1$=2.0 Hz, J$_2$=8.8 Hz, 1H), 7.57 (d, J=8.4 Hz, 1H), 7.4-7.2 (m, 5H), 5.2 (s, 2H); ESI-MS m/z=315 (M+H)$^+$; LCMS purity: 84.2%

3-Benzyl-6-(2-(tert-butyldimethylsilyloxy)ethyl-amino)quinazolin-4(3H)-one (97B)

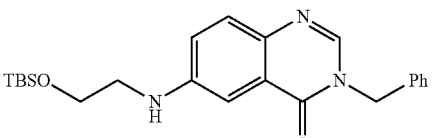

A mixture of product of Example 97A (0.4 g, 1.269 mmol), 2-(tert-butyldimethylsilyloxy)ethanamine (0.267 g, 1.523 mmol), cesium carbonate (1.241 g, 3.81 mmol), palladium acetate (0.014 g, 0.063 mmol) and X-PHOS (0.03 g, 0.063 mmol) in Toluene (10 mL) under Argon was refluxed at 110° C. for 16 h. The reaction mixture was cooled, diluted with ethyl acetate, and washed with water (2×15 mL) and saturated aqueous brine. The organic layer was dried over sodium sulfate, filtered and concentrated to obtain dark oil. The residue was purified by flash chromatography using 20% ethyl acetate in hexane to afford title compound (0.2 g, 31.9%) as an off-white solid.

N-(3-Benzyl-4-oxo-3,4-dihydroquinazolin-6-yl)-N-(2-(tert-butyldimethylsilyloxy)ethyl)-4,6-dichloropyrimidine-5-carboxamide (97C)

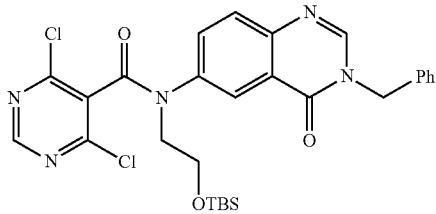

97C

To a stirred, cooled (0° C.) solution of product of Example 97B (1.2 g, 2.93 mmol) and TEA (1.225 mL, 8.79 mmol) in DCM (20 mL) was added drop wise a solution of 4,6-dichloropyrimidine-5-carbonyl chloride (0.61 g, 2.92 mmol) in DCM (5 mL) at −30° C. After 1 h, the reaction was concentrated in vacuo, diluted with ethyl acetate, and washed with water (2×15 mL) and saturated aqueous brine, The organic layer was dried over sodium sulphate, filtered and concentrated in vacuo to afford title compound (0.9 g, 25.8%) as a yellow solid.

N-(3-Benzyl-4-oxo-3,4-dihydroquinazolin-6-yl)-4,6-dichloro-N-(2-hydroxyethyl)pyrimidine-5-carboxamide (97D)

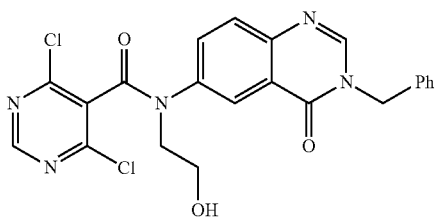

97D

A solution of product of Example 97C (0.9 g, 1.54 mmol), in 10 mL of methanolic solution of HCl (3 mL concentrated aqueous HCl in 97 mL of methanol) was stirred at room temperature for 1 h. Methanol was removed in vacuo, the residue was dissolved in ethyl acetate, and washed with saturated aqueous sodium bicarbonate solution and saturated aqueous brine. The organic layer was dried over sodium sulfate, filtered and concentrated in vacuo to afford title compound (0.5 g, 38%) as a solid, which was used in the next step without further purification.

6-(3-Benzyl-4-oxo-3,4-dihydroquinazolin-6-yl)-4-chloro-7,8-dihydropyrimido[5,4-f][1,4]oxazepin-5(6H)-one (97E)

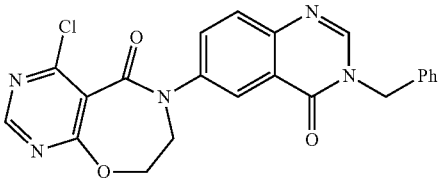

97E

A slurry of product of Example 97D (0.5 g, 1.063 mmol) and TEA (0.445 g, 3.19 mmol) in acetonitrile (10 mL) was stirred at 80° C. for 16 h. The reaction was cooled, concentrated in vacuo, diluted with ethyl acetate, and washed with water and saturated aqueous brine. The organic layer was dried over sodium sulfate, filtered and concentrated in vacuo to afford title compound (0.2 g, 38.8%) as a yellow solid. $^1$H NMR (300 MHz, DMSO-$d_6$): δ 8.84 (s, 1H), 8.63 (s, 1H), 8.18 (d, J=2.4 Hz, 1H), 7.93 (dd, $J_1$=2.1 Hz, $J_2$=8.7 Hz, 1H), 7.8 (d, J=8.4 Hz, 1H), 7.4-7.2 (m, 5H), 5.23 (s, 2H), 4.77 (t, J=4.5 Hz, 2H), 4.27 (t, J=4.2 Hz, 2H).

4-Amino-6-(3-benzyl-4-oxo-3,4-dihydroquinazolin-6-yl)-7,8-dihydropyrimido[5,4-f][1,4]oxazepin-5(6H)-one (97)

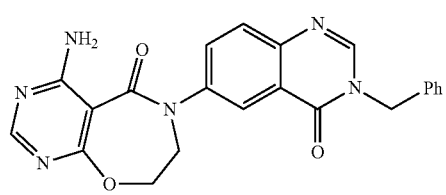

97

A solution of product of Example 97E (0.18 g, 0.415 mmol) in 0.5M ammonia in p-dioxane (10 mL) was stirred at room temperature for 5 h. The reaction mixture was concentrated in vacuo, diluted with ethyl acetate, and washed with water and saturated aqueous brine. The organic layer was dried over sodium sulfate, filtered and concentrated in vacuo to afford title compound (0.14 g, 76%) as a white solid. $^1$H NMR (300 MHz, DMSO-$d_6$): δ 8.61 (s, 1H), 8.18 (s, 1H), 8.11 (d, J=2.1 Hz, 1H), 7.87 (dd, $J_1$=2.1 Hz, $J_2$=8.7 Hz, 1H), 7.75 (d, J=9.0 Hz, 1H), 7.67 (bs, 2H), 7.4-7.2 (m, 5H), 5.22 (s, 2H), 4.63 (t, J=4.5 Hz, 2H), 4.08 (t, J=4.2 Hz, 2H). ESI-MS m/z=415 (M+H)$^+$; LCMS purity: 93%.

4-Amino-6-(4-oxo-3,4-dihydroquinazolin-6-yl)-7,8-dihydropyrimido[5,4-f][1,4]oxazepin-5(6H)-one (98)

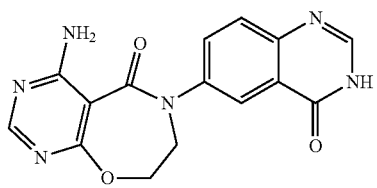

98

Pd/C (0.0514 g, 0.048 mmol) was added to a solution of Example 97 (0.1 g, 0.241 mmol) and ammonium formate (76 mg, 1.207 mmol) in ethanol (5 mL) at 25° C. The reaction mixture was heated to 80° C. for 16 h. Insoluble solids were filtered off, and filtrate was concentrated. Residue was partitioned between ethyl acetate and water. Organic layer was separated, washed with brine, dried over sodium sulphate, filtered and concentrated in vacuo. The crude product was purified by flash chromatography using 60% ethyl acetate in hexane to afford title compound (0.02 g, 23.51%) as a solid. $^1$H NMR (300 MHz, DMSO-d$_6$): δ 12.4 (s, 1H), 8.18 (s, 1H), 8.12 (d, J=3.0 Hz, 1H), 8.08 (d, J=1.8 Hz, 1H), 7.83 (dd, J$_1$=1.8 Hz, J$_2$=8.4 Hz, 1H), 7.75-7.65 (m, 3H), 4.64 (m, 2H), 4.08 (m, 2H); ESI-MS m/z=325 (M+H)$^+$; LCMS purity: 93%.

Example 99 was prepared by the methods described above for Example 96 or routine variations thereof starting from the requisite halo-substituted heterocycle ring system.

| Ex | Structure | Analytical Data | Mass/Purity |
|----|-----------|-----------------|-------------|
| 99 | 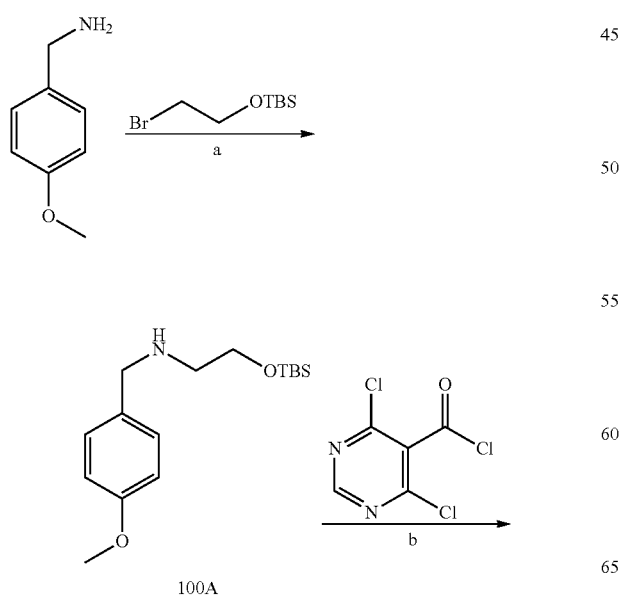 | $^1$H NMR (400 MHz, CDCl$_3$): δ 8.27 (s, 1H), 7.51 (d, J = 6.8 Hz, 1H), 7.35-7.28 (m, 5H), 7.18 (d, J = 3.2 Hz, 1H), 7.15-7.07 (m, 3H), 6.55 (d, J = 3.2 Hz, 1H), 5.27 (s, 2H), 4.75 (t, J = 4.0 Hz, 2H), 3.99 (t, J = 4.8 Hz, 2H). | ESI-MS m/z = 404 (M + H)$^+$; HPLC purity: 90.84%. |

Example 100

4-Amino-6-(5-propyl-5H-pyrrolo[3,2-d]pyrimidin-2-yl)-7,8-dihydropyrimido[5,4-f][1,4]oxazepin-5(6H)-one

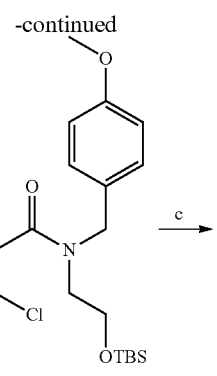
100B

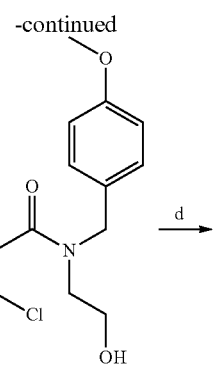
100C

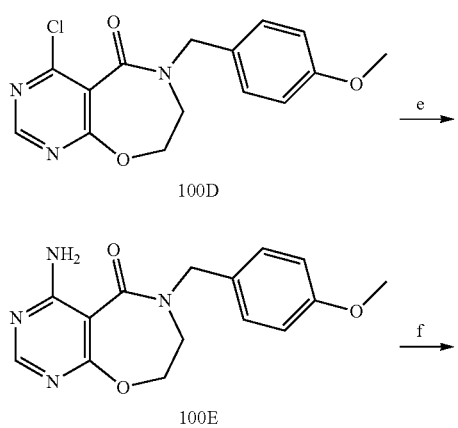
100D

100E

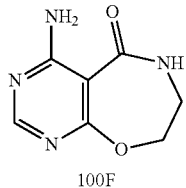

100F

Reagents and conditions: a) Br(CH$_2$)$_2$OTBDMS, K$_2$CO$_3$, ACN, 80° C., 16 h: b) DCM, Et$_3$N, -78° C.; c) 3% HCl-EtOH, RT, 1 h; d) CH$_3$CN, Et$_3$N, 80° C., 16 h; e) NH$_3$, Dioxane, RT, 2 h, f) TFA, anisole, 90° C., 16 h.

Procedures:

2-(tert-Butyldimethylsilyloxy)-N-(4-methoxybenzyl) ethanamine (100A)

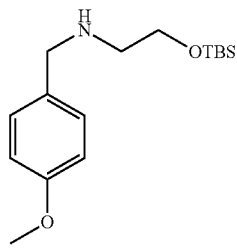

100A (2-bromoethoxy)(tert-butyl)dimethylsilane (20 g, 84 mmol) was added to a solution of (4-methoxyphenyl) methanamine (11.47 g, 84 mmol) in acetonitrile (200 mL) followed by K$_2$CO$_3$ (57.8 g, 418 mmol), and the mixture was stirred at 80° C. for 16 h. Insoluble solids were filtered off, filtrate was concentrated and partitioned between ethyl acetate and water. Organic layer was separated, washed with brine, dried over sodium sulphate and filtered. The filtrate was concentrated in vacuo and purified by flash chromatography using 30% ethyl acetate in hexane to afford title compound (19 g, 77%) as an oil. $^1$H NMR (300 MHz, DMSO-d$_6$): δ 7.22 (d, J=8.4 Hz, 2H), 6.82 (d, J=8.7 Hz, 2H), 3.77 (s, 3H), 3.62 (m, 4H), 2.56 (t, J=5.7 Hz, 2H), 2.5 (m, 1H), 0.85 (s, 9H), 0.02 (s, 6H).

N-(2-(tert-Butyldimethylsilyloxy)ethyl)-4,6-dichloro-N-(4-methoxybenzyl)pyrimidine-5-carboxamide (100B)

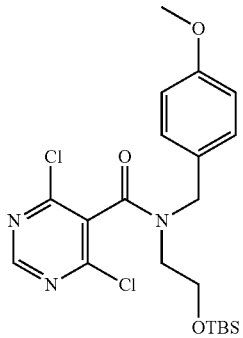

100B

To a stirred, cooled (0° C.) solution of product of Example 100A (7.66 g, 25.9 mmol) and TEA (5.42 mL, 38.9 mmol) in DCM (80 mL) was added drop wise a solution of 4,6-dichloropyrimidine-5-carbonyl chloride (5.46 g, 25.90 mmol) in DCM (10 mL). After 1 h, the reaction was concentrated in vacuo, diluted with ethyl acetate, and washed with water (2×60 mL) and saturated aqueous brine. The organic layer was dried over sodium sulphate, filtered and concentrated in vacuo to afford title compound (9.0 g, 48.4%) as a pale yellow solid.

4,6-Dichloro-N-(2-hydroxyethyl)-N-(4-methoxybenzyl)pyrimidine-5-carboxamide (100C)

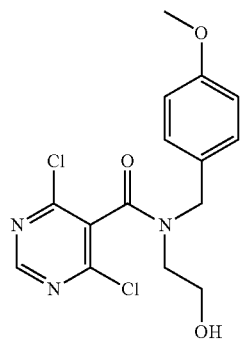

100C

A solution of product of Example 100B (9 g, 9.13 mmol) in 60 mL of ethanolic solution of HCl (3 mL concentrated aqueous HCl in 97 mL of ethanol) was stirred at room temperature for 2 h. Ethanol was removed in vacuo, the residue was dissolved in ethyl acetate, and washed with saturated aqueous sodium bicarbonate solution and saturated aqueous brine. The organic layer was dried over sodium sulfate, filtered and concentrated in vacuo to afford title compound (4.5 g, 66%) as a pale yellow solid, which was carried on to the next step without further purification.

4-Chloro-6-(4-methoxybenzyl)-7,8-dihydropyrimido[5,4-f][1,4]oxazepin-5(6H)-one (100D)

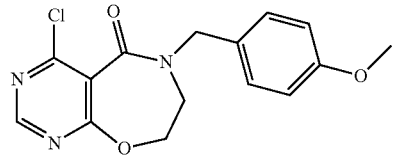

100D

A slurry of product of Example 100C (4.5 g, 12.63 mmol) and TEA (8.8 mL, 63.2 mmol) in acetonitrile (60 mL) was stirred at 80° C. for 16 h. The reaction was cooled, concentrated in vacuo, diluted with ethyl acetate, and washed with water and saturated aqueous brine. The organic layer was dried over sodium sulfate, filtered and concentrated in vacuo to afford title compound (3 g, 74.3%) as a white solid. $^1$H NMR (400 MHz, DMSO-d$_6$): δ 8.77 (s, 1H), 7.3 (d, J=8.0 Hz, 2H), 6.94 (d, J=8.4 Hz, 2H), 4.68 (s, 2H), 4.41 (t, J=4.8 Hz, 2H), 3.74 (s, 3H), 3.71 (t, J=3.6 Hz, 2H).

4-Amino-6-(4-methoxybenzyl)-7,8-dihydropyrimido[5,4-f][1,4]oxazepin-5(6H)-one (100E)

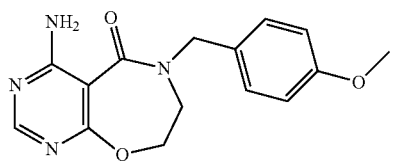
100E

A solution of product of Example 100D (3 g, 9.38 mmol) in 0.5M ammonia in p-dioxane (30 mL) was stirred at room temperature for 3 h. The reaction mixture was concentrated in vacuo, diluted with ethyl acetate, and washed with water and saturated aqueous brine. The organic layer was dried over sodium sulfate, filtered and concentrated in vacuo to afford title compound (2.5 g, 77%) as a white solid. $^1$H NMR (300 MHz, DMSO-$d_6$): δ 8.12 (s, 1H), 7.63 (bs, 2H), 7.28 (d, J=8.4 Hz, 2H), 6.91 (d, J=8.4 Hz, 2H), 4.65 (s, 2H), 4.31 (t, J=4.2 Hz, 2H), 3.74 (s, 3H), 3.56 (t, J=4.8 Hz, 2H).

4-Amino-7,8-dihydropyrimido[5,4-f][1,4]oxazepin-5(6H)-one (100F)

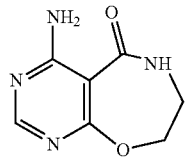
100F

TFA (15 mL, 195 mmol) was added to a solution of 100E (2.5 g, 8.32 mmol) in anisole (1 mL, 9.15 mmol) at 0° C., and the mixture was stirred for 2 h at 90° C. for 16 h in sealed-tube. The reaction mixture was concentrated to get the residue and it was triturated with 25 mL (50%) ethyl acetate in hexane to afford to afford title compound (1.0 g, 66.7%) as an off-white-solid. $^1$H NMR (400 MHz, DMSO-$d_6$-$D_2O$): δ 8.26 (s, 1H), 4.57 (t, J=3.9 Hz, 2H), 3.47 (t, J=4.2 Hz, 2H).

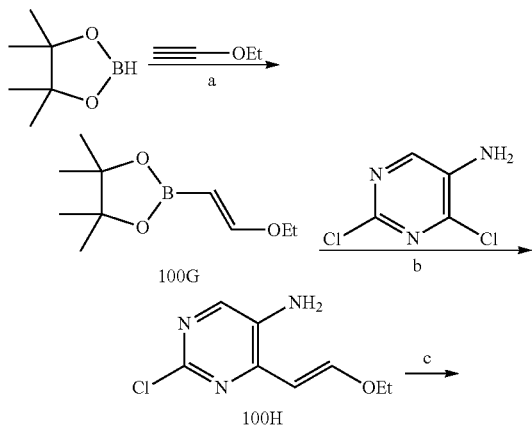

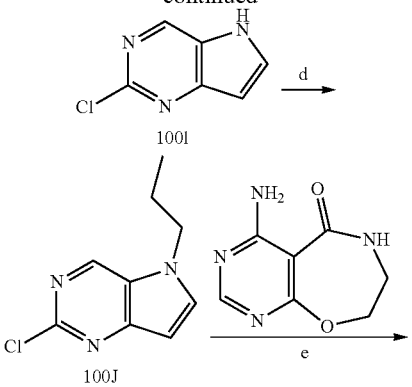

Reagents and conditions: a) di(cyclopenta-2,4-dien-1-yl)zirconium(IV) chloride, CH$_2$Cl$_2$, RT, 16 h, b) K$_3$PO$_4$ dibasic, Pd(OAc)$_2$, dicyclohexyl(2',6'-dimethoxy-[1,1'-biphenyl]-2-yl)phosphine, ACN, water, 80° C., 16 h, c), AcOH, 140° C., 4 h; d) n-propyl bromide, Cs$_2$CO$_3$, DMF, 25° C., 4 h, e) K$_3$PO$_4$ dibasic, CuI, (1S,2S)-cyclohexane-1,2-diamine, 1,4-dioxane, 110° C., 24 h.

Procedures:

4-Amino-6-(5-propyl-5H-pyrrolo[3,2-d]pyrimidin-2-yl)-7,8-dihydropyrimido[5,4-f][1,4]oxazepin-5(6H)-one

(E)-2-(2-Ethoxyvinyl)-4,4,5,5-tetramethyl-1,3,2-dioxaborolane (100G)

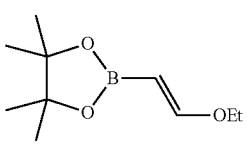
100G

Di(cyclopenta-2,4-dien-1-yl)zirconium(IV) chloride (0.685 g, 2.344 mmol) was added to a solution of 4,4,5,5-tetramethyl-1,3,2-dioxaborolane (5.0 g, 39.1 mmol) in dichloromethane (15 mL) followed by ethoxyethyne (3.01 g, 43.0 mmol) at 0° C., and the mixture was stirred for 16 h at 25° C. Insoluble solids were filtered off, and filtrate was concentrated. Residue was partitioned between ethyl acetate and water. Organic layer was separated, washed with brine, dried over sodium sulphate, filtered and concentrated in vacuo to afford title compound (6.04 g, 78.13%) as oil. $^1$H NMR (400 MHz, CDCl$_3$): δ 7.04 (d, J=14.0 Hz, 1H), 4.43 (d, J=14.8 Hz, 1H), 3.84 (q, J=7.2 Hz, 2H), 1.32-1.2 (m, 15H).

(E)-2-Chloro-4-(2-ethoxyvinyl)pyrimidin-5-amine (100H)

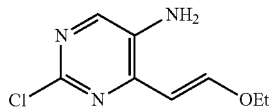

A mixture of 2,4-dichloropyrimidin-5-amine (2.0 g, 12.2 mmol), product of Example 100G (6.04 g, 30.5 mmol), potassium phosphate dibasic (5.31 g, 30.5 mmol), palladium (II) acetate (0.027 g, 0.122 mmol) and dicyclohexyl-(2',6'-dimethoxy-[1,1'-biphenyl]-2-yl)phosphine (0.050 g, 0.122 mmol) in acetonitrile (30 mL) and water (20 mL) under argon was refluxed at 80° C. for 16 h. The reaction mixture was cooled, diluted with ethyl acetate, and washed with water (2×30 mL) and saturated aqueous brine. The organic layer was dried over sodium sulfate and filtered. The filtrate was concentrated and purified by flash chromatography using 30% ethyl acetate in hexane to afford title compound (0.3 g, 12.32%) as an oil. $^1$H NMR (300 MHz, CDCl$_3$): δ 7.89 (s, 1H), 7.85 (d, J=11.7 Hz, 1H), 5.69 (d, J=11.7 Hz, 1H), 4.05 (q, J=7.2 Hz, 2H), 3.49 (bs, 2H), 1.37 (t, J=7.5 Hz, 3H).

2-Chloro-5H-pyrrolo[3,2-d]pyrimidine (100I)

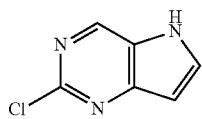

A solution of product of Example 100H (0.3 g, 1.503 mmol) in acetic acid (20 mL) was stirred at 140° C. for 4 h. Acetic acid was removed in high vacuo, the residue was co-distilled with toluene to afford title compound (0.22 g, 88%) as a yellow solid, which was carried on to the next step without further purification. $^1$H NMR (400 MHz, DMSO-d$_6$): δ 8.76 (s, 1H), 8.68 (bs, 1H), 7.69 (t, J=3.2 Hz, 1H), 6.72 (s, 1H).

2-Chloro-5-propyl-5H-pyrrolo[3,2-d]pyrimidine (100J)

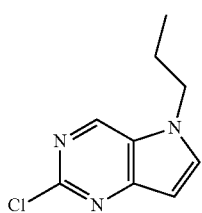

1-Bromopropane (132 mg, 1.074 mmol) was added to a solution of product of Example 100I (150 mg, 0.977 mmol) in DMF (10 mL) followed by cesium carbonate (0.477 g, 1.074 mmol), and the mixture was stirred at 25° C. for 4 h. Insoluble solids were filtered off, and filtrate was concentrated. Residue was partitioned between ethyl acetate and water. Organic layer was separated, washed with brine, dried over sodium sulphate, filtered and concentrated in vacuo. The crude product was purified by flash chromatography using 5% ethyl acetate in hexane to afford title compound (0.15 g, 74.6%) as a brown color syrup. $^1$H NMR (300 MHz, CDCl$_3$): δ 8.68 (s, 1H), 7.51 (d, J=3.0 Hz, 1H), 6.62 (d, J=2.7 Hz, 1H), 4.16 (t, J=6.9 Hz, 2H), 1.91 (m, 2H), 0.94 (t, J=7.5 Hz, 3H).

4-Amino-6-(5-propyl-5H-pyrrolo[3,2-d]pyrimidin-2-yl)-7,8-dihydropyrimido[5,4-f][1,4]oxazepin-5(6H)-one (100)

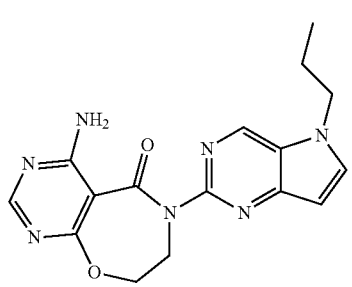

A mixture of product of Example 100J (0.195 g, 1.0 mmol), Example 100F (0.15 g, 0.833 mmol), potassium phosphate dibasic (0.29 g, 1.665 mmol), CuI (15.86 mg, 0.083 mmol) and trans (1S,2S)—N1,N2-dimethylcyclohexane-1,2-diamine (0.023 g, 0.167 mmol) in 1,4-dioxane (5 mL) under Argon was refluxed at 110° C. for 24 h in sealed-tube. The reaction mixture was diluted with methanol, insoluble solids were filtered off and filtrate was concentrated to get the residue. The residue was purified by flash chromatography using 3% methanol in ethyl acetate to afford title compound (0.02 g) as a yellow solid. $^1$H NMR (400 MHz, DMSO-d$_6$): δ 9.12 (s, 1H), 8.19 (s, 1H), 8.02 (d, J=3.6 Hz, 1H), 7.69 (bs, 2H), 6.62 (d, J=2.8 Hz, 1H), 4.61 (t, J=4.4 Hz, 2H), 4.29 (t, J=7.2 Hz, 2H), 4.15 (t, J=4.8 Hz, 2H), 1.83 (m, 2H), 0.83 (t, J=7.2 Hz, 3H); ESI-MS m/z=340.1 (M+H)$^{+-}$; LCMS Purity: 96.2%.

Example-101

4-Amino-6-(1-propyl-1H-pyrrolo[3,2-b]pyridin-5-yl)-7,8-dihydropyrimido[5,4-f][1,4]oxazepin-5(6H)-one

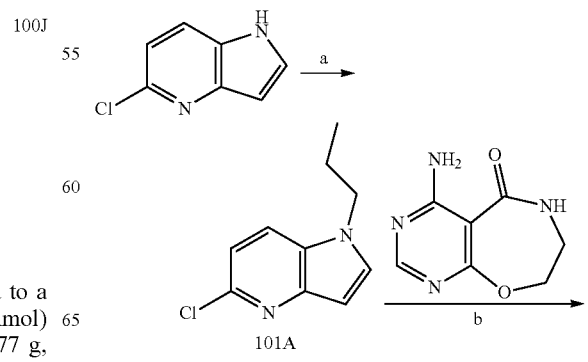

-continued

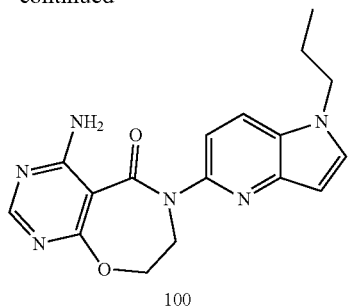

100

Reagents and conditions: a) n-propyl bromide, Cs₂CO₃, DMF, 70° C., 0.5 h; b) CuI, (1S,2S)-N,N'-Dimethyl cyclohexyl-1,2-diamine, K₃PO₄, Toluene, 120° C., 2.5 h;

Procedures:

4-Amino-6-(1-propyl-1H-pyrrolo[3,2-b]pyridin-5-yl)-7,8-dihydropyrimido[5,4-f][1,4]oxazepin-5(6H)-one 5-Chloro-1-propyl-1H-pyrrolo[3,2-b]pyridine (101A)

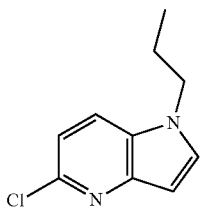

101A

1-Bromopropane (192 mg, 1.57 mmol) was added to a solution of 2-chloro-5H-pyrrolo[3,2-d]pyrimidine (200 mg, 1.31 mmol) in DMF (15 mL) followed by cesium carbonate (0.855 g, 2.63 mmol), and the mixture was stirred at 70° C. for 0.5 h. Insoluble solids were filtered off, filtrate was concentrated and partitioned between ethyl acetate and water. Organic layer was separated, washed with brine, dried over sodium sulphate and filtered. The filtrate was concentrated in vacuo to afford title compound (0.22 g, 86%) as an oil. ¹H NMR (300 MHz, CDCl₃): δ 7.59 (d, J=8.7 Hz, 1H), 7.34 (d, J=3.3 Hz, 1H), 7.10 (d, J=8.4 Hz, 1H), 6.62 (d, J=3.6 Hz, 1H), 4.07 (t, J=6.9 Hz, 2H), 1.86 (m, 2H), 0.91 (t, J=7.5 Hz, 3H).

4-Amino-6-(1-propyl-1H-pyrrolo[3,2-b]pyridin-5-yl)-7,8-dihydropyrimido[5,4-f][1,4]oxazepin-5(6H)-one (101)

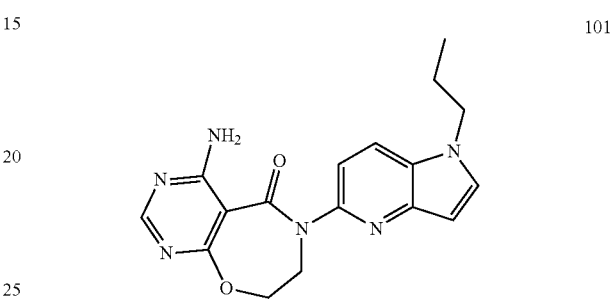

101

A mixture of product of Example 101A (0.064 g, 0.33 mmol), Example 100F (0.05 g, 0.27 mmol), potassium phosphate dibasic (0.117 g, 0.555 mmol), CuI (0.005 g, 0.027 mmol) and trans (1S,2S)—N1,N2-dimethylcyclohexane-1,2-diamine (0.0076 g, 0.055 mmol) in 1,4-dioxane (5 mL) under argon was refluxed at 110° C. for 24 h in sealed-tube. The reaction mixture was diluted with methanol, insoluble solids were filtered off and filtrate was concentrated to get the residue. The residue was purified by flash chromatography using 3% methanol in ethyl acetate to afford title compound (0.005 g) as a yellow solid. ¹H NMR (400 MHz, DMSO-d₆): δ 8.2 (bs, 1H), 8.01 (d, J=8.4 Hz, 1H), 7.71 (d, J=3.0 Hz, 1H), 7.60 (bs, 2H), 7.49 (d, J=8.7 Hz, 1H), 6.54 (d, J=3.0 Hz, 1H), 4.63 (m, 2H), 4.26 (m, 2H), 4.19 (t, J=6.9 Hz, 2H), 1.78 (m, 2H), 0.82 (t, J=7.2 Hz, 3H); ESI-MS m/z=339.1 (M+H)⁺;

Examples 102-105 were prepared by the procedures analogous to those described in Examples 65, 66, 82 or 83 using appropriately substituted starting materials.

| Ex | Structure | Analytical Data | Mass/Purity |
| --- | --- | --- | --- |
| 102 | 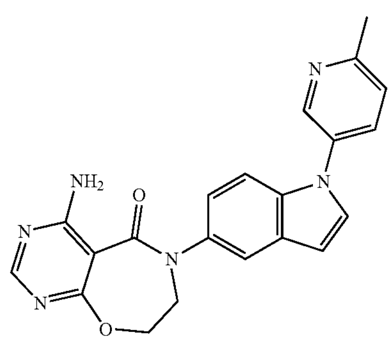 [SMILES: Cc1ccc(-n2ccc3cc(N4CCOc5ncnc(N)c5C4=O)ccc32)cn1] | ¹H NMR (400 MHz, DMSO-d₆): δ 8.71 (d, J = 2.4 Hz, 1H), 8.18 (s, 1H), 7.96 (dd, J₁ = 2.4 Hz, J₂ = 8.0 Hz, 1H), 7.74 (d, J = 2.8 Hz, 1H), 7.7-7.6 (m, 3H), 7.54 (d, J = 8.8 Hz, 1H), 7.48 (d, J = 8.4 Hz, 1H), 7.18 (dd, J₁ = 1.6 Hz, J₂ = 8.8 Hz, 1H), 6.77 (d, J = 2.8 Hz, 1H), 4.65 (t, J = 4.0 Hz, 2H), 4.01 (t, J = 4.4 Hz, 2H), 2.57 (s, 3H). | ESI-MS m/z = 387 (M + H)⁺; HPLC purity: 97%. |

| Ex | Structure | Analytical Data | Mass/Purity |
|---|---|---|---|
| 103 | 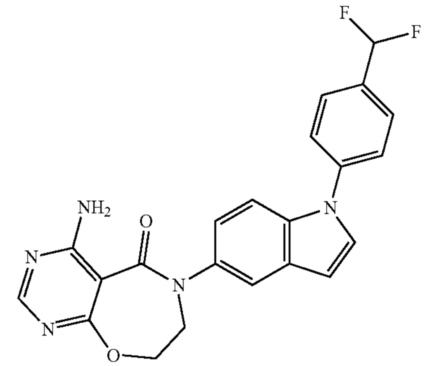 [SMILES: Nc1ncnc2c1C(=O)N(c1ccc3c(ccn3-c3ccc(C(F)F)cc3)c1)CCO2] | $^1$H NMR (400 MHz, DMSO-$d_6$): δ 8.18 (s, 1H), 7.82-7.76 (m, 5H), 7.68-7.60 (m, 4H), 7.21 (dd, $J_1$ = 2.0 Hz, $J_2$ = 8.8 Hz, 1H), 7.15 (t, J = 56 Hz, 1H), 6.78 (d, J = 2.8 Hz, 1H), 4.65 (t, J = 4.0 Hz, 2H), 4.02 (t, J = 4.4 Hz, 2H). | ESI-MS m/z = 422 (M + H)$^+$; LCMS purity: 95%. |
| 104 | 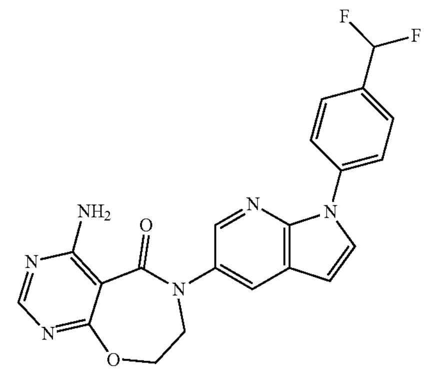 [SMILES: Nc1ncnc2c1C(=O)N(c1cnc3c(ccn3-c3ccc(C(F)F)cc3)c1)CCO2] | $^1$H NMR (300 MHz, DMSO-$d_6$): δ 8.34 (d, J = 2.4 Hz, 1H), 8.17 (s, 1H), 8.15-8.06 (m, 4H), 7.75 (d, J = 8.7 Hz, 2H), 7.65 (bs, 2H), 7.10 (t, J = 55.8 Hz, 1H), 6.80 (d, J = 3.9 Hz, 1H), 4.68 (t, J = 3.9 Hz, 2H), 4.05 (t, J = 3.9 Hz, 2H). | ESI-MS m/z = 423 (M + H)$^+$; LCMS purity: 97%. |
| 105 | 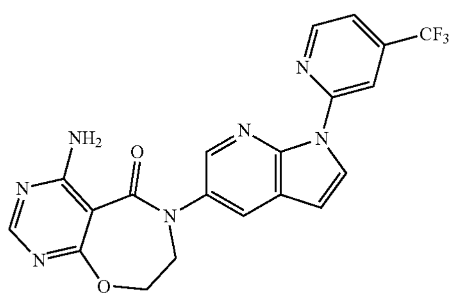 [SMILES: Nc1ncnc2c1C(=O)N(c1cnc3c(ccn3-c3cc(C(F)(F)F)ccn3)c1)CCO2] | $^1$H NMR (400 MHz, DMSO-$d_6$): δ 9.37 (s, 1H), 8.82 (d, J = 4.8 Hz, 1H), 8.54-8.50 (m, 2H) 8.21 (d, J = 2.4 Hz 1H), 8.19 (s, 1H), 7.72 (d, J = 5.2 Hz, 1H), 7.68 (bs, 2H), 6.88 (d, J = 4.0 Hz, 1H), 4.71 (t, J = 3.6 Hz, 2H), 4.09 (t, J = 4.4 Hz, 2H). | ESI-MS m/z = 442 (M + H)$^+$; LCMS purity: 99%. |

Biological Assay

Human DGAT1 was expressed in Sf9 insect cells using a baculovirus expression system. Microsomes were prepared and used as enzyme for in vitro inhibition testing in either of two formats measuring production of coenzyme A or tridecanoylglycerol product, respectively. All steps were performed at 21-23° C. All data for DGAT1 inhibition by test compounds were collected under conditions where product formation was linear with reaction time.

For inhibition of CoA product formation, test compounds were prepared in 100% DMSO, diluted 100-fold into assay buffer, and 10 uL added to 96-well half-area plates (Greiner 675076). An equal volume (10 uL) of 3× enzyme in buffer was added and the components incubated for 30 minutes pre-reaction incubation to allow enzyme and test compounds to attain binding equilibrium. The 3× enzyme mixture contained 30 uM {4-[4-(4-amino-7,7-dimethyl-7H-pyrimido[4,5-b][1,4]oxazin-6-yl)phenyl]cyclohexyl}acetic acid for fully inhibited control wells. Some assays were performed with inclusion of didecanoylglycerol in the pre-reaction incubation of test compound and enzyme. DGAT reactions (30 uL) were initiated upon addition of 10 uL of 3× substrate solution. Final reaction conditions consisted of 20 mM HEPES pH 7.5, 2 mM MgCl$_2$, 1 mM CHAPS, 50 uM didecanoylglycerol, 3 uM decanoyl-CoA, 1 ug/mL microsomal protein, and 1% DMSO. Following a 60 minute reaction incubation, reactions were stopped and CoA product derivatized with 30 uL of buffer containing 10 uM {4-[4-(4-amino-7,7-dimethyl-7H-pyrimido[4,5-b][1,4]oxazin-6-yl)phenyl]cyclohexyl}acetic acid and 50 uM 7-diethylamino-3-(4'-maleimidylphenyl)-4-methylcoumarin (CPM). Fluorescence was read using Envision reader at Ex 405 nm/Em 480 nm about 30 minutes after addition of final solution. Inhibition was normalized to controls containing DMSO or 10 uM {4-[4-(4-amino-7,7-dimethyl-7H-pyrimido[4,5-b][1,4]oxazin-6-yl)phenyl]cyclohexyl}acetic acid. IC$_{50}$s were fitted using GraphPad Prism to a sigmoidal dose response.

For inhibition of triacylglycerol product formation, 11 uL reactions were run in white Polyplate-384 (PerkinElmer6007300) starting with a 30 minute pre-reaction incubation of 5 uL of 2.2× enzyme and 1 uL of 100% DMSO containing test compound or control compound, {4-[4-(4-amino-7,7-dimethyl-7H-pyrimido[4,5-b][1,4]oxazin-6-yl)phenyl]cyclohexyl}acetic acid. Some assays were performed with inclusion of didecanoylglycerol in the pre-reaction incubation of test compounds and enzyme. Reactions were initiated after 30 minute pre-reaction incubation via addition of 5 uL of 2.2× substrate. Final reaction conditions consisted of 50 mM HEPES pH 7.5, 2 mM $MgCl_2$, 1 mM CHAPS, 25 uM didecanoylglycerol, 0.5 uM decanoyl-CoA, 0.3 nCi/uL [$^{14}$C]-decanoyl-CoA or 0.5 nCi/uL [$^{3}$H]-decanoyl-CoA, 0.05-4 ug/mL microsomal protein, and 1% DMSO. Following 60 minute reaction incubation, reactions were stopped with 40 uL of 45% isopropanol and 50 mM sodium carbonate in water and mixed. Extraction of tridecanoylglycerol product was accomplished via addition of 30 uL Microscint-E (Perkin Elmer) and 2 hours of incubation (sealed). Plates were read on a Microbeta Microplate reader. Inhibition was normalized to controls containing DMSO or 10 uM {4-[4-(4-amino-7,7-dimethyl-7H-pyrimido[4,5-b][1,4]oxazin-6-yl)phenyl]cyclohexyl}acetic acid. $IC_{50}$s were fitted using GraphPad Prism to a sigmoidal dose response.

Biological Data

Exemplified compounds of the present invention are inhibitors of DGAT1. All of the compounds except Example 101 were tested at one or more DGAT assays described above and were found to be inhibitors of DGAT1 with $IC_{50}$<10 uM or inhibition>50% at 10 uM. Data for some specific examples tested at the human DGAT1 fluorescene (CPM) or lipid extraction (LE) assays are listed below.

| Ex | hDGAT1 CPM Assay $IC_{50}$ (nM) | hDGAT1 LE Assay $IC_{50}$ (nM) |
| --- | --- | --- |
| 3 | 371.6 | |
| 6 | 85.8 | |
| 10 | 42.0 | |
| 11 | 6.3 | |
| 12 | 16.3 | |
| 33 | | 23.3 |
| 34 | 25.7 | |
| 59 | 49.5 | |
| 60 | | 14.8 |
| 63 | | 2.3 |
| 64 | | 8.8 |
| 65 | | 3.9 |
| 66 | 42.5 | |
| 68 | 2.8 | |
| 72 | | 9.3 |
| 74 | | 4.5 |
| 76 | 2.5 | |
| 78 | 7.3 | |
| 80 | | 3.6 |
| 81 | | 2.1 |
| 82 | 20.5 | |
| 83 | 40.0 | |
| 87 | 55.1 | |
| 94 | 872.5 | |
| 95 | 10.1 | |
| 96 | | 7.3 |
| 97 | | 200.8 |
| 98 | | 623.0 |

The invention claimed is:

1. A compound selected from the group consisting of:

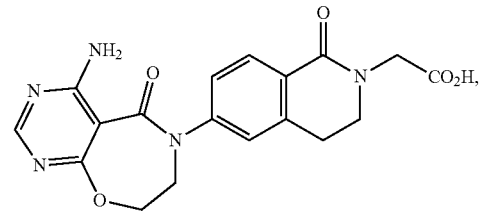

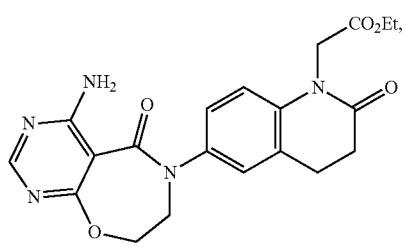

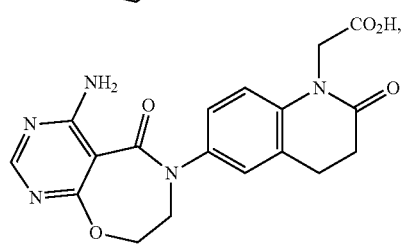

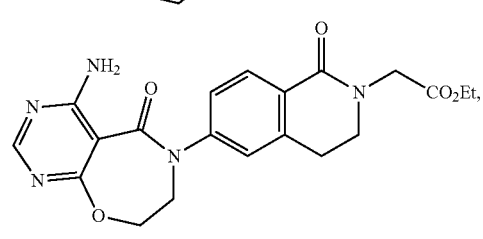

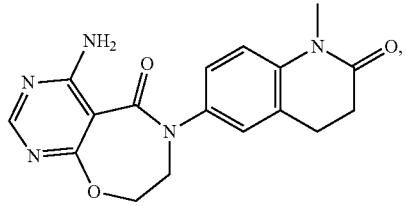

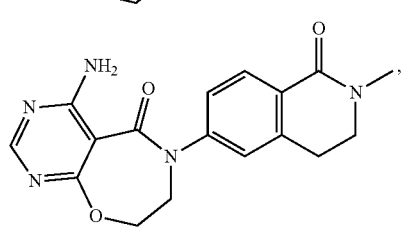

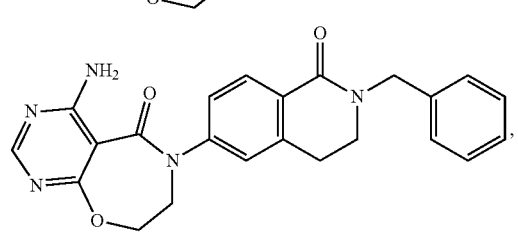

147
-continued
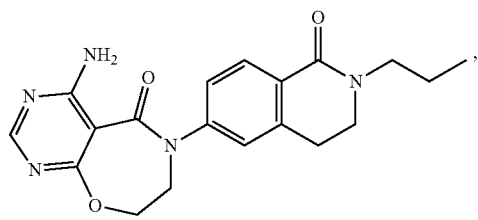
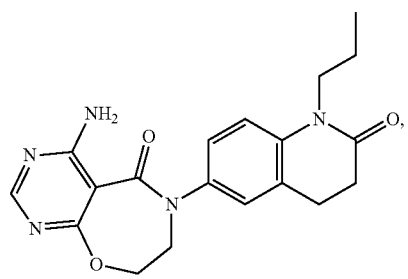
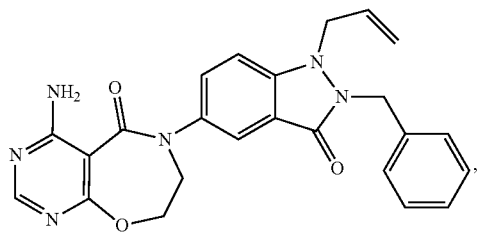
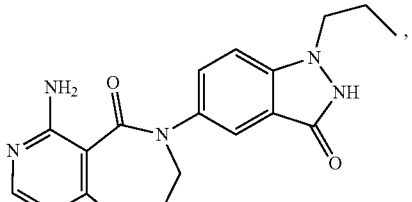
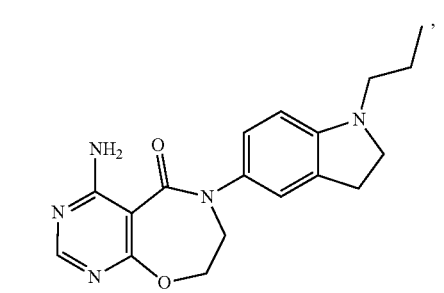
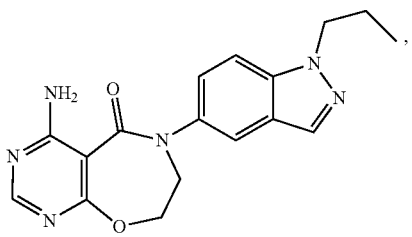
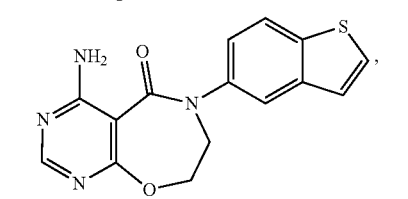
148
-continued
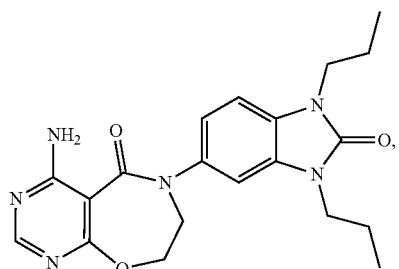
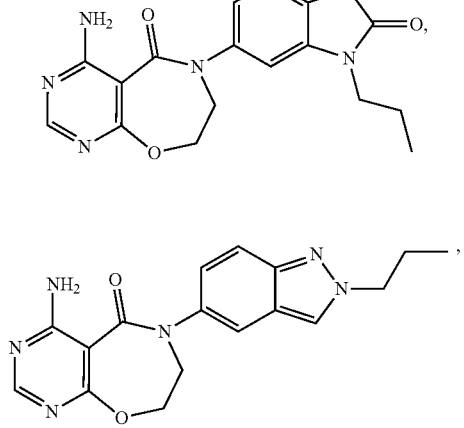
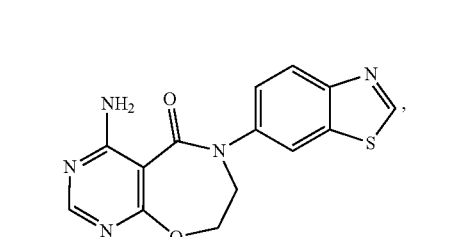
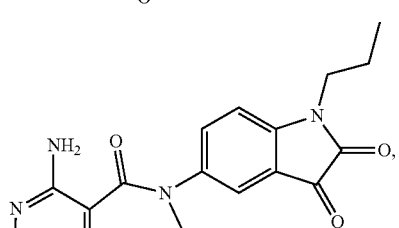
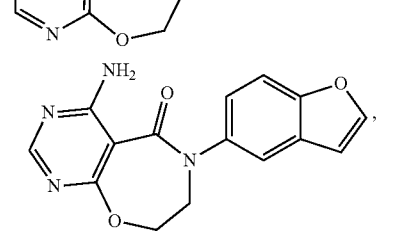
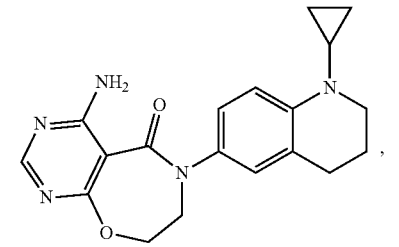
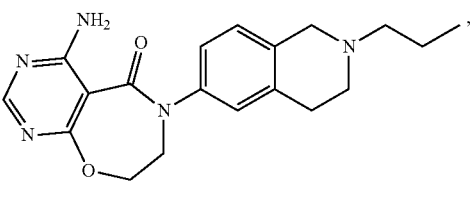

149
-continued
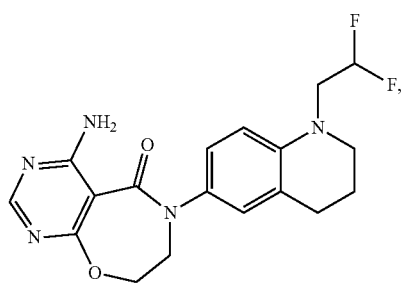
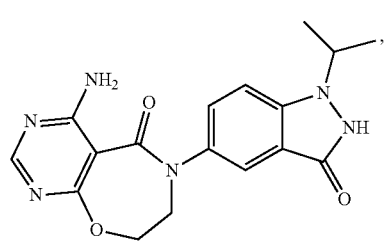
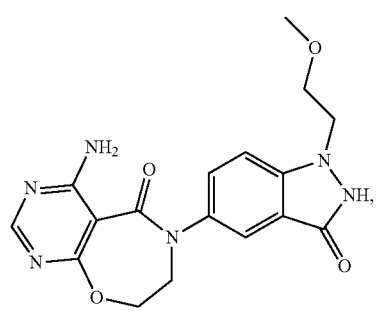
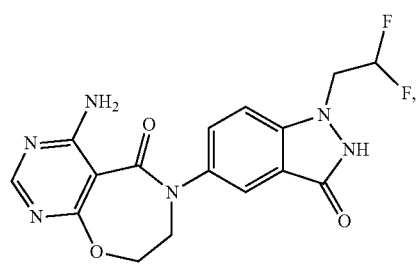
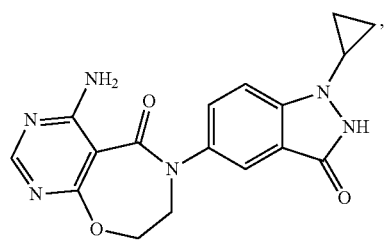
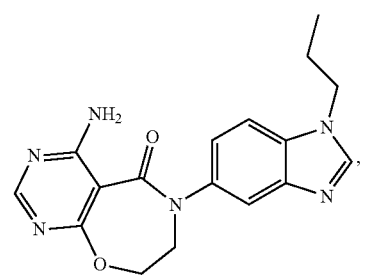
150
-continued
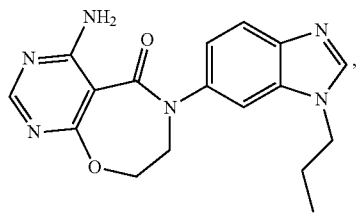
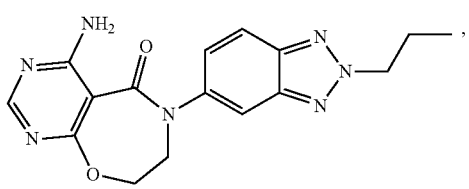
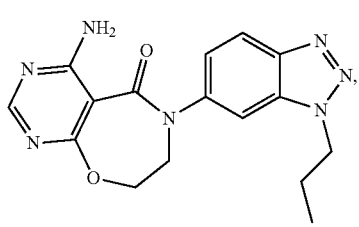
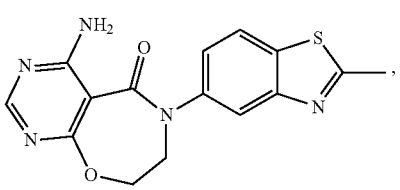
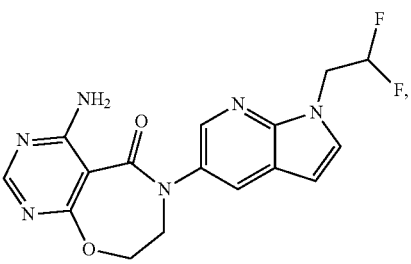
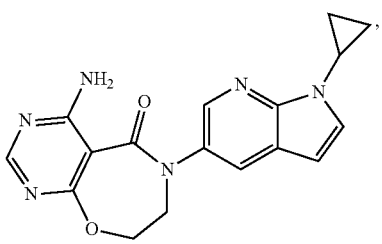
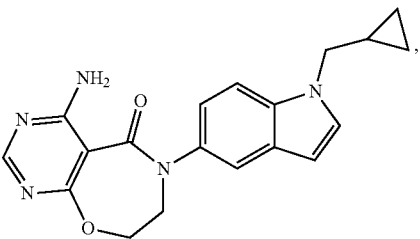

151
-continued
152
-continued
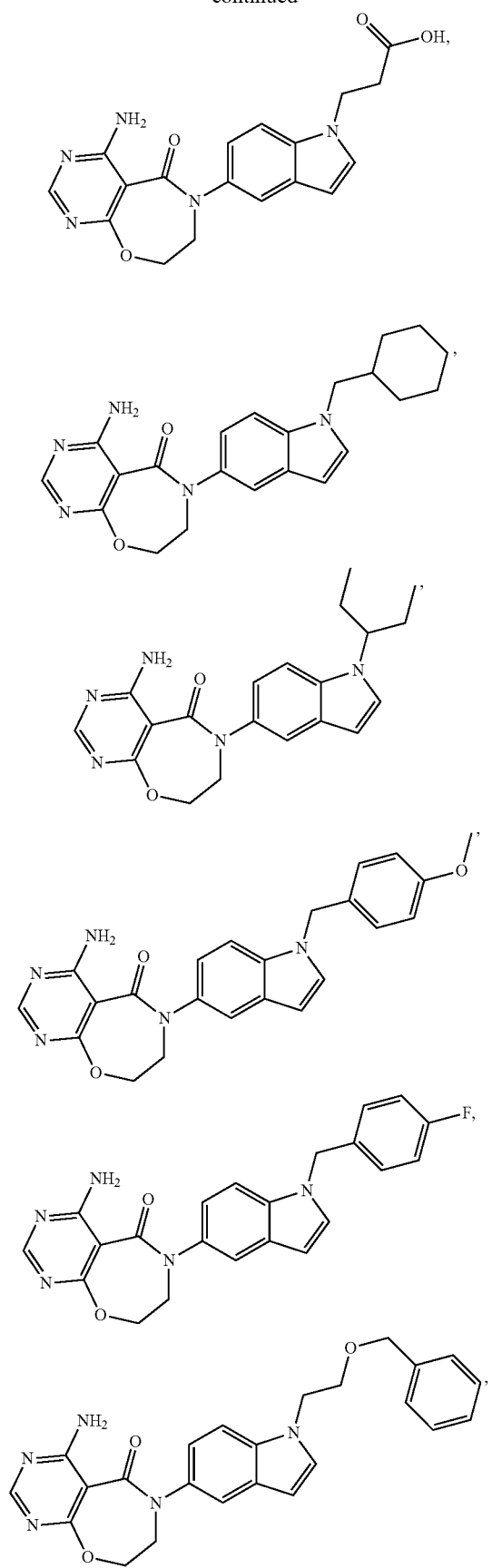
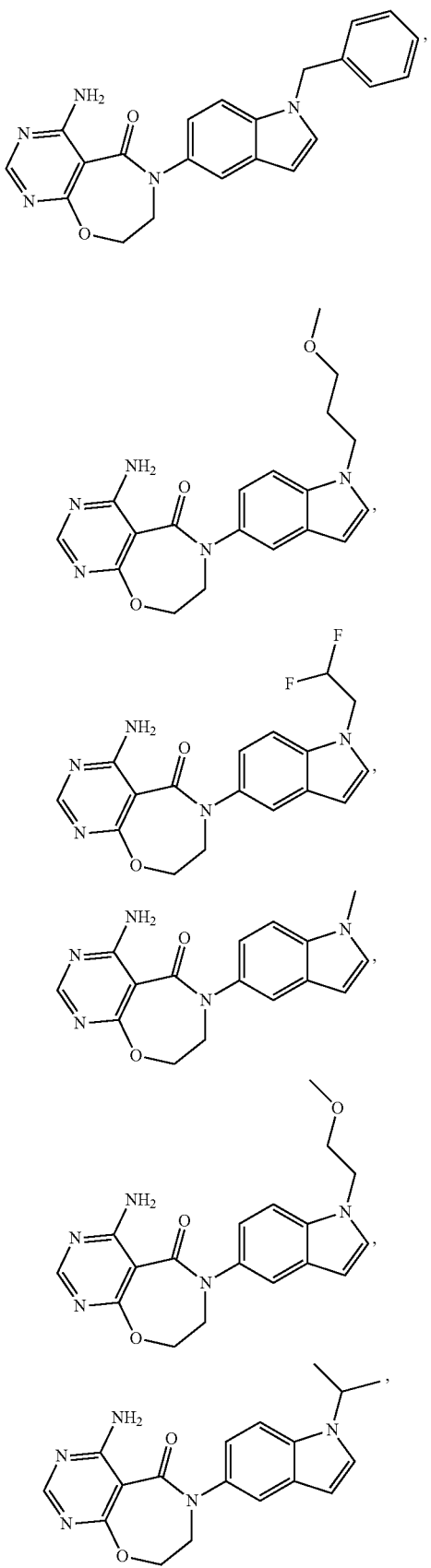

153
-continued
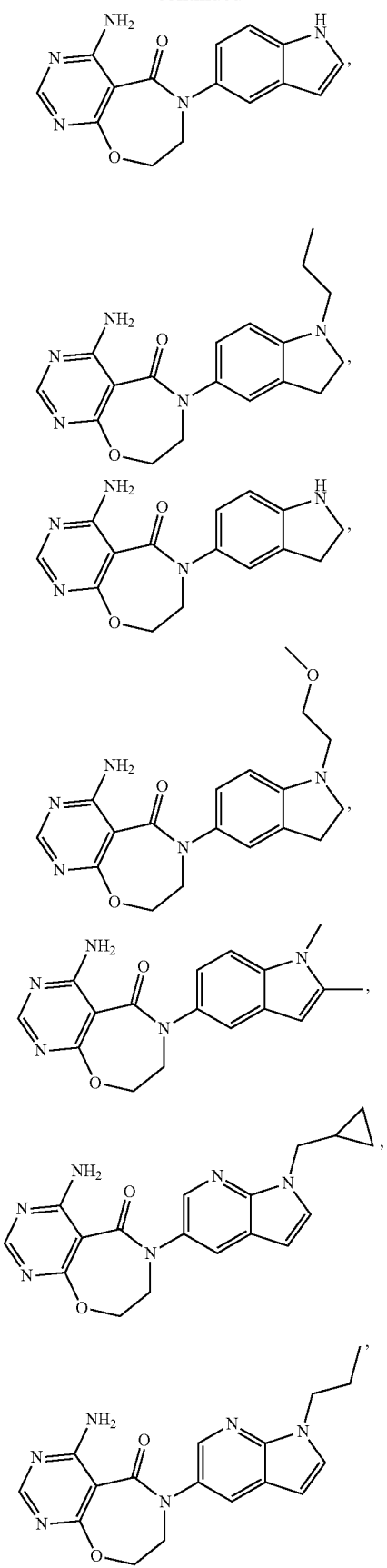
154
-continued
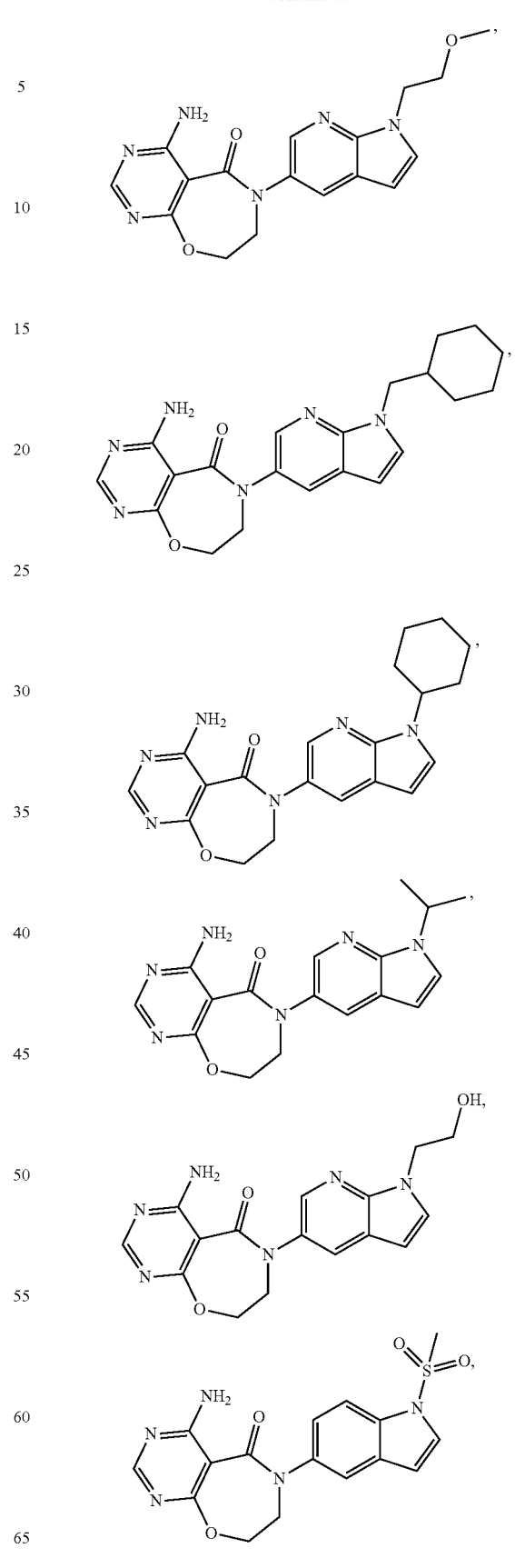

155
-continued
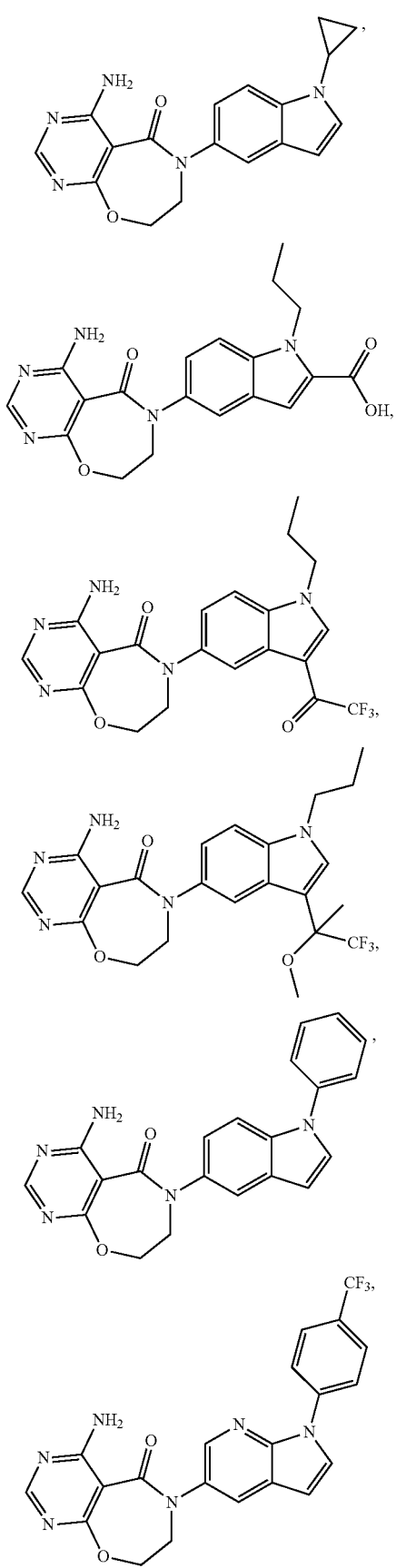
156
-continued
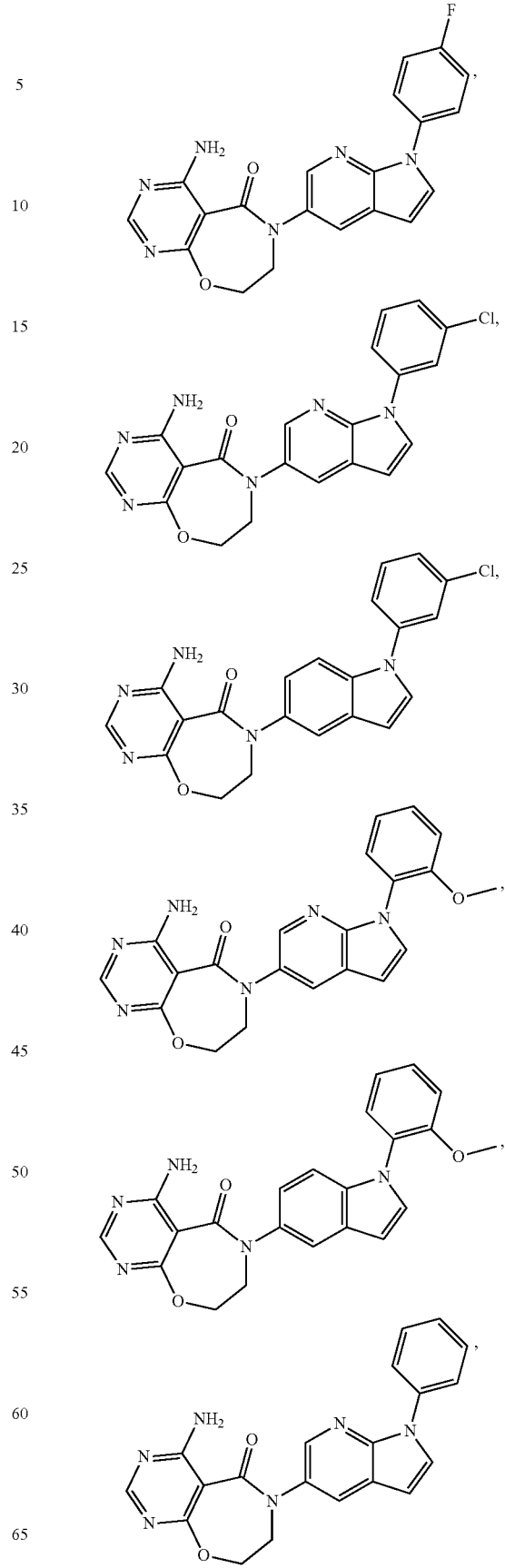

157
-continued
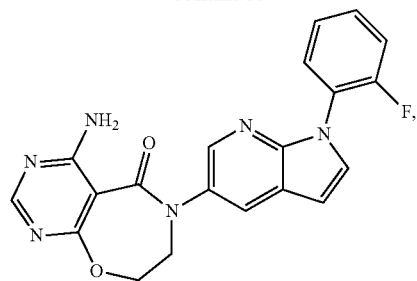
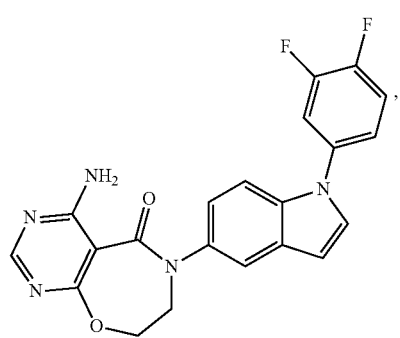
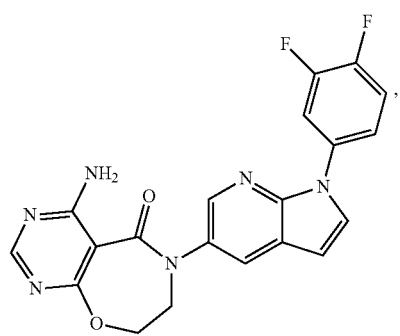
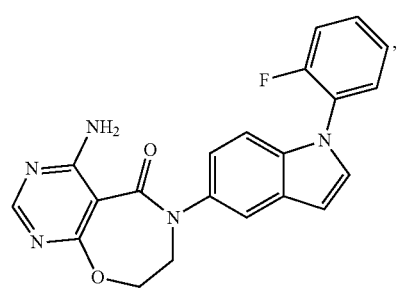
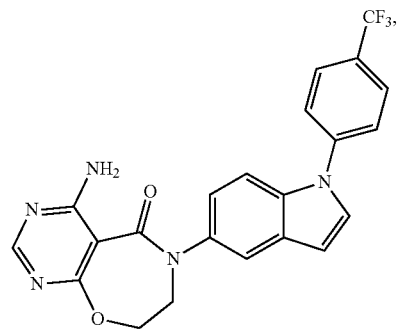
158
-continued
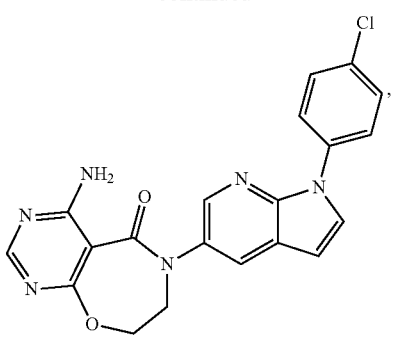
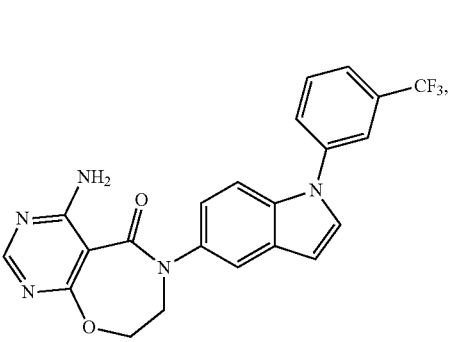
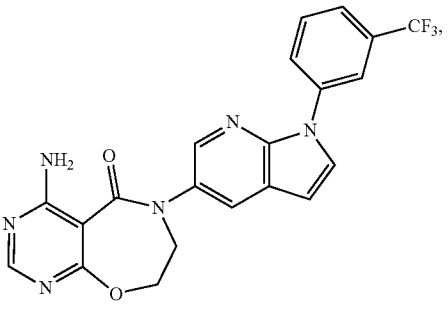
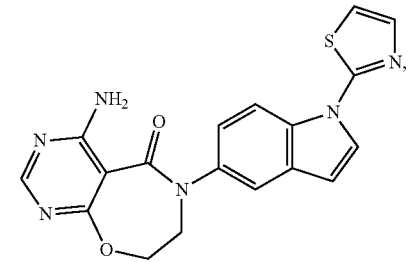
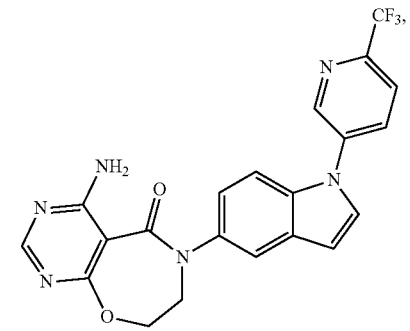

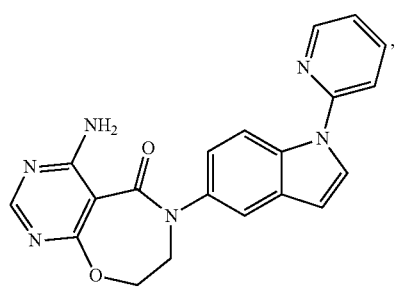
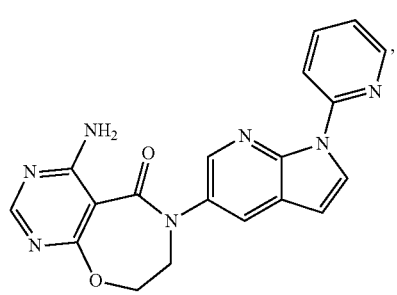
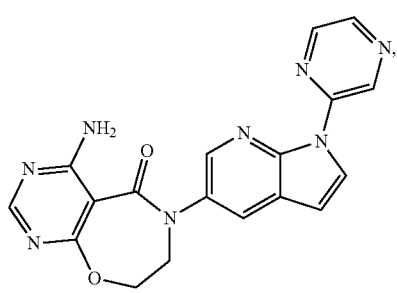
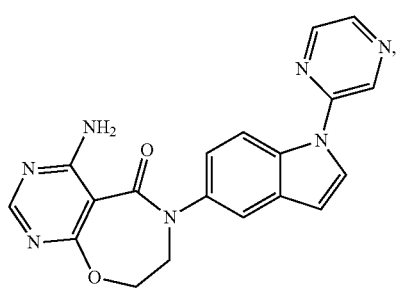
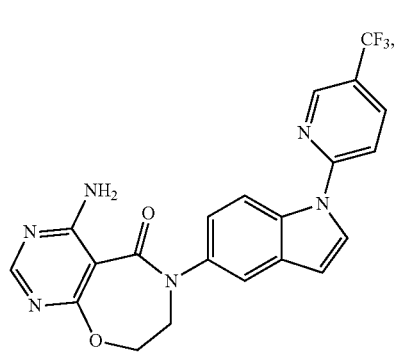
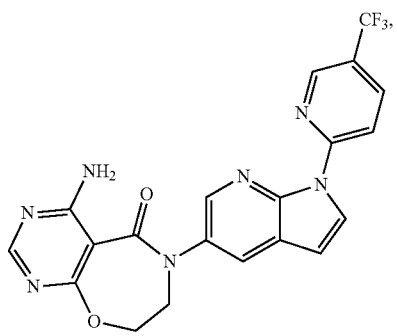
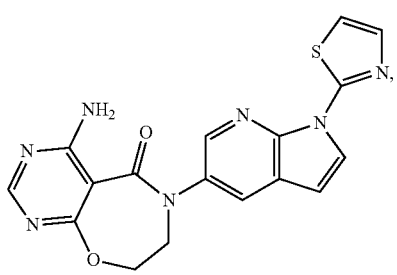
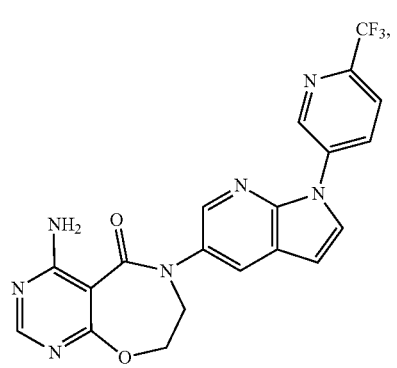
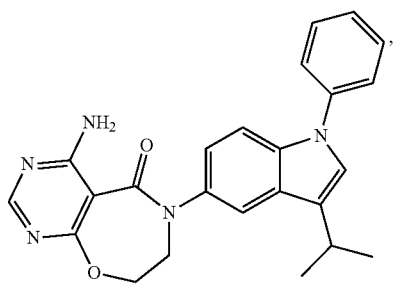
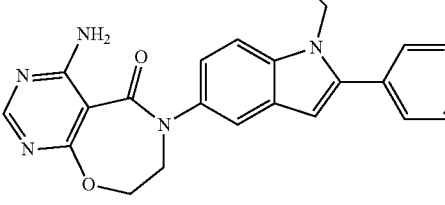

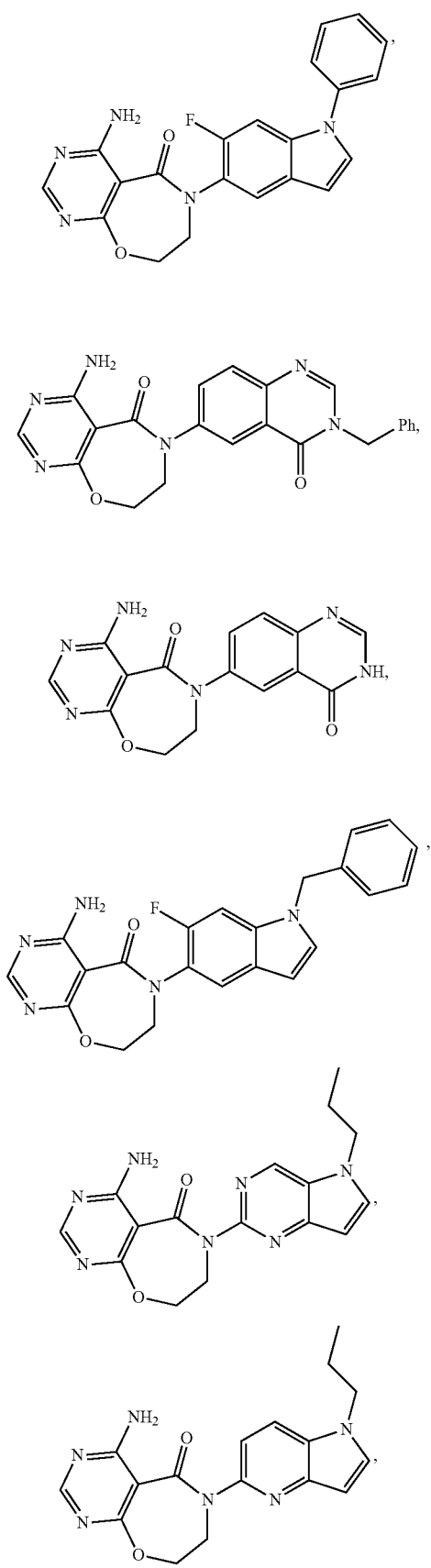

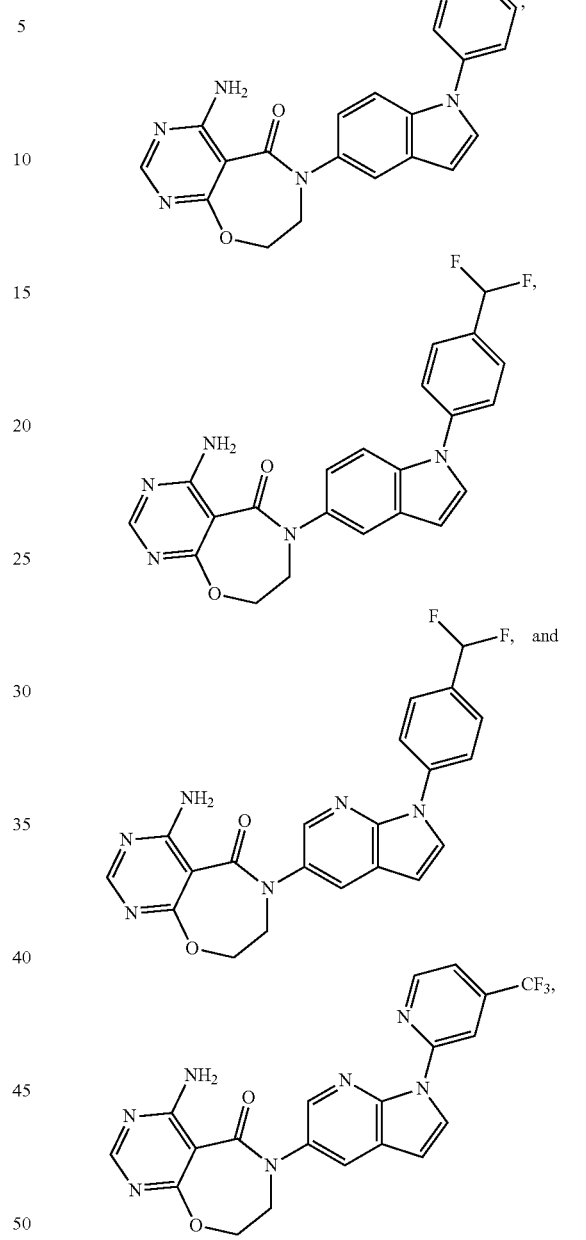

or a pharmaceutically acceptable salt thereof.

2. The compound according to claim 1 in free base form.

3. A pharmaceutical composition comprising the compound or salt according to claim 1, and a pharmaceutically acceptable carrier.

4. A pharmaceutical composition comprising the compound according to claim 2, and a pharmaceutically acceptable carrier.

5. A method of treating obesity comprising administering to a human in need thereof an effective amount of the compound or salt according to claim 1.

6. A method of treating obesity comprising administering to a human in need thereof an effective amount of the compound according to claim 2.

7. A method of treating acne comprising administering to a human in need thereof an effective amount of the compound or salt according to claim 1.

8. A method of treating acne comprising administering to a human in need thereof an effective amount of the compound according to claim 2.

9. The method according to claim 7 wherein the compound is:

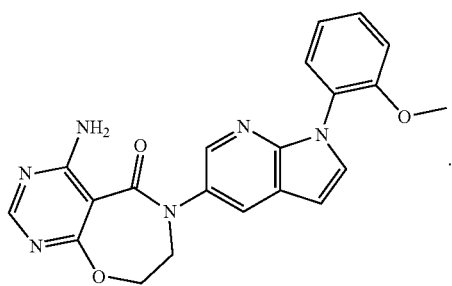 [SMILES: COc1ccccc1-n1ccc2cc(N3CCOc4ncnc(N)c4C3=O)cnc21]

10. The method according to claim 7 wherein the compound is:

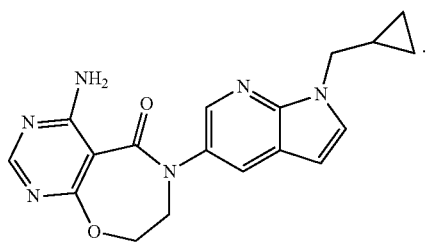 [SMILES: Nc1ncnc2c1C(=O)N(c1cnc3c(ccn3CC3CC3)c1)CCO2]

11. The method according to claim 8 wherein the compound is:

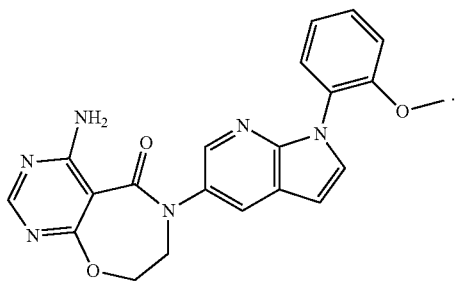 [SMILES: COc1ccccc1-n1ccc2cc(N3CCOc4ncnc(N)c4C3=O)cnc21]

12. The method according to claim 8 wherein the compound is:

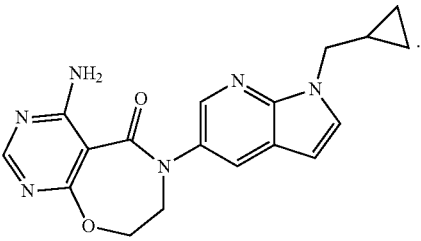 [SMILES: Nc1ncnc2c1C(=O)N(c1cnc3c(ccn3CC3CC3)c1)CCO2]

13. A method of treating obesity comprising administering to a human in need thereof an effective amount of the pharmaceutical composition according to claim 3.

14. A method of treating obesity comprising administering to a human in need thereof an effective amount of the pharmaceutical composition according to claim 4.

15. A method of treating acne comprising administering to a human in need thereof an effective amount of the pharmaceutical composition according to claim 3.

16. A method of treating acne comprising administering to a human in need thereof an effective amount of the pharmaceutical composition according to claim 4.

* * * * *